US009895534B2

(12) United States Patent
Stevenson et al.

(10) Patent No.: US 9,895,534 B2
(45) Date of Patent: Feb. 20, 2018

(54) MLCC FILTER ON AN AIMD CIRCUIT BOARD WITH CONDUCTIVE GROUND PIN ATTACHED TO A HERMETIC FEEDTHROUGH FERRULE

(71) Applicant: Greatbatch Ltd., Clarence, NY (US)

(72) Inventors: Robert A. Stevenson, Canyon Country, CA (US); Christine A. Frysz, Orchard Park, NY (US); Richard L. Brendel, Carson City, NV (US)

(73) Assignee: Greatbatch Ltd., Clarence, NY (US)

(*) Notice: Subject to any disclaimer, the term of this patent is extended or adjusted under 35 U.S.C. 154(b) by 0 days.

(21) Appl. No.: 15/375,235

(22) Filed: Dec. 12, 2016

(65) Prior Publication Data

US 2017/0087355 A1 Mar. 30, 2017

Related U.S. Application Data

(60) Continuation of application No. 14/503,583, filed on Oct. 1, 2014, which is a division of application No.
(Continued)

(51) Int. Cl.
*A61N 1/375* (2006.01)
*A61N 1/08* (2006.01)
(Continued)

(52) U.S. Cl.
CPC ............... *A61N 1/08* (2013.01); *A61N 1/375* (2013.01); *A61N 1/3718* (2013.01);
(Continued)

(58) Field of Classification Search
CPC ...... A61N 1/08; A61N 1/3718; A61N 1/3754; A61N 2001/086; H01G 4/35; H03H 1/0007
(Continued)

(56) References Cited

U.S. PATENT DOCUMENTS

| | | | |
|---|---|---|---|
| 3,681,612 A | 8/1972 | Kinzler et al. |
| 3,745,430 A | 7/1973 | Kerr et al. |

(Continued)

FOREIGN PATENT DOCUMENTS

| | | |
|---|---|---|
| JP | 6176962 | 6/1994 |
| JP | 7272975 | 10/1995 |

(Continued)

*Primary Examiner* — Michael Carey
(74) *Attorney, Agent, or Firm* — Michael F. Scalise

(57) ABSTRACT

An EMI/energy dissipating filter for an active implantable medical device (AIMD) is described. The filter comprises a first gold braze hermetically sealing the insulator to a ferrule that is configured to be mounted in an opening in a housing for the AIMD. A lead wire is hermetically sealed in a passageway through the insulator by a second gold braze. A circuit board substrate is disposed adjacent the insulator. A two-terminal chip capacitor disposed adjacent to the circuit board has an active end metallization that is electrically connected to the active electrode plates and a ground end metallization that is electrically connected to the at least one ground electrode plates of the capacitor. A ground path electrically extends between the ground end metallization of the chip capacitor and the ferrule. The ground path comprises a conductive pin electrically and mechanically connected to the ferrule by a third gold braze. The ground path comprises an internal ground plate disposed within the circuit board substrate, and the internal ground plate is electrically connected to both the conductive pin and the ground end metallization of the chip capacitor. An active path electrically extends between the active end metallization of the chip capacitor and the lead wire.

35 Claims, 82 Drawing Sheets

Related U.S. Application Data

13/873,832, filed on Apr. 30, 2013, now Pat. No. 8,868,189, which is a continuation of application No. 13/528,052, filed on Jun. 20, 2012, now Pat. No. 8,433,410, which is a continuation of application No. 12/407,402, filed on Mar. 19, 2009, now Pat. No. 8,195,295.

(60) Provisional application No. 61/038,382, filed on Mar. 20, 2008, provisional application No. 61/116,094, filed on Nov. 19, 2008, provisional application No. 61/144,102, filed on Jan. 12, 2009, provisional application No. 61/150,061, filed on Feb. 5, 2009.

(51) Int. Cl.

| | |
|---|---|
| ***A61N 1/37*** | (2006.01) |
| ***H01G 4/35*** | (2006.01) |
| ***H01G 4/40*** | (2006.01) |
| ***H01R 13/7195*** | (2011.01) |
| ***H03H 1/00*** | (2006.01) |
| ***H05K 9/00*** | (2006.01) |
| ***H03H 7/01*** | (2006.01) |
| ***H05K 5/00*** | (2006.01) |
| ***H05K 1/18*** | (2006.01) |
| ***H01G 4/06*** | (2006.01) |

(52) U.S. Cl.

CPC ............ *A61N 1/3754* (2013.01); *H01G 4/06* (2013.01); *H01G 4/35* (2013.01); *H01G 4/40* (2013.01); *H01R 13/7195* (2013.01); *H03H 1/0007* (2013.01); *H03H 7/1766* (2013.01); *H05K 1/181* (2013.01); *H05K 5/0095* (2013.01); *H05K 9/00* (2013.01); *A61N 1/086* (2017.08); *H03H 2001/0042* (2013.01); *H03H 2001/0085* (2013.01); *H05K 2201/10015* (2013.01)

(58) Field of Classification Search

USPC ........................................................ 607/36

See application file for complete search history.

(56) References Cited

U.S. PATENT DOCUMENTS

| | | | |
|---|---|---|---|
| 3,961,294 | A | 6/1976 | Hollyday |
| 4,424,551 | A | 1/1984 | Stevenson et al. |
| 4,858,064 | A | 8/1989 | Segawa et al. |
| 5,039,965 | A | 8/1991 | Higgins |
| 5,268,810 | A | 12/1993 | Dimarco et al. |
| 5,331,505 | A | 7/1994 | Wilheim |
| 5,333,095 | A | 7/1994 | Stevenson et al. |
| 5,450,090 | A | 9/1995 | Gels et al. |
| 5,491,300 | A | 2/1996 | Huppenthal et al. |
| 5,493,259 | A | 2/1996 | Blalock et al. |
| 5,620,476 | A | 4/1997 | Truex et al. |
| 5,650,759 | A | 7/1997 | Hittman et al. |
| 5,683,435 | A | 11/1997 | Truex et al. |
| 5,757,252 | A | 5/1998 | Cho et al. |
| 5,765,779 | A | 6/1998 | Hancock et al. |
| 5,782,891 | A | 7/1998 | Hassler et al. |
| 5,822,174 | A | 10/1998 | Yamate et al. |
| 5,905,627 | A | 5/1999 | Brendel et al. |
| 5,929,729 | A | 7/1999 | Swarup |
| 5,959,336 | A | 9/1999 | Barsan |
| 5,973,906 | A | 10/1999 | Stevenson et al. |
| 5,973,907 | A | 10/1999 | Reed |
| 6,137,161 | A | 10/2000 | Gilliland et al. |
| 6,146,743 | A | 11/2000 | Haq et al. |
| 6,373,673 | B1 | 4/2002 | Anthony |
| 6,424,234 | B1 | 7/2002 | Stevenson |
| 6,456,481 | B1 | 9/2002 | Stevenson |
| 6,459,935 | B1 | 10/2002 | Piersma |
| 6,473,314 | B1 | 10/2002 | Custer et al. |
| 6,512,666 | B1 | 1/2003 | Duva |
| 6,529,103 | B1 | 3/2003 | Brendel et al. |
| 6,566,978 | B2 | 5/2003 | Stevenson et al. |
| 6,660,116 | B2 | 12/2003 | Wolf |
| 6,765,680 | B2 | 7/2004 | Carr et al. |
| 6,765,779 | B2 | 7/2004 | Stevenson |
| 6,765,780 | B2 | 7/2004 | Brendel et al. |
| 6,768,630 | B2 | 7/2004 | Togashi |
| 6,806,806 | B2 | 10/2004 | Anthony |
| 6,888,715 | B2 | 5/2005 | Stevenson et al. |
| 7,038,900 | B2 | 5/2006 | Stevenson et al. |
| 7,046,499 | B1 | 5/2006 | Imani et al. |
| 7,110,227 | B2 | 9/2006 | Anthony et al. |
| 7,113,387 | B2 | 9/2006 | Stevenson et al. |
| 7,199,995 | B2 | 4/2007 | Stevenson |
| 7,236,834 | B2 | 6/2007 | Christopherson et al. |
| 7,301,748 | B2 | 11/2007 | Anthony et al. |
| 7,310,216 | B2 | 12/2007 | Stevenson et al. |
| 7,322,832 | B2 | 1/2008 | Kronich et al. |
| 7,327,553 | B2 | 2/2008 | Brendel |
| 7,363,090 | B2 | 4/2008 | Halperin et al. |
| 7,423,860 | B2 | 9/2008 | Anthony et al. |
| 7,428,136 | B2 | 9/2008 | Barnett |
| 7,433,168 | B2 | 10/2008 | Anthony |
| 7,436,672 | B2 | 10/2008 | Ushijima et al. |
| 7,439,449 | B1 | 10/2008 | Kumar et al. |
| 7,446,996 | B2 | 11/2008 | Togashi |
| 7,450,396 | B2 | 11/2008 | Ye et al. |
| 7,495,884 | B2 | 2/2009 | Togashi |
| 7,586,728 | B2 | 9/2009 | Anthony |
| 7,593,208 | B2 | 9/2009 | Anthony et al. |
| 7,675,729 | B2 | 3/2010 | Anthony et al. |
| 7,679,926 | B2 | 3/2010 | Hsu et al. |
| 7,702,387 | B2 | 4/2010 | Stevenson et al. |
| 7,719,854 | B2 | 5/2010 | Youker et al. |
| 7,733,621 | B2 | 6/2010 | Anthony et al. |
| 7,957,806 | B2 | 6/2011 | Stevenson et al. |
| 8,219,208 | B2 | 7/2012 | Stevenson et al. |
| 8,463,375 | B2 | 6/2013 | Dabney et al. |
| 2003/0179536 | A1 | 9/2003 | Stevenson et al. |
| 2005/0092507 | A1* | 5/2005 | Marshall ............. A61N 1/3754 174/50.59 |
| 2005/0201039 | A1 | 9/2005 | Stevenson et al. |
| 2005/0219787 | A1 | 10/2005 | Stevenson et al. |
| 2006/0028784 | A1* | 2/2006 | Brendel ............... A61N 1/3754 361/302 |
| 2006/0032665 | A1 | 2/2006 | Ice |
| 2006/0085043 | A1 | 4/2006 | Stevenson |
| 2006/0212096 | A1 | 9/2006 | Stevenson |
| 2007/0112398 | A1 | 5/2007 | Stevenson et al. |
| 2007/0123949 | A1 | 5/2007 | Dabney et al. |
| 2007/0179554 | A1 | 8/2007 | Lyer et al. |
| 2007/0203529 | A1 | 8/2007 | Iyer et al. |
| 2007/0203530 | A1 | 8/2007 | Hubing et al. |
| 2007/0288058 | A1 | 12/2007 | Halperin et al. |
| 2008/0049376 | A1 | 2/2008 | Stevenson et al. |
| 2008/0049410 | A1 | 2/2008 | Kawaguchi et al. |
| 2008/0071313 | A1 | 3/2008 | Stevenson et al. |
| 2008/0116997 | A1 | 5/2008 | Dabney et al. |
| 2008/0132987 | A1 | 6/2008 | Westlund et al. |
| 2008/0158746 | A1 | 7/2008 | Anthony et al. |
| 2008/0161886 | A1 | 7/2008 | Stevenson et al. |
| 2008/0195180 | A1 | 8/2008 | Stevenson et al. |
| 2008/0239622 | A1 | 10/2008 | Hsu et al. |
| 2008/0247111 | A1 | 10/2008 | Anthony et al. |
| 2008/0247116 | A1 | 10/2008 | Kawano et al. |
| 2008/0247117 | A1 | 10/2008 | Elam et al. |
| 2008/0264685 | A1 | 10/2008 | Park et al. |
| 2008/0277153 | A1 | 11/2008 | Teshome et al. |
| 2009/0097219 | A1 | 4/2009 | Cho et al. |
| 2009/0107717 | A1 | 4/2009 | Hsu et al. |
| 2009/0116167 | A1 | 5/2009 | Stevenson et al. |
| 2009/0128976 | A1 | 5/2009 | Anthony |
| 2009/0139760 | A1 | 6/2009 | Tanaka |
| 2009/0180237 | A1 | 7/2009 | Hou et al. |
| 2009/0187229 | A1 | 7/2009 | Lavie |
| 2009/0236141 | A1 | 9/2009 | Kim et al. |
| 2009/0243756 | A1 | 10/2009 | Stevenson et al. |

(56) References Cited

U.S. PATENT DOCUMENTS

| | | | |
|---|---|---|---|
| 2010/0046135 A1 | 2/2010 | Niki et al. | |
| 2010/0046137 A1 | 2/2010 | Adachi | |
| 2010/0109958 A1 | 5/2010 | Haubrich et al. | |
| 2010/0109966 A1 | 5/2010 | Mateychuk et al. | |
| 2010/0149042 A1 | 6/2010 | Utsi et al. | |
| 2010/0151113 A1 | 6/2010 | Shelton | |
| 2010/0179606 A1* | 7/2010 | Iyer ...................... | A61N 1/3754 607/2 |
| 2011/0029036 A1 | 2/2011 | Yamamoto et al. | |

FOREIGN PATENT DOCUMENTS

| | | |
|---|---|---|
| JP | 2001068958 | 3/2001 |
| JP | 2004254257 | 9/2004 |
| JP | 2004289760 | 10/2004 |
| JP | 2005117606 | 4/2005 |
| JP | 2007129565 | 5/2007 |

* cited by examiner

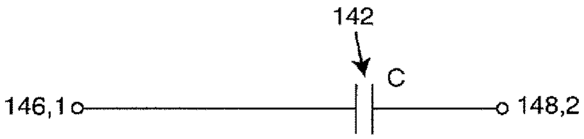
FIG. 15
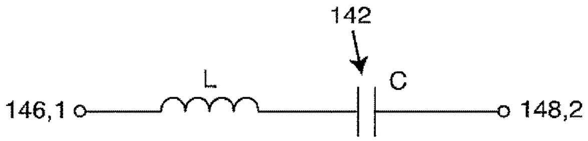
FIG. 16
$$f_r = \frac{1}{2\pi\sqrt{LC}}$$
Where $f_r$ = MLCC Self Resonance Frequency in Hertz
L = Induction in Henries
C = Capacitance in Farads
FIG. 17
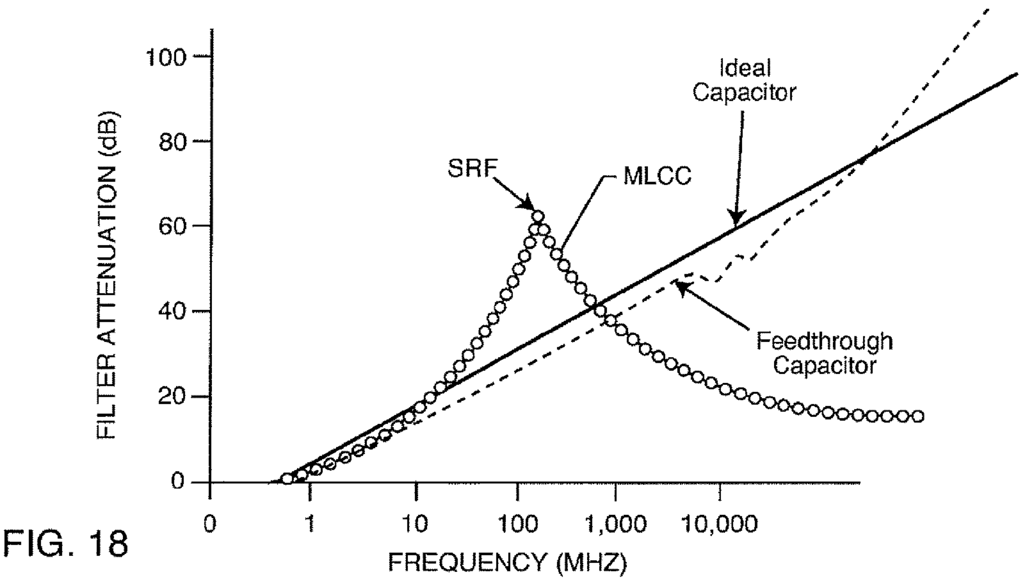
FIG. 18

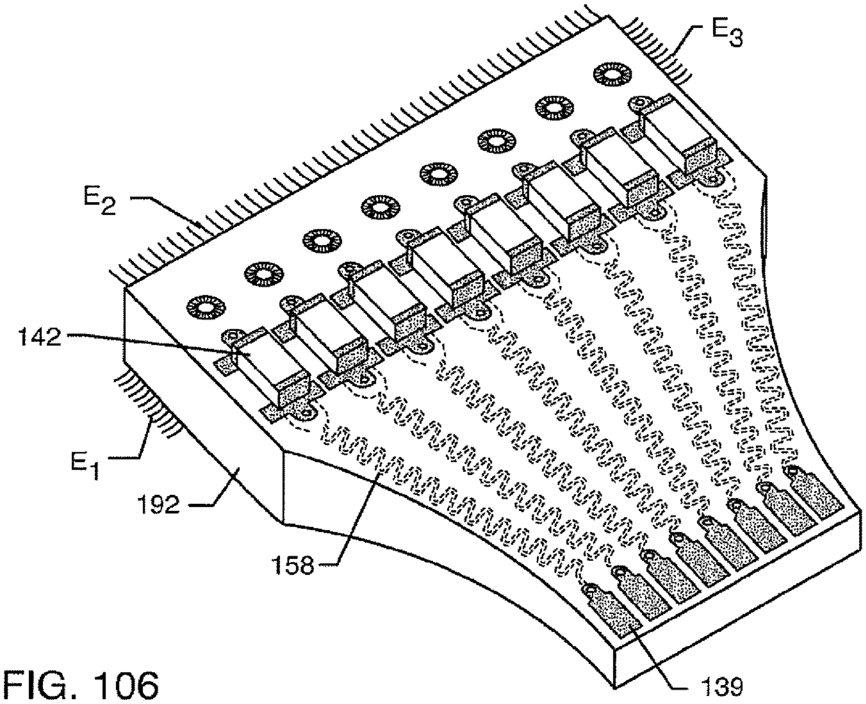
FIG. 106
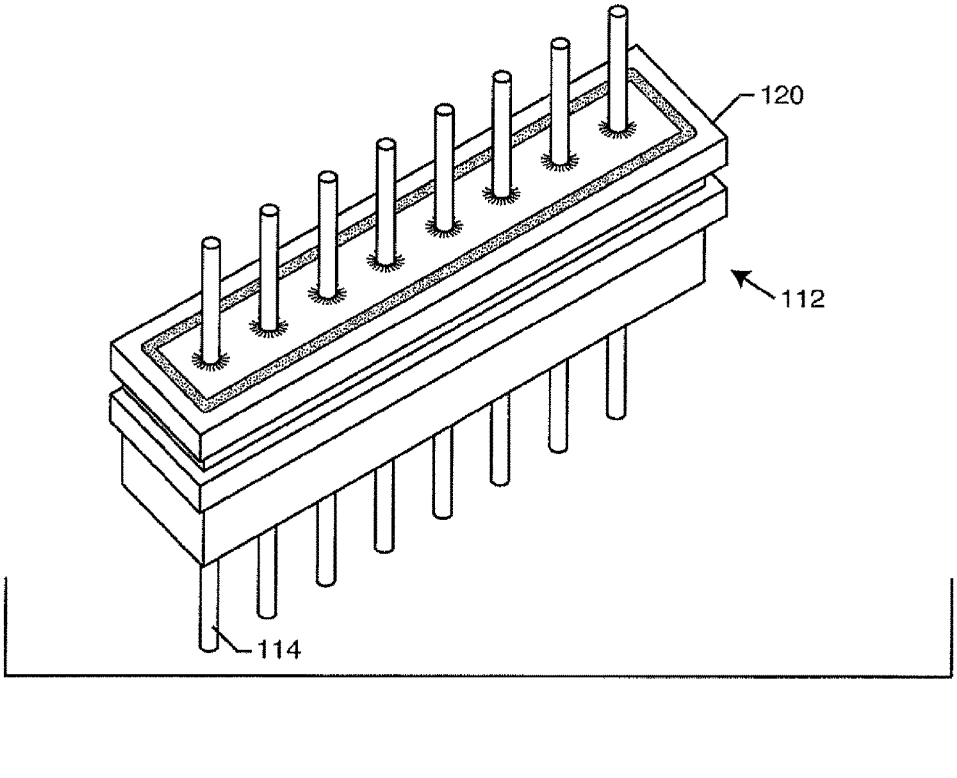

WHERE C = CAPACITANCE IN FARADS
L = INDUCTANCE IN HENRYS
R = RESISTANCE (INCLUDES RESISTANCE OF INDUCTOR, HOOK-UP WIRE & CAPACITOR EQUILIVANT SERIES RESISTANCE (ESR)

RESONANT FREQUENCY $= f_r$

WHERE $f_r = \frac{1}{2\Pi\sqrt{LC}}$

WHERE $f_r$ IS IN HERTZ

MLCC FILTER ON AN AIMD CIRCUIT BOARD WITH CONDUCTIVE GROUND PIN ATTACHED TO A HERMETIC FEEDTHROUGH FERRULE

CROSS REFERENCE TO RELATED APPLICATIONS

This is a continuation application of U.S. patent application Ser. No. 14/503,583, filed on Oct. 1, 2014, which is a divisional application of U.S. patent application Ser. No. 13/873,832, filed on Apr. 30, 2013, now U.S. Pat. No. 8,868,189, which is a continuation application of U.S. patent application Ser. No. 13/528,052, filed on Jun. 20, 2012, now U.S. Pat. No. 8,433,410, which is a continuation application of U.S. patent application Ser. No. 12/407,402, filed on Mar. 19, 2009, now U.S. Pat. No. 8,195,295, which claims priority from U.S. Provisional Pat. App. Ser. Nos. 61/038,382, filed on Mar. 20, 2008; 61/116,094, filed on Nov. 19, 2008; 61/144,102, filed on Jan. 12, 2009; and 61/150,061, filed on Feb. 5, 2009, the contents of which are fully incorporated herein with this reference.

BACKGROUND OF THE INVENTION

The present invention relates generally to feedthrough filter capacitor EMI filters. More particularly, the present invention relates to a hybrid EMI filter substrate and/or flex cable assembly which embodies embedded shielded flat-through/feedthrough filters and/or energy dissipating circuit elements. This invention is applicable to a wide range of connectors, terminals and/or hermetic seals that support lead wires as they ingress/egress into electronic modules or shielded housings. In particular, the present invention applies to a wide variety of active implantable medical devices (AIMDs).

FIGS. 1-40 provide a background for better understanding the significance and novelty of the present invention.

FIG. 1 illustrates various types of active implantable and external medical devices 100 that are currently in use. FIG. 1 is a wire formed diagram of a generic human body showing a number of implanted medical devices. 100A represents a family of hearing devices which can include the group of cochlear implants, piezoelectric sound bridge transducers and the like. 100B represents a variety of neurostimulators and brain stimulators. Neurostimulators are used to stimulate the Vagus nerve, for example, to treat epilepsy, obesity and depression.

Brain stimulators are pacemaker-like devices and include electrodes implanted deep into the brain for sensing the onset of the seizure and also providing electrical stimulation to brain tissue to prevent the seizure from actually occurring. The lead wires associated with a deep brain stimulator are often placed using real time MRI imaging. 100C shows a cardiac pacemaker which is well-known in the art. 100D includes the family of left ventricular assist devices (LVAD's), and artificial hearts, including the recently introduced artificial heart known as the Abiocor. 100E includes an entire family of drug pumps which can be used for dispensing of insulin, chemotherapy drugs, pain medications and the like. Insulin pumps are evolving from passive devices to ones that have sensors and closed loop systems. That is, real time monitoring of blood sugar levels will occur. These devices tend to be more sensitive to EMI than passive pumps that have no sense circuitry or externally implanted lead wires. 100F includes a variety of bone growth stimulators for rapid healing of fractures. 100G includes urinary incontinence devices. 100H includes the family of pain relief spinal cord stimulators and anti-tremor stimulators. 100H also includes an entire family of other types of neurostimulators used to block pain. 1001 includes a family of implantable cardioverter defibrillator (ICD) devices and also includes the family of congestive heart failure devices (CHF). This is also known in the art as cardio resynchronization therapy devices, otherwise known as CRT devices. 100J illustrates an externally worn pack. This pack could be an external insulin pump, an external drug pump, an external neurostimulator or even a ventricular assist device. 100K illustrates the insertion of an external probe or catheter. These probes can be inserted into the femoral artery, for example, or in any other number of locations in the human body. 100L illustrates one of various types of EKG/ECG external skin electrodes which can be placed at various locations. 100M are external EEG electrodes placed on the head.

FIG. 2 is a prior art unipolar discoidal feedthrough capacitor, which has an active internal electrode plate set 102 and a ground electrode plate set 104. The inside diameter termination surface 106 is connected electrically to the active electrode plate set 102. An outside diameter termination surface 108 is both solderable and electrically conductive, and it is connected to the outside diameter of electrode plate sets 104.

FIG. 3 is a cross-section of the discoidal feedthrough capacitor of FIG. 2 shown mounted to a hermetic seal 112 of an active implantable medical device (AIMD). In prior art discoidal feedthrough capacitor devices, the lead wire 114 is continuous. The hermetic seal 112 is attached to, typically, a titanium housing 116, for example, of a cardiac pacemaker. An insulator 118, like alumina ceramic or glass, is disposed within a ferrule 120 and forms a hermetic seal against body fluids. The terminal pin or lead wire 114 extends through the hermetic seal 112, passing through aligned passageways through the insulator 118 and the capacitor 110. A gold braze 122 forms a hermetic seal joint between the terminal pin 114 and the insulator 118. Another gold braze 124 forms a hermetic seal joint between the alumina insulator 118 and the titanium ferrule 120. A laser weld 126 provides a hermetic seal joint between the ferrule 120 and the housing 116. The feedthrough capacitor 110 is shown surface mounted in accordance with U.S. Pat. No. 5,333,095, and has an electrical connection 128 between its inside diameter metallization 106 and hence the active electrode plate set 102 and lead wire 114. There is also an outside diameter electrical connection 130 which connects the capacitor's outside diameter metallization 108 and hence the ground electrodes 104 to the ferrule 120. Feedthrough capacitors are very efficient high frequency devices that have minimal series inductance. This allows them to operate as EMI filters over very broad frequency ranges. Referring once again to FIG. 3, one can see that another way to describe a prior art discoidal feedthrough capacitor 110 is as a three-terminal capacitor. Three-terminal devices generally act as transmission lines. Referring to FIG. 3, one can see that there is a current "I" that passes into lead wire 114. For a prior art AIMD, on the body fluid side there is generally an implanted lead which can undesirably act as an antenna which can pick up energy from environmental emitters. This energy is known as electromagnetic interference (EMI). Cell phones, microwave ovens and the like have all been implicated in causing interference with active implantable medical devices. If this interference enters lead wire 114 at point X (FIG. 3), it is attenuated along its length by the feedthrough capacitor 110. Upon exiting, the undesirable high frequency EMI has been cleaned off of the normal low frequency (LF) circuit current (such as pacemaker pacing pulses or biologic frequency sensors) so that the high frequency EMI has been significantly attenuated. Another way of looking at this is as the high frequency energy passes from terminal 1 to terminal 2 (FIGS. 3 and 4), it is diverted through the feedthrough capacitor 110 to the ground terminal which is also known as the third terminal or terminal 3. The feedthrough capacitor 110 also performs two other important functions: a) its internal electrodes 102 and 104 act as a continuous part of the overall electromagnetic shield housing of the electronic device or module which physically blocks direct entry of high frequency RF energy through the hermetic seal 112 or equivalent opening for lead wire ingress and egress in the otherwise completely shielded housing (such RF energy, if it does penetrate inside the shielded housing can couple to and interfere with sensitive electronic circuitry), and; b) the feedthrough capacitor 110 very effectively shunts undesired high frequency EMI signals off of the lead wires to the overall shield housing where such energy is dissipated in eddy currents resulting in a very small temperature rise.

FIG. 4 is a schematic diagram showing the discoidal feedthrough capacitor 110 previously described in connection with FIGS. 2 and 3. As one can see, it is a three-terminal device consistent with terminals 1, 2 and 3 illustrated in FIG. 3.

FIG. 5 is a quadpolar prior art feedthrough capacitor 132 which is similar in construction to that previously described in FIG. 2 except that it has four through holes.

Throughout this description, functionally equivalent elements will be given the same reference number, irrespective of the embodiment being shown.

FIG. 6 is a cross-section showing the internal electrodes 102, 104 of the capacitor 132 of FIG. 5.

FIG. 7 is a schematic diagram showing the four discrete feedthrough capacitors comprising the quadpolar feedthrough capacitor 132 of FIGS. 5 and 6.

FIG. 8 is an exploded electrode view showing the inner and outer diameter electrodes of the unipolar feedthrough capacitor 110 of FIGS. 2 and 3. One can see the active electrode plates set 102 and the ground electrode plate set 104. Cover layers 134 are put on the top and bottom for added electrical installation and mechanical strength.

FIG. 9 is an exploded view of the interior electrodes of the prior art quadpolar feedthrough capacitor 132 previously illustrated in FIG. 5. As shown in FIG. 9, the active electrode plate sets are shown as 102 and the ground electrode plates are shown as 104. Cover layers 134 serve the same purpose as previously described in connection with FIG. 8.

FIG. 10 illustrates a prior art quadpolar feedthrough capacitor 132 mounted on top of a hermetic insulator 118 wherein a wire bond substrate 136 is attached to the top as shown. Wire bond pads 138, 138', 138'', 138''' and 140 are shown for convenient connection to the internal circuitry of the AIMD. This is more thoroughly described in FIGS. 75 and 76 of U.S. Pat. Nos. 7,038,900 and 7,310,216, the contents of which are incorporated herein.

FIG. 11 is a cross-section taken generally from section 11-11 from FIG. 10. In FIG. 11, the internal circuit traces T.sub.1 through T.sub.4 to the wire bond pads 138-138''' are shown. Referring back to FIG. 10, there is an additional wire bond pad 140 shown on the left side of the wire bond substrate 136. This is also shown in FIG. 11. This is a ground connection to the outside diameter of the hermetic seal ferrule 120 and provides a convenient connection point for electronic circuits and the like that need a ground attachment point on the inside of the AIMD.

FIG. 12 is a schematic diagram of the prior art wire bond pad quadpolar hermetic feedthrough 132 of FIG. 10.

FIG. 13 is a prior art monolithic ceramic capacitor (MLCC) 142. These are made by the hundreds of millions per day to service the consumer electronics and other markets. Virtually all cell phones and other types of electronic devices have many of these. In FIG. 13, one can see that the MLCC 142 has a body 144 generally consisting of a high dielectric constant ceramic such as barium titanate. It also has solderable termination surfaces 146 and 148 at either end. These termination surfaces 146 and 148 provide a convenient way to make a connection to the internal electrode plates of the MLCC capacitor 142. FIG. 13 can also take the shape and characteristics of a number of other types of capacitor technologies, including rectangular, cylindrical, round, tantalum, aluminum electrolytic, stacked film or any other type of capacitor technology.

FIG. 14 is a sectional view taken from section 14-14 in FIG. 13. The left hand electrode plate set is shown as 150 and the right hand electrode plate set is shown as 152. One can see that the left hand electrode plates 150 are electrically connected to the external metallization surface 146. The opposite electrode plate set (or right hand plate set) 152 is shown connected to the external metallization surface 148. One can see that prior art MLCC and equivalent chip capacitors are also known as two-terminal capacitors. That is, there are only two ways electrical energy can connect to the body of the capacitor. In FIGS. 13 and 14, the first terminal “1” is on the left side and the second terminal “2” is on the right side.

FIG. 15 is an ideal schematic diagram of the prior art MLCC capacitor 142 of FIG. 13.

FIG. 16 is a more realistic schematic diagram showing the fact that the MLCC 142 structure as illustrated in FIG. 13 has series inductance L. This inductive property arises from the fact that it is a two-terminal device and does not act as a transmission line. That is, its lead wires and associated internal electrodes all tend to add series inductance to the capacitor. It is well known to electrical engineers that MLCC capacitors will self-resonate at a particular frequency. FIG. 17 gives the formula for this resonant frequency. There is always a point at which the capacitive reactance as shown in FIG. 16 is equal and opposite to the inductive reactance. It is this point that these two imaginary components cancel each other out. If it weren’t for resistive losses, at the resonant frequency the impedance between 146,1 and 148,2 as shown in FIG. 16 would go to zero. However, the resistive losses of the inductor L and the equivalent series resistance of the capacitor C prevent this from happening. This is better understood by referring to FIG. 18.

Shown in FIG. 18 are three curves. An ideal capacitor curve is shown which is very similar to the response of a feedthrough capacitor, such as shown in FIG. 3. One can see that the attenuation goes up fairly linearly with frequency all the way up to very high frequencies even above 10,000 megahertz (MHz). The MLCC curve is for the capacitor of FIG. 13. At low frequencies, in this case below 100 MHz, the MLCC curve tracks very closely to an ideal or a feedthrough capacitor. However, as the MLCC nears its self-resonant frequency (SRF), its attenuation tends to go up dramatically. This is because when one refers back to FIG. 16, the inductive and capacitive reactance elements are tending to cancel each other out. As previously mentioned, if it weren’t for its resistive losses at resonance (SRF), the MLCC chip would look like a short circuit, in which ideal case its attenuation would be infinite. This means that if it weren’t for these resistive losses, we would have infinite attenuation at the SRF. Instead what we have is a peak of approximately 60 dB as shown. Above resonance, the MLCC capacitor becomes increasingly inductive and the attenuation drops dramatically. This is an undesirable effect and this is why feedthrough capacitors have generally been the preferred choice for use in EMI broadband filters.

FIG. 19 shows three different size MLCC capacitors C.sub.1-C.sub.3 connected around a unipolar feedthrough pin or lead wire 114. Self-resonant frequency is dependent upon the internal inductance of a capacitor. This was illustrated and described in connection with FIG. 16. One can reduce the amount of inductance by using a physically smaller MLCC capacitor. For example, referring to FIG. 19, one could have one each of what is known in the art as a size 0402, a 0603 and a 0805 MLCC capacitor. This is an EIA designation wherein, for example, 0805 would be 0.080 inches long and 0.050 inches wide. Accordingly, these three MLCC capacitors C.sub.1-C.sub.3 would have three different resonant frequencies. This is more thoroughly described in U.S. Pat. No. 5,973,907 and U.S. Pat. No. 5,959,336 the contents of which are incorporated herein by reference. FIG. 20 is the schematic diagram for the three MLCC capacitors of FIG. 19.

FIG. 21 shows the attenuation response for the three chip capacitor unipolar hermetic terminal in FIG. 19. These three capacitors C.sub.1-C.sub.3 are acting in parallel as shown in the schematic diagram of FIG. 20. Referring to FIG. 21, we can see that there are now three resonant peaks representing the self-resonant frequency of each of these individual MLCC capacitors acting together in parallel. Shown for reference is the ideal capacitor response curve previously shown in FIG. 18. The SRF for C.sub.1, C.sub.2 and C.sub.3 are also shown. The physically largest capacitor C.sub.1 will have the lowest self-resonant frequency whereas the physically smaller capacitor (C.sub.3) will have the highest self-resonant frequency. This is because, in general, the smaller the MLCC capacitor, the lower its internal inductance. Secondary factors that determine the value of the undesirable equivalent series inductance (ESL) of an MLCC capacitor include the number and spacing of internal electrodes, geometry, form factor and circuit board mounting techniques.

Referring once again to FIG. 19, the reason why this approach has never been commonly practiced in the AIMD market is the fact that this is a complicated design and is also costly. Because of the space limitations and reliability implications, packing this many components into such a small place becomes impractical.

FIG. 22 shows a different method of mounting MLCC capacitors, for example, those previously shown in FIG. 19. In the industry, this is known as the tombstone mounting position, which is a highly undesirable thing to do when the capacitor is to be used as an EMI filter or an RF decoupling device (bad mounting and bad form factor). This is because the capacitor's inductive loop area L.sub.1 tends to increase. The increased inductive loop area (integral of area bounded under the loop) has the effect of directly raising the inductance L as previously described in connection with FIG. 16. The reason this is undesirable is this particular capacitor will tend to self-resonate at a much lower frequency (and thereby becomes a less effective high frequency device or EMI filter).

FIG. 23 illustrates a more desirable way to mount the MLCC capacitor 142 of FIG. 22. This is a conventional flat surface mount technique, which has a much lower inductive loop area L.sub.2 as shown (area bounded under the loop). Accordingly, even though the two capacitors are identical in size and capacitance value, the MLCC capacitor 142 as shown in FIG. 23 will resonate at a much higher frequency before it starts to become undesirably inductive.

FIG. 24 is known in the art as a reverse geometry MLCC capacitor 142'. For comparative purposes, the physical size of the MLCC capacitor illustrated in FIG. 24 is exactly the same dimensions as the MLCC capacitors 142 previously shown in FIGS. 22 and 23. The important thing is the location of the termination surfaces 146' and 148'. The MLCC capacitor 142' in FIG. 24 has been terminated along its long sides. Accordingly, its inductive loop area or the area bounded underneath the loop L.sub.3 is the smallest of all the loop configurations. Thus, the capacitor 142' of FIG. 24 will self-resonate at a much higher frequency as compared to the MLCC capacitors 142 shown in FIGS. 22 and 23. A good treatment of this is found in a technical paper entitled, A CAPACITOR'S INDUCTANCE, which was given at the Capacitor and Resistor Technology Symposium in Lisbon, Portugal, Oct. 19-22, 1999. This paper was co-authored by Robert Stevenson and Dr. Gary Ewell of Aerospace Corporation. A related paper was given entitled, A CAPACITOR'S INDUCTANCE: CRITICAL PROPERTY FOR CERTAIN APPLICATIONS and was given by the same authors at the 49.sup.th Electronic and Components Technology Conference of the institute of Electrical and Electronic Engineers held Jun. 1-4, 1999 in San Diego, Calif.

FIG. 25 is the same electrical schematic diagram as previously illustrated in FIG. 16, but additionally showing the equivalent circuit model for an MLCC. Added are resistors IR and ESR. IR is the insulation resistance of the capacitor C. For electronic circuit analysis reasons, this IR resistor can generally be ignored. The reason for this is that it is typical that the value of IR is in excess of 10 Gigaohms (10,000,000,000 ohms). This number is so high compared to the values of the other components of the capacitor circuit model that it can be safely ignored. Also added to the complete schematic model shown in FIG. 25 is the capacitor series resistance (ESR). This is the total ESR including the dielectric loss tangent of the ceramic materials themselves and all ohmic losses and other electrical connections within and external to the capacitor itself. As previously stated, the presence of resistor ESR is why at the self-resonant frequency, the insertion loss does not go to infinity.

FIG. 26 is a prior art chip transient suppression diode 154, such as a transorb or the like.

FIG. 27 is a schematic diagram showing the diode chip 154 of FIG. 26 connected between an active medical device lead wire 114 and circuit ground. The dashed line shown in FIG. 27 illustrates the shielded housing of the AIMD. The reason for diode chip 154 (or multiple diode arrays) is to help protect the sensitive electronic circuits of the AIMD from external high voltage insults. These could be electrostatic discharges or the application to the patient of automatic (high voltage) external defibrillation (AED). AEDs are commonly now found in government buildings, airports, airplanes and the like. It is very important that a pacemaker not be burned out during the application of an AED external defibrillation event. The diode chip 154 shown in FIGS. 26 and 27 basically is typically an avalanche type diode which is also known in the art as a zener diode. In other words, they do not forward bias or short out until a certain voltage threshold is reached. These are also known in the art as transorbs and also have other market names. Such diodes can be back to back and placed in parallel in order to suppress biphasic high voltage AED defibrillation pulses.

FIG. 28 is a prior art inductor chip 156. There are many manufacturers of these. These can either have ferrite elements or be non-ferromagnetic. They come in a variety of sizes, inductance values and voltage ratings.

FIG. 29 is a schematic diagram of the inductor chip 156 of FIG. 28.

Referring to FIG. 30, one can see that an inductor circuit trace 158 is printed or deposited right on top of a prior art MLCC capacitor 142 to form an MLCC-T 160. The advantage here is that low cost MLCC's which have been produced from very high volume commercial capacitor operations could be utilized and the inductor trace 158 could be printed on as a supplemental operation. This forms a parallel inductor (L)-capacitor (C) resonant L-C circuit which creates a very high impedance at its resonant frequency. This is effective for suppressing a single RF frequency, such as that from Magnetic Resonance Imaging (MRI) equipment, or the like. This is more thoroughly described in U.S. Patent Application Publication No. US 2007-0112398 A1, the contents of which are incorporated herein by reference.

FIG. 31 shows yet another way to deposit an inductor shape 158 onto a separate substrate 162 to form a parallel L-C resonant circuit. For example, the substrate 162 could be of alumina ceramic or other suitable circuit board material. This could then be bonded with a thin adhesive layer 164 to a prior art MLCC capacitor 142. The composite MLCC-T structure 160', including corresponding metallization surfaces 146 and 148 on opposite ends, is illustrated in the electrical schematic diagram of FIG. 34 where it is evident that the structure forms a parallel L and C "tank" or bandstop circuit FIG. 32 is an isometric view of a novel composite monolithic ceramic capacitor-parallel resonant tank (MLCC-T) 160" which forms a bandstop or tank filter 166 in accordance with previously referenced U.S. patent application Ser. No. 11/558,349. Viewed externally, one can see no difference between the MLCC-T 160" of the present invention and prior art MLCC capacitor 142 as shown in FIG. 13. However, the novel MLCC-T 160" has an embedded inductor 162 which is connected in parallel across the capacitor between its opposite termination surfaces 146 and 148.

FIG. 33 illustrates an exploded view of the various layers of the novel MLCC-T tank filter 160" shown in FIG. 32. The novel MLCC tank (MLCC-T) 160" includes an embedded inductor 162. At low frequencies, the embedded inductor 162 shorts out the capacitor from one end to the other. However, at high frequency, this forms a parallel tank circuit 166 which is again better understood by referring to the schematic diagram in FIG. 34. Referring once again to FIG. 33, one can see that as the capacitor stacks up from the top, we have an area of blank cover sheets 168 followed by one or more embedded inductor layers 162. These inductor traces can have a variety of shapes as further illustrated in FIG. 83 of U.S. Patent Application Publication No. US 2007-0112398 A1. It will be obvious to those skilled in the art that there are a variety of optional shapes that could also be used. Then there are a number of other blank interleafs 170 before one gets to the capacitor electrode plate sets, 150 and 152. One can see the capacitor electrode plate set 150 which connects to the left hand termination 146 and one can also see the capacitor electrode plate set 152 which connects to the right hand termination 148. In FIG. 33, only single electrodes are shown as 150, 152. However, it will be obvious to those skilled in the art that any number of plates "n" could be stacked up to form the capacitance value that is desired. Then bottom blank cover sheets 168 are added to provide insulative and mechanical strength to the overall TANK filter MLCC-T 160".

After sintering the composite structure at high temperature, the last step, referring back to FIG. 32, is the application of the solderable termination surfaces 146 and 148. These termination surfaces can be a thick film ink, such as palladium silver, glass frit, gold plating, or the like and applied in many processes that are known in the art. Once again, the overall MLCC-T 160", which is illustrated in FIG. 32, looks identical to a prior art MLCC 142 as shown in FIG. 13. However, embedded within it is a novel parallel inductor structure 162 creating a novel parallel tank or bandstop filter 166 shown in the schematic diagram of FIG. 34.

Referring to schematic drawing FIG. 34, one can see that the inductor L has been placed in parallel with the capacitor C which is all conveniently located within the monolithic structure MLCC-T 160" shown in FIG. 32.

In FIG. 35 only one pole of a quadpolar feedthrough capacitor 132 is shown, which is better understood by referring to its schematic diagram shown in FIG. 36. One can see that there is a feedthrough capacitor 132 which is also known as a broadband EMI filter shown as $C_1$, $C_2$, $C_3$ and $C_4$ in FIG. 36. In line with each one of these circuits is a parallel resonant bandstop filter MLCC-T 160 to block MRI pulsed RF frequencies or frequencies from similar powerful emitters. The function of these bandstop filters is better understood by referring to the complete description in U.S. Pat. No. 7,363,090, the contents of which are incorporated herein.

Referring once again to FIG. 35, one can see that there is a metallic ferrule 120 which is attached to a hermetic insulator 118 by means of gold braze 124. There are also two lead wires 114 and 114' as shown. Lead wire 114 is mechanically and hermetically attached to insulator 118 by means of gold braze material 122. The bandstop filter or tank filter MLCC-T 160 is held in place with an insulative spacer plate 172. The feedthrough capacitor 132 is mounted on top as shown. Lead wire 114' is attached to the other end of the tank filter MLCC-T 160. A capacitor outside diameter metallization 108 connects to the capacitor's internal ground electrodes 104. Electrical connection 126 is made between the capacitor's outside diameter metallization 108 and both the metal of the ferrule 120 and gold braze material 124.

FIG. 37 is a different type of prior art MLCC feedthrough capacitor 142 that is built into a special configuration. It is known in the art by some as a flat-through capacitor (it also has other trade names). It will be referred to herein as a flat-through capacitor 174. At low frequencies, the flat-through capacitor 174 exhibits ideal capacitance behavior versus frequency. That is, its attenuation curve versus frequency is nearly ideal. This is because it is truly a three-terminal device which acts as a transmission line in a manner similar to those of prior art discoidal feedthrough capacitors 110. This is better understood by referring to its internal electrode plate geometry as shown in FIG. 38. Shown is a through or active electrode plate 175 that is sandwiched between two ground electrode plates 178 and 178'. The through or active electrode plate 175 is connected at both ends by termination surfaces 180 and 182. When the capacitor is mounted between circuit trace lands 184 and 186 as shown in FIG. 37, this connects the circuit trace together between points 184 and 186. Referring to the active circuit trace 175 in FIG. 38, one can see that there is a current $i_1$ that enters. If this is a high frequency EMI current, it will be attenuated along its length by the capacitance of the flat-through capacitor and emerge as a much smaller in amplitude EMI signal at terminal 2 as $i_1$. Similar to discoidal feedthrough capacitors, the flat-through capacitor 174 is also a three-terminal capacitor as illustrated in FIG. 37. The point of current input $i_1$ is terminal 1, the point of circuit current egress $i_1$ is known as terminal 2 and ground is known as terminal 3. In other words, any RF currents that are flowing down the circuit trace must pass through the electrodes 175 of the capacitor 174. This means that any RF signals are exposed for the full length of the electrode plate 175 between the ground electrodes 178 and the capacitance that is formed between them. This has the effect of making a very novel shape for a three-terminal feedthrough capacitor. One negative to this type of capacitor 174 is that it is not conveniently mountable in such a way that it becomes an integral part of an overall shield. There is always a frequency at which undesirable RF coupling 188 across the device will occur. This usually does not happen until 100 MHz or above. At very high frequencies, such as above 1 GHz, this problem becomes quite serious. Another negative, as compared to prior art discoidal feedthrough capacitors 110 (where the circuit current passes through a robust lead in a feedthrough hole), is that the flat-through capacitor circuit currents must flow through the electrodes of the flat-through capacitor itself (in prior art discoidal/feedthrough capacitors, the only current that flows in the electrodes is high frequency EMI currents). Monolithic ceramic manufacturing limitations on electrode thickness and conductivity means that prior art flat-through capacitors 174 have relatively high series resistance and can only be rated to a few hundred milliamps or a few amps at best (however, an implantable defibrillator must deliver a high voltage pulse of over 20-amps). Prior art MLCC and flat-through electrodes must be kept relatively thin to promote ceramic grain growth through the electrodes in order to keep the capacitor layers from delaminating during manufacturing or worse yet, during subsequent mechanical or thermal shocks which can cause latent failures.

FIG. 39 is the schematic diagram of the prior art flat-through capacitor 174 as illustrated in FIG. 37. Note that its schematic diagram is the same as that for the feedthrough capacitor 110 shown in FIGS. 2 and 3. The difference is that feedthrough capacitors are inherently configured to be mounted as an integral part of an overall shield which precludes the problem of RF coupling (see FIGS. 5-7).

FIG. 40 illustrates the attenuation versus frequency response curve which is shown generically for the flat-through capacitor of FIG. 37. If it weren't for cross-coupling of RF energy, it would perform as an ideal or nearly perfect capacitor would. However, because of this cross-coupling, there is always going to be a certain frequency at which the attenuation starts to parasitically drop off as shown. This drop off is very undesirable in active implantable medical device (AIMD) applications in that there would be less protection against high frequency EMI emitters such as cellular phones and the like. This parasitic drop off in attenuation due to cross-coupling is even a worse problem in military and space applications where EMI filter attenuation requirements of up to 10 or even 18 GHz, is important (implantable medical applications don't generally require filtering much above 3 GHz due to the effective reflection and absorption of human skin of RF energy at frequencies above 3 GHz). Space and military circuits have to operate in the presence of extremely high frequency emitters, such as GHz radars and the like. Accordingly, there is a need for a flat-through type of capacitor that eliminates the problems associated with this parasitic attenuation degradation due to RF cross-coupling across (or outside of around) the capacitor. In addition, there is also a need for flat-through capacitors that can handle much higher circuits through their "through" electrodes. The present invention fulfills these needs and provides other related advantages.

SUMMARY OF THE INVENTION

A primary objective of the present invention is to provide a novel shielded three-terminal flat-through EMI/energy dissipating filter which embodies one or more flat-through capacitors whose internal electrodes are high frequency shielded, are much thicker (compared to prior art MLCC flat-through thick film electrode technology) and higher in both cross-sectional and surface area (robust and able to carry much higher through circuit currents), whose electrodes can be configured with integral co-planar inductor elements, and can be optionally configured to accept a variety of surface mounted electronic components (like additional discrete or embedded capacitors, inductors, diodes, RFID chips, and the like). The higher surface area of the novel shielded three-terminal flat-through EMI/energy dissipating filter of the present invention maximizes the value of the flat-through capacitance. The present invention resides in a shielded three-terminal flat-through EMI/energy dissipating filter which comprises an active electrode plate through which a circuit current passes between a first terminal and a second terminal, and a plurality of shield plates substantially enveloping the active electrode plate, wherein the shield plates are conductively coupled to a grounded third terminal. Preferably, the plurality of shield plates include a first shield plate on a first side of the active electrode plate, and a second shield plate on a second side of the active electrode plate opposite the first shield plate. The active electrode plate is insulated from the shield plates by a dielectric material such that the active electrode plate and the shield plates cooperatively form a flat-through capacitor. A lead wire typically extends through at least one of the shield plates in non-conductive relation. The lead wire is conductively coupled to the active electrode plate to form the first terminal. A shielded fixture may be provided through which the lead wire extends in non-conductive relation. The fixture may comprise an hermetic seal for, for example, an active implantable medical device (AIMD). The surface area of the active electrode plate is maximized to increase parasitic capacitance and minimize resistance to current flow.

In some embodiments, a plurality of active electrode plates are provided which each have a first shield plate on a first side thereof and a second shield plate on a second side thereof opposite the first shield plate. Each active electrode plate is insulated from its adjacent shield plates by a dielectric material such that each active electrode plate and its adjacent shield plates cooperatively form a flat-through capacitor. The shield plates are conductively coupled to a common ground. A plurality of lead wires are provided which each extends through at least one of the shield plates in non-conductive relation. Each lead wire is conductively coupled to a respective active electrode plate to form the first terminal for said active electrode plate.

The shielded three-terminal flat-through EMI/energy dissipating filter may further include an adjacent feedthrough capacitor through which the lead wire extends prior to conductively coupling to the active electrode plate to form the first terminal.

A conductive pad may be conductively coupled to the active electrode plate to form the second terminal. The conductive pad may comprise a wire bond pad disposed on an exterior surface of a body of dielectric material through which the active electrode plate extends.

The shielded three-terminal flat-through EMI/energy dissipating filter may include a plurality of co-planar active electrode plates insulated from the shield plates by a dielectric material such that each active electrode plate and the shield plates cooperatively form a flat-through capacitor. Moreover, at least one of the co-planar active electrode plates may comprise an inductor. In several illustrated embodiments, a co-planar third shield plate extends between the co-planar active electrode plates.

In various embodiments, a lead wire or pin extends through at least one of the shield plates in non-conductive relation, wherein the lead wire or pin conductively couples to the active electrode plate to form the second terminal. A monolithic chip capacitor (MLCC) may be conductively coupled between the active electrode plate and at least one of the grounded shield plates. Further, a third shield plate may be disposed generally co-planarly with the active electrode plate, wherein the third shield plate is conductively coupled to the grounded third terminal. The third shield plate may substantially surround the active electrode plate and be disposed between the first and second shield plates.

The shielded three-terminal flat-through EMI/energy dissipating filter may further be modified such that at least a portion of the active electrode plate comprises an inductor. The inductor may comprise a spiral circuit trace.

In various embodiments of the EMI/energy dissipating filter, at least one via hole is provided for conductively coupling the shield plates to one another. The via holes may be disposed about the periphery of the active electrode plate to enhance its shielding characteristics.

In various embodiments, the active electrode plate may be configured to form at least a component of an "L", "π" (π), "T", "LL", "5 element" or an "n" element passive electronic low pass filter. Moreover, the active electrode plate may be configured to form at least a component of a band stop filter, a diode array, or an RFID chip. When used in connection with an active implantable medical device, the shielded three-terminal flat-through EMI/energy dissipating filter utilizes passive electronic device components which are optimized for use at MRI frequencies.

In some embodiments, the active electrode plate and the first and second shield plates are disposed generally perpendicularly to a lead wire conductively coupled to the active electrode plate to form the first terminal. In another embodiment, the active electrode plate and the first and second shield plates are disposed generally parallel to a lead wire conductively coupled to the active electrode plate to form the first terminal.

The active electrode plate and the shield plates are typically at least partially disposed within a hybrid flat-through substrate. This hybrid flat-through substrate may include surface metallization forming the third terminal. In many of the illustrated embodiments, the hybrid flat-through substrate is disposed adjacent to a hermetic seal for an implantable medical device such that the surface metallization is conductively coupled to a housing for the implantable medical device through a conductive ferrule of the hermetic seal.

The hybrid flat-through substrate may comprise a flex cable section, a rigid section, or a composite of both types. The flex cable section may comprise a polyimide, Kapton or acrylic material. The rigid section may comprise a high dielectric constant ceramic, alumina, fiberglass or FR4 material.

The rigid section of the hybrid substrate may include at least one passive electronic component conductively coupled to the active electrode plate. The passive electronic component may comprise an RFID chip, a capacitor, an inductor, a band stop filter, an L-C trap filter, a diode, or a diode array. The capacitor typically comprises a monolithic chip capacitor, and the inductor typically comprises a monolithic chip inductor or a toroidal inductor.

The second terminal of the active electrode plate may be conductively coupled to a circuit board for an electronic device, such as the internal circuit board of an AIMD.

In another embodiment, the hybrid flat-through substrate comprises a dielectric material with the active electrode plate embedded therein. The active electrode plate is conductively coupled to surface metallization for at least one via hole through the substrate. The shield plates comprise surface metallization applied to exterior surfaces of the hybrid flat-through substrate. A conductive cap may be provided which is configured to capture the hybrid flat-through substrate and conductively couple the shield plates to a ground. Such structure may be utilized in connection with a hermetic seal for an implantable medical device. The hermetic seal would typically include a conductive ferrule to which the conductive cap is conductively attached, at least one lead wire extending through the ferrule in non-conductive relation and conductively coupled to the surface metallization of the via hole.

The shielded three-terminal flat-through EMI/energy dissipating filter may be constructed such that all external components thereof comprise biocompatible materials designed for direct body fluid exposure. Moreover, the aforementioned RFID chips may include a wake-up feature for initializing AIMD RF telemetry circuits.

The aforementioned shielded three-terminal flat-through EMI/energy dissipating filters may be incorporated into a passive component network for an implantable lead of an active implantable device (AIMD). The passive component network comprises at least one lead wire having a length extending between and to a proximal end and a tissue-stimulating or biological-sensing electrode at a distal end, an energy dissipative surface disposed adjacent to tissue or within the blood or lymph flow of a patient at a point distant from the electrode, and a diversion circuit associated with the lead wire, for selectively diverting high-frequency energy away from the electrode to said energy dissipative surface for dissipation of said high frequency energy as heat. The passive component network may include an impeding circuit associated with the diversion circuit for raising the high frequency impedance of the lead wire. The impeding circuit is typically disposed between said diversion circuit and the distal end of said at least one lead wire, and typically comprises an inductor or a band stop filter.

The at least one lead wire may comprise a portion of a probe or a catheter. Moreover, the energy dissipative surface may comprise a sheath, an insulative body, or a thermally conductive element. Moreover, the at least one lead wire may comprise at least a pair of lead wires each having a length extending between and to a proximal end and a tissue stimulating or biological-sensing electrode at a distal end. The diversion circuit couples each of said lead wires to said energy dissipative surface. The diversion circuit may further be coupled between the pair of lead wires.

The high frequency energy typically comprises an RF pulse frequency of a magnetic resonance scanner in a preferred embodiment. The high frequency energy may further comprise a range of selected RF pulsed frequencies.

The diversion circuit may comprise a low pass filter including at least one of a C filter, and L filter, a T filter, a pi (π) filter, an LL filter, a 5-element filter, or an "n" element filter. The diversion circuit may further comprise at least one series resonant L-C trap filter. Moreover, the impeding circuit may include a non-linear circuit element. In this case, the non-linear circuit element may comprise a diode or a transient voltage suppressor. In various embodiments, the diversion circuit may comprise at least one series resonant L-C trap filter, and wherein the impeding circuit comprises an inductor or a band stop filter.

It will be appreciated that the basic point of novelty of the three-terminal flat-through EMI/energy dissipating filter is that it comprises an active electrode plate through which a circuit current passes between a first terminal and a second terminal, a first shield plate on a first side of the active electrode plate, and second shield plate on a second side of the active electrode plate opposite the first shield plate, wherein the first and second shield plates are conductively coupled to a grounded third terminal. The effective capacitance area or overlapping surface area of the active electrode plate and its surrounding grounded shield plates have been relatively maximized in order to achieve a higher value of capacitance of the three-terminal flat-through capacitor. The dielectric constant of the insulating layers between the active electrode plate and the surrounding ground shied plates have also been substantially raised in order to achieve a higher capacitance value for the three-terminal flat-through capacitor. Preferably, the dielectric thickness separating the active electrode plate and the surrounding ground shield plate is relatively minimized in order to achieve a higher capacitance value. A number of redundant parallel layers of the active electrode plate and surrounding grounded shield plates are provided to increase the total capacitance value of the three-terminal flat-through capacitor.

Other features and advantages of the present invention will become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 15 is an electrical schematic diagram of an ideal MLCC capacitor as illustrated in FIG. 13.

FIG. 16 is a more realistic electrical schematic diagram of the MLCC structure of FIG. 13.

FIG. 17 is a chart giving the formula for resonance frequency.

FIG. 18 is a graph showing filter attenuation versus frequency.

FIG. 106 is an exploded perspective view of an in-line octapolar hermetic terminal with a shielded three-terminal flat-through EMI/energy dissipating filter hybrid flat-through substrate embodying the present invention.

FIG. 123 is an attenuation versus frequency chart showing impedance characteristics of various types of filters.

FIG. 124 is a schematic diagram of a series inductor-capacitor filter commonly known in the industry as an L-C trap filter.

FIG. 125 is a chart giving the resonant frequency equation for an L-C series trap filter.

FIG. 126 illustrates the impedance Z in ohms versus frequency of the series resonant L-C trap filter of FIG. 124.

FIG. 127 is similar to the chart similar to FIG. 126, illustrating the impedance in ohms versus frequency of two discrete series resonant L-C trap filters.

FIG. 128 is an overall outline drawing showing a cardiac pacemaker with endocardial lead wires implanted into a human heart.

FIG. 129 is a cross-sectional view of a human head showing a deep brain stimulator electrode.

FIG. 130 is a schematic illustration of a unipolar lead system for an AIMD.

FIG. 131 is an illustration similar to FIG. 130, including an L-C trap filter.

FIG. 132 is another illustration similar to FIG. 130, wherein the frequency selective components comprise capacitive elements.

FIG. 133 is another illustration similar to FIGS. 130 and 132, wherein the capacitance value C has been selected such that the capacitive reactance will be equal and opposite to the inductive reactance of the implanted lead.

FIG. 134 illustrates prior art hermetic and non-hermetic connectors that are typically used in the military, aerospace, medical, telecommunication and other industries.

Figure 135:
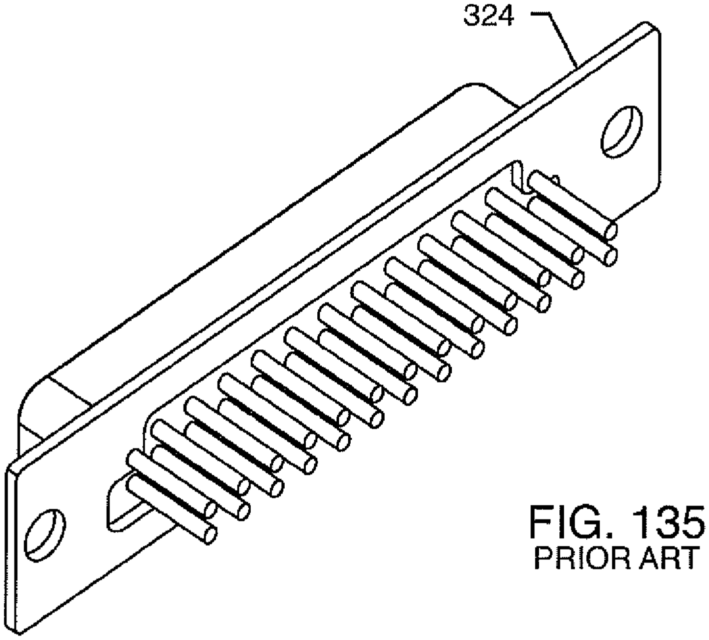
Figure 136:
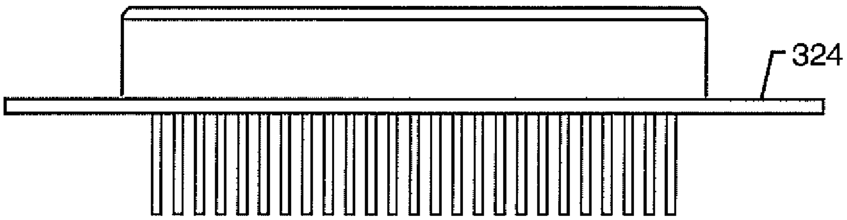

FIGS. 135 and 136 illustrate a prior art sub D-type connector.

Figure 137:
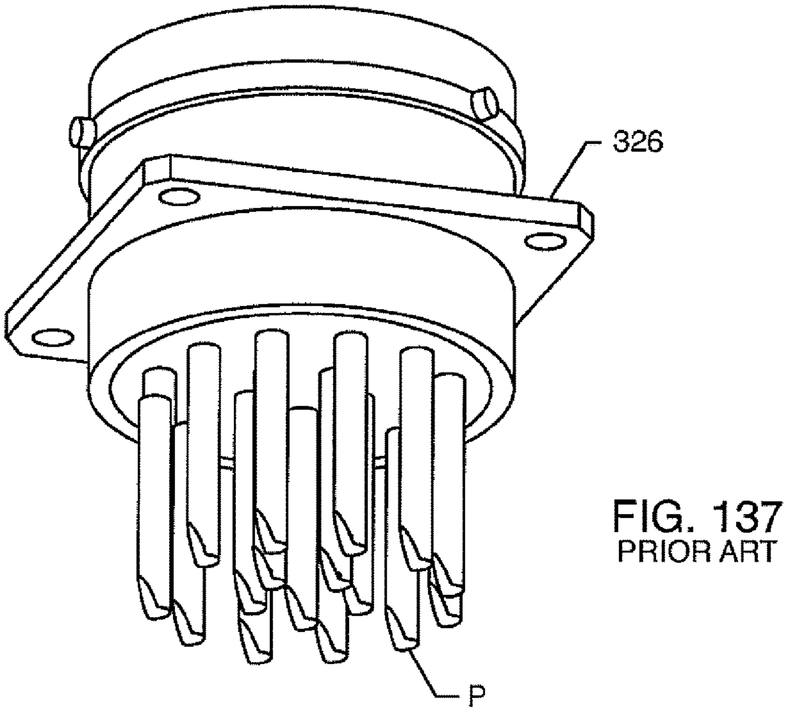
Figure 138:
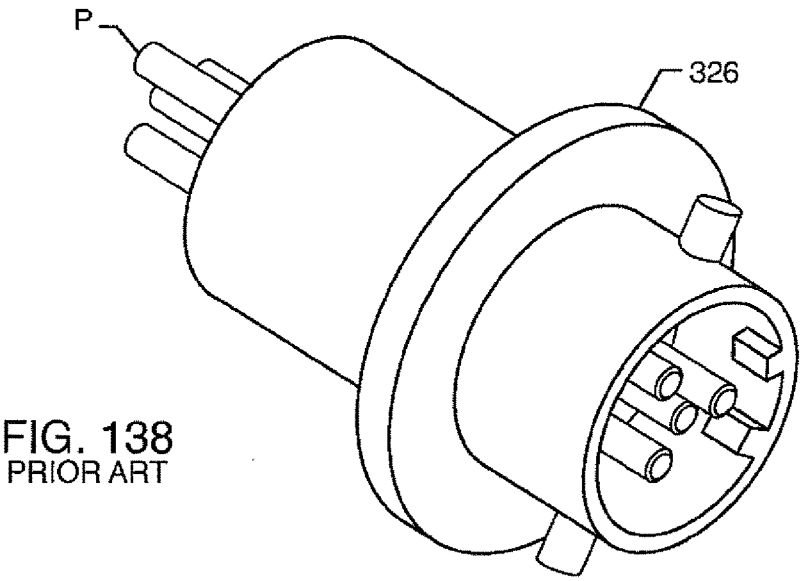

FIGS. 137 and 138 show prior art hermetic connectors.

Figure 139:
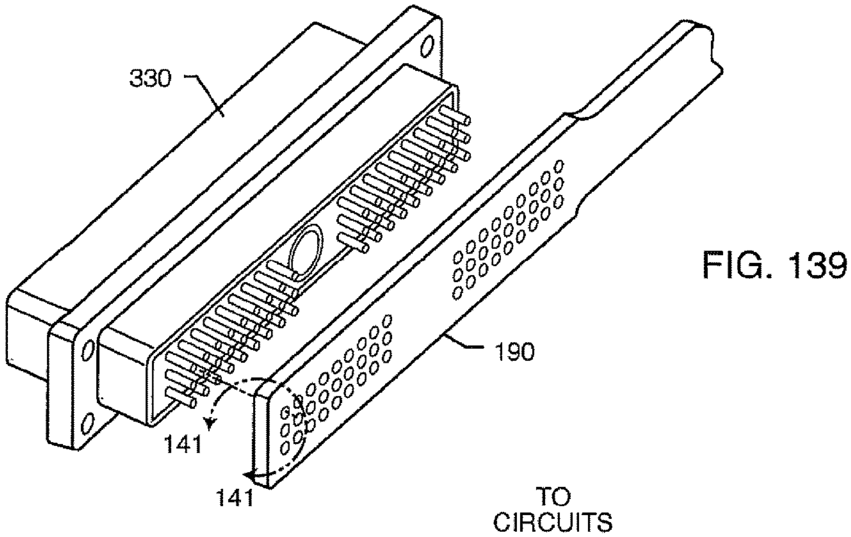

FIG. 139 shows an exploded view of a prior art multi-pin connector and a shielded three-terminal flat-through EMI filter.

Figure 140:
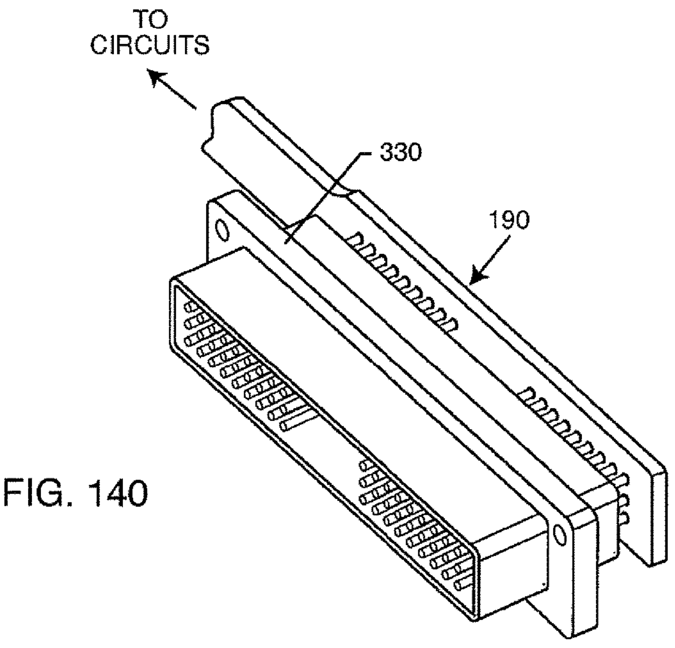

FIG. 140 is similar to FIG. 139 except that the shielded three-terminal flat-through EMI filter of the present invention has been attached.

Figure 141:
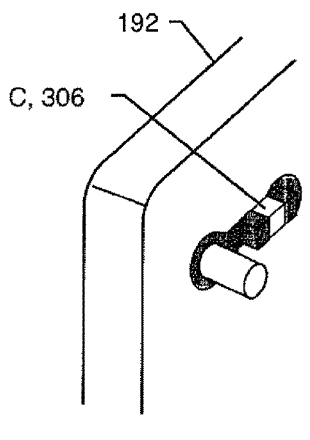

FIG. 141 is an exploded view taken generally from section 141-141 of FIG. 139 showing a surface mounted MLCC capacitor.

DETAILED DESCRIPTION OF THE PREFERRED EMBODIMENTS

As shown in the drawings for purposes of illustration, the present invention is concerned with shielded three-terminal flat-through EMI/energy dissipating filters 190 which can be embodied in substrates or flex cable assemblies. The novel concept resides in designing an embedded flat-through capacitor wherein optional surface mounted passive or active components can be attached while at the same time providing an interconnection circuit. The novel shielded three-terminal flat-through EMI/energy dissipating filters 190 embody a flat-through capacitor that has similar characteristics to prior art feedthrough EMI filter capacitors. The flat-through EMI/energy dissipating filter 190 of the present invention provides three-terminal capacitive filtering while simultaneously providing shielding of circuits and signals passing through the robust high current capability electrodes of the flat-through capacitor. The flat-through EMI/energy dissipating filter 190 of the present invention functions in a very equivalent manner to prior art feedthrough capacitors in that: a) its internal ground plates act as a continuous part of the overall electromagnetic shield housing of the electronic device or module which physically blocks direct entry of high frequency RF energy through the hermetic seal or equivalent opening for lead wire ingress and egress in the otherwise completely shielded housing (such RF energy, if it does penetrate inside the shielded housing can couple to and interfere with sensitive electronic circuitry); and, b) like prior art feedthrough capacitors, the flat-through EMI/energy dissipating filter 190 of the present invention very effectively shunts undesired high frequency EMI signals off of the lead wire (electrodes) to the overall shield housing where such energy is dissipated in eddy currents resulting in a very small temperature rise. Of course, unlike for prior art discoidal/feedthrough capacitors, in the present invention the circuit currents (for example pacemaker pacing pulses or ICD HV defibrillation high current shocks) must pass through the internal electrodes of the embedded flat-through capacitor. By integrating flat-through technology into prior art circuit boards, substrates or flex cables, the flat-through electrodes can be manufactured with much thicker electrodes (like copper sheet) which greatly increases their capability to safely carry relatively higher through circuit currents (like external or internal cardiac defibrillation pulses).

Figure 10:
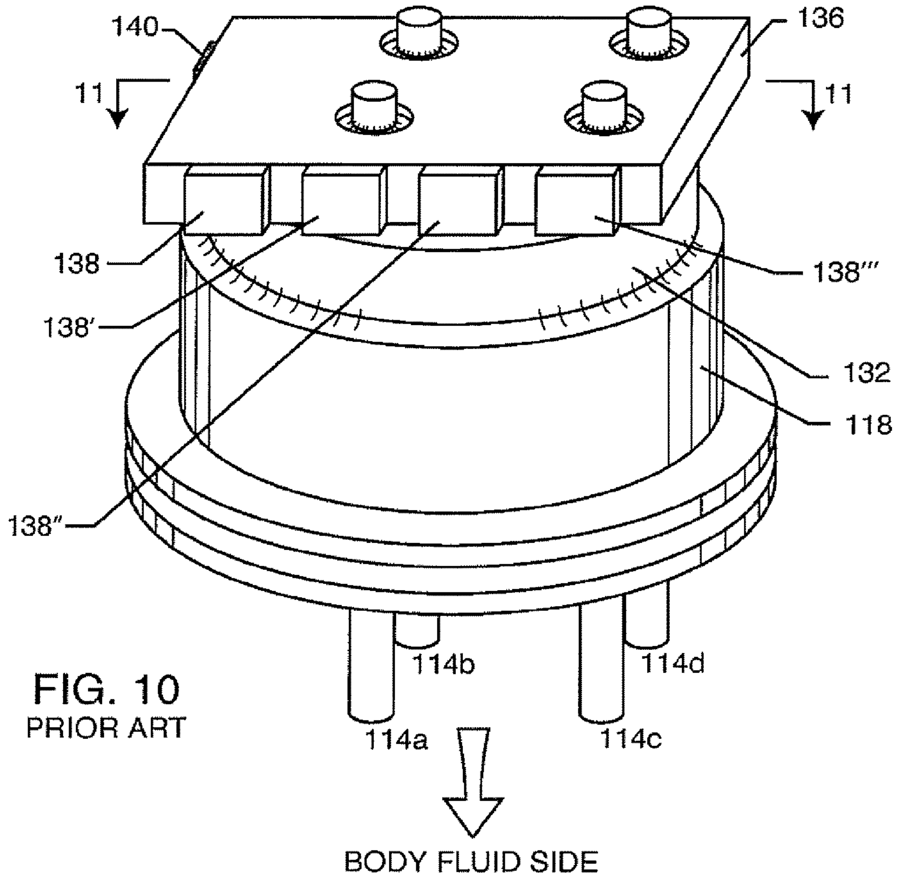
FIG. 10 is a perspective view of a quadpolar feedthrough capacitor mounted on top of a hermetic seal.
Figure 11:
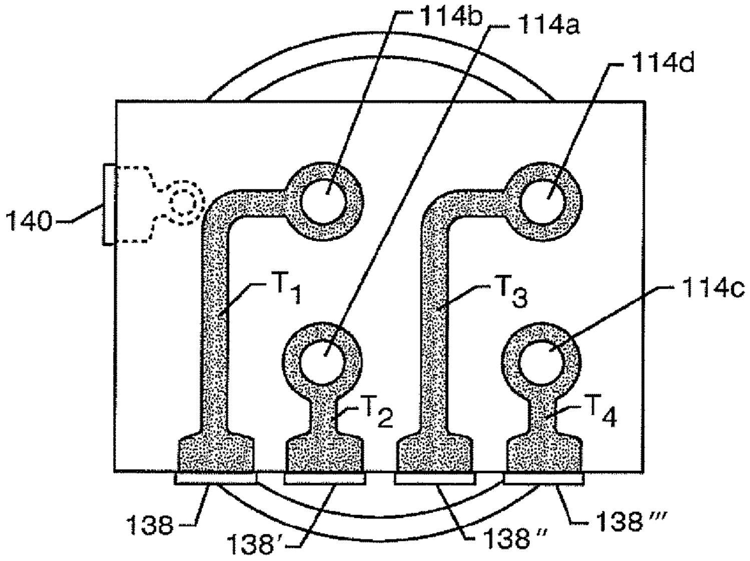
FIG. 11 is a sectional view taken generally along the line 11-11 of FIG. 10.
Figure 12:
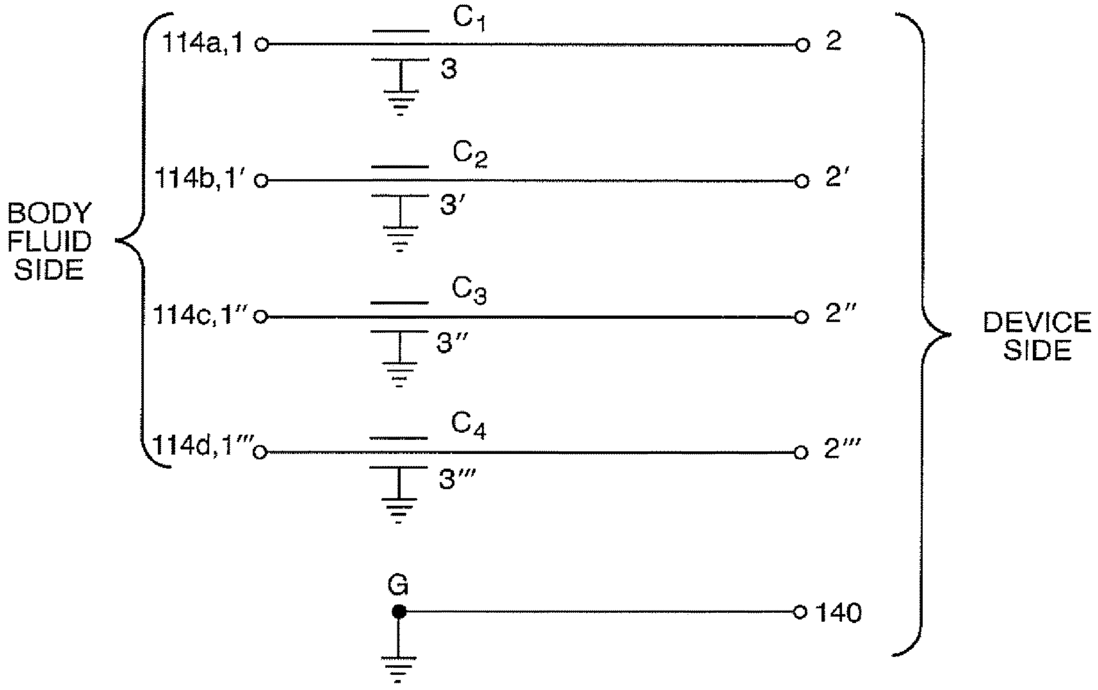
FIG. 12 is an electrical schematic diagram of the quadpolar hermetic feedthrough terminal shown in FIG. 10.
Figure 41:
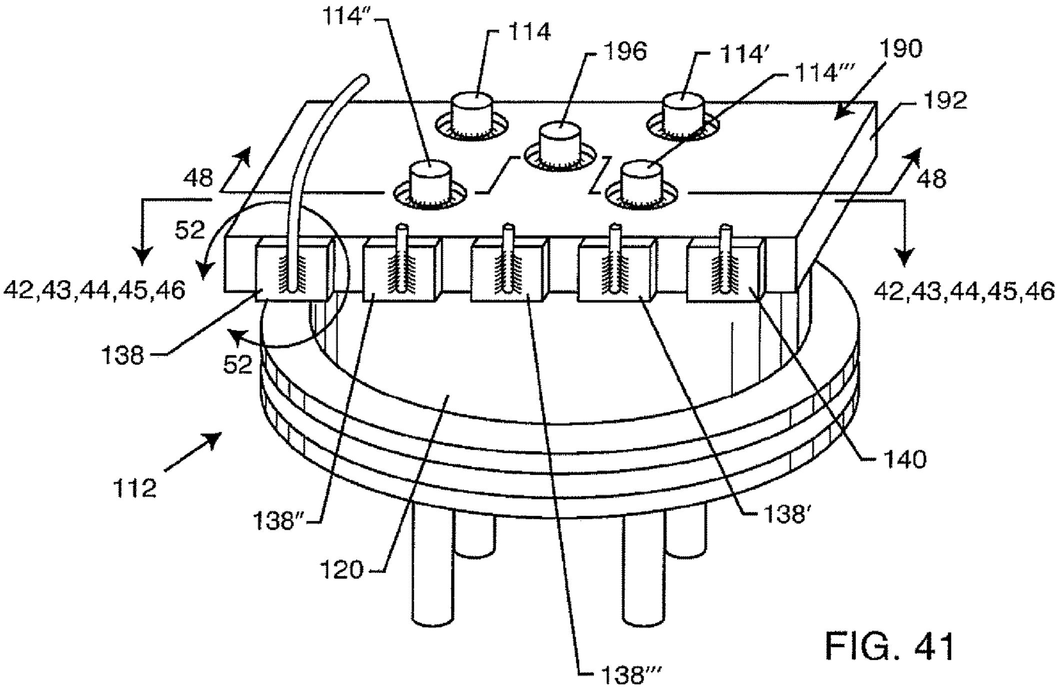
FIG. 41 is a perspective view of a quadpolar EMI filter hermetic seal similar to that shown in FIG. 10, but embodying a shielded three-terminal flat-through EMI/energy dissipating filter of the present invention.

FIG. 41 is a very similar to the quadpolar EMI filtered hermetic seal that was illustrated in FIG. 10. In FIG. 41, in accordance with the present invention, the feedthrough capacitor element has been completely eliminated, thus significantly reducing the cost of manufacture. The feedthrough capacitor 132 and its associated wire bond substrate 136 that were described in FIG. 10 have been replaced by a novel shielded three-terminal flat-through EMI/energy dissipating filter 190. In FIG. 41, wire bond pads 138, 138', 138", 138'" and 140 are very similar to the wire bond pads illustrated in FIG. 10. They are attached to a relatively higher K ceramic or suitable hybrid substrate 192. Novel parasitic flat-through capacitors of the present invention are integrated into the substrate 192. This is better understood by referring FIGS. 42 through 46.

Figure 42:
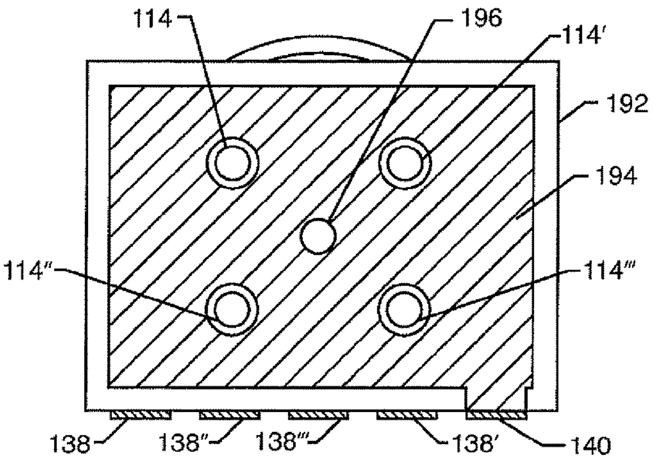
FIG. 42 is a sectional view taken generally along the line 42-42 of FIG. 41.
Figure 43:
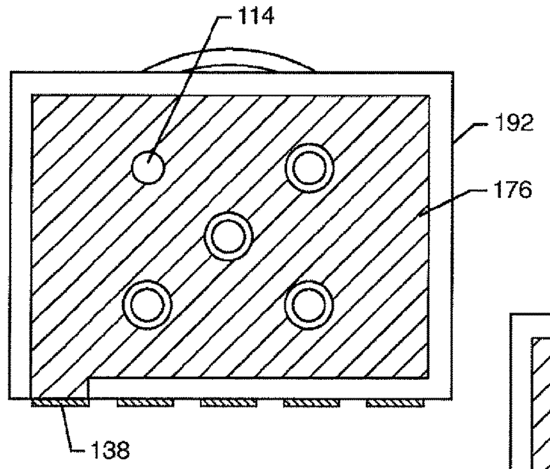
FIG. 43 is a sectional view taken generally along the line 43-43 of FIG. 41.
Figure 44:
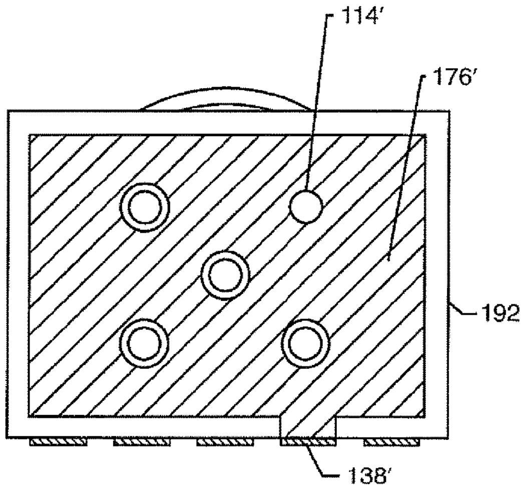
FIG. 44 is a sectional view taken generally along the line 44-44 of FIG. 41.
Figure 45:
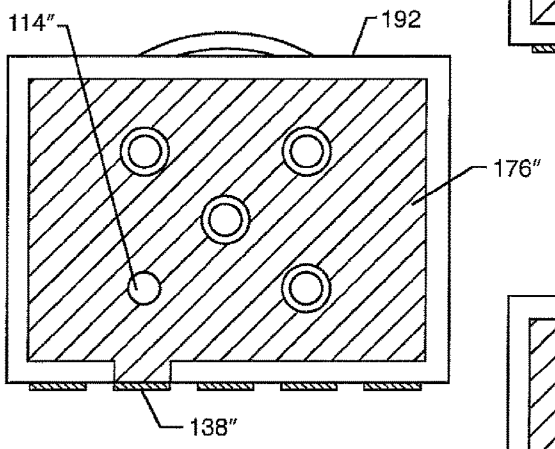
FIG. 45 is a sectional view taken generally along the line 45-45 of FIG. 41.
Figure 46:
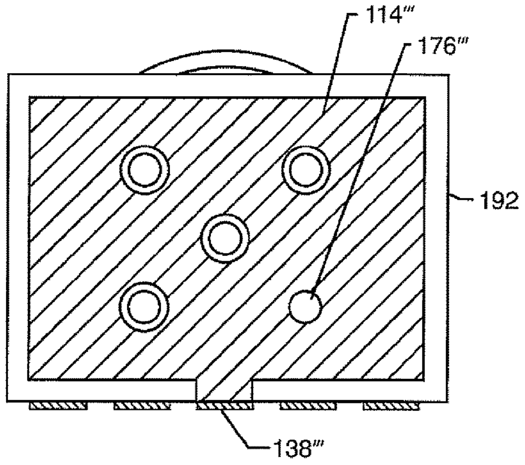
FIG. 46 is a sectional view taken generally along the line 46-46 of FIG. 41.
Figure 48:
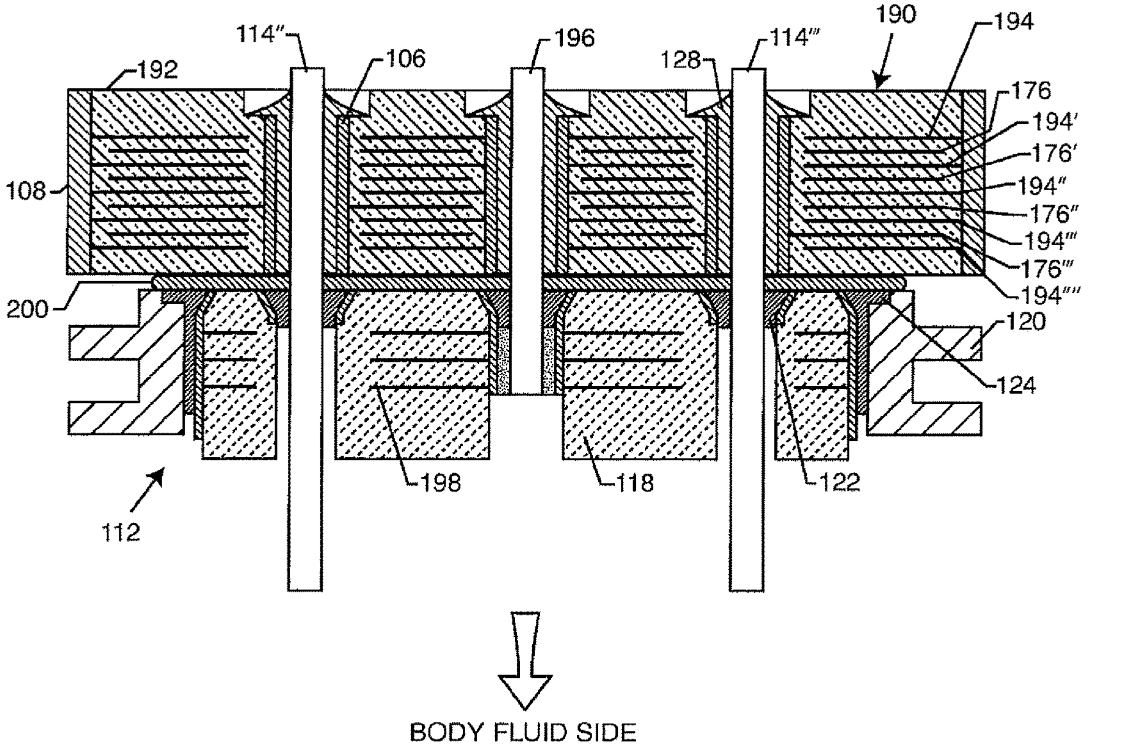
FIG. 48 is a sectional view taken generally along the line 48-48 of FIG. 41.

FIG. 42 illustrates a grounded shield plate 194. In this case, the center pin 196 is grounded. That is, there is a web plate (not shown) underneath the substrate 192 wherein the ground pin 196 is electrically coupled to the metallic ferrule 120 of the hermetic seal 112. It is important that this be a low inductance RF ground. In other words, the web plate would be a high surface area plate with clearance holes only for the pass through of lead wires 114, 114', 114" and 114'". This RF grounded web plate, could, for example, have its outer diameter laser welded to the ferrule 120 of the hermetic terminal and its inside diameter hole welded or soldered to the grounded lead wire or pin 196. An alternative methodology of grounding the center pin 196 is illustrated with embedded ground plates within the hermetic seal as shown in FIG. 48. Referring to FIG. 48, one can see that there is a hermetic insulator 118 through which the lead wires pass in non-conductive relation to the metallic ferrule 120. Shown are ground plates 198 embedded in the insulative portion 118 of the hermetic seal 112 which are attached by gold brazing to the center ground pin 196. Grounding this centered pin 196 using plates embedded in the insulator 118 of the hermetic seal 112 has been described in U.S. Pat. No. 7,199,995, the contents of which is incorporated herein by reference. Other methods of grounding pin 196 are further described in U.S. Pat. Nos. 5,905,627 and 6,529,103, the contents of which are also incorporated herein by reference.

FIGS. 43 through 46 illustrate the internal active electrode plate layouts 176, 176', 176" and 176'". The overlap area which is otherwise known as the effective capacitance area (ECA) of each of these active electrode plates has been maximized in order to maximize the flat-through capacitance. Maximizing the thickness and the area of the active electrode plates 176-176'" also has an added benefit in that their overall resistance is lowered (and its current rating is greatly increased). This is important because circuit currents of the novel shielded three-terminal flat-through EMI/energy dissipating filter 190 must pass through the respective electrode plates 176-176'" in order to accomplish the novel shielded flat-through capacitor characteristics.

Figure 37:
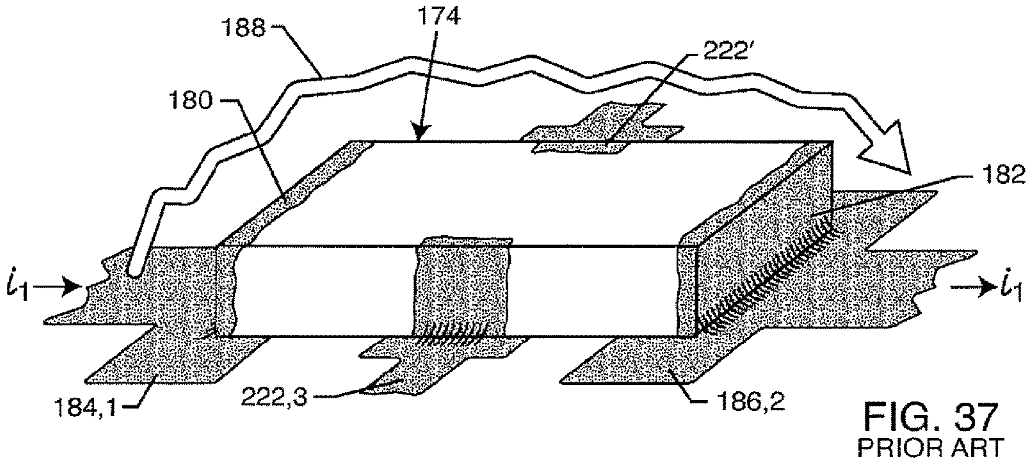
FIG. 37 is a perspective view of a prior art flat-through capacitor.
Figure 38:
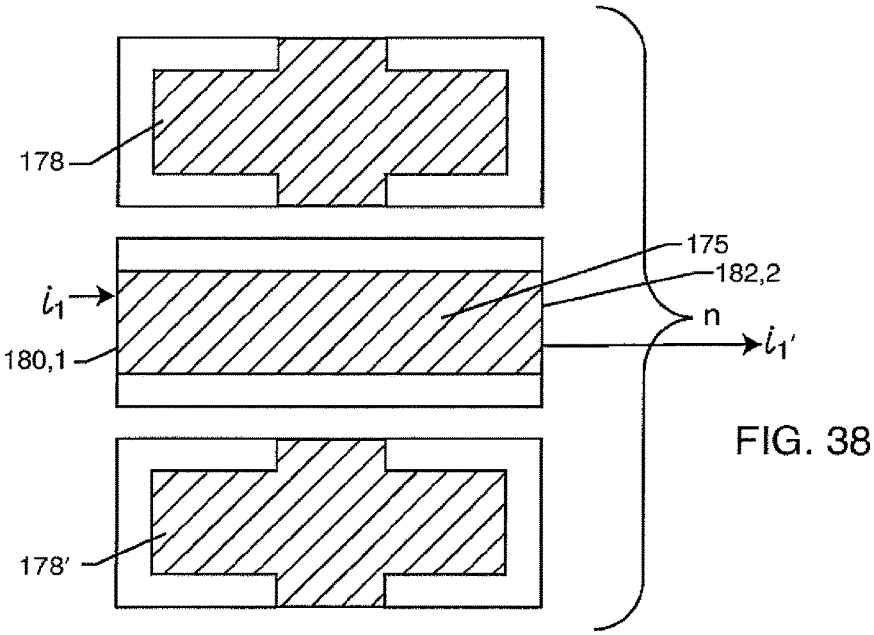
FIG. 38 is a diagram showing the internal electrode array of the flat-through capacitor of FIG. 37.
Figure 39:
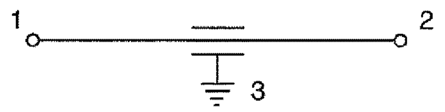
FIG. 39 is an electrical schematic diagram of the prior art flat-through capacitor of FIGS. 37 and 38.

As previously mentioned, one serious negative to prior art flat-through capacitors 174, such as shown in FIG. 37, is that it is not conveniently mountable in such a way that it becomes an integral part of an overall electromagnetic shield. There is always a frequency at which undesirable RF coupling 188 across the device will occur. This usually does not happen until 100 MHz or above. At very high frequencies, such as above 1 GHz, this problem becomes quite serious. A second negative, as compared to prior art discoidal feedthrough capacitors 110 and 132, where the circuit current runs through a robust lead in a feedthrough hole, is that the flat-through circuit currents must flow through the electrodes of the flat-through capacitor 174 itself. Limitations on electrode thickness and conductivity means that prior art flat-through capacitors 174 have relatively high series resistance and can only be rated to a few milliamps, or at best, a few amps. However, a patient's pacemaker lead undergoing external (AED) defibrillation or an implantable defibrillator must deliver a high voltage pulse of over 20-amps. The novel shielded three-terminal flat-through EMI/energy dissipating filter 190 of the present invention overcomes both of the foregoing negatives associated with prior art flat-through capacitors by incorporating grounded shield plates 194 surrounding on at least the top and bottom sides a novel high surface area and relatively thick flat-through active electrode plate 176 through which circuits of up to 30-amps or greater can pass. As will be seen in subsequent drawings, the novel high surface area electrodes 176 of the shielded three-terminal flat-through EMI/energy dissipating filter 190 can optionally include inductor sections which not only desirably add series inductance to the filter but also increase the flat-through capacitance by increasing the effective capacitance area (ECA).

Figure 47:
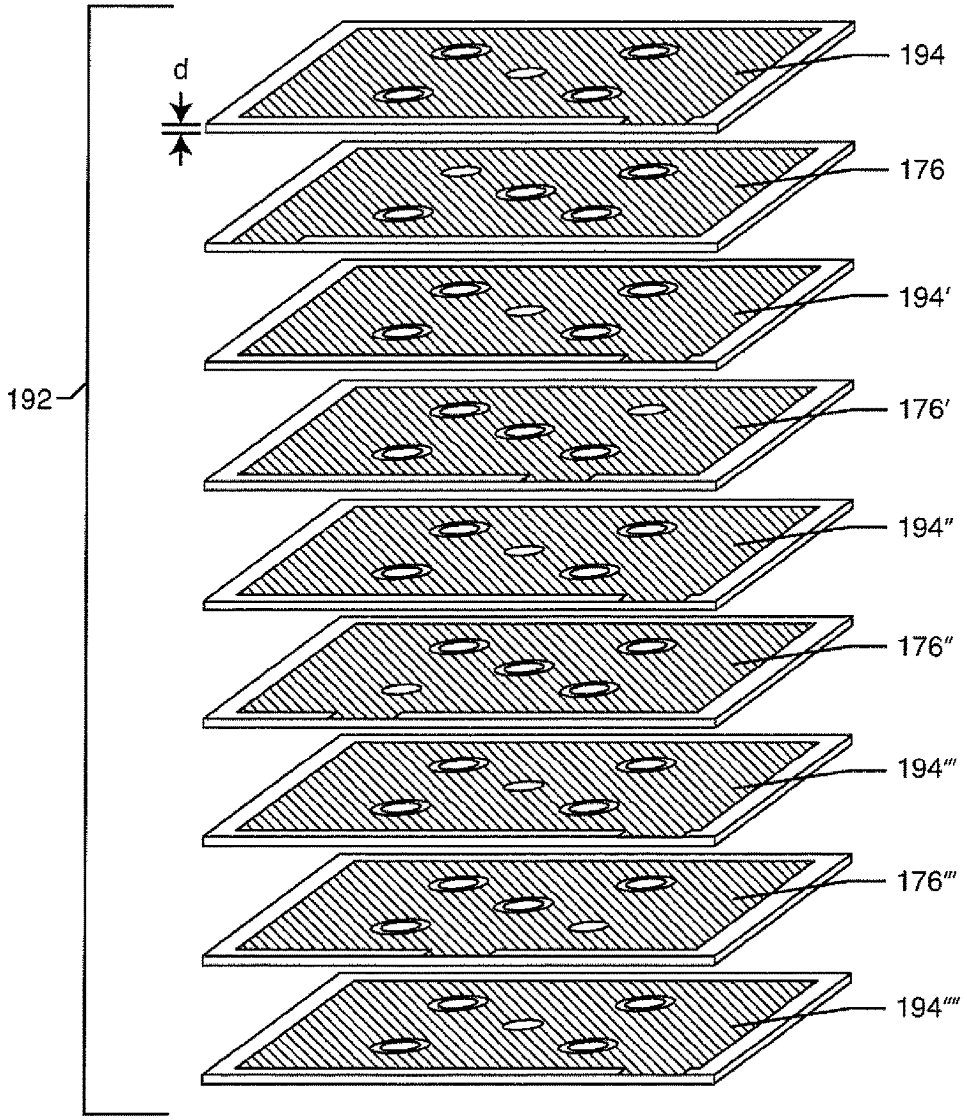
FIG. 47 is an exploded perspective view of the plates forming the flat-through EMI/energy dissipating filter of FIGS. 41-46.

The overall internal construction of the novel hybrid substrate 192 is best understood by referring to the exploded view shown in FIG. 47. One can see that each one of the flat-through active electrodes 176 through 176'" are sandwiched between a plurality of grounded shield plates 194, 194', 194", 194'", 194"" and 194'"" as shown. The resulting high ECA has the effect of creating a very high value of flat-through capacitance for EMI filtering (typically several tens or hundreds of picofarads). In contrast, the narrow (low surface area) circuit trace-type flat-through designs taught by U.S. Pat. Nos. 5,683,435 and 6,473,314 are not effective capacitor electrodes. This results in a flat-through capacitance that is nearly zero (only a stray picofarad which offers no effective EMI filter attenuation by itself). In addition, by creating the flat-through capacitance between overlapping grounded shield plates 194, the problem that was previously described in connection with the prior art structure of FIG. 37 has been eliminated. In FIG. 37, it was shown that for a typical prior art flat-through capacitor, there is a frequency at which coupling 188 will occur. This is where the RF signal can, through stray capacitance, antenna action or mutual inductance, avoid passing through electrode plate 175 and instead be coupled directly across the circuit traces or couple to adjacent circuit traces. This is best understood as previously described in FIG. 40 as the degradation in attenuation due to cross-coupling. By shielding the high surface area electrodes 176 of the novel shielded three-terminal flat-through EMI/energy dissipating filter 190 of the present invention with RF grounded shield plates 194 on both sides (and optionally co-planar sides as well), this stray coupling problem and associated high frequency attenuation degradation has been completely eliminated. Again, referring to FIG. 37, one can see that there is really no shield barrier from end-to-end of a prior art flat-through capacitor 174. At some frequency, for example around 100 MHz to 1 GHz, EMI or RF will undesirably cross-couple across the prior art flat-through capacitor 174 or, potentially worse yet, couple to adjacent circuits.

Referring back to the novel construction as illustrated in FIGS. 41 through 48, the flat-through capacitance is very well shielded. In this case, the flat-through capacitance will act as an ideal capacitor and will be free of resonances and parasitic RF coupling degradation. In FIG. 48, one can see an optional external metallization 108 that is connected to the interior grounded shield electrode plates 194. This is useful to help prevent edge re-radiation of high frequency RF energy which could couple to sensitive electronic circuits inside the overall shielded housing of the electronic device. In a preferred embodiment, the external metallization 108 would be directly electrically connected to gold braze 124 (in this case, the diameter of the ferrule 120 would need to be enlarged). Accordingly, the RF grounding and impedance would be lowered between the ferrule 120 and the outer metallization 108 of the shielded three-terminal flat-through EMI/energy dissipating filter 190. In this case, it will be obvious that the center ground pin 196 could be eliminated and the internal ground electrodes 198 within the hermetic insulator 118 could also be eliminated. In other words, the grounding of the shield electrode plates 194 could be accomplished either by the center pin 196 as shown in FIG. 48, or be done around the outside perimeter or circumference with an attachment between the external metallization 108 and for example, gold braze 124. Adding metallization 108 means that the embedded active flat-through electrode plates 176 are RF shielded by top and bottom plates 194 and on their co-planar edges by the shielding effect of metallization 108. This means that the active electrode plates 176 are completely shielded such that RF re-radiation or cross coupling cannot occur.

Referring once again to FIG. 48, there is an insulative washer 200 which is disposed between the shielded three-terminal flat-through EMI/energy dissipating filter 190 and the hermetic insulator body 118. This is to make sure that the electrical connection materials 128 cannot migrate underneath the hybrid substrate 192 and cause shorting between adjacent pins. For example, if electrical conductive material 128 were to migrate between pins 114" and 114" this could short out the output of a cardiac pacemaker. Insulating layer 200, in a preferred embodiment is also an adhesive. This is desirable during manufacturing such that the shielded three-terminal flat-through EMI/energy dissipating filter 190 is firmly affixed to the hermetic seal 112. This makes the subsequent electrical attachment operations by soldering, centrifuging of thermally conductive polyamides or epoxies or the like, more convenient.

Referring once again to FIG. 48, the body fluid side is shown on the bottom side of hermetic insulator 118. It is typical that electronic circuits for AIMDs be inside the hermetic and electromagnetically shielded housing. However, the present invention is not limited to only placing the shielded three-terminal flat-through EMI/energy dissipating filter 190 on the inside of the housing of the AIMD. If one were to construct the shielded three-terminal flat-through EMI/energy dissipating filter 190 of entirely biocompatible materials, there is no reason that it could not be disposed on the body fluid side. Reference is made to U.S. Pat. No. 7,113,387 the contents of which are hereby incorporated herein, which describes EMI filter capacitors designed for direct body fluid exposure. For example, active flat-through electrodes and their corresponding electrode shield plates could all be disposed within a non-lead containing high dielectric material and with connections and electrodes and shield plates made of biocompatible materials such as pure platinum, gold, niobium, tantalum, titanium or the like. In other words, the structure of FIG. 48 could be constructed such that it would be adapted for direct body fluid exposure. In FIG. 48, insulator 118 is hermetically sealed to lead wire 114', 114" by metallization 106' and gold braze 122, to ground pin 196 by metallization 106" and gold braze 122', and to ferrule 120 by metallization 106'" and gold braze 124.

Figure 49:
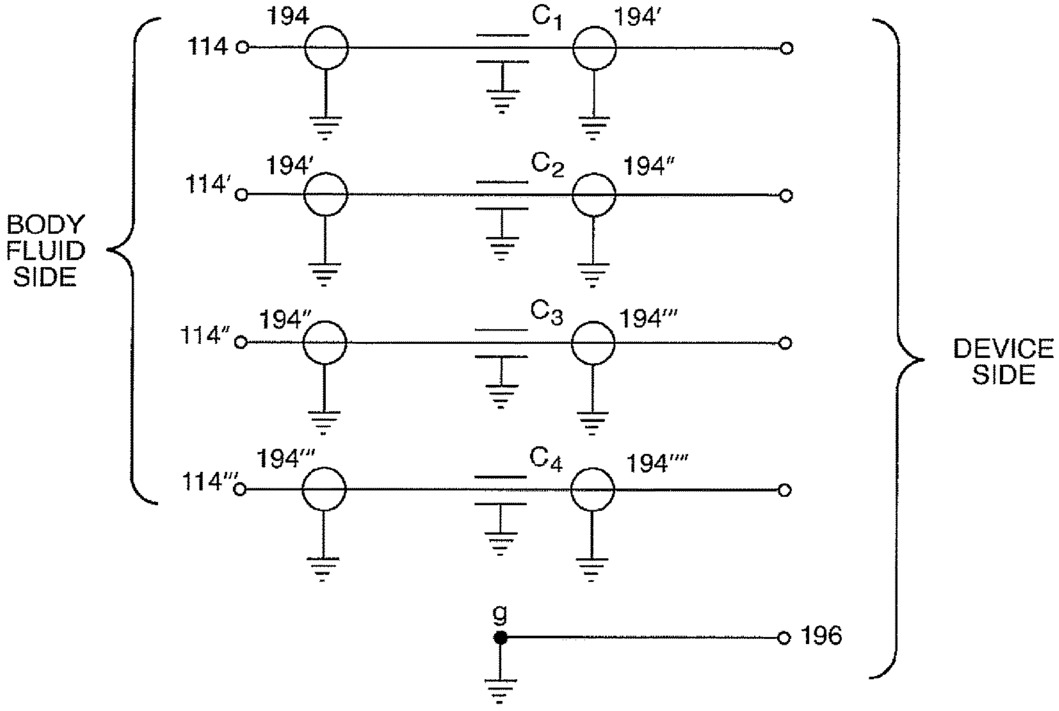
FIG. 49 is an electrical schematic drawing of the flat-through EMI/energy dissipating filter of FIG. 41.

FIG. 49 is a schematic drawing of the novel shielded three-terminal flat-through EMI/energy dissipating filter 190 of FIG. 41. Shields 194 through 194"" illustrate the fact that the high surface area active electrode plates 176 are surrounded at least on top and bottom by grounded shield electrode plates 194 that form the flat-through effective capacitance overlap area and at the same time prevent undesirable RF coupling across the flat-through capacitive filter. The feedthrough capacitances $C_1$, $C_2$, $C_3$ and $C_4$ have been formed by the overlap area (ECA) between each of the active electrodes 176 and the corresponding shield plates 194 that surround the active electrodes on both top and bottom. For example, referring back to FIG. 47, one can see that active electrode plate 176-176'" have been surrounded on top and bottom by grounded shield plates 194-194'". The grounded shield plates 194" can be deposited by metal plating, thick film deposition (silk-screening), discrete metal sheets or similar processes on to a dielectric layer which has a specific dielectric thickness d. It is well known to capacitor designers that the formula for the total flat-through capacitance is given by the formula $C=kA(n_{-1})/d$. In this formula, k is the permittivity or dielectric constant of the insulative dielectric material itself; A is the effective capacitance area in $in_2$ or $mm_2$ (ECA) determined by the overlap of the grounded shield plates 194 and 194' and, for example, the active electrode 176; n is the number of total electrode areas; and, d is the dielectric thickness. Referring to FIG. 47, we can add insulative dielectric cover sheets (not shown) which can be the same or different insulating and/or dielectric material that forms the dielectric layer on each of the electrode layers (this is to add additional electrical and mechanical protection). It will be obvious to those skilled in the art of designing capacitors that blank cover sheets (as many as needed) could also be inserted between the active electrode layers 176 and the associated or surrounding grounded shield plate layers 194. This would cause the dielectric thickness d to become greater which would have two effects. The first effect would be to increase the dielectric thickness and therefore the voltage rating of the flat-through capacitor. Thin dielectric layers tend to break down at relatively lower voltages. Therefore, for a high voltage application, such as that of an implantable cardioverter defibrillator (ICD), one would want a dielectric thickness that would be relatively greater than say, for example, a low voltage pacemaker. When one examines the equation for capacitance, the dielectric thickness d appears in the denominator. So as one increases the dielectric thickness then the total flat-through capacitance would drop. Accordingly, the first decision a designer makes is what is the required dielectric thickness for the voltage rating of the application and then adjust the ECA such that the desired flat-through capacitance is achieved. In some cases, not enough flat-through capacitance will be achieved to adequately filter all frequencies. As will be described in connection with subsequent drawings, it will be shown how to add, by surface mounting or embedding or thick film deposition, commercially available discrete capacitors, inductors, diodes and other components to enhance its overall performance of the present invention, and in particular, the low frequency (LF) performance of the novel shielded three-terminal flat-through EMI/energy dissipating filter 190.

Figure 50:
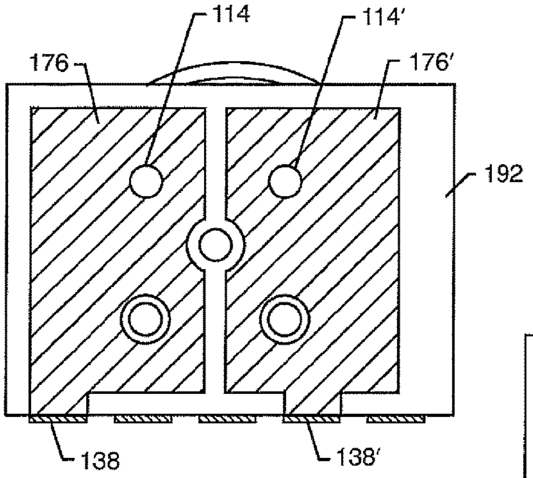
FIG. 50 is a sectional view similar to FIGS. 43 and 44 illustrating incorporation of stacked layers $L_1$ and $L_2$ into a single co-planar layer.

FIG. 50 illustrates a way to produce the novel hybrid EMI filter substrate 192 of FIG. 41 with less layers and a correspondingly lower overall substrate thickness. This is accomplished by incorporating two (or more) active electrodes 176 and 176' onto a single co-planar layer. Putting multiple active electrode plates on co-planar layers has the desired effect of making the shielded three-terminal flat-through EMI/energy dissipating filter 190 thinner, easier to manufacture and less expensive. However, this has the undesirable effect of reducing the effective capacitance area (ECA) for each active electrode plate 176. However, when high K materials are used, the effective capacitance area is so large that this is really not a detriment. Also, subsequent drawings will show methods of adding co-planar inductor-electrodes to boost the filter attenuation. It will be obvious to those skilled in the art that in a similar manner, active electrodes 176" and 176'" could also be incorporated into a single combined layer. The novel shielded three-terminal flat-through EMI/energy dissipating filter 190, and particularly its hybrid substrate 192, can be constructed of prior art flex circuit techniques (like polyimide flex circuits), multi-layer rigid substrates (like alumina or FR4 board), thick film deposition onto a substrate or carrier, or the like. For each of these manufacturing techniques, there is a practical limit to the number of layers that can be built up. This limitation has to do with limitations of the inherent manufacturing process. For example, when one builds up a sufficient number of layers (more than 8 to 10), then a flex circuit starts to become fairly rigid. In fact, it's common in flex cable design that a portion of the flex cable be built up and become a portion known as "rigid-flex." The present invention allows the shielded three-terminal flat-through EMI/energy dissipating filter technology to be used in completely flexible substrates, hybrid substrate designs that have both a flexible and a rigid layer, or in a completely rigid board.

Figure 51:
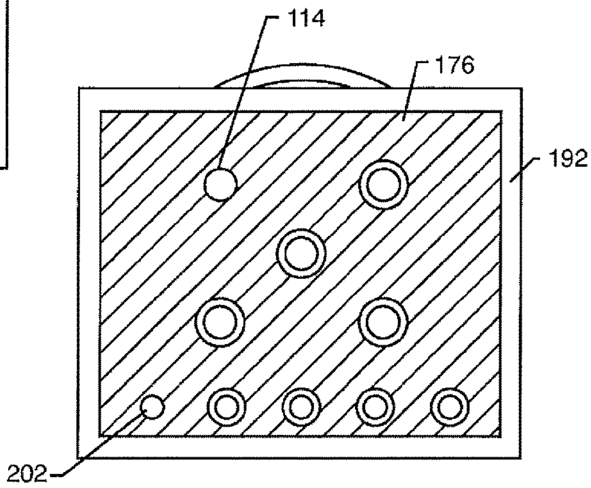
FIG. 51 is a sectional view similar to FIGS. 42-46, showing modification of the active electrode plates for connection to a via hole.
Figure 52:
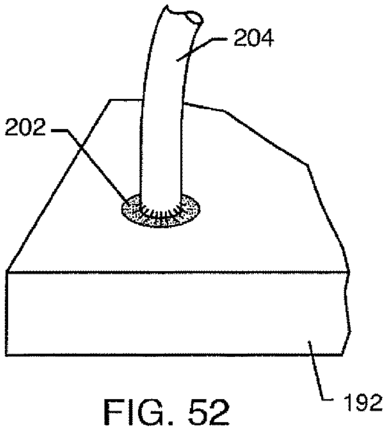
FIG. 52 is a fragmented perspective view illustrating a lead wire extending into one of the via holes of FIG. 51.
Figure 53:
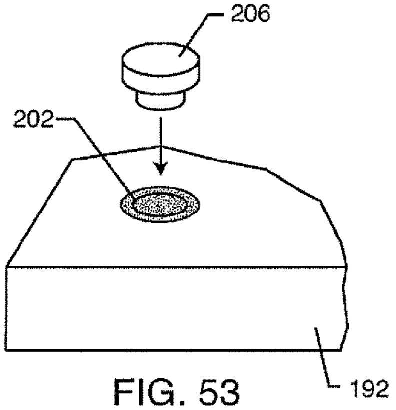
FIG. 53 is a view similar to FIG. 52, showing an alternative bond pad in place of the wire.

Referring back to FIG. 41, one can see that there are wire bond pads 138 through 140 as shown. The addition of wire bond pads adds a circuit connection convenience and an additional expense. In comparison, FIG. 51, shows that, for example, the active electrode plate 176 shown in FIG. 43 could be modified such that it was connected to a via hole 202. This via hole 202 provides for a convenient connection of either a lead wire 204, as shown in FIG. 52, or a round (or rectangular, square or other not shown) wire bond pad 206 as illustrated in FIG. 53.

Figure 3:
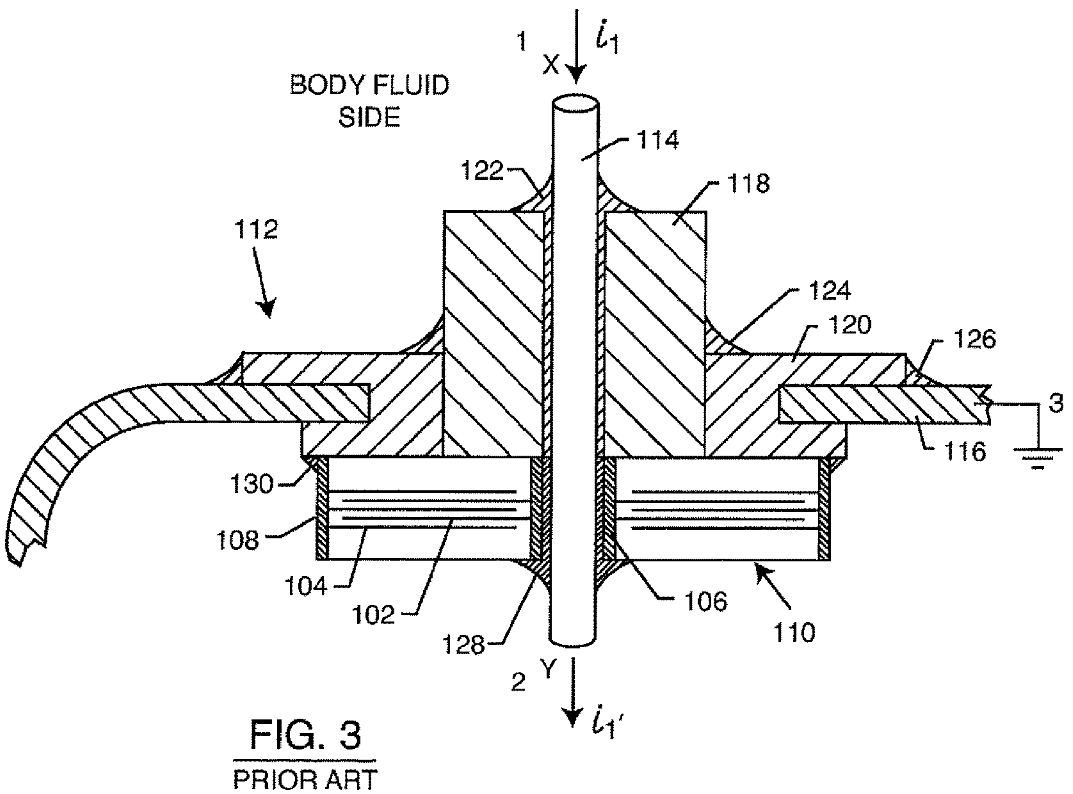
FIG. 3 is a sectional view of the feedthrough capacitor of FIG. 2 shown mounted to a hermetic seal of an active implantable medical device (AIMD).
Figure 4:
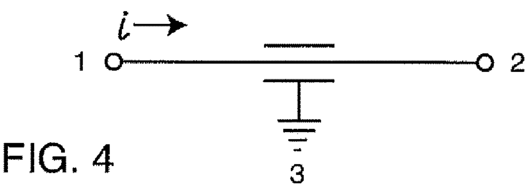
FIG. 4 is a schematic diagram showing the feedthrough capacitor shown in FIGS. 2 and 3.
Figure 54:
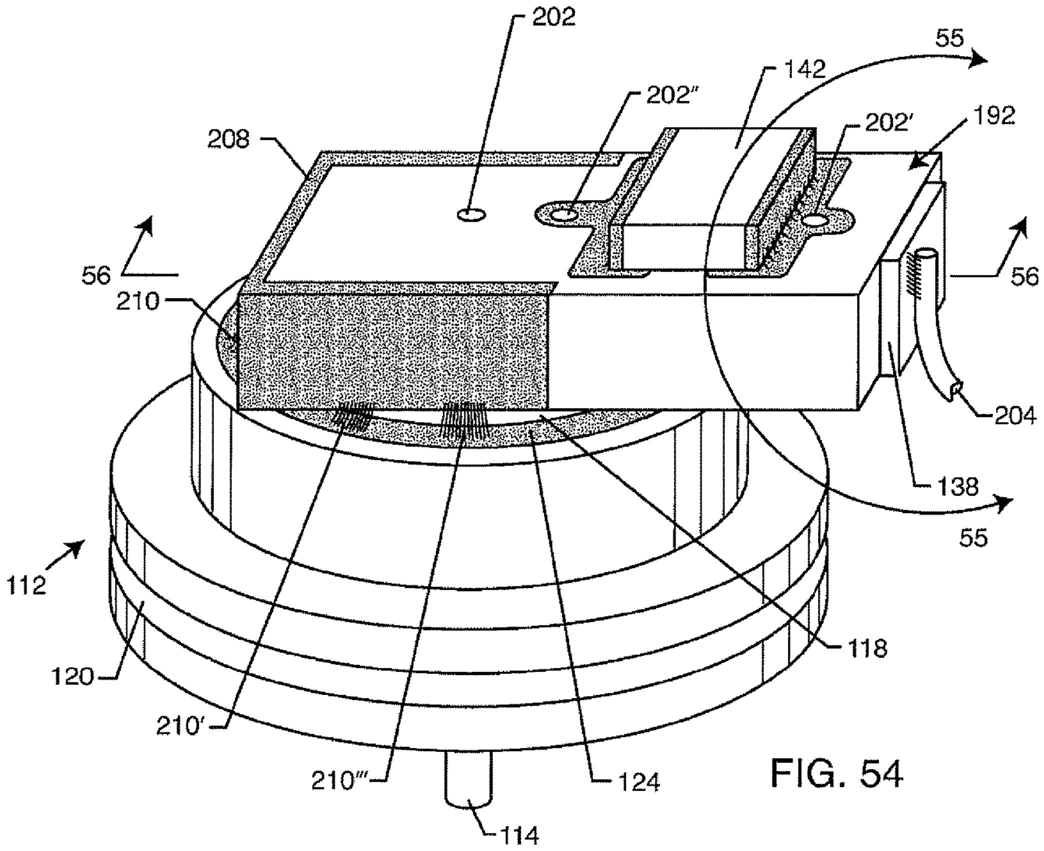
FIG. 54 is a perspective view of a unipolar hermetic seal similar to that shown in FIG. 3, except that it is inverted with the feedthrough capacitor replaced with a shielded three-terminal flat-through EMI/energy dissipating filter of the present invention.

FIG. 54 is an isometric drawing of a unipolar pacemaker hermetic seal 112 that is similar to that shown in FIG. 3 except that the feedthrough capacitor has been replaced with a shielded three-terminal flat-through EMI/energy dissipating filter 190 of the present invention shown mounted on top of the insulator 118 and gold braze 124. The hybrid substrate 192 of the shielded three-terminal flat-through EMI/energy dissipating filter 190 can be manufactured from any number of the techniques previously described herein. The body of the hybrid substrate 192 could be a conventional substrate consisting of high dielectric constant ceramic, alumina, ceramic, fiberglass, FR4 or any other rigid type of multi-layer board technology. In addition, it could be made of a number of flexible or flex cable variances. These could include flex cables that are laminated together based on polyimide, Kapton and acrylic construction. Another embodiment would be polyimide flex cables with all polyimide connections which are laminated together at high temperature. All of these types of boards and/or substrates and/or flex cables are known in the art. What is described herein is a very novel adaptation of those boards and substrates to flat-through filter technology. Hereinafter, the novel substrates incorporating various forms of novel shielded flat-through EMI filter technologies will be referred to as the hybrid substrates 192.

Figure 56:
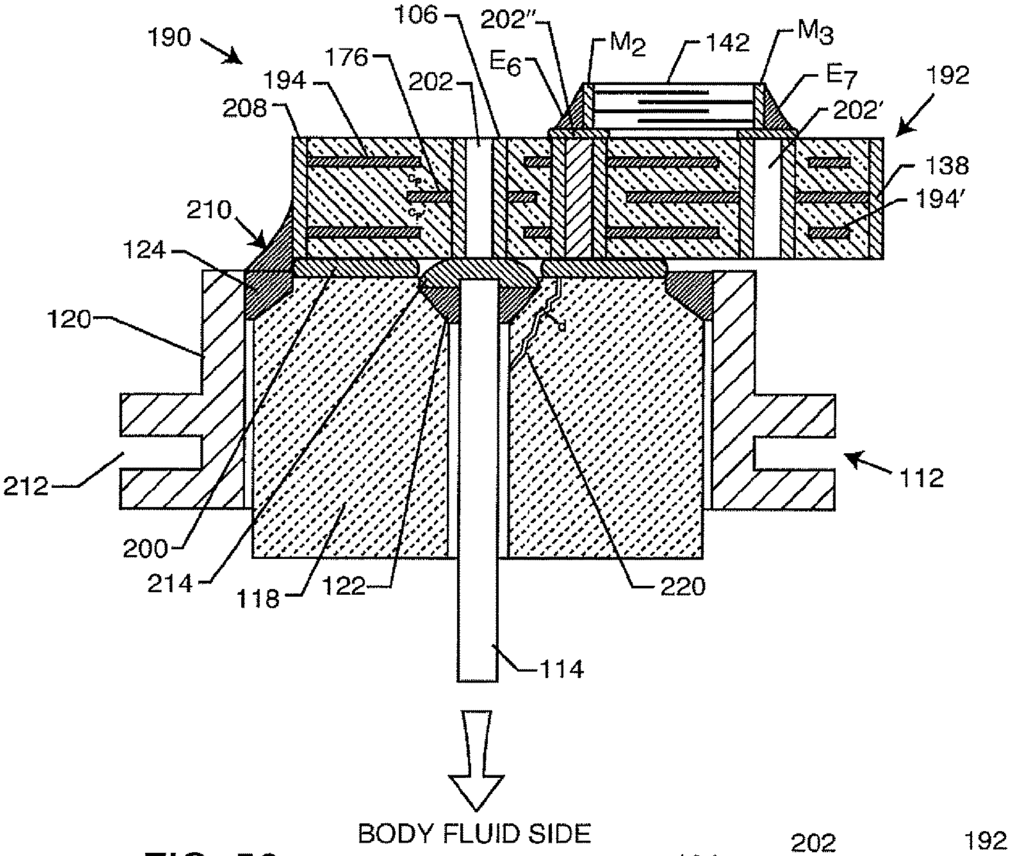
FIG. 56 is a sectional view taken generally along the line 56-56 of FIG. 54.

In FIG. 54, one can see that there is a metalized area 208 on the hybrid substrate 192. This wrap-around metalized area 208 makes connection to internal ground shield plates 194 and 194' embedded within the hybrid substrate 192 as shown in FIG. 56. One can see in FIG. 54 a plurality of electrical connections 210, 210' and 210' as shown (the equivalent electrical connections 210" and 210" on the opposite side of substrate 192 are not shown). These electrical connections connect to gold braze 124 that is part of the hermetic seal and provides an "oxide-free" RF ground multi-point connection. This is better understood by referring to FIG. 56 which is taken from section 56-56 of FIG. 54. The importance of connecting to a gold braze instead of connecting directly to the titanium ferrule 120 can be better understood by referring to U.S. Pat. Nos. 6,765,779 and 6,765,780 the contents of which are incorporated herein. From FIG. 56, one can see that there is a prior art hermetic seal 112 which includes a metal ferrule 120 which is typically of titanium or the like. There is a flange area 212 shown which is convenient for laser welding to the titanium housing of an AIMD, such as a cardiac pacemaker or the like. There is a hermetic insulator 118 which can be of alumina, ceramic materials, glass or equivalent. In this particular embodiment, there is a gold braze 124 which forms a mechanical and hermetic seal between the insulator 118 and the ferrule 120. A gold braze 122 makes a similar mechanical and hermetic seal between the lead wire 114 and the insulator 118. In this example, the body fluid side would be towards the bottom of the cross-sectional illustration of FIG. 56. An electrical connection is made between lead wire 114 and the metalized via hole 202 which is part of the novel hybrid substrate 192. The via hole 202 makes electrical connection to internal active electrode (otherwise known as the flat-through electrode) plate 176 as shown, which in turn is connected to via hole 202'. The grounded electrode shield plates 194 and 194' are connected to the outside metallization surface 208 of the hybrid substrate 192. In turn, this metallization 208 is electrically connected via material 210 to the gold braze 124 of the hermetic seal 112. As previously stated, this direct connection to gold makes a reliable oxide free low impedance connection, the importance of which is described thoroughly in U.S. Pat. Nos. 6,765,779 and 6,765,780. One can also see that by wrapping metallization surface 208 around the sides of the hybrid substrate 192, one prevents any chance that EMI being conducted on active electrode 176 could radiate or cross-couple into the interior of the AIMD. By keeping the EMI "bottled up" between the grounded shield plates 194 and 194', one forms a nearly complete faraday cage shield which is the ideal solution. Due to the thin geometry, substrate edge re-radiation of RF energy is a very minor concern which, if the dielectric thickness between layers 176 and 194, 194' becomes large, can be solved by co-planar edge shields which will be described in connection with FIG. 60. This novel method of shield containment is applicable to any of the embodiments described herein.

Referring once again to FIG. 54, one can see that a prior art monolithic ceramic chip capacitor (MLCC) 142 has been electrically connected to lands which are in turn connected to via holes 202' and 202". This is better understood by referring to the exploded view of FIG. 54 shown in FIG. 58. One can see that via hole 202' is connected to the active circuit electrode 176. The other side of the MLCC capacitor 142 is connected by via hole 202" to both of the grounded shield electrode plates 194 and 194'. It is important that a very low impedance connection has been made to both sides of the MLCC capacitor 142. In this embodiment, any type of chip capacitor could be used. That is, monolithic ceramic, stacked film, tantalum, electrolytic or the like. It will also be obvious to those skilled in the art that the ground (left) side of MLCC capacitor 142 need not be connected to RF ground by way of the via 202" as shown. Instead, an enlarged land on the left side of the MLCC 142 could be RF grounded directly to the external wrap-around metallization surfaces 208.

Figure 55:
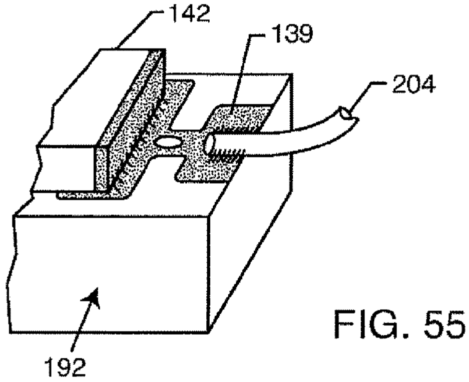
FIG. 55 is a fragmented view of the area indicated by line 55-55 in FIG. 54, illustrating an alternative way of attaching a lead wire.

In FIG. 54, one can see that there is a wire bond pad 138 which is affixed to the hybrid substrate 192. This makes for a convenient mounting pad for attachment of lead wire 204. Lead wire 204 would be routed to the internal circuits of the general electronic device or an AIMD. Lead wire 204 can be affixed to wire bond pad 138 by thermal or ultrasonic welding, soldering or the like. FIG. 55 shows an alternative arrangement wherein the wire bond pad 138 (which would typically be made of Kovar) has been eliminated. In FIG. 55, there is a different type of plated of metal deposited wire bond pad 139. In this case, no separate attachment of a Kovar block 138 is required as illustrated in FIG. 54. In this case, in FIG. 55, wire bond pad 139 can be an integral part of an external circuit trace and deposited by plating, thick film deposition technique and the like.

Referring once again to FIG. 56, active electrode plate 176 is sandwiched between the two grounded electrode shield plates 194 and 194'. The prior art MLCC capacitor 142 is connected between via hole 202' (which is also connected to the active circuit plate 176) and via hole 202" which is in electrically conductive relationship with both the ground shields 194 and 194'. Electrically speaking, this means that the MLCC capacitor 142 connects from the active circuit plate 176 to ground. Accordingly, it acts as an electrical bypass low-pass filter element to provide additional EMI filtering to complement the flat-through capacitance as previously described.

Referring once again to FIG. 56, one can see that there is an electrical connection material 214 that is disposed between the lead wire 114 and the via hole 202. This can be of a thermal setting conductive polymer, such as a conductive epoxy or a conductive polyimide or the like. Material 214 could also be of solder or braze, which is known in the art as solder bump construction or even ball grid array (BGA). It is shown in the reflowed position so it is not obvious that this started out as a round ball. In order to provide electrical isolation between this material 214 and the gold braze 124, one or more adhesive backed insulative washers 200 are disposed between the hermetic seal 112 and the hybrid substrate 192. Typically this washer 200 would be an adhesive backed polyimide or the like to make sure that electrical conductive materials such as 214 stay in place and could not short and/or migrate to areas where they were not desired (like a short to ground). As described in U.S. Pat. No. 7,327,553, the contents of which are incorporated herein by reference, a laminar leak detection path can be provided between the washer 200 to facilitate helium leak testing of the hermetic seal.

There is a similar electrical connection material 210 disposed between metallization surface 208 and gold braze 124. Material 210 is also typically a thermal setting conductive adhesive, solder, low temperature braze, laser weld, or the like. A wire bond pad 138 is shown connected to the active electrode plate 176. At this point, any electrical noise (EMI) that was entering from the body fluid side on lead wire 114 has been decoupled by the filtering action of the flat-through capacitances shown in FIG. 56 as $C_P$ and $C_P'$ and the MLCC 142 working together. The flat-through capacitance is relatively lower in value than the MLCC 142; however, it is very effective for attenuating high frequencies. Lower frequencies are attenuated by the higher capacitance value MLCC capacitor 142. Wire bond pad 138 is convenient for connection of one or more lead wires 204 to internal circuit components inside of the general electronic shielded module or an AIMD.

Figure 57:
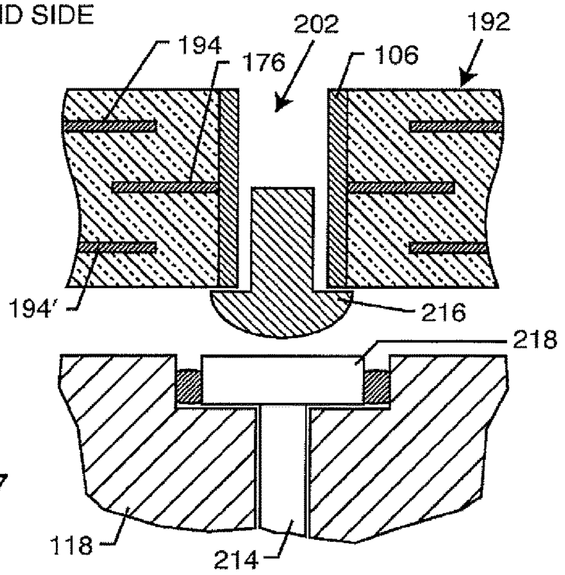
FIG. 57 is a fragmented sectional view showing an alternative connection methodology wherein a via hole is filled and then attached to a solder bump.

In FIG. 56 one can see that via hole 202 is connected to lead wire 114 by means of an electrical conducting material 214 which can be solder, a low temperature braze, a thermal-setting conductive adhesive or the like. An alternative methodology is shown in FIG. 57 wherein the via hole 202 is filled and then attached to a solder bump 216 as shown. The solder bump 216 makes contact to the metallization 106 of via hole 202. By raising the entire assembly to an elevated temperature, the solder bump 216 wets to the nail head lead 218 forming a reliable electrical and mechanical connection.

Figure 58:
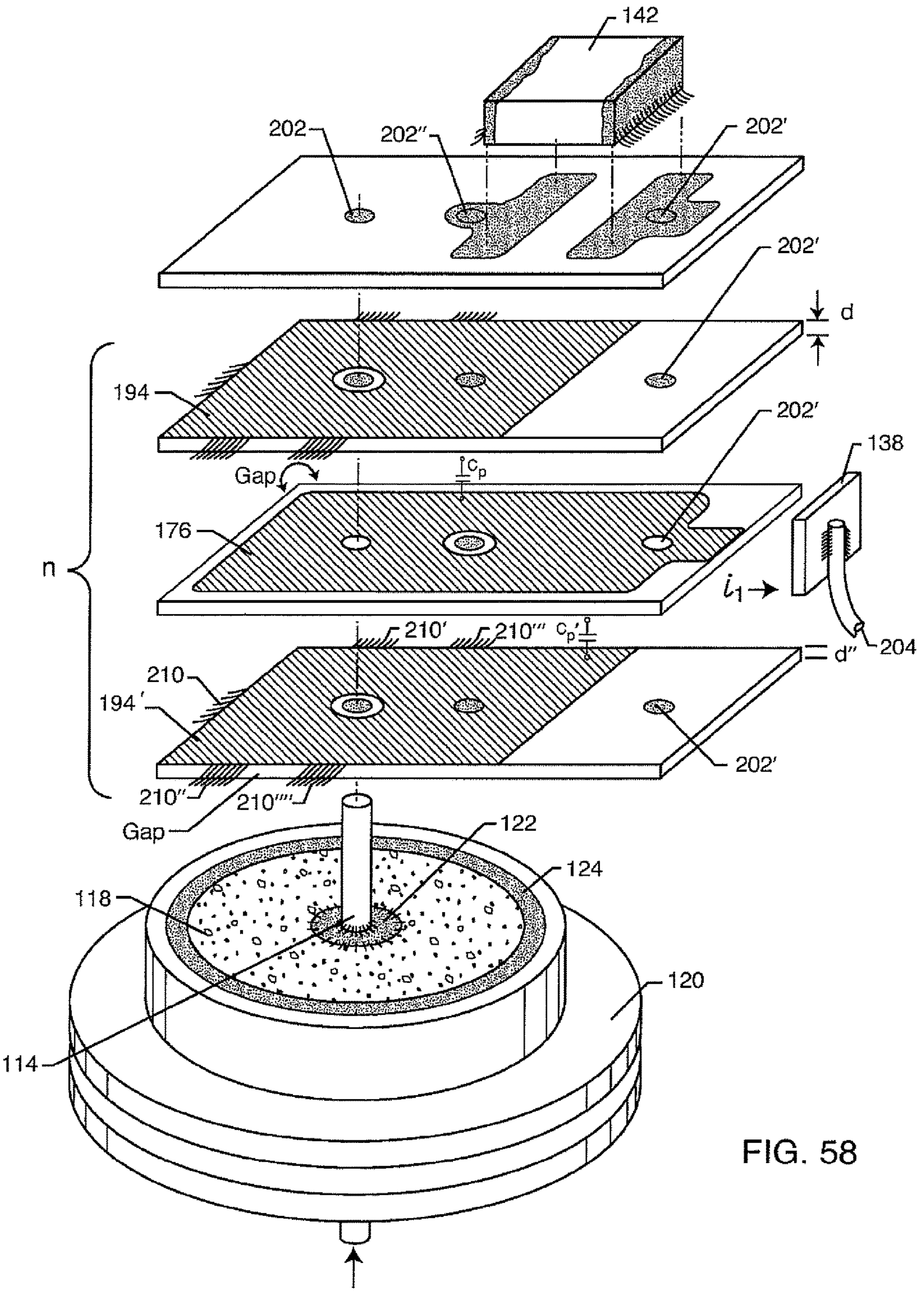
FIG. 58 is an exploded perspective view of various components forming the structure of FIGS. 54 and 56.

FIG. 58 is an exploded view of FIG. 54. A low impedance RF electrical connection to the ground shield plates 194 and 194' is very important. Accordingly, one can see that there are multiple electrical attachments 210 to 210". This, of course, could be one long continuous connection all around the ground metallization 208 to the gold braze 124. However, it is desirable to not block a helium leak path. The integrity of these hermetic terminals is critical to preclude the entry of body fluid into the AIMD.

Referring once again to FIG. 56, one can see that if there were a crack 220 or other defect in the hermetic terminal insulator 118 or in the corresponding gold braze 122 then body fluid (moisture) may be able to enter into the enclosed electronic housing or worse yet, the hermetic housing of an AIMD like a cardiac pacemaker. It is very common in the art to test these terminals using helium as a leak detection medium. However, a concern is that the installation of adjunct components, such as the hybrid substrate 192 of the present invention, could temporarily block the flow of helium. Typically a helium leak test is performed in a few seconds. Therefore any adjunct sealant, such as a continuous coverage of conductive thermal setting adhesive 210 or the like, could slow down the flow of helium through such coverings. Accordingly, in the preferred embodiment of the present invention, it is desirable to leave open gaps as shown in FIGS. 54 and 58 between areas of electrical attachment. In this way, if there are any defects 220 in the hermetic terminal insulator 118 or its associated gold brazes 122 and 124, the helium will be free to pass and be detected by the leak test equipment. As taught by U.S. Pat. No. 6,566,978, the contents of which are incorporated herein by reference, it will be obvious to those skilled in the art that strategically placed open via holes through the hybrid substrate 192 could be provided in order to pass helium during hermetic seal testing.

Figure 59:
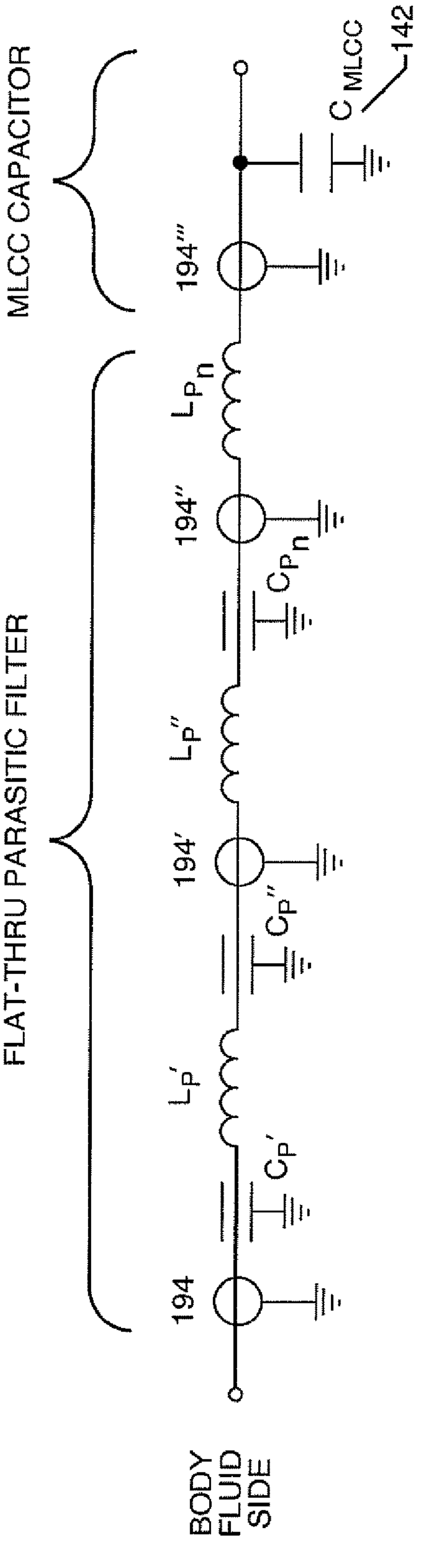
FIG. 59 is an electrical schematic for the structure of FIGS. 54, 56 and 58.

Referring once again to FIG. 58, a novel aspect of the present invention is that flat-through capacitance develops between the circuit active electrode plate 176 and the surrounding grounded shield electrode plates 194 and 194'. This capacitance is shown as $C_P$ and $C_P'$. The capacitance value of this flat-through capacitance is dependent upon the typical capacitance equation, which is given by C=kA(.η.−1)/d. Where k is the dielectric constant of the material. As previously mentioned, the novel hybrid substrate 192 shown in FIG. 56 could be constructed of a variety of different materials. For example, the dielectric constant of a polyimide material would be between 3 and 4 whereas an alumina ceramic material could be as high as 9 to 11. Barium and strontium titanate dielectric bodies can have dielectric constants in excess of 5000. In the equation, A stands for the area, which is the effective capacitance area (ECA). This is calculated by the sandwiched overlap between the area of circuit active electrode plate 176 and the corresponding ground electrode shield plates 194 and 194'. Ignoring fringe effects, a simplified way of calculating this area is simply the area of active electrode plate 176 that is bounded between the sandwiched grounded shields 194 and 194'. In the equation, .η. is the total number of repetitive electrode plates. In this case, there are three plates consisting of 194, 176 and 194'. This gives us η−1 which yields two parasitic flat-through capacitances $C_P$ and $C_P'$. The dielectric thickness d is simply the thickness of the dielectric material that separates 194 and 176; and 176 and 194' as shown. The presence of the flat-through capacitances $C_P$ and $C_P'$ is extremely important to the overall broadband EMI filtering performance of the present invention. This can be understood by referring to the schematic diagram of FIG. 59. In addition to the flat-through capacitances $C_P$, $C_P'$ . . . $C_{Pn}$, there is also parasitic inductance formed along the length of the active electrode plate 176. This is shown as $L_P$, $L_P'$, and $L_{\cdot Pn}$. It will be obvious to those skilled in the art that the higher the amount of the effective capacitance area that overlaps between the active electrode plate 176 and the adjoining ground shield plates 194 and 194', the higher the parasitic capacitance $C_P$ will be. In this case, the parasitic inductance is very small and really does not aide in filtering. It will also be obvious to those skilled in the art that the parasitic inductance of the active electrode 176 will be proportional to both its length and its width. In other words, the longer the active electrode 176 is, the greater its inductance $L_P$ will be. The presence of series inductance is very important as this will improve the overall high frequency performance of the shielded three-terminal flat-through EMI/energy dissipating filter 190. There are ways of making this slight series parasitic inductance much higher as will be described below.

Referring back to schematic FIG. 59, one can see that in a number of locations there is a shield symbol 194-194''' (sometimes shown as "Sh"). This is an indication that the entire assembly consisting of the flat-through capacitance $C_P$ and the capacitance C contributed by the MLCC capacitor 142, in general, has its active electrode all contained (sandwiched between) within the shield plates 194. As previously mentioned, this is very important so that undesirable electromagnetic interference at high frequency cannot bypass or jump across from the body fluid side and thereby enter into the electronic device or AIMD housing and possibly interfere with sensitive electronic circuits. The importance of filtering for AIMDs, such as cardiac pacemakers, has been described by U.S. Pat. Nos. 4,424,551, 5,333,095 and 5,905,627 the contents of which are incorporated herein. In this regard, the shielded three-terminal flat-through EMI/energy dissipating filter 190 of the present invention acts in equivalent way to prior art feedthrough capacitors in that the shielded three-terminal flat-through EMI/energy dissipating filter 190 is not only an effective filter and energy dissipation element, it's ground electrode plates 194 act as an effective part of the overall electromagnetic shield housing of the AIMD or other equivalent shielded electronic circuit.

Referring back to FIG. 58, one can see that in the present configuration, the inductance, although quite small, is relatively maximized due to the relatively long length of active electrode plate 176 and the fact that it is relatively narrow. One will also notice that the flat-through (parasitic) capacitance is the sum of the parallel combination of $C_P$ and $C_P'$, and is relatively maximized due to the large area of the active electrode 176 and the high ECA achieved by its overlap with the grounded shield plates 194 and 194'. One way to further increase the total amount of flat-through (parasitic) capacitance would be to increase the number of layers in FIG. 58. In a monolithic construction, repeating the number of redundant layers would increase the capacitance by the .η.−1 term of the capacitance equation. Additional ways to increase the amount of flat-through capacitance would be to further increase the effective capacitance overlap area ECA, increase the dielectric constant or decrease the dielectric thickness (d).

Figure 2:
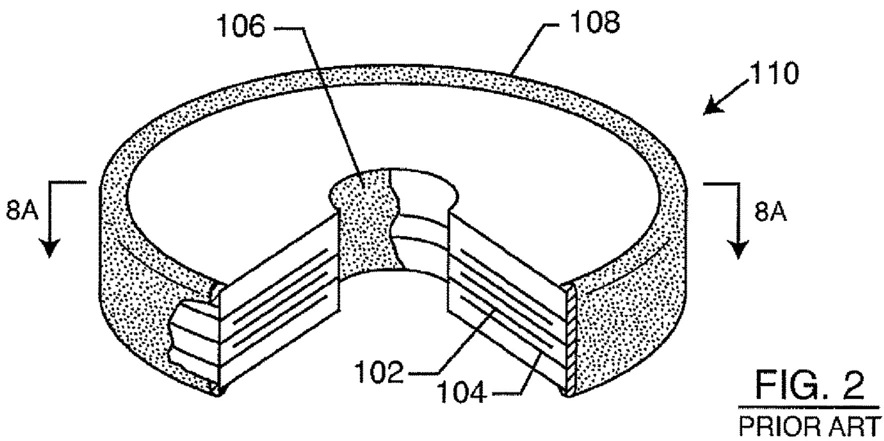
FIG. 2 is a fragmented perspective view of a prior art unipolar discoidal feedthrough capacitor.
Figure 5:
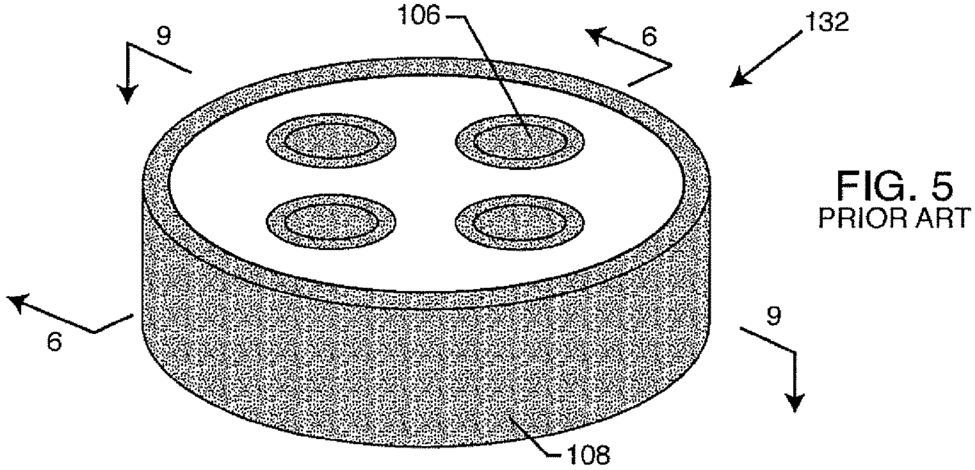
FIG. 5 is a perspective view of a quadpolar feedthrough capacitor.
Figure 6:
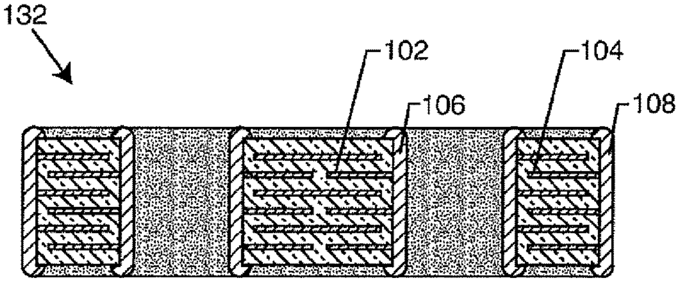
FIG. 6 is sectional view taken along the line 6-6 of FIG. 5.
Figure 7:
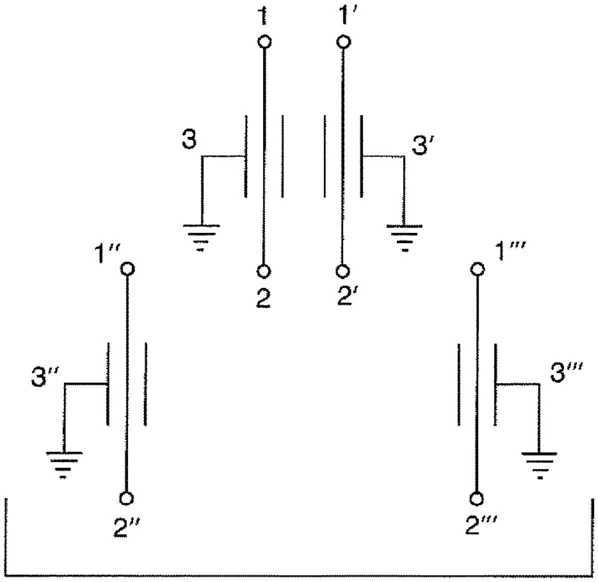
FIG. 7 is an electrical schematic diagram of the quadpolar feedthrough capacitor of FIGS. 5 and 6.
Figure 8:
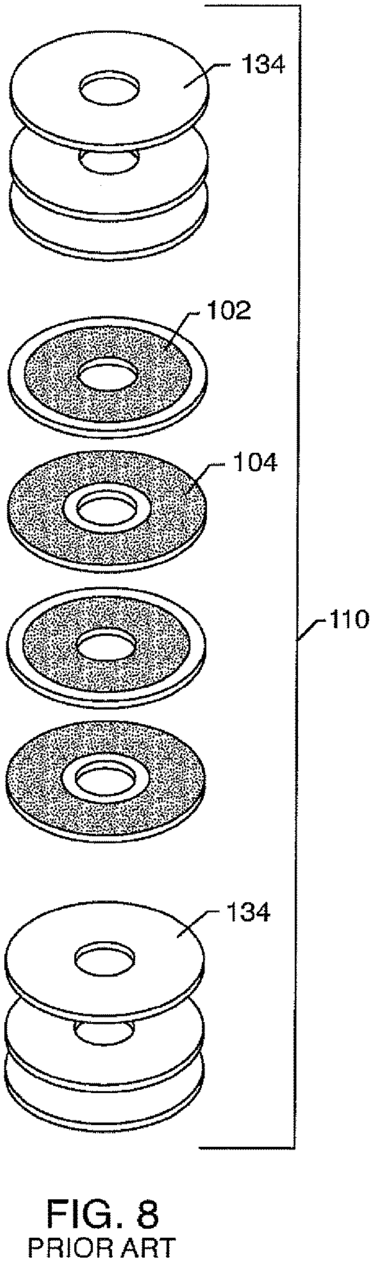
FIG. 8 is an exploded electrode view showing the inner and outer diameter electrodes of the unipolar feedthrough capacitor of FIGS. 2 and 3.
Figure 9:
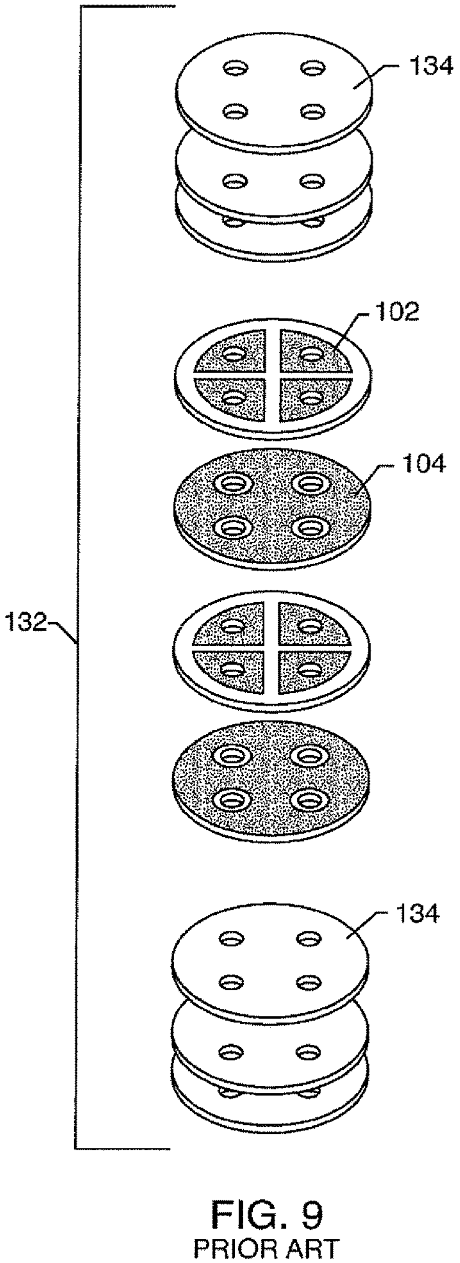
FIG. 9 is an exploded view of the interior electrodes of the quadpolar feedthrough capacitor show in FIG. 5.
Figure 13:
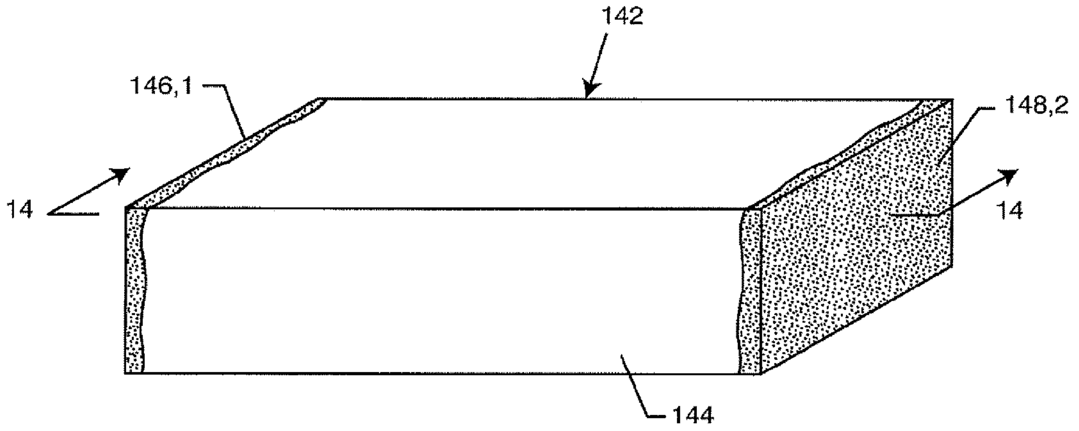
FIG. 13 is a perspective view of a monolithic ceramic capacitor (MLCC).
Figure 14:
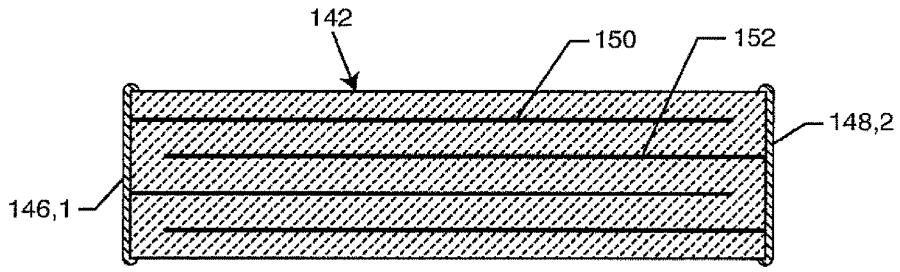
FIG. 14 is a sectional view taken generally along the line 14-14 of FIG. 13.
Figure 19:
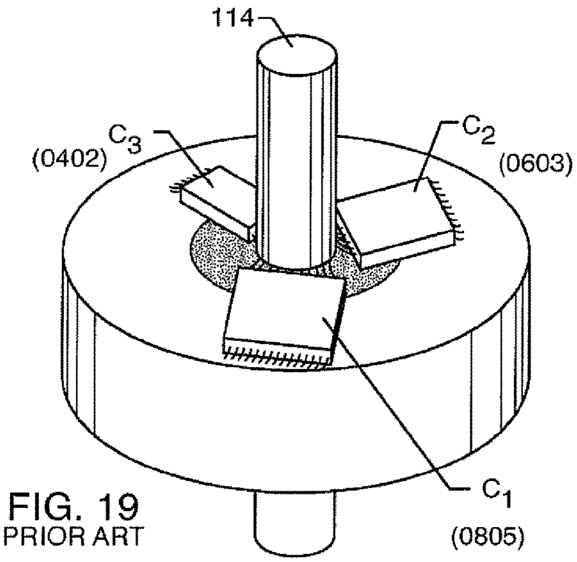
FIG. 19 is a perspective view of a unipolar terminal having three different size MLCC capacitors connected to the feedthrough pin.
Figure 20:
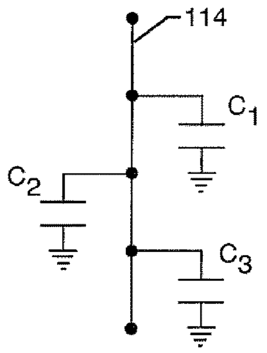
FIG. 20 is an electrical schematic diagram of the structure shown in FIG. 19.
Figure 21:
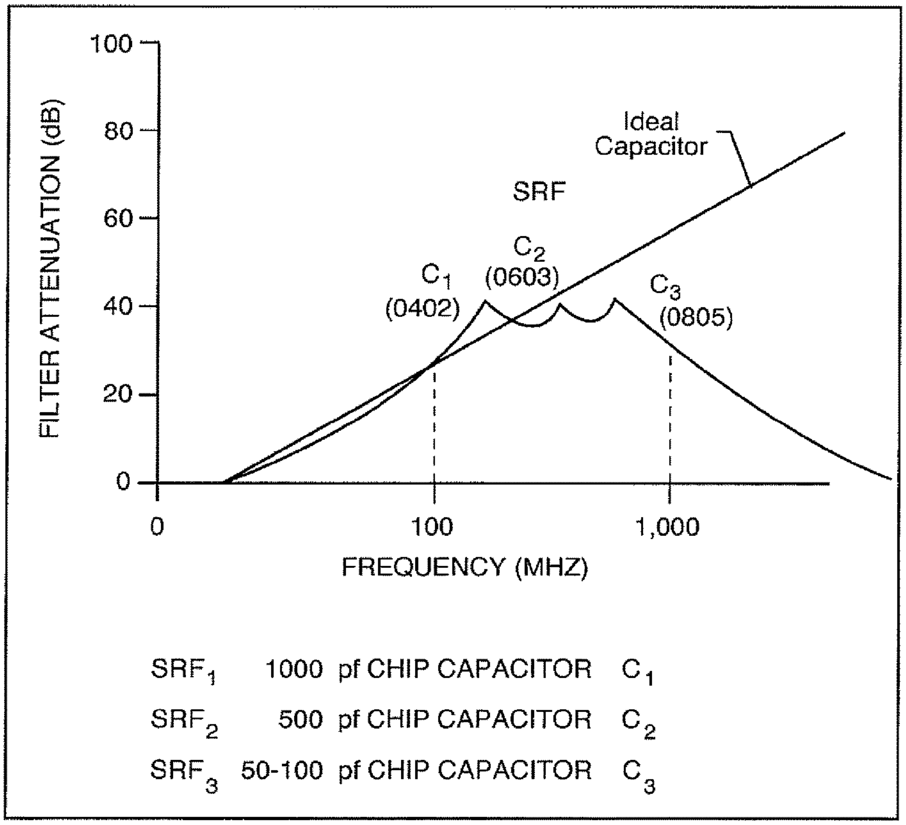
FIG. 21 is a graph showing the attenuation response for the three chip capacitor unipolar hermetic terminal shown in FIG. 19.
Figure 22:
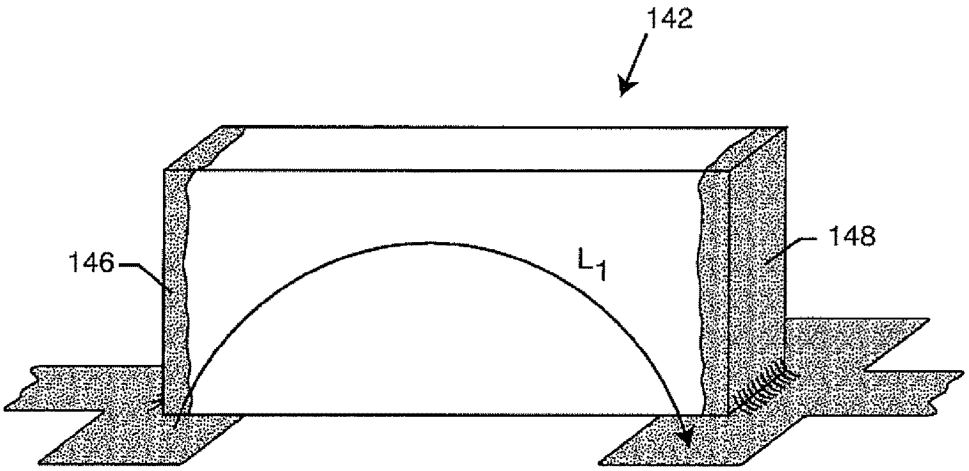
FIG. 22 illustrates a different method of mounting the MLCC capacitors such as those shown in FIG. 19.
Figure 23:
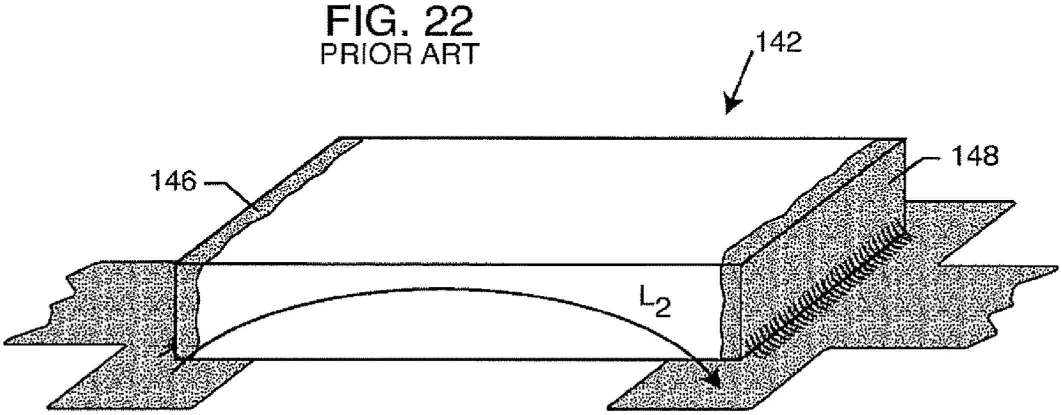
FIG. 23 illustrates a more desirable way to mount the capacitor of FIG. 22.
Figure 24:
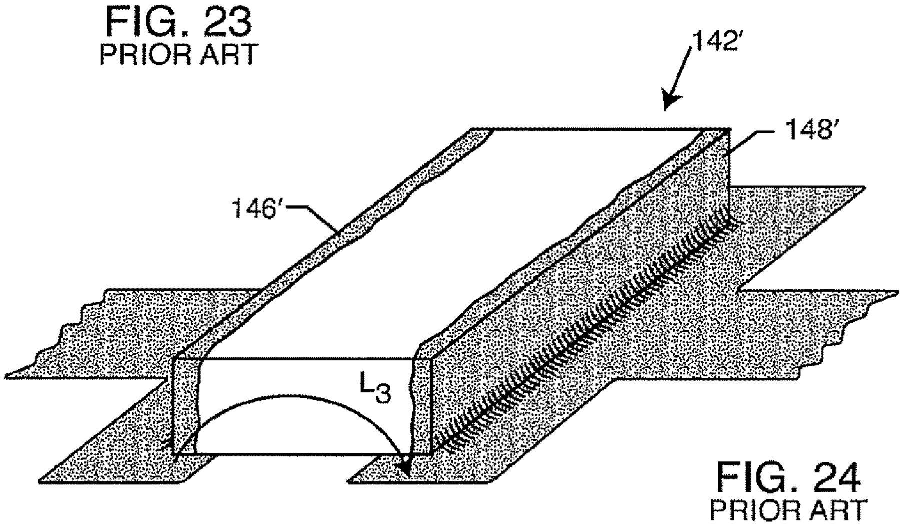
FIG. 24 shows yet another way of mounting the MLCC capacitor of FIGS. 22 and 23.
Figure 25:
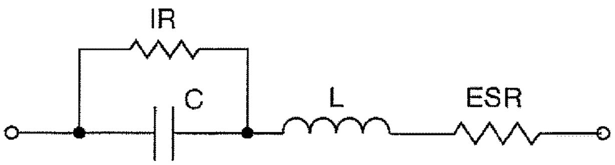
FIG. 25 is an electrical schematic diagram showing an equivalent circuit model for the MLCC chip capacitor.
Figure 26:
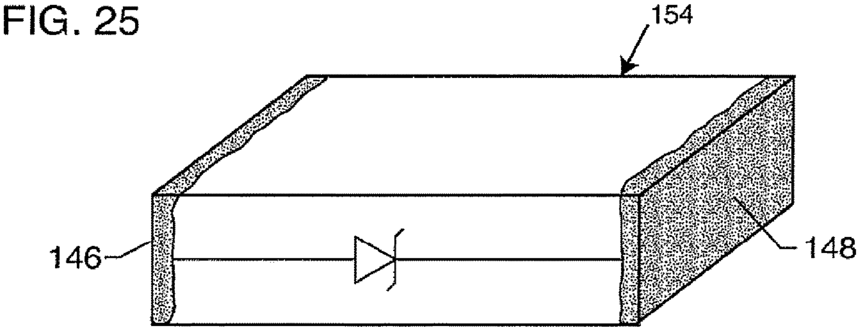
FIG. 26 is a perspective and schematic view of a prior art MLCC transient suppressant diode.
Figure 27:
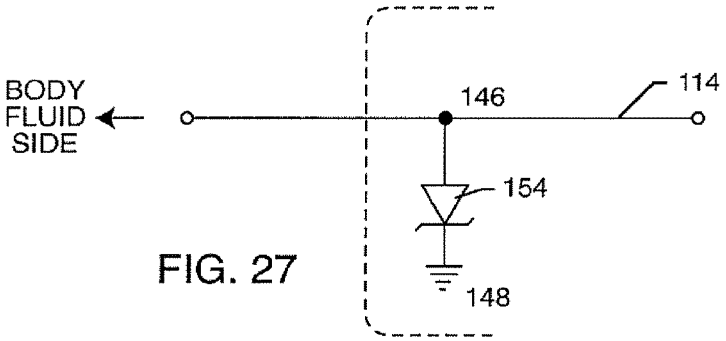
FIG. 27 is an electrical schematic diagram of the diode of FIG. 26.
Figure 28:
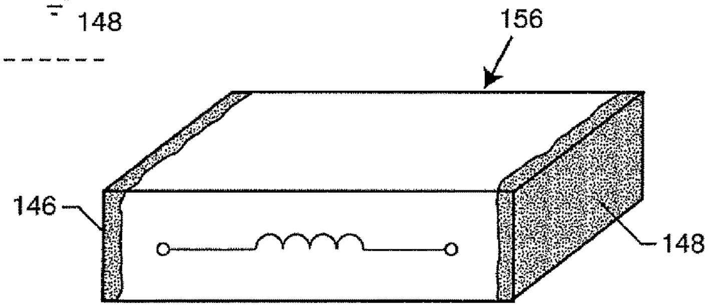
FIG. 28 is a perspective and schematic diagram of a prior art chip inductor.
Figure 29:
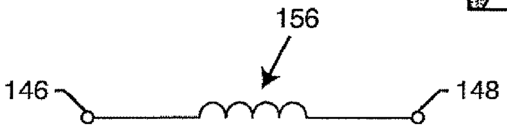
FIG. 29 is an electrical schematic diagram of the inductor chip of FIG. 28.
Figure 30:
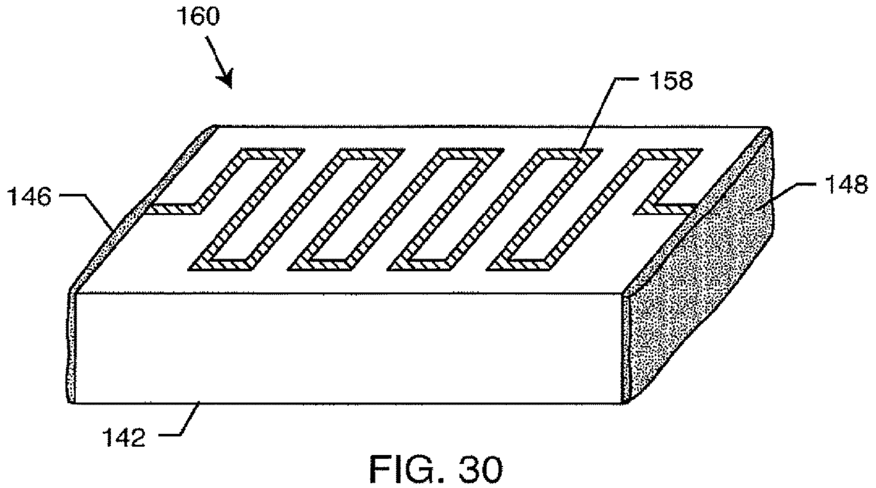
FIG. 30 is a perspective view of an MLCC capacitor having an inductor circuit trace deposited thereon.
Figure 31:
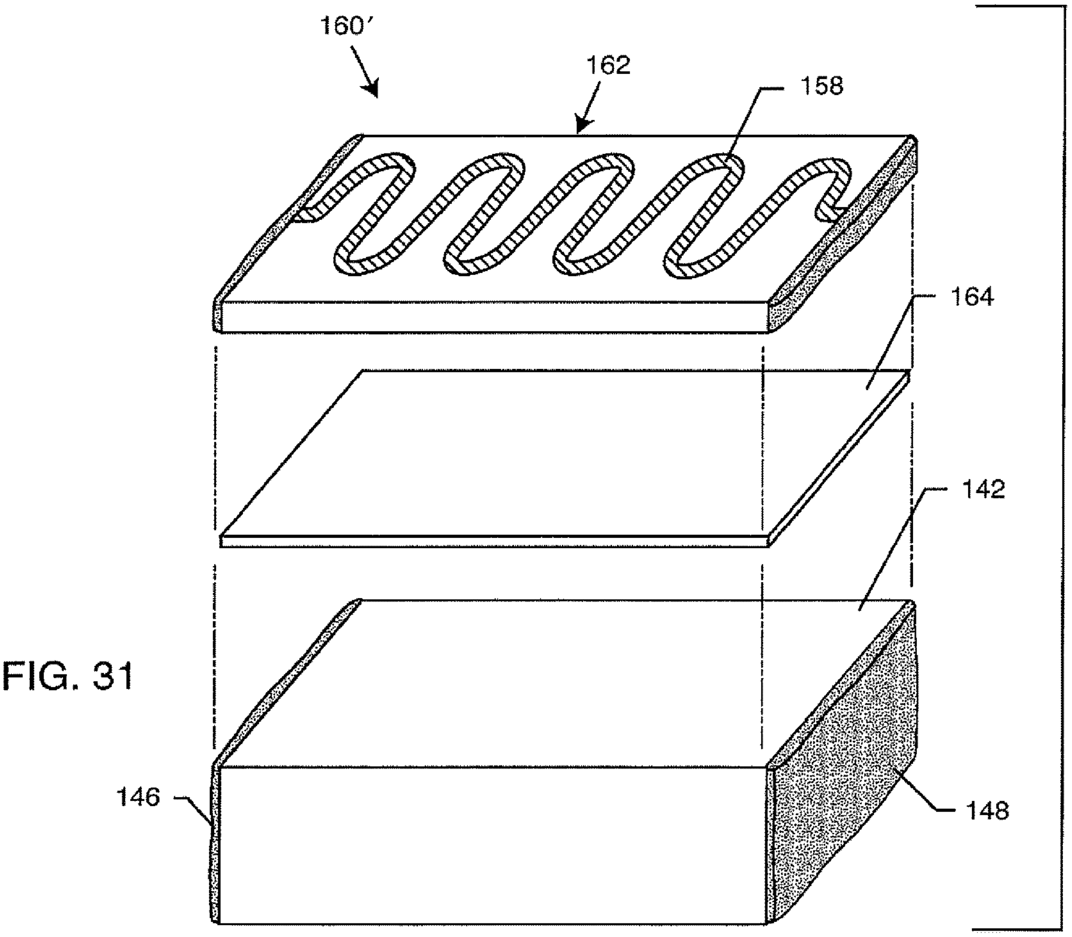
FIG. 31 is an exploded perspective view of a structure similar to FIG. 30 showing another way to deposit the inductor shape onto a separate substrate.
Figure 32:
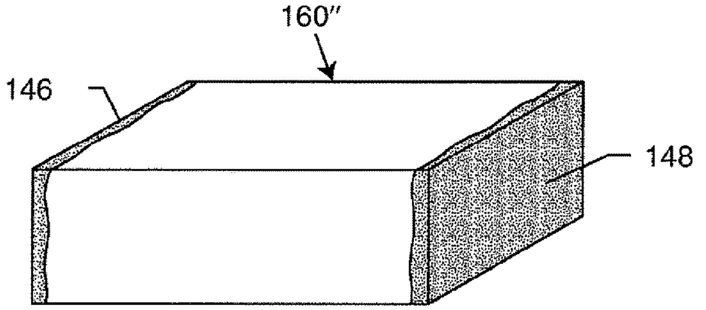
FIG. 32 is a perspective view of a composite monolithic ceramic capacitor-parallel resonant tank (MLCC-T) or bandstop filter.
Figure 33:
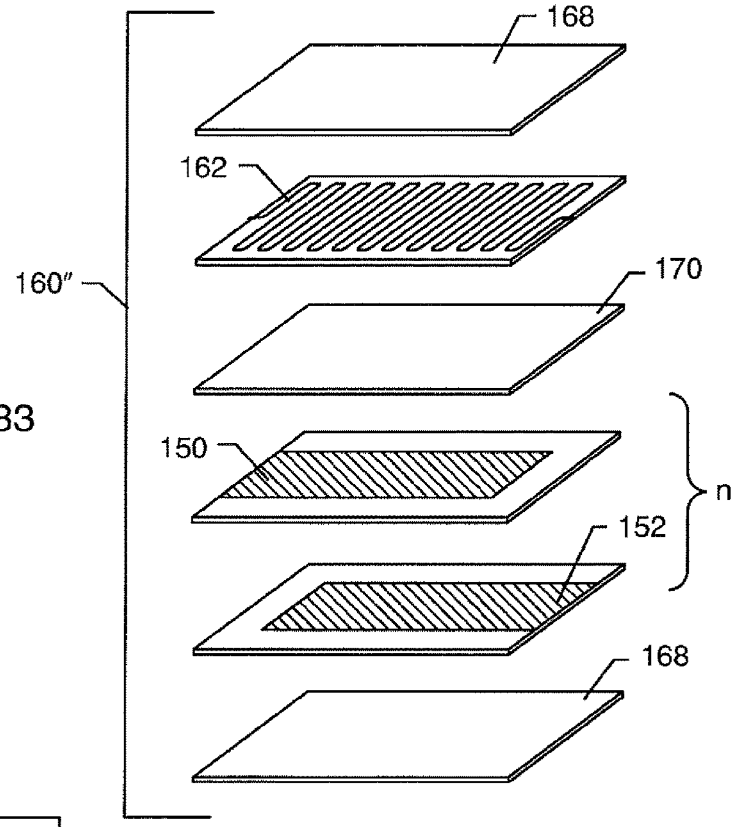
FIG. 33 is an exploded perspective view of the various layers of the MLCC-T tank filter of FIG. 32.
Figure 34:
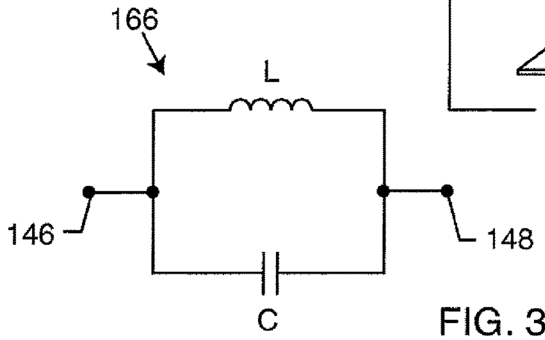
FIG. 34 is an electrical schematic diagram of the MLCC-T tank or bandstop filter of FIGS. 32 and 33.
Figure 35:
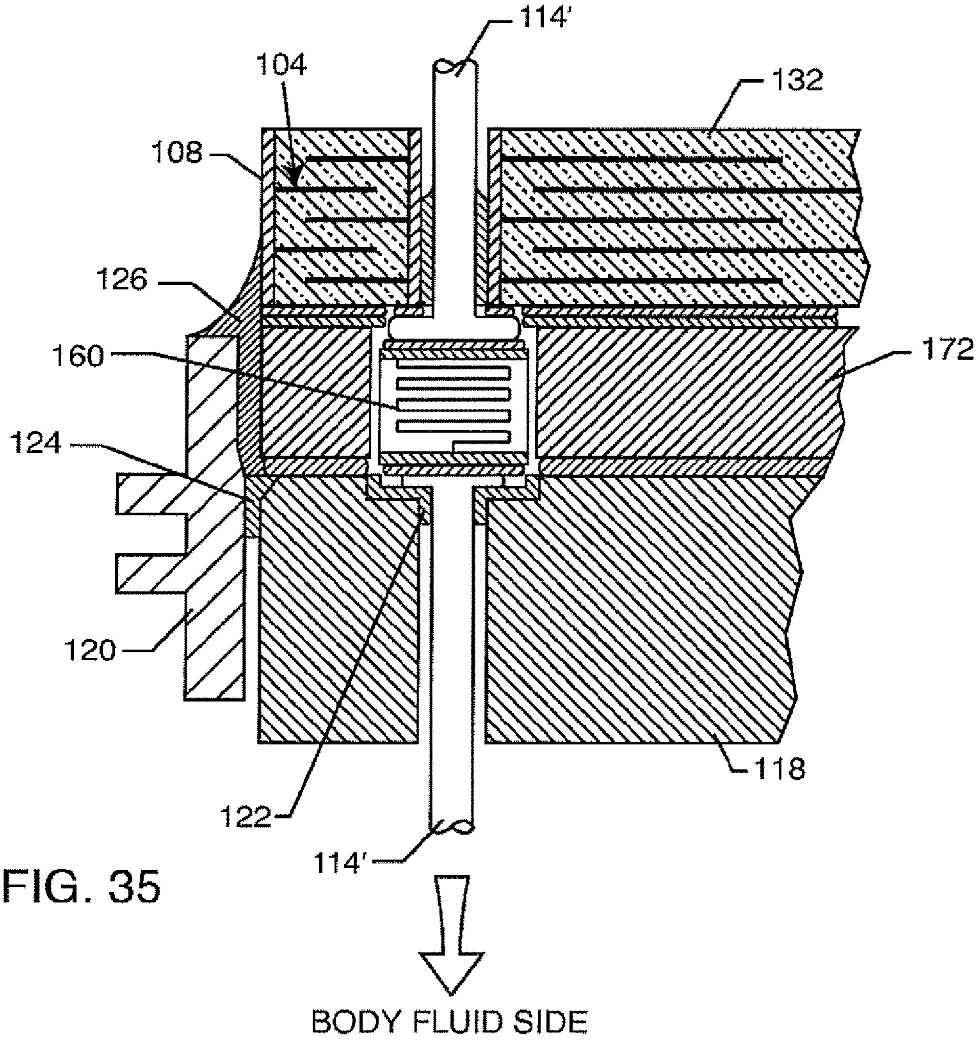
FIG. 35 is a sectional view of one pole of a quadpolar feedthrough capacitor embodying an MLCC-T filter.
Figure 36:
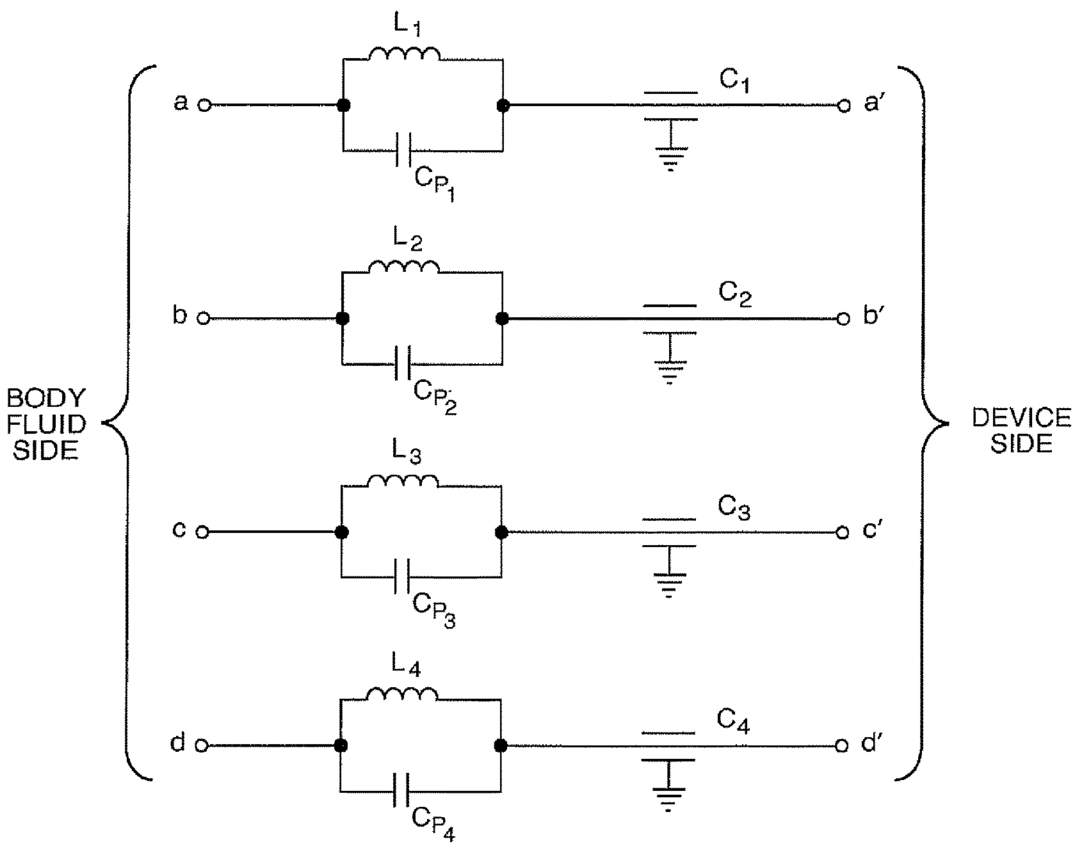
FIG. 36 is an electrical schematic diagram of the quadpolar device partially shown in FIG. 35.
Figure 40:
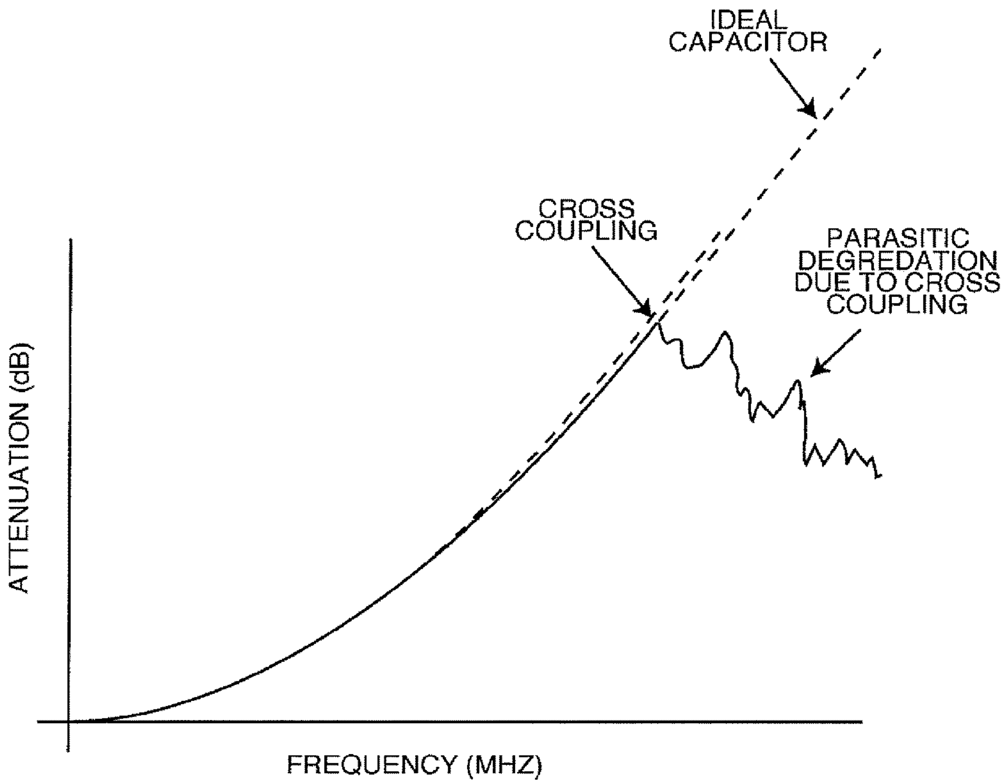
FIG. 40 illustrates the attenuation versus frequency response curve of the typical flat-through capacitor of FIGS. 37 and 38.

Prior art feedthrough capacitors, as illustrated in FIGS. 2 and 5 and shown in the assembly in FIG. 10, make for very low inductance broadband low-pass filters. This is why they have generally been the preferred EMI filter at the point of lead wire ingress and egress for AIMDs and other devices. However, feedthrough capacitors are generally built in low volumes in the industry. Because of this, they tend to be relatively high in price when compared to the much higher volumes MLCC capacitors. It is not unusual for a single feedthrough capacitor to cost several dollars, wherein an MLCC capacitor can cost just a few cents. In addition, prior art feedthrough capacitors tend to be quite low in capacitance value (primarily in the range from 400 to 4000 picofarads). This means that prior art feedthrough capacitors make very effective high frequency filters above 25 MHz, but off little attenuation at low frequencies (below 5 MHz). Feedthrough capacitors, in general, can be a hundreds of times more costly than equivalent value MLCC capacitors. However, referring back to FIG. 13, for the MLCC capacitor and its high frequency performance curve, as illustrated in FIG. 18, this does not produce a broadband low-pass filter. In general, MLCCs are marginal or insufficient for attenuating high frequency emitters that AIMD patients can be exposed to. This includes cellular telephones, RF identification (RFID), airport radars, microwave ovens and the like. As described in connection with FIG. 37, one possible solution would be to use flat-through capacitor technology. However, the parasitic degradation of attenuation due to cross-coupling as illustrated in FIG. 40 is a serious problem. Another problem associated with the prior art flat-through capacitor of FIG. 37 is that it is relatively costly. This is not just because it is produced in relatively low volumes. There are additional costs required for the additional flat-through terminations 222 and 222' as shown in FIG. 37. These added terminations are difficult to automate and add significant hand work and additional expense. By incorporating the flat-through capacitor electrode plate 176 as a distributive parasitic element sandwiched between ground shield plates 194 and 194', as illustrated in FIG. 58, a number of desirable goals are achieved. First of all, the problem of cross-coupling across the flat-through capacitor has been eliminated. This is because it is contained or sandwiched within an entirely shielded structure. Therefore, there is no way for high frequency EMI to couple across the novel shielded three-terminal flat-through EMI/energy dissipating filter 190 of the present invention. In addition, flex cables for circuit boards are already commonly used in prior art electronic devices including AIMDs. In other words, by not adding any additional structures, one can embed a flat-through capacitance and then combine it with an MLCC capacitor 142 (or additional components) as shown in FIG. 58. The MLCC capacitor 142 is effective for low frequency attenuation and the parasitic flat-through capacitance $C_P$ works to attenuate high frequencies. The parasitic capacitance or flat-through capacitance works in parallel with the capacitance of the discrete MLCC capacitor 142 which results in a very effective broadband low-pass filter from kilohertz (kHz) frequencies all the way to 10 gigahertz (GHz) or higher. This is all summarized by the schematic diagram shown in FIG. 59. Shields 194-194" are illustrative to indicate that the entire flat-through filter is sandwiched between RF shield plates in such a way that high frequency EMI signals cannot re-radiate from the active electrode plate(s) 176. This is a very important concept. Until the undesirable EMI energy is decoupled to ground, it cannot be left unshielded inside the overall electromagnetically shielded housing of the electronic device or AIMD. If left unshielded, such high frequency noise could cross-couple into sensitive AIMD sense circuits. For example, if a cardiac pacemaker senses such high frequency noise as a heartbeat, the pacemaker could inhibit which could be life-threatening for a pacemaker-dependent patient.

Figure 60:
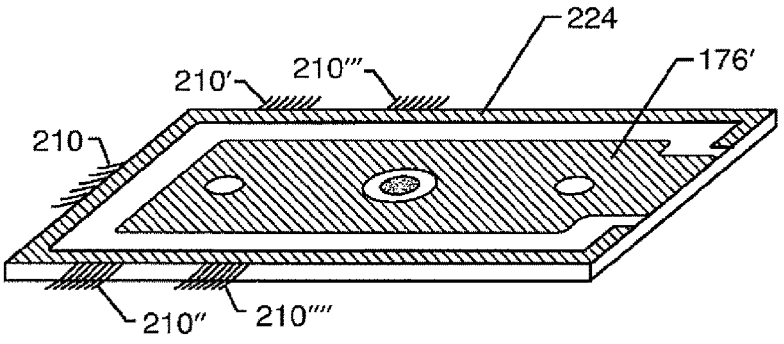
FIG. 60 is a perspective view showing modification of an active electrode plate layer shown in FIG. 58.

FIG. 60 illustrates an alternative active electrode layer to that which was previously described as 176 in FIG. 58. Referring to FIG. 60, one has to imagine removing the exploded active electrode view layer 176 in FIG. 58 and replacing it with the active electrode 176'. The active electrode plate 176' itself is not much different from that previously illustrated in FIG. 58 (its surface area is slightly smaller). What is different is that a grounded or third shield trace 224 has been deposited around the active electrode 176' on the same co-planar surface. The purpose of the surrounding grounded shield trace 224 on the same plane as active electrode 176' is to further aid in the coaxial shielding of the active electrode plate 176'. When one considers that the active electrode 176' is already sandwiched between grounded shield plates 194 and 194', this means that it is now shielded top, bottom and on both sides. The addition of the optional edge shield 224 prevents edge radiation of high frequency from the shielded three-terminal flat-through EMI/energy dissipating filter 190.

Figure 61:
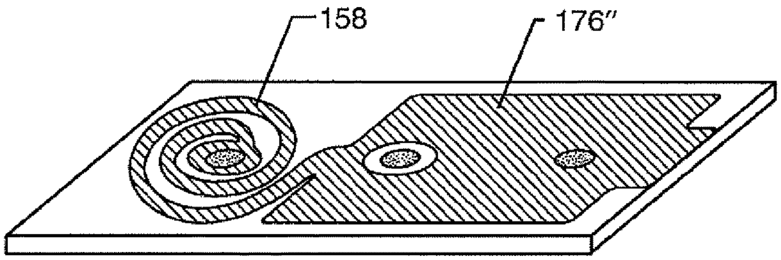
FIG. 61 is a view similar to FIG. 60, wherein the active electrode plate has been modified by adding a spiral inductor element.

The filter performance of the flat-through capacitor can be further improved by additional low-pass circuit elements. Referring to FIG. 61, one can see that the active electrode plate 176" has been modified by adding a Wheeler spiral inductor element 158. Wheeler spiral inductors are well known in the prior art for a variety of other applications. Wheeler spiral design equations are also readily available. The spiral inductor circuit trace 158 adds substantial series inductance to the active electrode plate 176" and also increases the flat-through capacitance overlap area (ECA) as well. In FIG. 61, by also having a wide active electrode plate area 176", one also maximizes the parasitic flat-through capacitance as previously described. In other words, the increased total effective overlap area (ECA) between the inductor circuit trace of 158 and the active electrode plate 176" as they are sandwiched between the two ground shield plates 194 and 194' greatly increases the flat-through capacitance $C_P$ and $C_P'$. In the art of EMI filter design, when one places an inductor in series with the circuit along with a capacitance to ground, this is known as an L-section low-pass filter. The schematic for the L-section filter of FIG. 61 is shown in FIG. 62.

Figure 62:
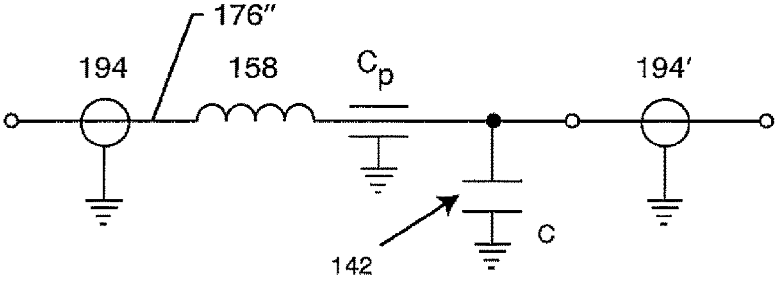
FIG. 62 is an electrical schematic for the inductor-capacitor filter formed by the substrate of FIG. 61.

Referring to FIG. 62, one can see the Wheeler inductor spiral 158 is in series with the active electrode 176" which has in parallel to ground both the flat-through parasitic capacitance $C_P$, and the MLCC capacitor 142 to form an L-filter. Not shown in FIG. 62 is the fact that the parasitic capacitance $C_P$ is really a distributive element and should be shown throughout the circuit. Accordingly, FIG. 62 should be considered a relatively low frequency model wherein a high frequency model would be of a distributed transmission line.

Figure 63:
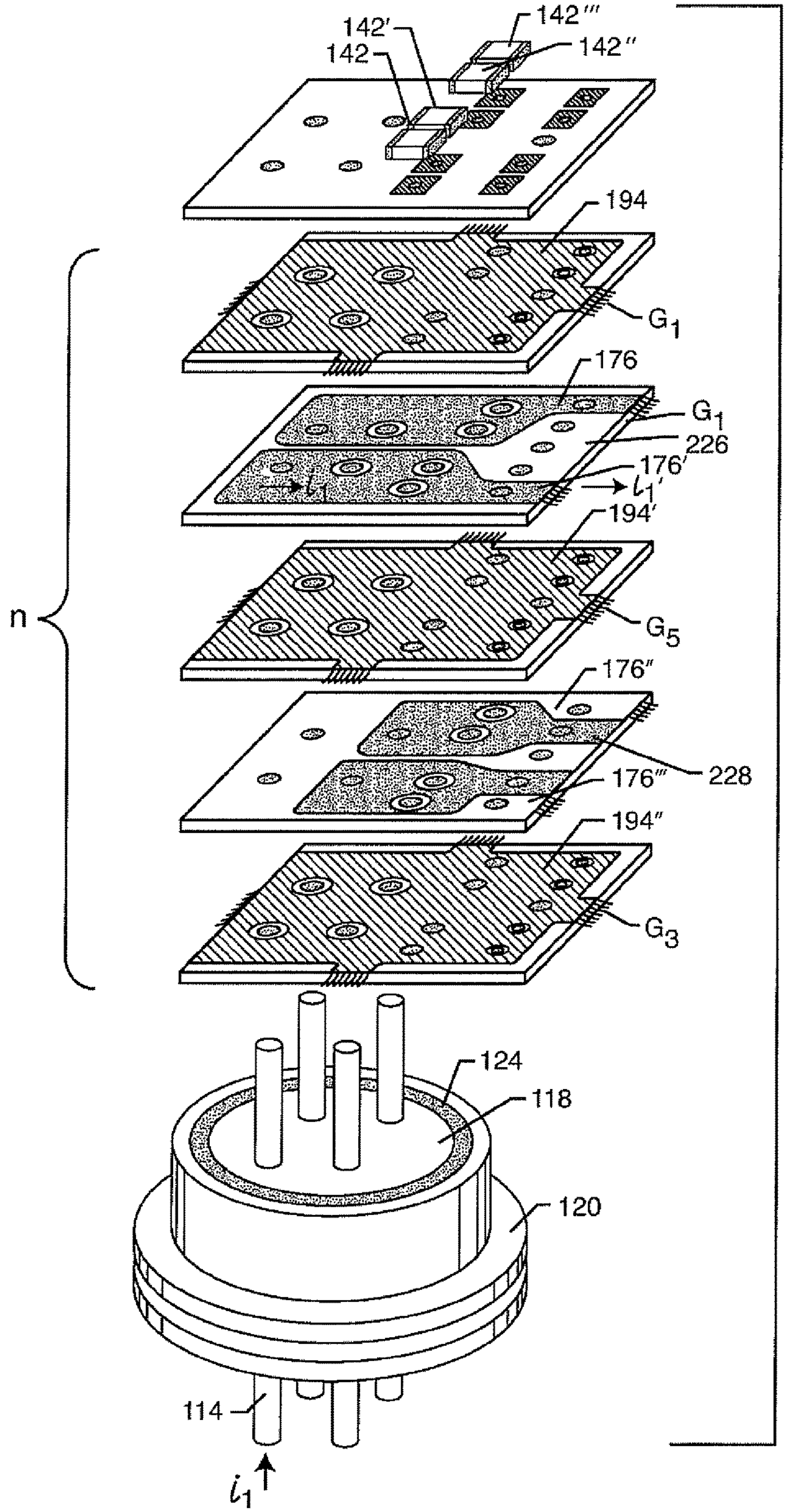
FIG. 63 is an exploded perspective view of a quadpolar filter assembly incorporating a shielded three-terminal flat-through EMI/energy dissipating filter in accordance with the present invention.
Figure 64:
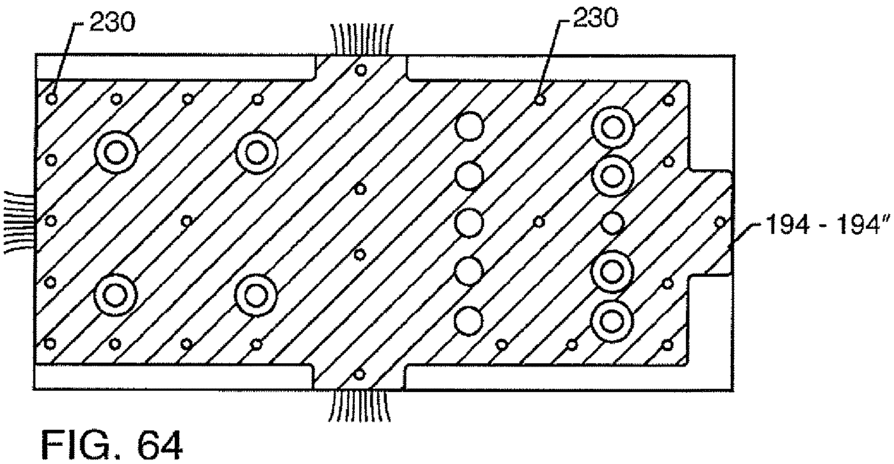
FIG. 64 is a top plan view showing a modification of the grounded shield plates of FIG. 63.

FIG. 63 illustrates a quadpolar filtered feedthrough assembly in accordance with the present invention. It is very similar in construction as previously described for the unipolar device of FIGS. 54, 56 and 58. In FIG. 63, one can see that there are multiple ground electrode shield plates 194, 194' and 194". The associated via holes will be obvious to those skilled in the art. Sandwiched between these ground electrode shield plates are active circuit electrode layers 226 and 228. Flat-through electrode circuits 176 and 176' are contained on electrode circuit trace layer 226. As previously described, parasitic capacitances or flat-through capacitances are formed due to the ECA overlap area on both sides. The spacing of the ground shields 194 and 194' is quite important in that they should not be spaced too far apart or high frequency RF leakage could occur due to the electromagnetic interference signals re-radiating from the flat-through electrode plates 176 and 176' out through the outside edge. This RF leakage was prevented in the unipolar design of FIG. 54 by wrapping the metallization surface 208 around the outside. This can also be accomplished by stitching through a number of conductive filled via holes 230 as shown in FIG. 64. FIG. 64 is a modification of the ground shields 194-194" of FIG. 63. One can see that there are a plurality of these stitching vias 230 or grounding vias all around the perimeter and even inside. The purpose of these stitching vias 230 is to electrically connect the three (or .eta.) ground shield layers 194-194" together in a multi-point low inductance configuration. These stitching vias form another very important purpose in that they decrease the effective length when one looks at the side view of this laminated sandwiched structure. It is a common principle in waveguide engineering that the cutoff frequency of a waveguide is dependent upon its geometry. For rectangular waveguides, the length-to-width ratios are very important. By shortening the length, one greatly increases the frequency at which the waveguide could start to pass electromagnetic signals through it. Accordingly, by including many stitching vias 230, one is guaranteed that the sandwiched construction maintains RF shielding as to edge re-radiation integrity up into the 5 to 10 GHz region. This is well above the effective filtering frequency required for AIMDs. The upper frequency for AIMDs is defined by experts in the art as 3 GHz. The reason that attenuation above 3 GHz is not required for AIMD EMI filters has to do with the reflection and absorption of body tissues at very short wavelengths. Accordingly, it is generally accepted by the implantable medical device EMC community that electromagnetic filters need to be very effective up to 3 GHz, but not beyond. References for this is made to published ANSI/AAMI standard PC69.

Referring once again to FIG. 63, it will be obvious to those skilled in the art that multiple layers n could be stacked up. The reason for this would be two fold. That is, to increase effective capacitance area (ECA) for the flat-through capacitances formed between the active electrode plates 176″ and the surrounding ground shields 194″ and also to increase the current handling capability of the active circuit electrode plates by putting additional redundant electrodes in parallel. This would tend to decrease the series resistance of said active circuit electrodes and, at the same time, increase their current and power handling capabilities.

Referring once again to FIG. 64, another purpose for the multiple vias 230 is to increase the mechanical integrity of a flexible hybrid substrate 192. By having multiple vias 230 stitching through, it becomes much more unlikely that said structure could delaminate. Another way to accomplish this is shown in FIG. 65, by the use of slot patterns 232.

Figure 65:
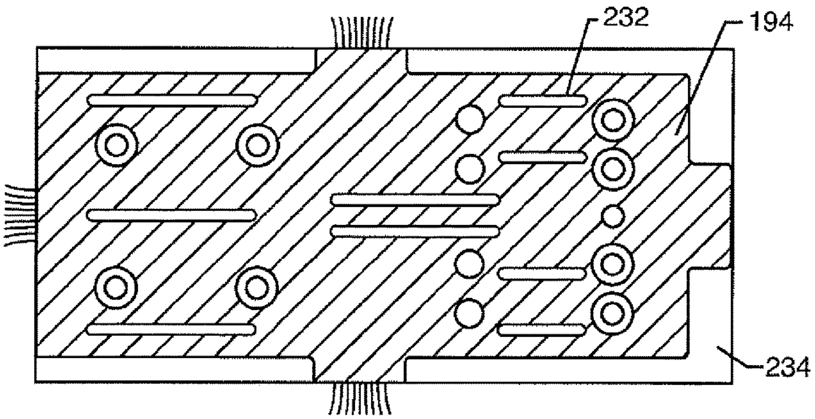
FIG. 65 is a view similar to FIG. 64 of the grounded shield plates, showing additional modifications.

In FIG. 65, there are multiple slots 232 as shown. These slots can be placed in a number of areas. The slots 232 are generally not filled in the same way that a via hole is filled. However, it does allow the adhesive binder layers to contact through the metalized electrode shield. For example, in a typical polyimide flex cable arrangement, multiple layers of polyimide are laid up with an acrylic binder. In this way, by providing for the slots 232, the acrylic binder can contact the underlying substrate material 234.

Referring back to FIG. 65, in the present invention it is preferable to align the slots 232 in the direction of active electrode circuit current flow such that torturous paths are not created for current flow. This also tends to maintain the inductive integrity of the ground plate. By way of example, if the shielded three-terminal flat-through EMI/energy dissipating filter 190 of the present invention were used at the point of lead wire ingress of a cardiac pacemaker, then the active electrodes must be low loss in order to conduct both the pacemaker pacing pulses and also conduct the biologic sensing signals. In other words, a modern cardiac pacemaker actively detects and monitors the electrical activity of the heart. One purpose for low loss active electrodes is as an AIMD battery saving purpose. Some patients are not pacemaker dependent, meaning that they only need to be paced at certain critical times when their heart rate drops too low. Therefore the pacemaker electronic circuits constantly monitor the heart. When a pacing pulse is needed, the pacemaker activates and delivers the pacing pulse through implanted leads to the appropriate cardiac tissue. The stimulation pulse then restores the heart to its natural sinus rhythm. Accordingly, it is very important that the active electrodes, such as those shown in layers 226 and 228 of FIG. 63, be relatively low loss. That is, the resistivity of the active electrodes should not be so high that pacing pulses or sensing signals are significantly attenuated.

Figure 66:
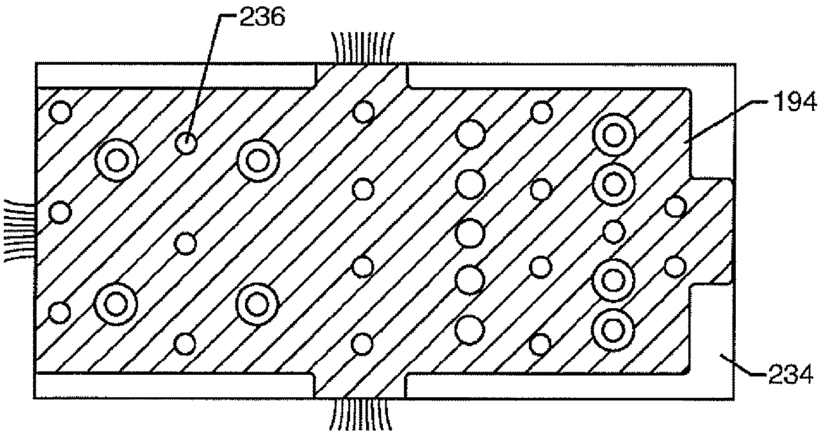
FIG. 66 is similar to FIGS. 64 and 65, showing an alternative configuration of the grounded shield plates.

FIG. 66 illustrates a methodology of putting multiple holes 236 in the metalized electrode shield. These multiple holes 236 serve the same purpose as the previously described slots 232 in FIG. 65.

Figure 67:
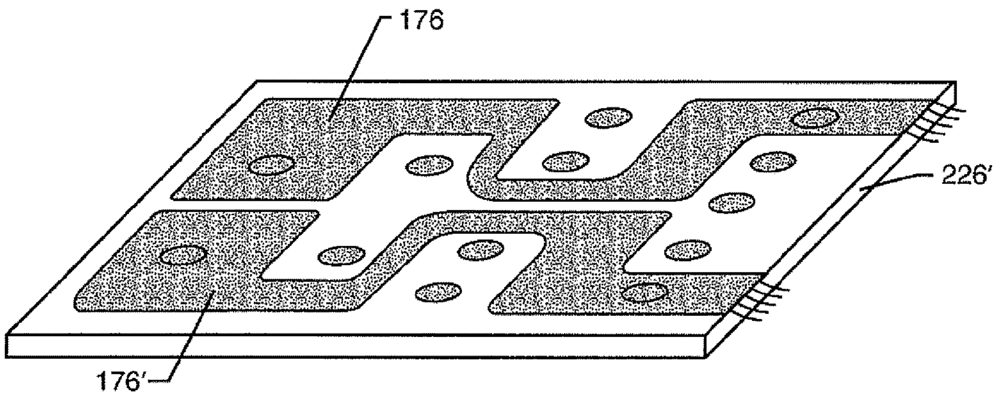
FIG. 67 is a perspective view of an alternative arrangement of the active electrode plate substrate of FIG. 63.

FIG. 67 shows an alternative arrangement for the active electrode layer 226 previously shown in FIG. 63. In FIG. 67, one could imagine that this layer 226' could replace layer 226 in FIG. 63.

Figure 68:
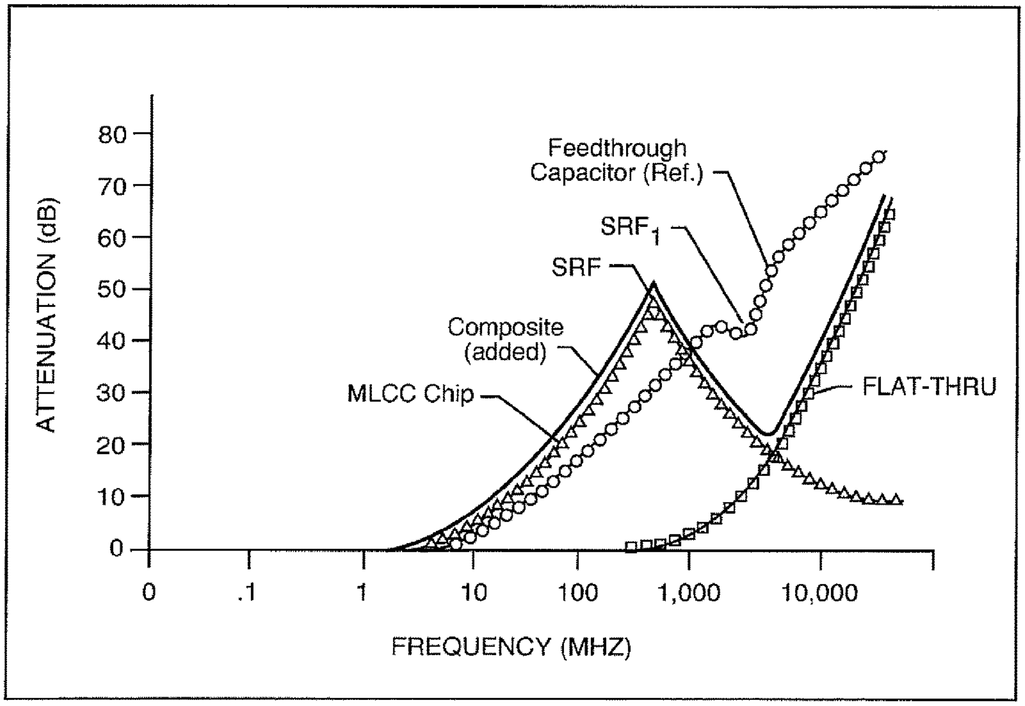
FIG. 68 is a graph illustrating attenuation versus frequency comparing the performance of the shielded three-terminal flat-through EMI/energy dissipating filter of FIG. 63 with other technologies.

FIG. 68 is a graph illustrating attenuation versus frequency comparing the performance of the shielded three-terminal flat-through EMI/energy dissipating filter 190 of FIG. 63 with a prior art feedthrough capacitor and a prior art MLCC. One can see significant differences in the comparison of a conventional feedthrough capacitor with that of an MLCC capacitor and the shielded three-terminal flat-through EMI/energy dissipating filter of the present invention. In FIG. 68, the feedthrough capacitor and the MLCC are of equal capacitance value. The capacitance value of the shielded three-terminal flat-through EMI/energy dissipating filter is significantly less. The feedthrough capacitor exhibits a small self-resonant dip shown as $SRF_1$. Feedthrough capacitors are unique in that after they go through this type of transmission line self resonance, they continue to function as a very effective broadband filter. The opposite is true for a prior art MLCC capacitor. The MLCC capacitor actually outperforms at its resonant frequency SRF other capacitor technologies, however, at frequencies above its self-resonant frequency SRF, it very rapidly becomes inductive at which point the attenuation decreases versus frequency. This is highly undesirable, as high frequency emitters, such as cell phones, would not be properly attenuated. The flat-through capacitance in the present invention is a parasitic capacitance and it tends to be a relatively low capacitance value. That means that its effective 3 dB point (or point where it starts to become an effective filter) is relatively high in frequency. In this case, the 3 dB point is approximately 1000 MHz. In accordance with the design of FIG. 63, when one combines the MLCC capacitor response curve with the flat-through parasitic curves (these two capacitances are added in parallel). FIG. 68, illustrates the composite or added response attenuation curve (which for active electrode 176 is the addition of all of the capacitive elements in parallel) illustrated in FIG. 59 (parasitic inductances $L_P$ are so small in value that they can be ignored). When one compares this solid composite curve with that of a prior art feedthrough capacitor, one sees that the prior art feedthrough capacitor outperforms the composite curve at frequencies above 1000 MHz. It will be obvious to those skilled in the art that one way around this would be to increase the capacitance value of the flat-through parasitic capacitor so that it could start performing at a lower frequency. An effective way to increase the capacitance value of the parasitic capacitor is to increase the dielectric constant of the surrounding dielectric materials. Referring back to dielectric substrate layers 226 and 228 of FIG. 63, that would mean, for example, using a high dielectric constant (k) dielectric, such as barium titanate or strontium titanate for the insulative substrate material 234. This would raise the dielectric constant (k) up into the area above 2000. Accordingly, the value of the flat-through capacitance would go up so high that one would not even need to include the MLCC capacitance. Another way to accomplish the same thing and to use lower cost materials would be to use flex cable technology, such as polyimide or Kapton flex as previously described. The problem with this is that the dielectric constant of these materials is relatively low (typically below 10). However, one way to make up for this would be to increase the effective capacitance area in the overlap area of the active electrode plates 176 and their surrounding sandwiched ground shields 194 and 194' (and/or reduce the dielectric thickness, d).

Figure 69:
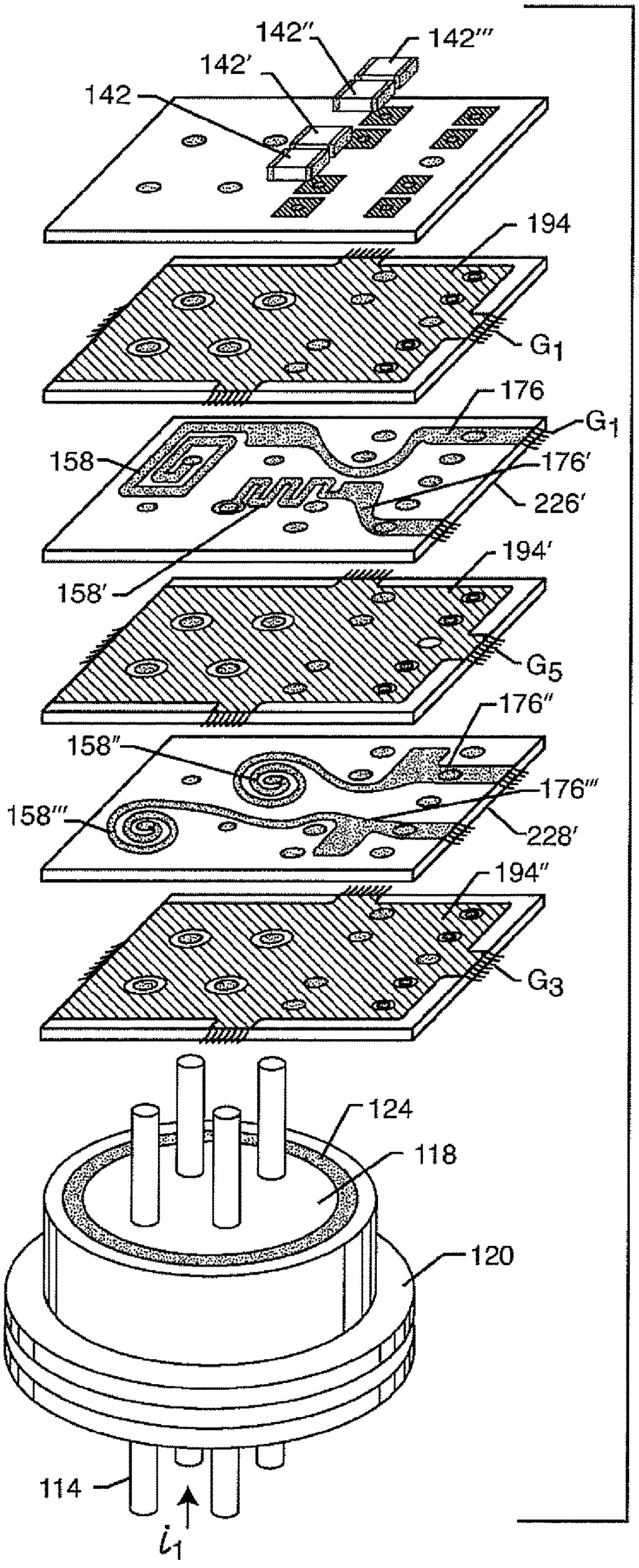
FIG. 69 is an exploded isometric view that is similar to FIG. 63 wherein the active electrodes have been modified to include inductors.

FIG. 69 is an exploded view of the quadpolar hybrid EMI filter of the present invention that is similar to that previously shown in FIG. 63. In FIG. 69, the circuit layers 226 and 228 of FIG. 63 have been modified to add inductor traces 158-158'''. These inductor traces are included as part of and are in series with active electrodes 176-176'''. It will be obvious to those skilled in the art that one would most likely select one inductor pattern and stay with that. For example, in electrode plate 176, there is a rectangular Wheeler spiral inductor 158. In electrode plate 176', we have by way of example, an inductor meander 158' which can be one of many patterns, including those illustrated in FIG. 74. In electrode plates 176" and 176'", we have round Wheeler spiral inductors 158" and 158'" as shown. Embedding co-planar inductors in series with the active electrodes is virtually a no-cost addition. The reason for this has to do with the manufacturing methods typically employed to produce flex cables or even solid substrates. That is, a solid metal layer is laid over the entire surface by plating or other metal-deposition processes and then resistive materials are laid down by silk-screening or similar processes. Then chemical etchings are used to remove all of the metal except for the desired electrode patterns. Accordingly, once a setup is made, adding inductor elements 158-158'" as shown in FIG. 69 becomes very inexpensive and easy to do. Advantages of adding the inductors as shown in FIG. 69 include making the low-pass EMI filter from a single element into what is known as a dual element L-section low-pass filter. A dual element filter has a steeper attenuation slope and is therefore more efficient. There is another advantage from adding the inductor shapes as shown in FIG. 69. By doing this, one increases the ECA and therefore the parasitic flat-through capacitance at the same time. Therefore one ends up with a very efficient distributive filter consisting of the inductance in series with the active electrode(s) and parasitic capacitances in parallel to ground.

Figure 70:
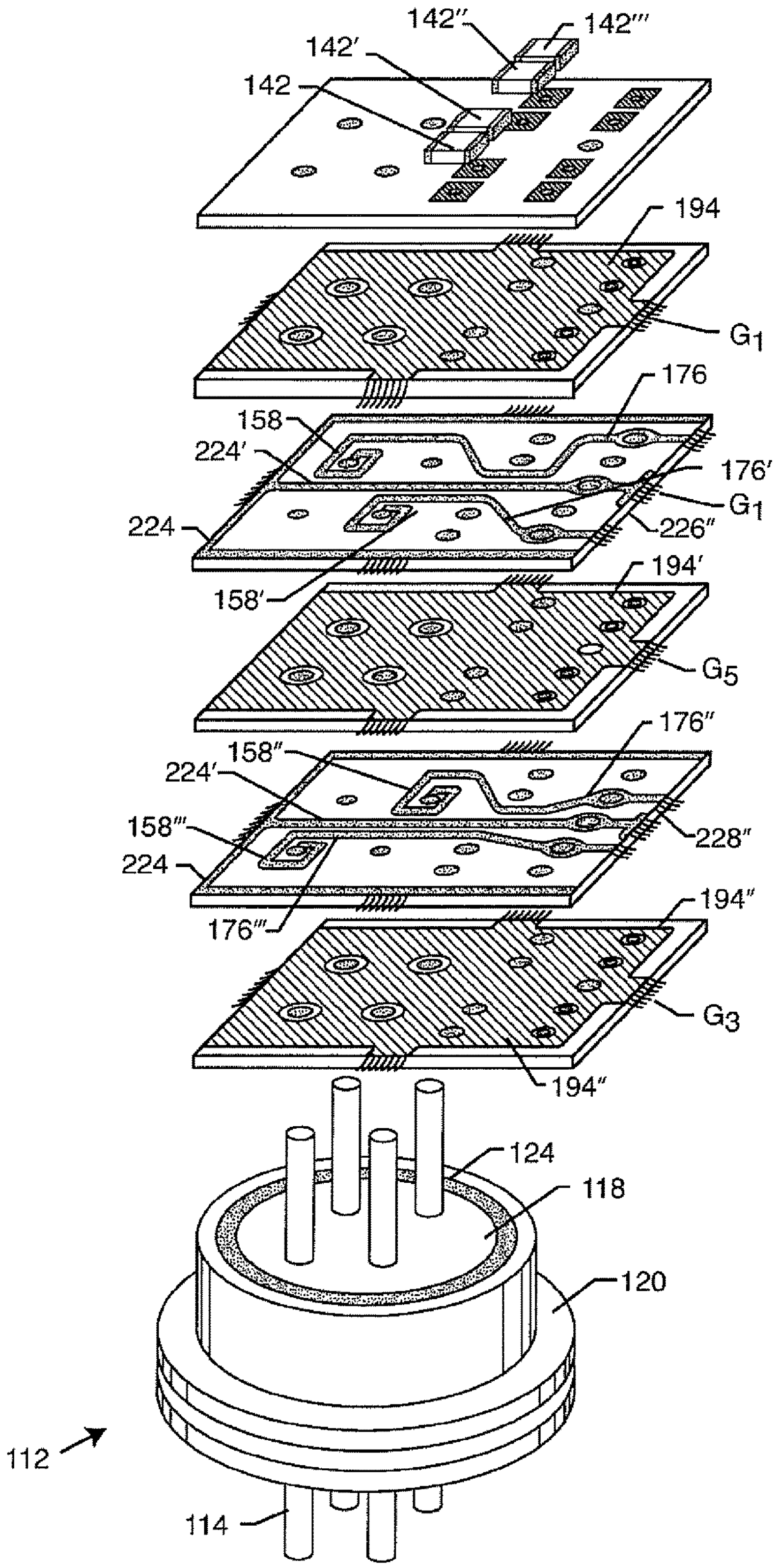
FIG. 70 is an exploded view very similar to FIGS. 63 and 69 except that edge shields and optional separating shields have been placed to prevent EMI radiation from the active electrode plates or optionally between co-planar electrode plates.

FIG. 70 is very similar to FIG. 69 except that the active electrode trace layers 226" and 228" have been modified by adding an optional surrounding co-planar ground shield 224. This surrounding ground shield concept to prevent substrate edge re-radiation was previously described in relation to FIG. 60. However, the difference in FIG. 70 is that an optional co-planar ground shield 224' has also been disposed on layers 226" and 228" between each of the active electrode traces 176 and 176' and also 176" and 176'". For example, with reference to layer 226" of FIG. 70, one can see a co-planar ground shield 224' that is disposed between circuit traces 176 and 176'. This would be used in the case where it was important to prevent cross-talk between adjacent circuit traces 176 and 176'. For example, this might be important in a cochlear implant to keep each digital or analog voice channel that stimulates the auditory nerve free of distorting noise from an adjacent channel. This becomes particularly important when the dielectric layer 226" on which the circuit electrodes 176 and 176' are deposited, are of high k dielectric materials. The use of high k dielectric materials increases the parasitic capacitance that would occur between circuit electrode layers 176 and 176'. The presence of a co-planar grounded shield trace 224' prevents the cross-talk between the adjacent circuit traces. This cross-talk shield 224' can be used in conjunction with, as shown in FIG. 70, or without (not shown) with the surrounding edge shield 224. The cross-talk shield 224' also need not be used on all active electrode layers in a particular shielded three-terminal flat-through EMI/energy dissipating filter 190, but only in those layers where cross-talk is a concern between adjacent circuits. In other words, the cross-talk shield 224' may be used on layer 226" but not be needed on layer 228". It will be obvious to those skilled in the art that on a particular substrate layer, that the number of circuit active electrodes (and optional cross-talk shields) is not limited to two (such as 176 and 176' as shown in FIG. 70), but can be of any number, n.

Figure 71:
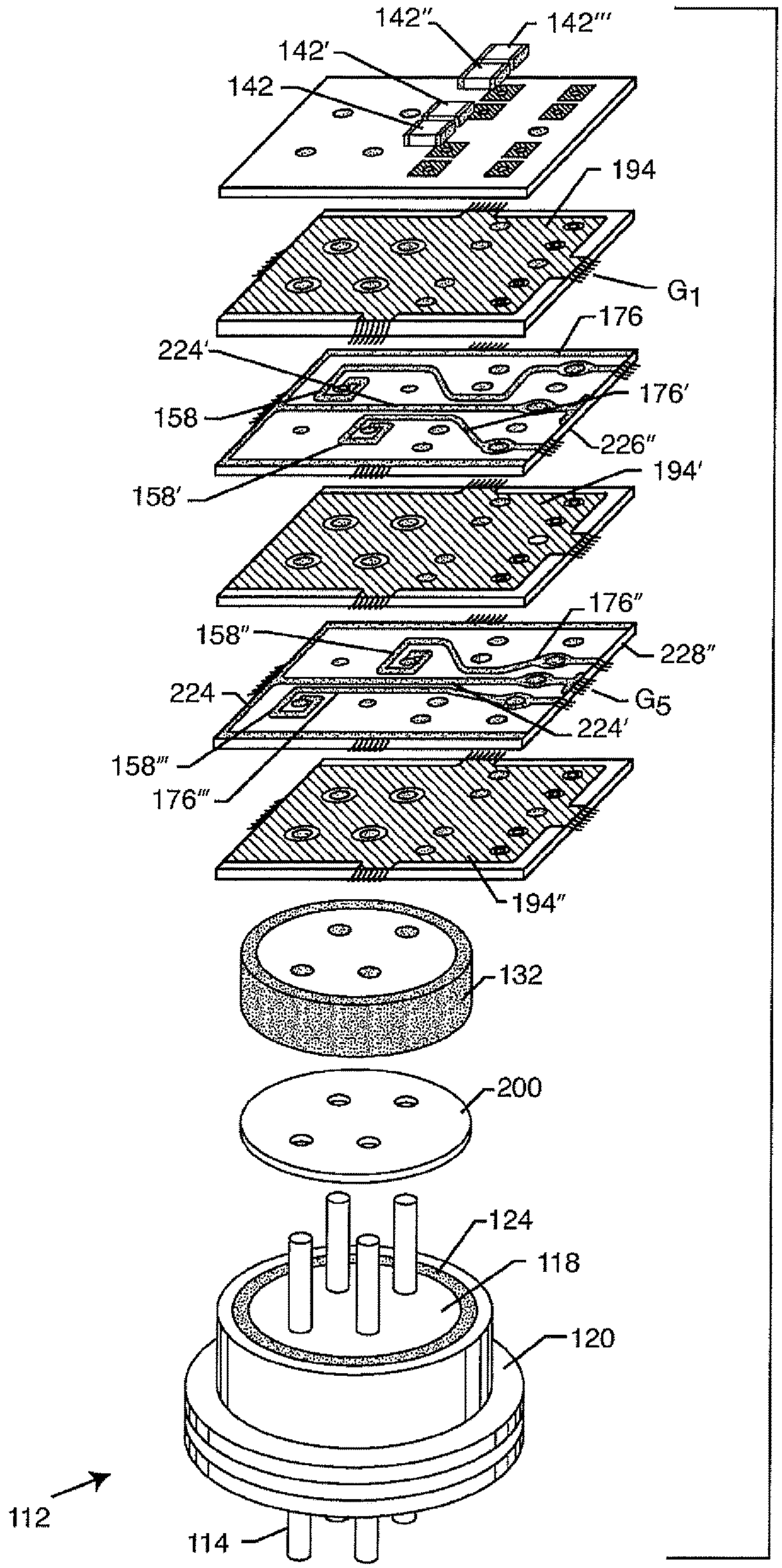
FIG. 71 is an exploded perspective view of an alternative form of the shielded three-terminal flat-through EMI/energy dissipating filter similar to FIG. 63.

FIG. 71 is yet another alternative to the quadpolar shielded three-terminal flat-through EMI/energy dissipating filter 190 as previously described in relation to FIG. 70. The difference between FIG. 70 and FIG. 71 is the addition of a feedthrough capacitor 132 which is bonded to the hermetic terminal 112 by way of an insulative adhesive washer 200. Feedthrough capacitors 132 are well known in the prior art and provide very effective high frequency filtering. FIG. 71 illustrates that these prior art feedthrough capacitors can be used in combination with the novel shielded three-terminal flat-through EMI/energy dissipating filter technology of the present invention. In a preferred embodiment, the structure as illustrated in FIG. 71 would allow for the elimination of the MLCC capacitors 142-142'" as illustrated (or they could be replaced by higher value MLCCs, film chip capacitors, tantalum technology or the like). In other words, there would be sufficient capacitance from the feedthrough capacitor 132 in combination with the flat-through capacitances of the hybrid substrate electrodes such that it is unlikely that additional filtering would be required for high frequency (above 100 MHz) attenuation. However, if one were to desire extremely low frequency filtering, one could use a monolithic ceramic feedthrough capacitor as illustrated in FIG. 71 along with the shielded three-terminal flat-through EMI/energy dissipating filter technology and surface mounted very high capacitance value tantalum capacitors. This would yield a filter that would be effective from all the way down in the kHz frequency range all the way up through 10 GHz. For AIMD applications, this would be very important for filtering for low frequency emitters such as those created from electronic article surveillance (EAS) gates or low frequency RFID readers (in the 125 to 132 kHz or 13.56 MHz range). These EAS gates are the pedestals that a person, including a pacemaker patient, typically encounters when exiting a retail store. These detect tags on articles and goods such as to prevent theft. One common system is manufactured by Sensormatic which operates at 58 kHz. It has been demonstrated through numerous publications that these EAS gates can interfere with pacemakers and ICDs. The present invention as illustrated in FIG. 71 would be effective in attenuating signals at 58 kHz all the way up through cell phone frequencies in the GHz range.

Figure 72:
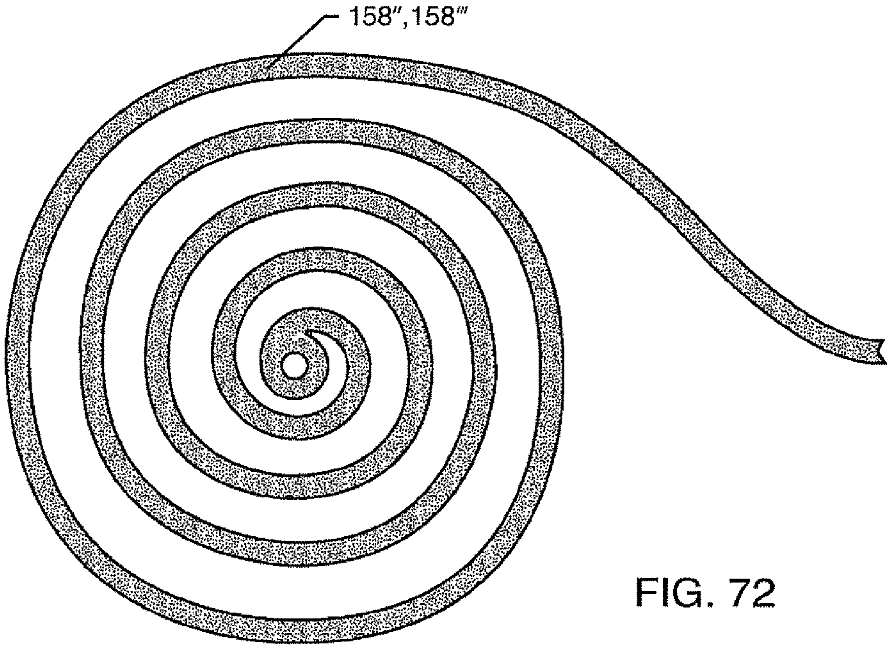
FIG. 72 is an enlarged view of a round Wheeler spiral shown forming a portion of an active electrode plate in FIG. 69.

FIG. 72 is a blown up view of the round Wheeler spirals 158" and 158' of FIG. 69.

Figure 73:
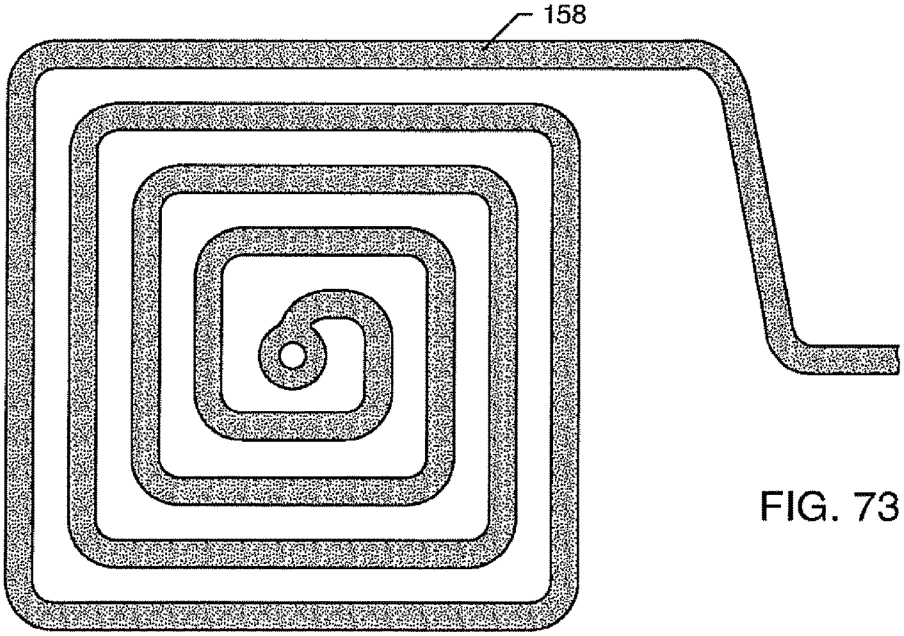
FIG. 73 is similar to FIG. 72, showing a square Wheeler spiral such as those shown forming portions of the active electrode plates in FIGS. 69, 70 and 71.

FIG. 73 is a square Wheeler spiral which is very similar to the rectangular Wheeler spiral 158 previously shown in FIG. 69.

Figure 74:
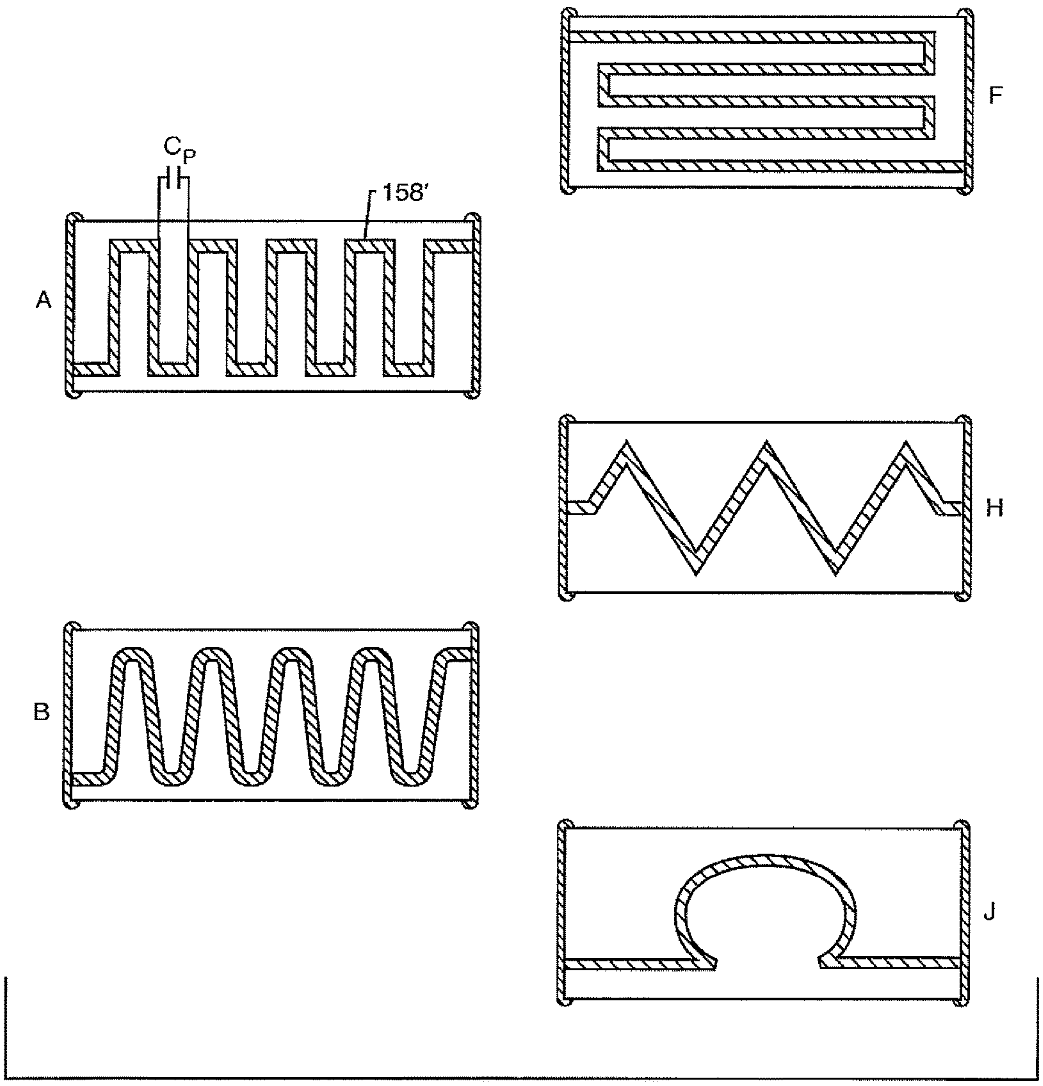
FIG. 74 illustrates several typical inductor meander shapes.

FIG. 74 shows some typical inductor meander shapes 158'. It will be obvious to those skilled in the art that any number of different inductor shapes can be easily deposited on the same co-planar substrate layer in series and an integral part of the active electrode plate(s) 176 of the shielded three-terminal flat-through EMI/energy dissipating filter 190 technology of the present invention.

Figure 75:
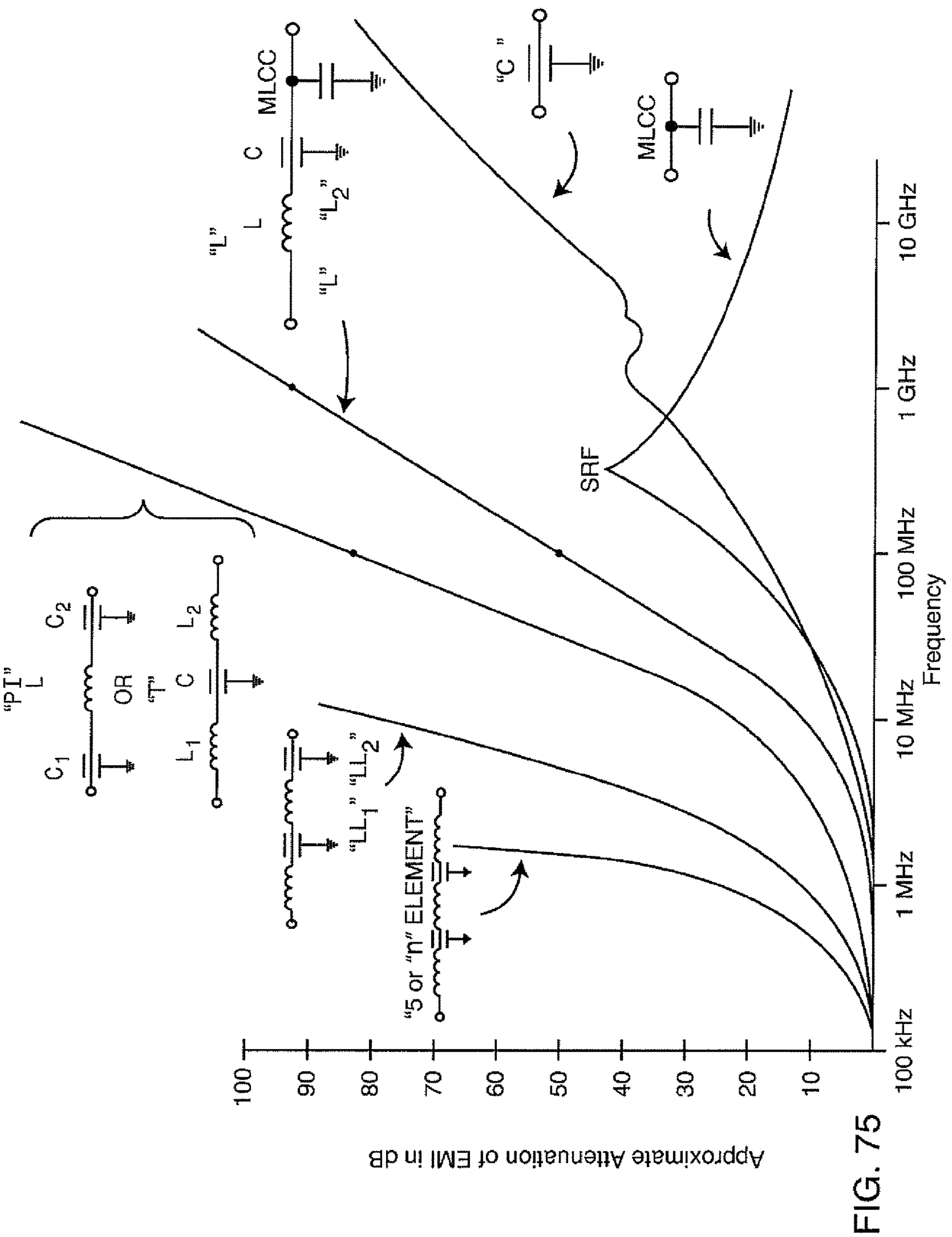
FIG. 75 illustrates the attenuation curves for various types of low-pass filters.

The advantage of adding additional elements to a low-pass filter is dramatically illustrated by FIG. 75, which illustrates the attenuation curves for various types of low-pass filters. By way of reference, a typical MLCC capacitor curve is shown. As one can see, the MLCC undesirably goes through a self resonant frequency SRF after which its attenuation declines versus frequency (the MLCC undesirably becomes increasingly inductive). However, for shielded three-terminal flat-through EMI/energy dissipating filters of the present invention, one achieves broadband filter performance all the way up to and including 10 GHz. As one can see, a single element or C section filter has an attenuation slope of 20 dB per decade. When one adds a series inductor to this, as shown in the L section filter, the attenuation slope increases to 40 dB per decade. The addition of a third element, which makes the filter into either a .π. or T section, increases the attenuation slope to 60 dB per decade. Going further, one could have a double L, which is shown as a $LL_1$ or an $LL_2$, meaning that the inductor can point either towards the body fluid side or to the device side, has an attenuation slope of 80 dB per decade. One can add any number of elements in this way. For example, a 5-element filter will have 100 dB per decade attenuation slope. It will be obvious to those skilled in the art that any number of elements could be used.

Referring once again to FIG. 69, the structure shown has an electrical schematic as shown in on FIG. 62 as an L section circuit. The capacitance of this L section consists of the sum of the parasitic flat-through capacitance $C_P$ which is formed between the active electrode plate 176 including the ECA formed from the inductors 158, and the opposing grounded shields 194 and 194'. The MLCC capacitor 142 in FIG. 62 represents the capacitors 142-142''' surface mounted onto the hybrid substrate 192. The MLCC capacitor is effective up to its resonant frequency; however, that is where the flat-through capacitance takes over yielding the relatively smooth curve shown in FIG. 75 for the L section filter. It will be obvious to those skilled in the art that the L section could be reversed. In other words, the inductor spiral could be designed and put on the other side of the capacitor as opposed to towards the body fluid side as presently shown in FIGS. 61 and 62. In addition, it will be obvious to those skilled in the art that multiple inductors could be placed inside of the novel hybrid substrate 192 in order to form a ".π.", "T", "LL" or even a "5" or "n" element device. Accordingly, the present invention includes a new method of constructing prior art low-pass EMI filter circuits that are already well known in the art. In other words, the feedthrough capacitor, the L, the .π., the T and LL filters are already well known. However, this is the first time, to the knowledge of the inventors, that a flat-through capacitance has been embedded within grounded shields 194 and 194'.

Figure 76:
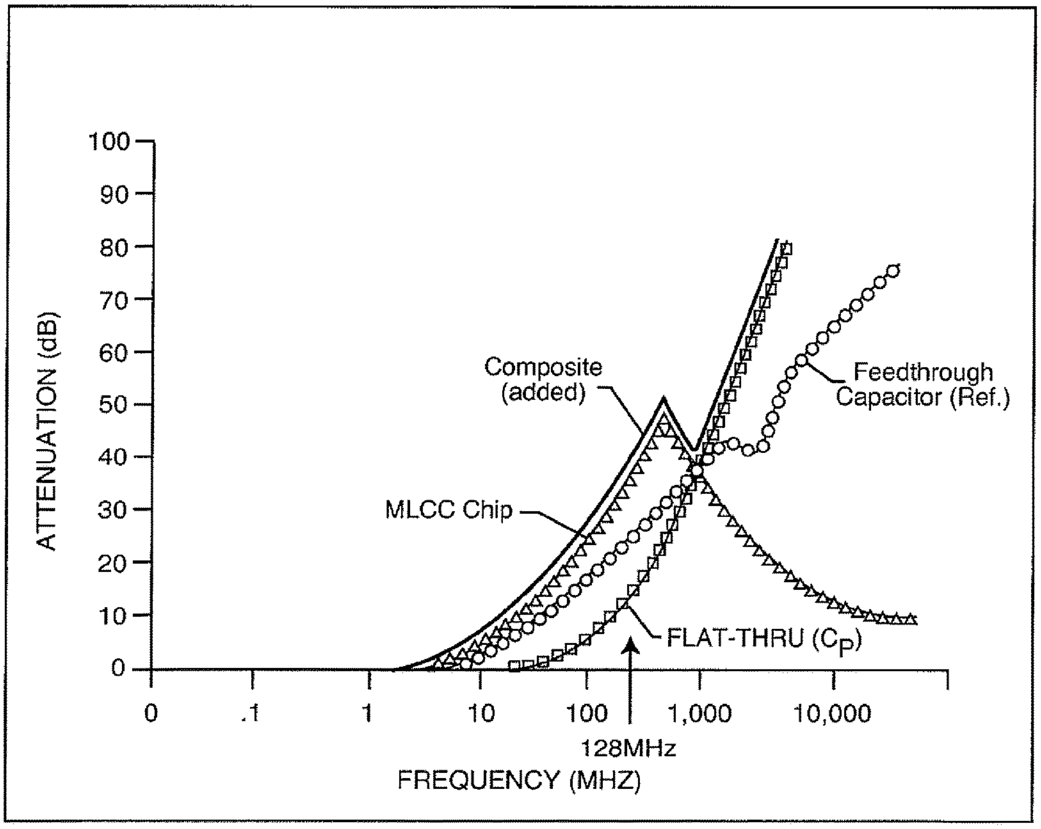
FIG. 76 is a family of filter attenuation curves similar to that shown in FIG. 68.

FIG. 76 is a family of filter attenuation curves similar to that previously shown in FIG. 68. In FIG. 74, one can see that the 3 dB cutoff point, or the point at which the flat-through ($C_P$) curve of the shielded three-terminal flat-through EMI/energy dissipating filter starts to become effective, has been moved substantially downward in frequency (to the left). In this case, its 3 dB point is approximately 40 MHz. In addition, since it is now part of an L section filter, its attenuation slope rate has been increased from 20 to 40 dB per decade. In FIG. 76, the referenced feedthrough capacitor curve is unchanged as well as the MLCC curve (these are discrete component comparison curves only). However, the composite curve, which is the addition of the MLCC curve, which is surface mounted to the shielded three-terminal flat-through EMI/energy dissipating filter substrate to the shielded three-terminal flat-through EMI/energy dissipating filter active electrode flat-through curve, is now substantially improved. At all points, the composite curve of the shielded three-terminal flat-through EMI/energy dissipating filter with the surface mounted MLCC(s) outperforms (has higher attenuation than) the referenced prior art feedthrough capacitor. In many cases, the amount of improvement is very substantial. For example, at MRI frequencies which are 64 MHz for 1.5 Tesla machines and 128 MHz for 3 Tesla machines, there is an improvement anywhere from 10 to over 20 dB. This is very significant and very important to protect an active implantable medical device from interference during MRI scans.

Figure 77:
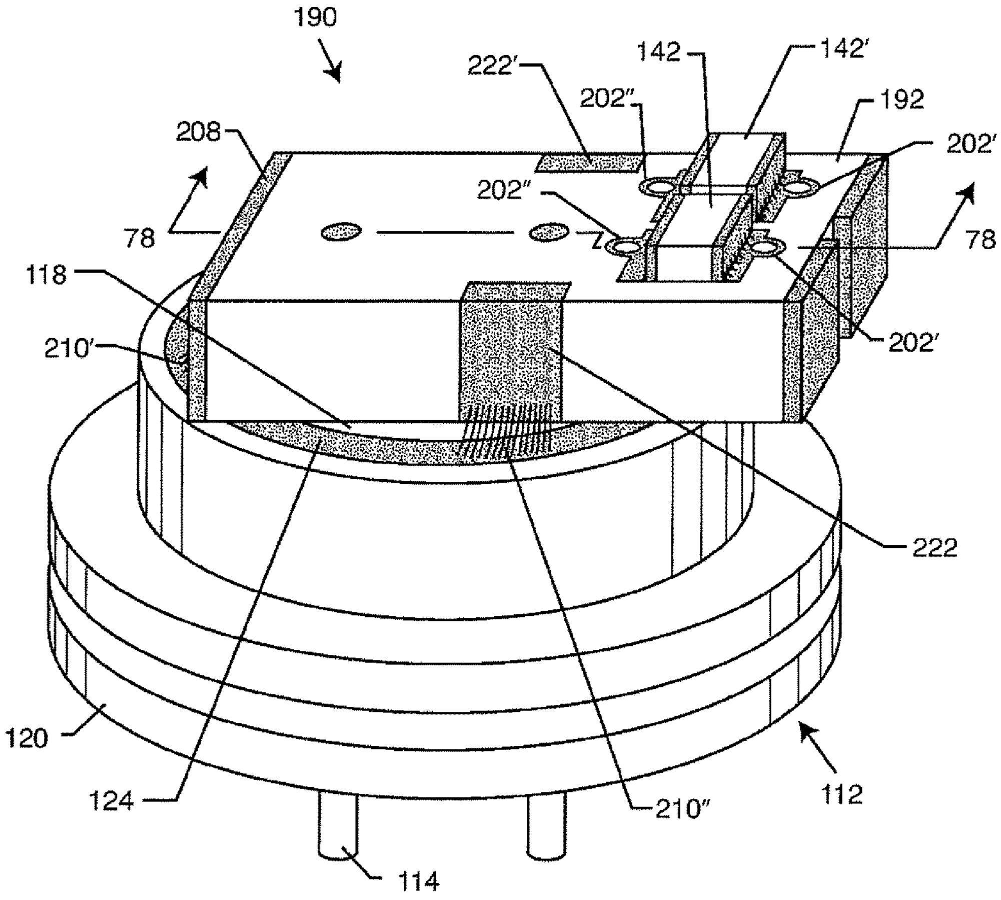
FIG. 77 is a perspective view of a bipolar hermetically sealed filter embodying the shielded three-terminal flat-through EMI/energy dissipating filter present invention.

FIG. 77 illustrates a bipolar hermetically sealed hybrid substrate filter 190 of the present invention.

Figure 78:
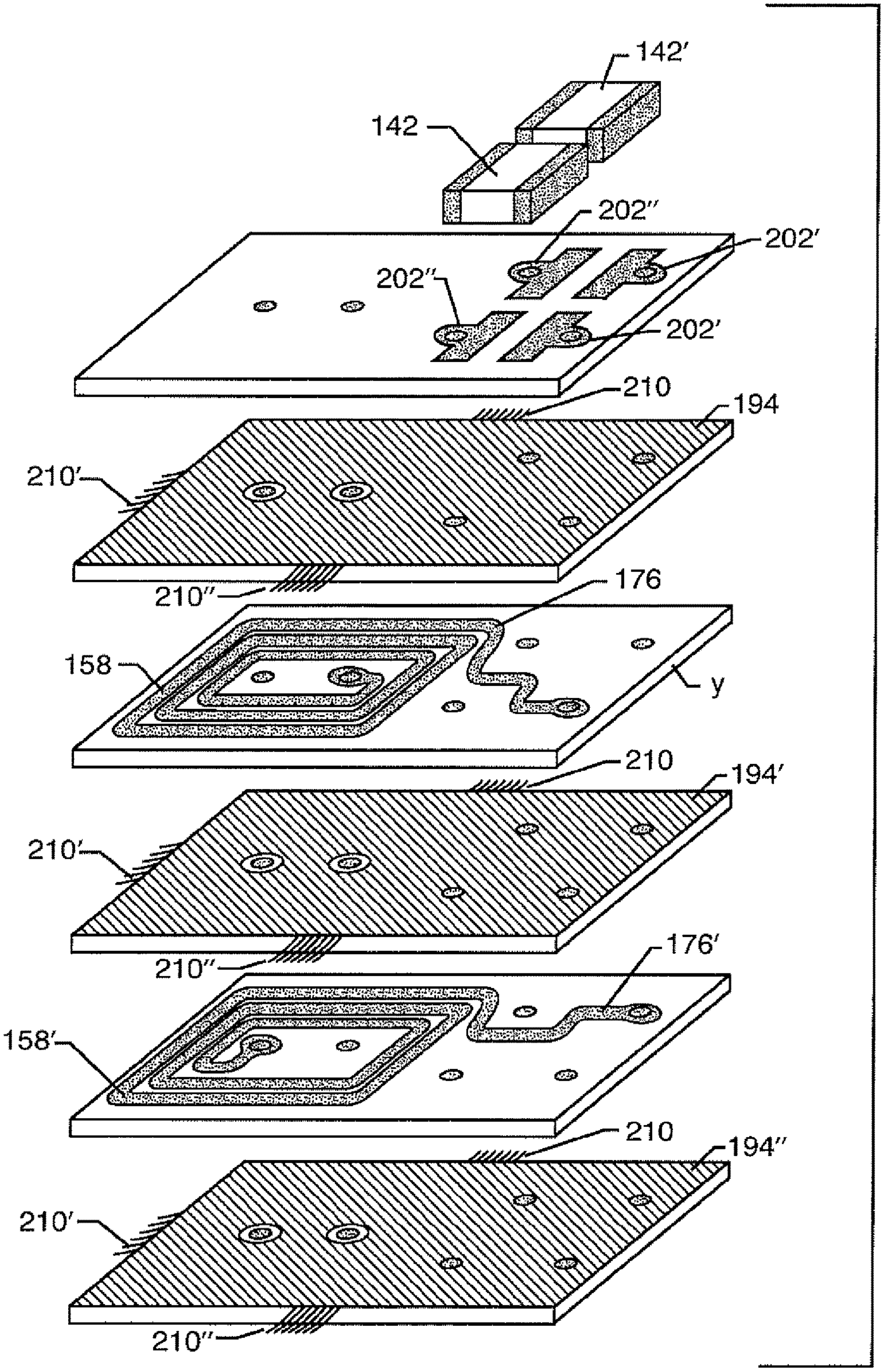
FIG. 78 is an exploded perspective view of the internal layers of the shielded three-terminal flat-through EMI/energy dissipating filter of FIG. 77.

FIG. 78 is an exploded view of the internal layers taken along line 78-78 in FIG. 77. One can see that in active electrode plates 176 and 176', the square Wheeler spirals 158 and 158' have been greatly enlarged. In order for the grounded shield plates 194-194" to be proper EMI shields and RF grounds, it is essential that they be properly grounded via electrical connection material 210-210" to the gold braze ring 124 of the ferrule 120 of the hermetic seal 112 as shown in FIG. 77. For AIMDs, ferrule 120 is typically of titanium, stainless steel or suitable non-corrosive material. Unfortunately, during manufacturing or over time, titanium can build up undesirable oxides. These oxides can act as an electrical insulator or even a semi-conductor. Attachment of electrical components to this oxide can cause undesirable circuit behavior. In the case of a low-pass EMI filter, this can cause degradation of the EMI filter performance. Therefore, it is essential that a connection be made to a non-oxidizing surface. Fortunately, the presence of gold braze 124, as shown in FIG. 77, forms a convenient non-oxidizable surface for such attachment. Attachment to this gold braze is described in U.S. Pat. Nos. 7,038,900 and 7,310,216 the contents of which are hereby incorporated by reference.

In FIG. 77, one can see that there is an electrical connection material 210" that connects between metallization band 222 and the gold braze material 124. On the opposite side, there is a similar electrical connection 210 that is made between metallization band 222' and the same gold braze material. On the left hand side of the hybrid substrate 192, electrical connection material 210' is also connected from metallization band 208 and the same gold braze material 124. One can also see this in the exploded view of FIG. 78 by looking at the electrical connections 210-210" for the ground shields layers 194-194". In this case, this is known as a three point ground system which forms an adequate (but not ideal) RF ground for the present invention. The more contact there is between these electrical attachments 210-210", the better. This is because as one increases the contact area to the grounded shield plates 194-194" it will reduce the electrical impedance and therefore improve their shielding efficiency, particularly at high frequency.

Figure 79:
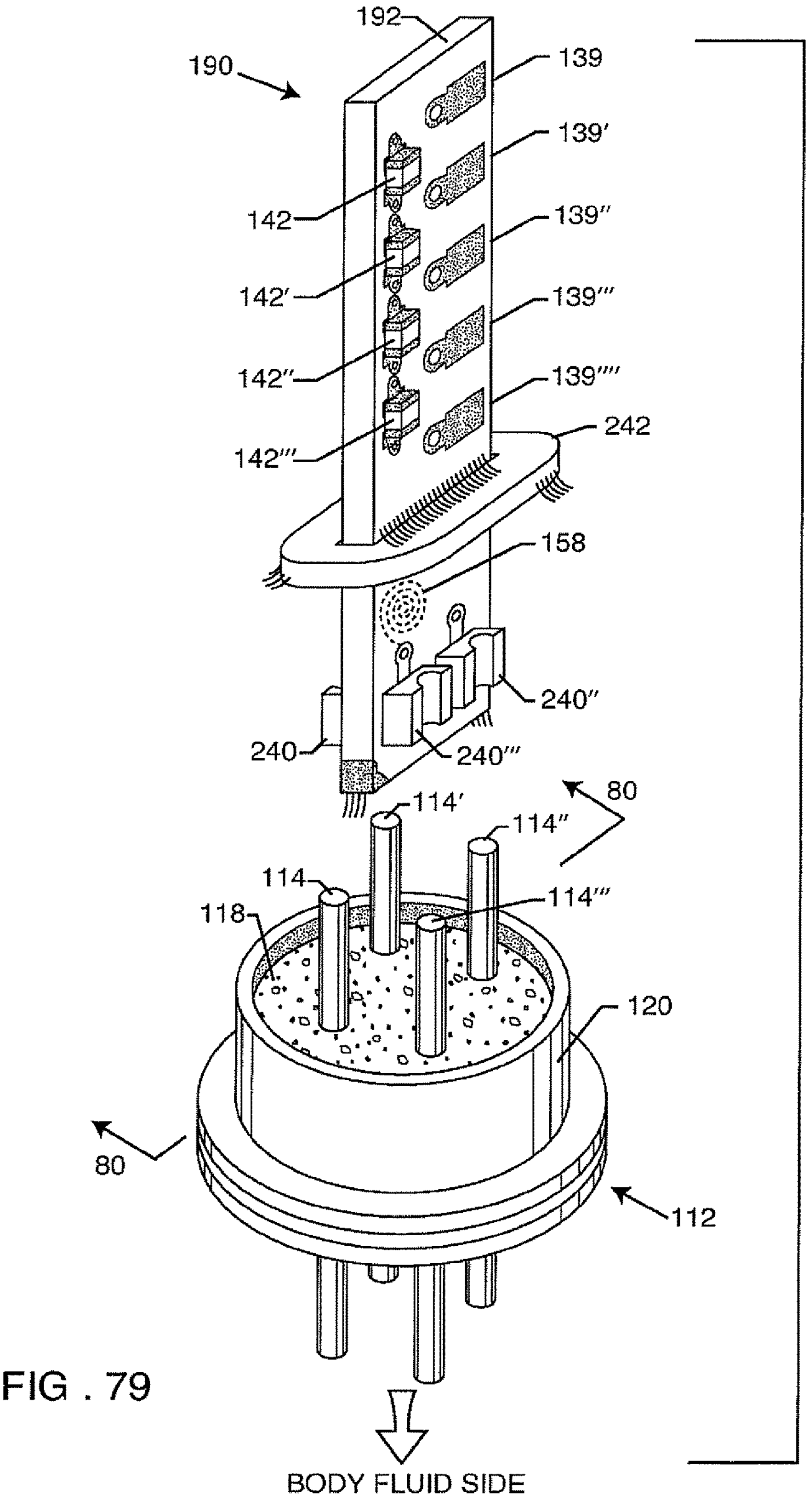
FIG. 79 is an exploded perspective view of an alternative embodiment embodying the shielded three-terminal flat-through EMI/energy dissipating filter of the present invention.

FIG. 79 is an alternative embodiment showing the hybrid substrate 192 of the present invention designed to be inserted partially into the ferrule 120 of the hermetic seal assembly 112 as shown in exploded view. There are convenient wire bond or electrical connection pads 139-139"" as shown. In this case, 139"" would be a ground pad, and pads 139-139''' would be circuit connections. The MLCC capacitors 142-142''', as previously described, would connect from the active electrode plates (not shown) of the shielded three-terminal flat-through EMI/energy dissipating filter through vias internally to internal grounded shield plates (also not shown). As previously described, if enough flat-through parasitic capacitance can be generated within the hybrid substrate 192, then the MLCC capacitors 142-142''' would not be required. Also shown is an optional embedded Wheeler spiral inductor 158. There would be one of these in series with each of the MLCC capacitors 142-142''' as previously described. A shield ring 242 is provided so that it will be connected through laser welding, brazing, soldering or the like to the ferrule 120. This is important so that electromagnetic interference cannot directly penetrate through the insulator 118 and re-radiate to the interior of the electronic device (a hermetic insulator forms a hole in the titanium electromagnetic shield housing of a cardiac pacemaker). The shield ring 242 is connected via soldering to via holes to the internal ground shield plates of the shielded three-terminal flat-through EMI/energy dissipating filter structure. Connection pads 240 through 240''' are designed to be electrically connected to lead wires 114 through 114'''.

Figure 80:
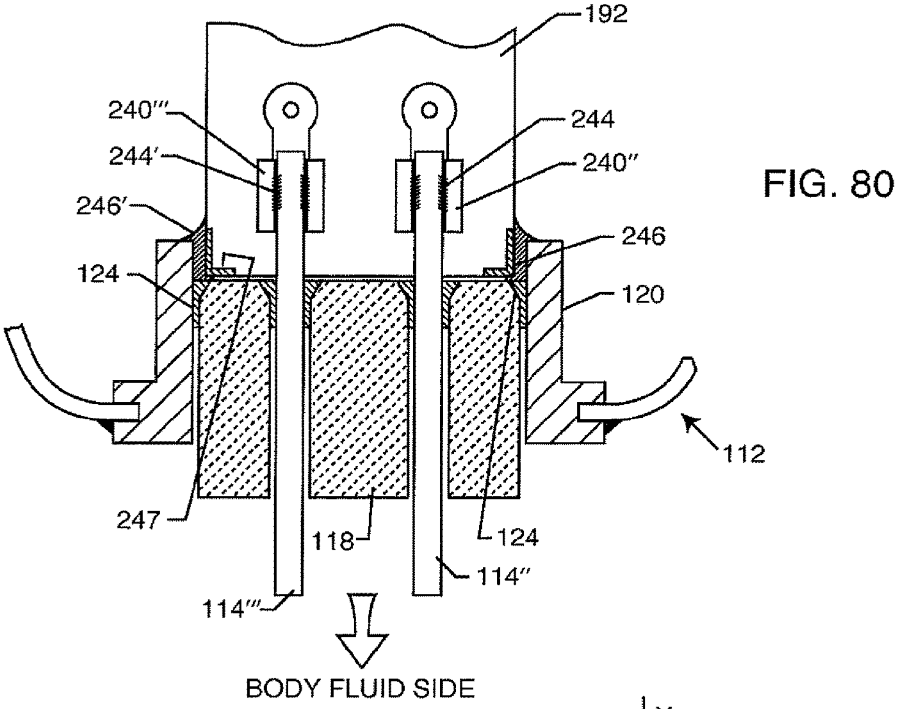
FIG. 80 is a partially fragmented view of the assembled section of FIG. 79 taken along the line 80-80 of FIG. 79.

FIG. 80 is a partially fragmented view taken from FIG. 79. In this case, the leads 114'' and 114''' are typically welded, brazed or soldered 244 and 244' into the lead wire retaining blocks 240'' and 240''' as shown. One can also see that there is an optional electrical connection 246 and 246' inside of the flange 120 of the hermetic seal 112. This electrical connection makes contact to the internal grounded shield plates (not shown) of the hybrid substrate 192. One can see that the electrical connection material 246 and 246' not only makes contact to the titanium flange 120, but it also makes intimate contact to the gold braze 124 such that there is an oxide free electrical connection in order to guarantee high frequency performance. In FIG. 80, one can see that the external shield ring 242 has been eliminated and replaced by a metallization layer 247. The metallization area 247 forms a circumferential ring over the non-conductive insulator 118 such that re-radiation of EMI through the hermetic seal 112 is prevented.

Figure 81:
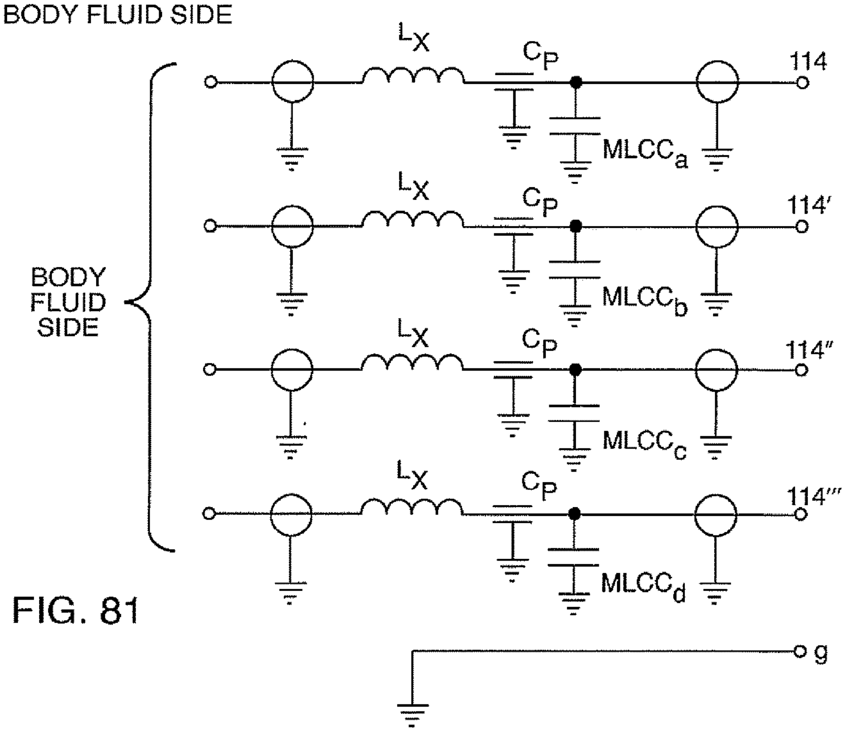
FIG. 81 is an electrical schematic diagram of the quadpolar shielded three-terminal flat-through EMI/energy dissipating filter shown in FIGS. 79 and 80.

FIG. 81 is the electrical schematic diagram of the quad-polar hybrid EMI filter of FIGS. 79 and 80. FIG. 81 illustrates an L-section low-pass filter.

Figure 82:
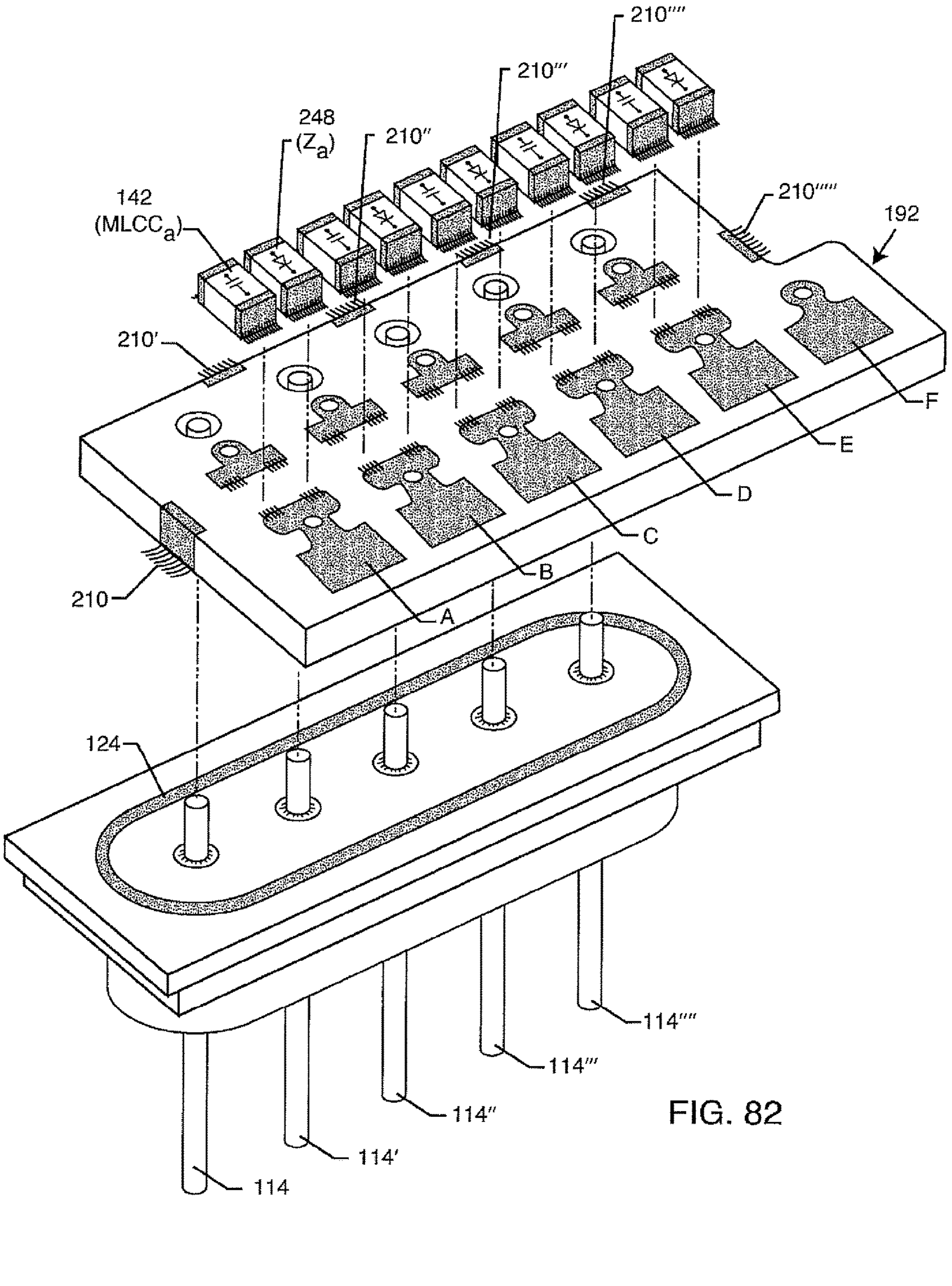
FIG. 82 is an exploded perspective view of an inline hybrid substrate embodying the shielded three-terminal flat-through EMI/energy dissipating filter of the present invention.

FIG. 82 illustrates an inline hybrid substrate 192 of the present invention. In this case, there are internal grounded shield plates (not shown) that have already been well described. There are multiple electrical connection points to the gold braze 124 consisting of 210-210''''. In this case, back-to-back MLCC capacitors 142 and voltage suppression diodes 248 (also known as zener diodes) have been incorporated in parallel. This is best understood by referring to the electrical schematic diagram of the structure shown in FIG. 83. Starting from the outside of an electronics module of the body fluid side of an AIMD (on the left), one can see that as EMI enters, it first encounters a flat-through capacitance C.sub.P in accordance with the novel through electrodes of the shielded three-terminal flat-through EMI/energy dissipating filter of the present invention. Then, as you move to the right in FIG. 83, the EMI encounters an inductance $L_1$ which is typically from an embedded co-planar Wheeler spiral inductor (not shown) contained within the active electrode plates of the hybrid substrate 192. Then it encounters the parallel combination of the MLCC capacitor 142 and the high voltage suppression diode 248. Then there can be another inductor (optional) $L_2$ that would be embedded within the hybrid substrate 192 and an additional flat-through capacitance $C_P'$ before one reaches the electrical connection pads a through g as illustrated.

Figure 83:
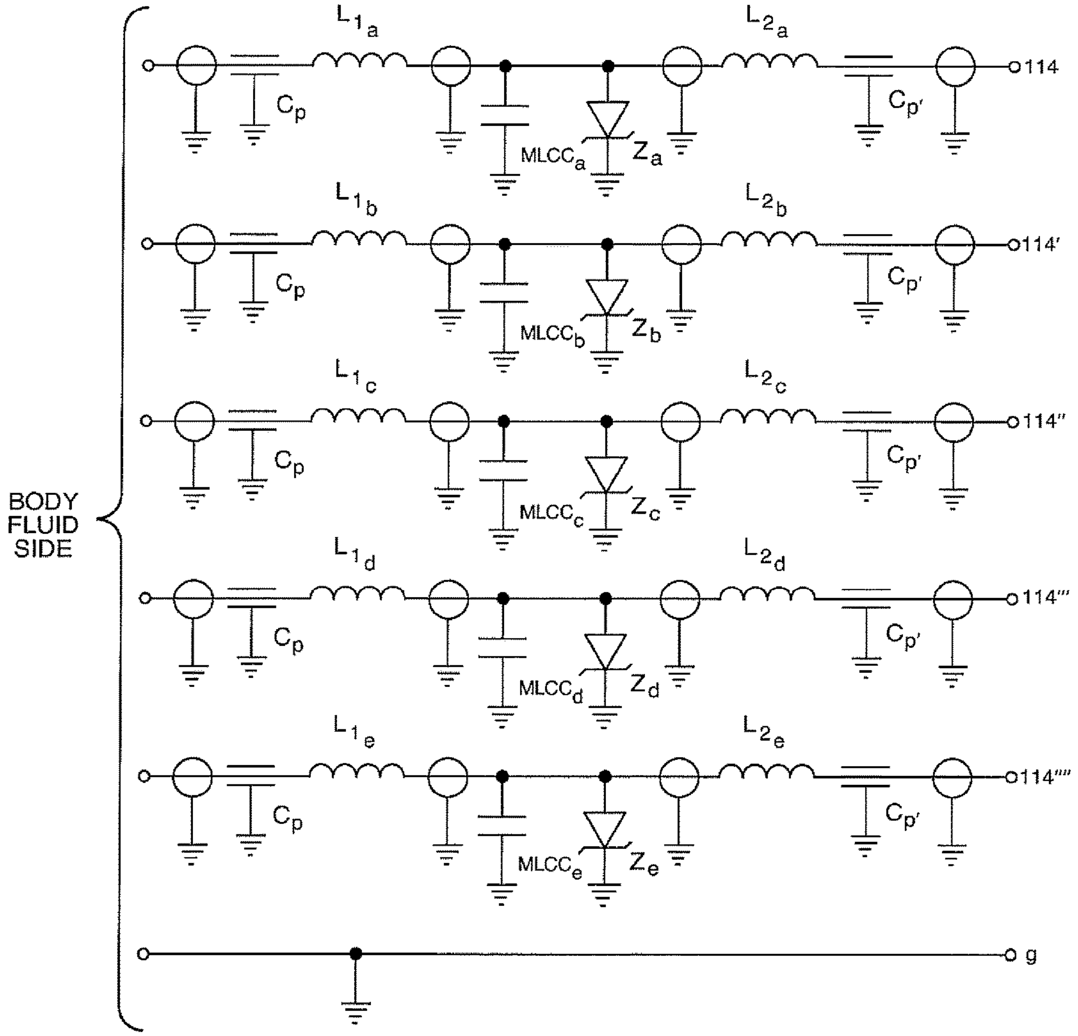
FIG. 83 is an electrical schematic diagram of the structure shown in FIG. 82.

Referring once again to FIGS. 82 and 83, the inductors, for example inductor $L_{1a}$ and $L_{2a}$, could be constructed of square, rectangular or a round Wheeler spirals or any of the other meander shapes previously described. FIG. 83 illustrates a very efficient five element low-pass filter.

Figure 84:
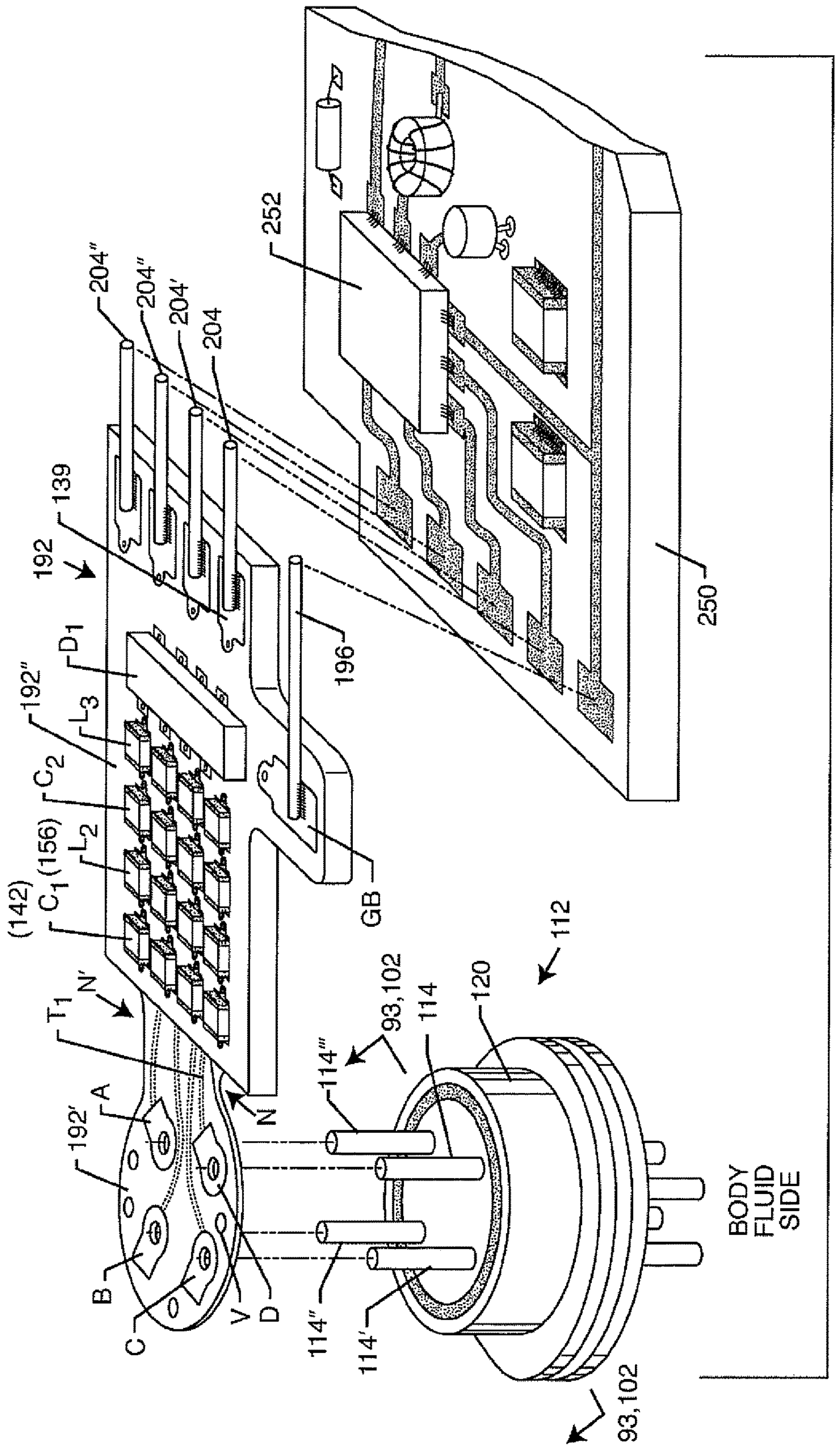
FIG. 84 is an exploded perspective view of another form of a shielded three-terminal flat-through EMI/energy dissipating filter embodying the present invention.

FIG. 84 illustrates another form of the novel hybrid substrate 192 of the present invention. The shielded three-terminal flat-through EMI/energy dissipating filter includes a hybrid substrate 192 is divided into two sections: 192' and 192''. Section 192' is a relatively thin area of flex cable and is therefore very flexible. Section 192'' can be made of similar or same materials as section 192' (or it can be a rigid board or substrate to which flexible section 192' is connected), but its thickness is built up until it forms what is known in the art as a section of "rigid" cable. This rigid section 192'' could be of polyimide, Kapton or other typical flex cable construction. It will also be obvious to those skilled in the art that this could also be a piece of rigid multilayer substrate or circuit board, including any of the ceramics or FR4 board or the like. The flex cable section 192' is designed to slip down over the pins 114-114''' of a hermetic seal 112 of an AIMD or any other electronic device (hermetic or not), such as those typically used in telecommunications, consumer electronics, military or even space applications). The hermetic seal 112 can be any type of terminal, including non-hermetic terminals or even plastic terminals. The present invention is applicable to any electronic assembly or a point at which any lead wires ingress and egress an electronic assembly, subassembly or housing. The methods of attachment to the terminal pins 114-114''' of the hermetic seal 112 and to the ground pin 196 will be described in connection with subsequent drawings.

Referring now to the rigid section 192'', one sees that a number of passive or active surface mounted electronic components can be mounted (they can also be embedded which is also well known in the prior art of multilayer substrate design). In this particular case, the hybrid substrate 192 of FIG. 84 has been designed with convenient lead wires 204-204''' and 196 for easy connection to lands of a circuit board 250 perhaps with an integrated circuit or microchip 252 within the active implantable medical device. The circuit board 250 is not part of the present invention, but is important in that the present invention be capable of connecting and interfacing with it.

Figure 85:
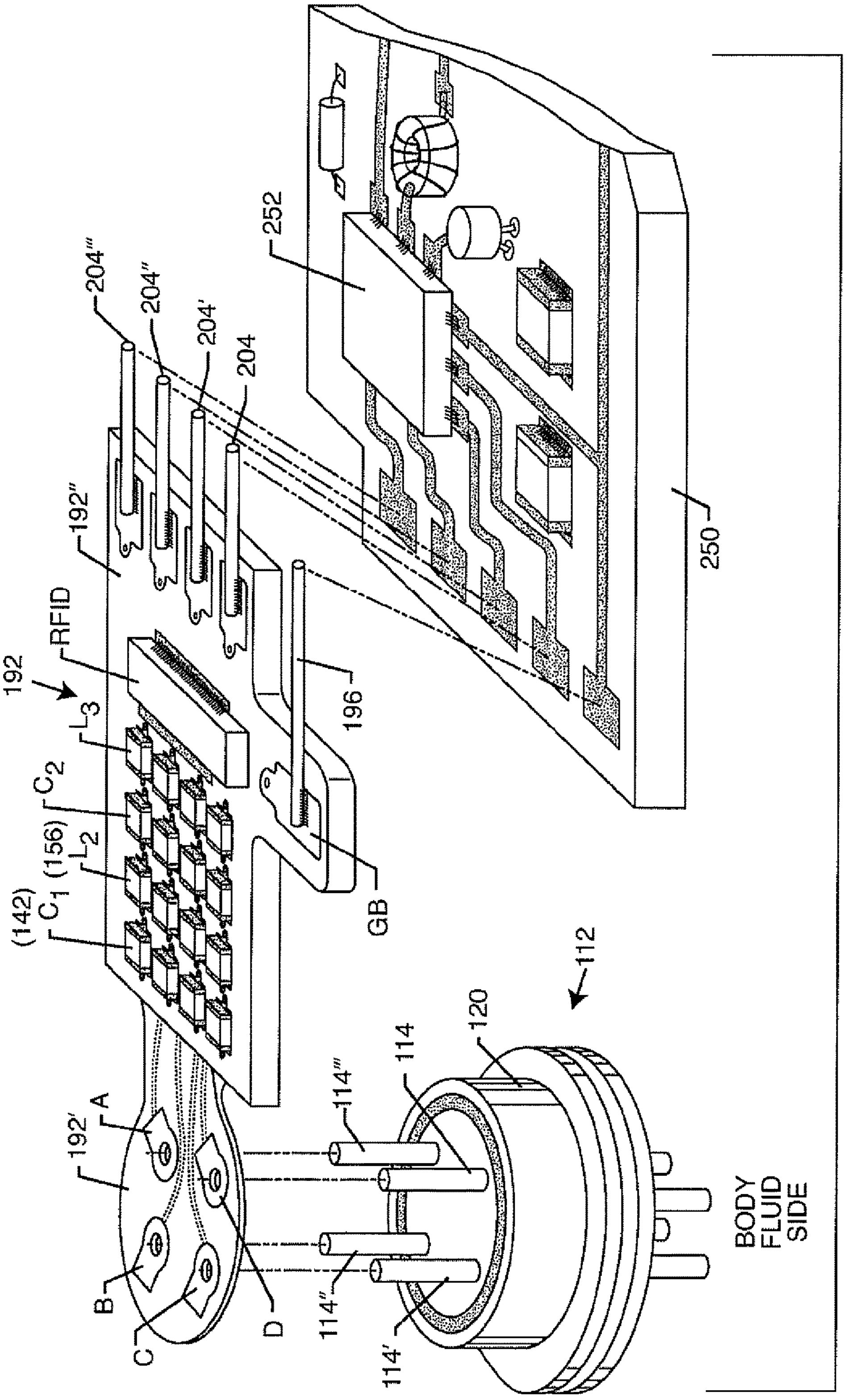
FIG. 85 is similar to FIG. 84 except that the diode array has been replaced with an RFID chip.

FIG. 85 is very similar to FIG. 84 except the diode array $D_1$ has been replaced with either a passive or an active RFID chip (RFID). In the preferred embodiment, this would be a low frequency passive RFID chip meaning that it would operate at a frequency that could easily penetrate the titanium electromagnetic shield of a typical AIMD or other EMI shielded electronic device. In a preferred embodiment, the RFID chip would operate in the International Standards Organization (ISO) band of 125 to 135 kHz. The RFID chip could be used for a number of different purposes, including identification of the model number, serial number of the AIMD, important patient or implanting physician information and the like. See U.S. Patent Application Publication No. US 2006-0212096 A1, the contents of which are incorporated herein by reference.

The RFID chip as illustrated in FIG. 85 could be simply mounted but not electrically connected to the active electrodes of the shielded three-terminal flat-through EMI/energy dissipating filter. No electrical connections are required for a passive RFID chip. In other words, when an external interrogator/reader was used, a powerful electromagnetic field would activate an antenna within RFID chip and it would automatically use the received power to turn on its microchip and transmit a return pulse. However, in another embodiment, the RFID chip, as shown in FIG. 85 could be electrically connected to power circuits embedded within the shielded three-terminal flat-through EMI/energy dissipating filter such that it received power from the internal battery of the AIMD. In this case, it would be known as an active RFID chip. With an active (powered) RFID chip, it could embody a much more sensitive receiving circuit and also transmit a much more powerful return pulse. In another embodiment, the RFID chip as shown in FIG. 85 could be used as a wake-up feature for AIMD RF telemetry circuits.

In the past, pacemaker and ICD and neurostimulator telemetry was done by close-coupled magnetic coils. In this older art, it was typical that the AIMD would have a multiple turn wire antenna within the titanium housing of the AIMD. There were even AIMDs that use an external loop antenna of this type. To interrogate or reprogram the AIMD, the physician or other medical practitioners would bring a wand, with a similar antenna embedded in it, very close to the AIMD. For example, for a typical pacemaker application, the telemetry wand would be placed directly over the implant with a wire connected to an external programmer. The medical practitioner would move the wand around until the “sweet-spot” was located. At this time, the external programmer would become active and electrograms and other important information would be displayed. Typically, the wand would be right against the patient’s skin surface or at most a couple of centimeters away. In the last few years, distance RF telemetry is becoming increasingly common. In this case, for example for a cardiac pacemaker, there would be a high frequency antenna that would be embedded within the plastic header block of the AIMD (outside the EMI shielded titanium housing). This would communicate with an external RF receiver-transmitter programmer. A typical band for such communication would be in the 402 to 405 MHz (known as the MICS band). Other devices use even higher frequencies for distance RF telemetry. A problem with such distance telemetry circuits is the energy consumption of the receiver circuitry which must be on all the time. There is one methodology which is known in the art as the Zarlink chip. The Zarlink chip uses a higher frequency (in the GHz range) to wake-up the lower frequency RF telemetry circuit. The higher frequency is more efficient; however, the device or chip still consumes an amount of idling energy from the AIMD battery to always be alert for its wake-up call. An alternative of this resides in the present invention where a passive RFID chip is used as a wake-up feature. This RFID can be integrated into the hybrid substrate 192 of the present invention (or mounted anywhere else inside or outside the housing of the AIMD). In a preferred embodiment, the external RF programmer can incorporate a low frequency RFID reader which would transmit a signal which would penetrate right through the titanium housing of the AIMD and activate the embedded passive RFID chip. The circuitry of the RFID chip would be connected to the telemetry circuits contained within the AIMD. For an example, in the case of a pacemaker, the external programmer would send the RFID signal as a wake-up call to turn on the telemetry receiving circuits so that the pacemaker could communicate with the external programmer.

Figure 86:
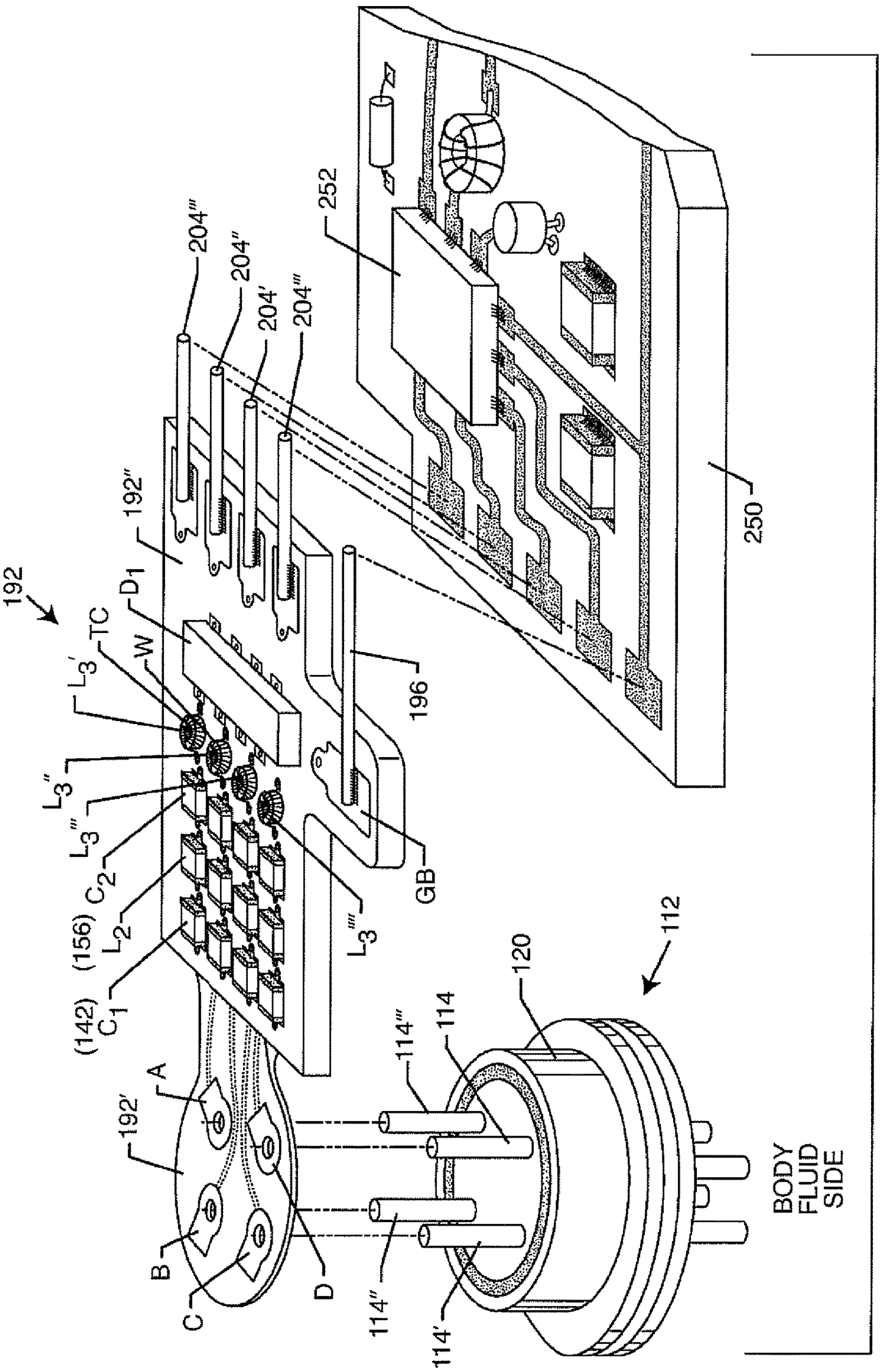
FIG. 86 is similar to FIG. 84, wherein toroidal inductors have been used to replace a series of surface mount chip inductors.

FIG. 86 is very similar to FIG. 84. In this case, toroidal inductors L3-L3''' have been used to replace the surface mount chip inductors. Chip inductors are low in both their inductance value and their current rating. Chip inductors can be acquired in two main forms: a) with a ferrite core, and; b) without a ferrite core. For exposure in MRI applications, it is usually desirable to eliminate ferrite material as it will saturate due to the main static field of the MR scanner. See U.S. Patent Application Publication No. US 2007-0112398 A1 and U.S. Pat. No. 7,363,090, the contents of which are incorporated herein. In FIG. 86, one can see that the toroidal inductor L3' does have a ferrite core TC with many turns of wire W wrapped around it. This makes for a very large inductor value. However, as mentioned, in an MRI environment, the inductance would drop to a very low value due to the saturation of the ferrite element TC itself. It is a feature of the present invention that the ferrite element would be selected so that it would not exhibit permanent remnants. That is, once the device was removed from the magnetic resonance (MR) scanner, the magnetic dipoles would return to their scattered state and the inductor would continue to operate as previously intended. The purpose of the toroidal inductors L3-L3''' would be to provide a very high inductance value for a low-pass filter so that its 3 dB cutoff frequency would be very low in frequency (for example, below 1 MHz or even down to 58 kHz for EAS gates). In fact, it will be obvious to those skilled in the art that inductor chips could also be large value wound inductors with powdered iron or ferrite toroidal cores. In an MR scanner, the electromagnetic field environments are quite harsh, but are also well known. For example, for a 1.5 Tesla scanner, the pulsed RF field is at 64 MHz. Accordingly, the shielded three-terminal flat-through EMI/energy dissipating filter could be designed such that its parasitic flat-through capacitance along with MLCC capacitors $C_2$ would provide sufficient attenuation at 64 MHz so that the AIMD could be free from EMI and be operated safely in an MR scanner. Accordingly, it would not matter that the cores of the toroidal inductors 156 saturated and that low frequency filtering is thereby not available during the time of the MR scans. Obviously, a person in an MR scanner is not likely to encounter an EAS gate or RFID reader typically found when exiting retail stores. What is important is that after the patient is removed from the MR scanner is that the toroidal inductors (or chip inductors with ferrite cores or layers) not exhibit permanent remnance and return to their original state so that they will continue to provide effective low frequency filtering against emitters that the patient may find in their every day environment.

Figure 87:
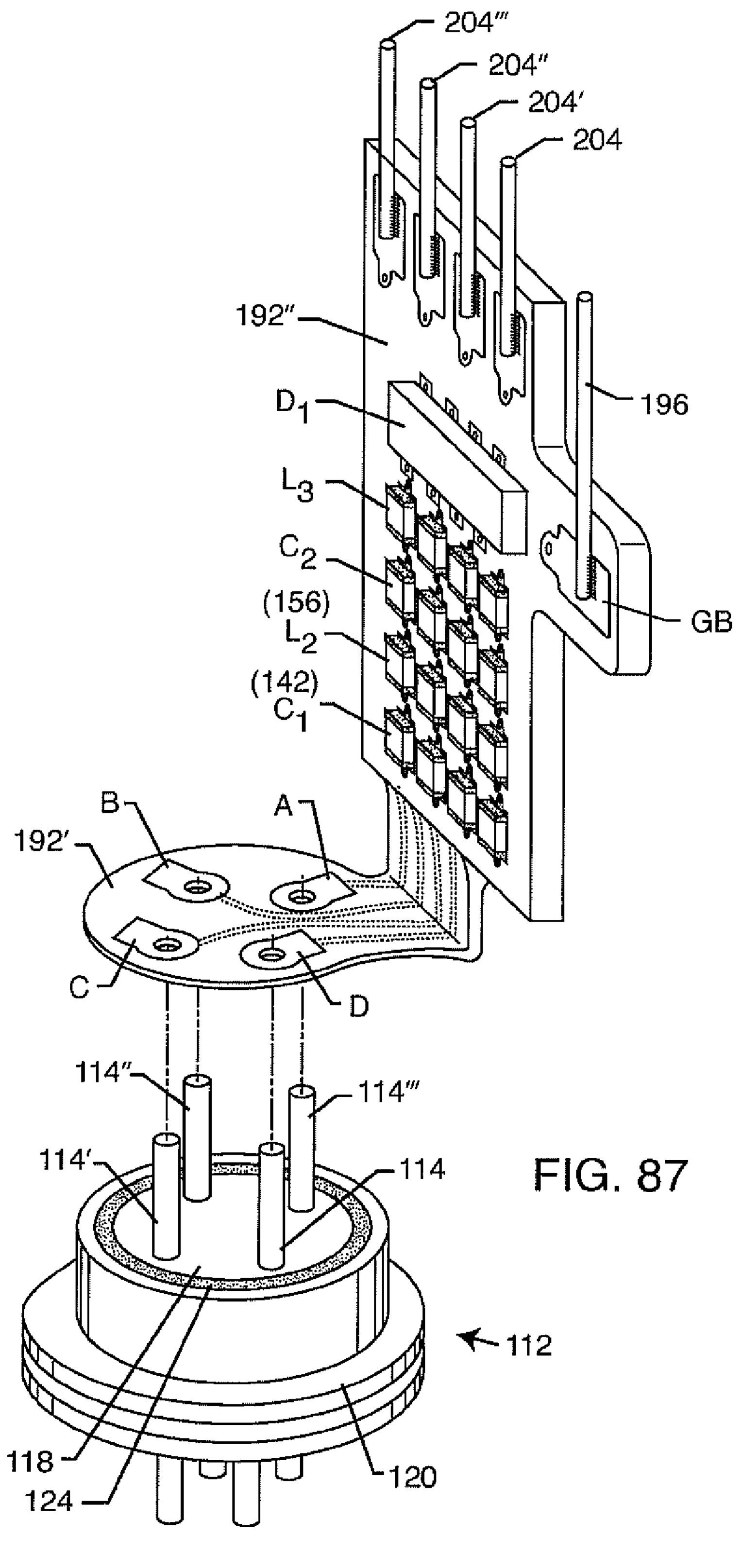
FIG. 87 is a view similar to FIG. 84, illustrating the flexibility of a portion of a hybrid substrate.

FIG. 87 illustrates the flexibility of section 192'. As one can see, it is very easy to bend the entire flex section 192' into a right angle. This is important so that the entire assembly can easily fit inside the typical spaces and geometries of active implantable medical devices, including cardiac pacemakers and the like.

Figure 88:
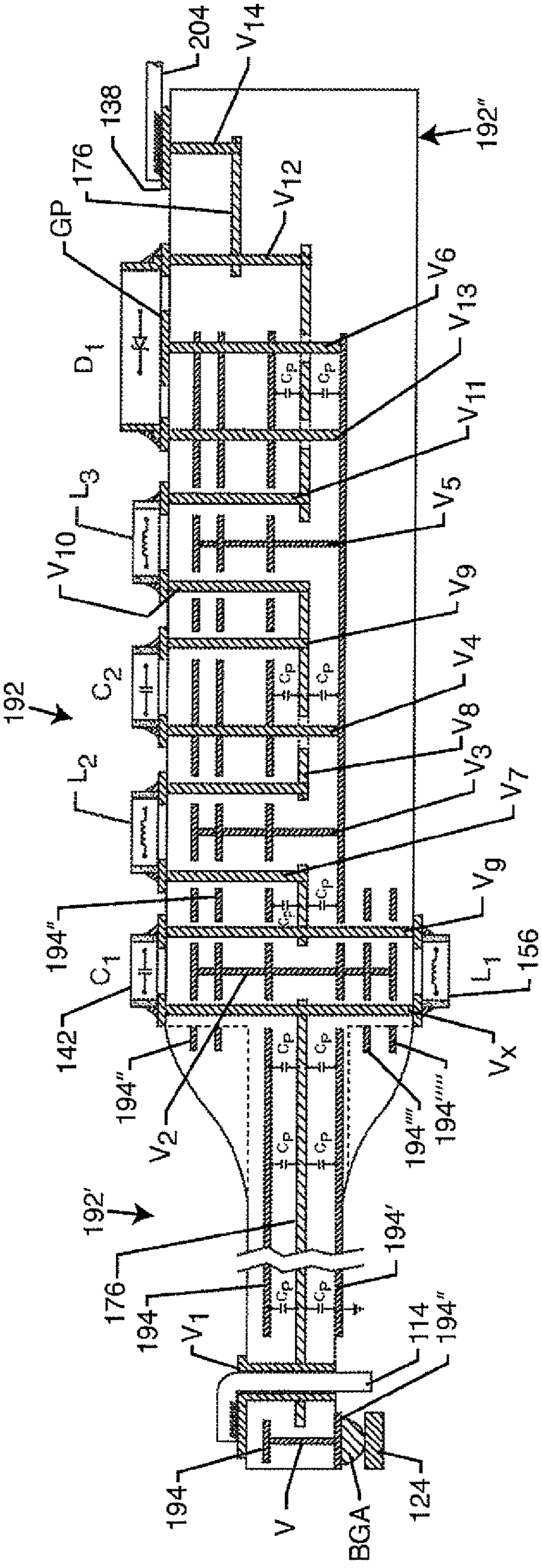
FIG. 88 is an internal diagrammatic view of the novel hybrid substrate of FIG. 84.

FIG. 88 is an internal sectional diagrammatic view taken of the hybrid substrate 192 of FIG. 84. In FIG. 88, one can see that the gold braze 124 of the hermetic seal 112 is shown on the left. An electrical connection BGA is made between internal ground via V to shield plates 194 and 194' and the gold braze material 124. These electrodes/RF shield plates 194 and 194' extend full width throughout the flexible portion 192' and the rigid portion 192" as illustrated in accordance with the present invention. Other circumferential via holes V (not shown) are used to provide a low impedance attachment to additional points between ground shield plates 194 and 194' to the gold braze 124 of the hermetic seal as shown. There are also additional ground shields connected by via hole $V_2$ to optional/additional RF shields plates 194"-194"" as shown. As previously mentioned, it is very important that the electrical connection BGA to the gold braze 124 be multi-point connections in such that a very low impedance is achieved so that the ground shields can properly function as a faraday cage shield at high frequencies.

Starting from the left and moving along to the right on FIG. 88, we will now follow flat-through capacitor active electrode plate 176. On the left side, active electrode plate 176 is electrically connected to lead wire 114 from the hermetic terminal by means of via hole and eyelet $V_1$. For simplicity, we are only going to trace one of the quadpolar circuits 176, although it will be obvious to those skilled in the art that the other three are of similar or identical flat-through capacitor construction techniques described herein. Parasitic flat-through capacitances $C_P$ are formed due to the ECA that is formed along the length of active electrode plate 176 which is sandwiched between the opposed grounded shield plates 194 and 194'. Via holes $V_2$, $V_3$, $V_4$, $V_5$, $V_6$, and $V_{13}$ (and others not shown) are part of a multipoint ground system so that the ground plates 194 and 194' are kept at the same low impedance shield potential.

Going further to the right, one encounters via hole $V_x$ and $V_y$, which connect MLCC 142 in parallel with inductor chip 156 forming a novel resonant tank filter for attenuating MRI RF signals and the like as previously described in U.S. Pat. No. 7,363,090, and U.S. Patent Application Publication Nos. US 2007-0288058 A1, US 2008-0071313 A1, US 2008-0049376 A1, US 2008-0161886 A1, US 2008-0132987 A1 and US 2008-0116997 A1, the contents of which are incorporated herein by reference. As one can see, this parallel combination of inductor chip 156 and chip capacitor 142 form a parallel combination which is electrically in series with active electrode plate 176 in accordance with the referenced co-pending patent serial numbers. Having MLCC 142 and inductor chip 156 placed on opposite sides (top and bottom) of the hybrid substrate 192 is just one way to form the parallel resonant combination. For example, if one refers to FIG. 80, 85 or 87 of U.S. Patent Application Publication No. US 2007-0112398A1, any of these novel integrated L-C chips could be used as a single element on top (or the bottom) of hybrid substrate 192 that would replace both MLCC 142 and inductor 156. It will be obvious to those skilled in the art that the parallel bandstop filter formed by $C_1$ and $L_1$ can be placed anywhere in the active electrode circuit of the shielded three-terminal flat-through EMI/energy dissipating filter. In other words, it could be moved further to the right, for example, after $L_2$ or even after $L_3$. It will also be obvious to those skilled in the art that any combination of circuit elements is possible, including placing circuit elements 142 and 156 in series as an inductor-capacitor (L-C) trap filter anywhere between the active electrode 176 and ground 194, 194'.

Referring once again to FIG. 88, active electrode plate 176 is then routed through via hole $V_7$ through inductor $L_2$ and then back down through via hole $V_8$ back to active electrode plate 176. Active electrode plate 176 is then electrically continuous to another via hole $V_9$ which is connected to the right hand termination surface of MLCC capacitor $C_2$. The other termination end of the capacitor $C_2$ is connected through via hole $V_4$ to grounded shield substrates 194-194'''. This makes for a very low impedance RF ground connection for capacitor $C_2$. The active electrode plate 176 then continues to via hole $V_{10}$ and up and to the right through inductor $L_3$ whose other end termination returns through via hole $V_{11}$ putting $L_3$ in series with active electrode plate 176. As previously described, inductors $L_2$ and $L_3$ can be chip inductors, including ferrite chip inductors or they can be toroidal wound inductors or other types of inductors. Active electrode plate 176 is then connected through via hole $V_{12}$ to the right hand side of the high voltage suppression diode array $D_1$. The left hand side of the diode array $D_1$ is connected through via hole $V_{13}$ such that it makes connection with grounded shield plates 194-194'''. Active electrode plate 176 then exits to the right from via hole $V_{12}$ over to via hole $V_{14}$ and then up to wire bond pad 138 which is very convenient for connection of lead wire 204 as shown. A ground pad GP on top of the hybrid substrate 192 has been provided which connects by via hole $V_6$ to the embedded grounded shield plates 194-194'''.

Referring now back to FIG. 84, one can see ground wire 196 which has been connected to the bond pad area GB. This is not required for all AIMDs, however, it is a very convenient point for connection of integrated circuit substrate 250 ground circuit trace or traces to the housing of the AIMD via lead 196 and then to the ground shield plates 194, 194' of the hybrid flex shielded three-terminal flat-through EMI/energy dissipating filter. As previously described, the ground shield plates are connected to the gold braze 124 of the hermetic seal 112 which is typically laser welded into the overall titanium housing/can of the AIMD (shown as 300 in FIG. 114). The housing can act as an EMI shield, an electrode or an energy dissipation surface. In all cases, a low impedance RF ground is required which is accomplished by the grounded shield plates of the shielded three-terminal flat-through EMI/energy dissipating filter 190 of the present invention. Referring back to FIG. 88, one can see that there are a number of parasitic flat-through capacitances $C_P$ that are formed in accordance with the present invention between shield plates 194 and 194' which surround active electrode plate 176 on top and bottom as shown.

Figure 89:
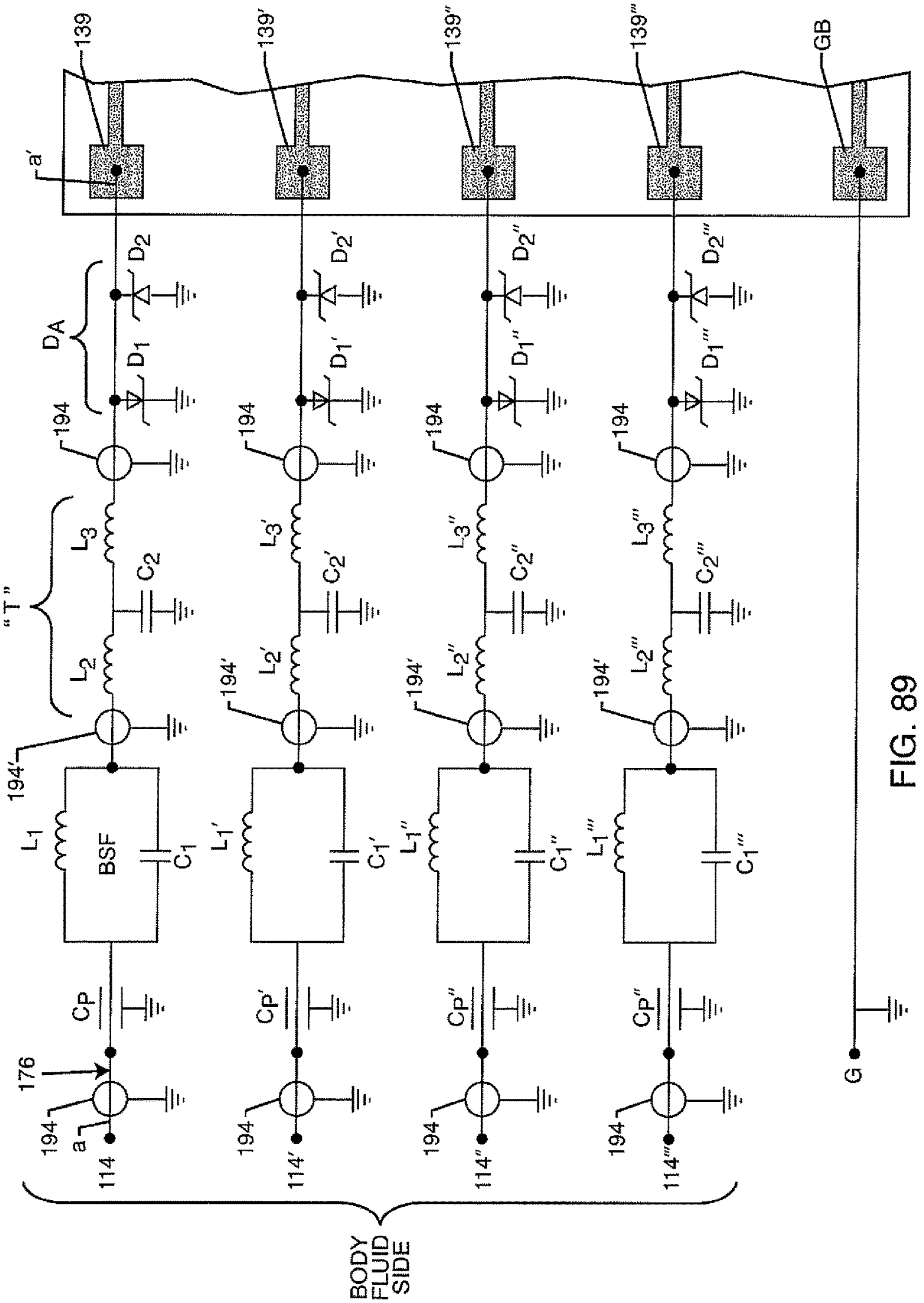
FIG. 89 is an electrical schematic diagram of the novel hybrid substrate of FIG. 84.

FIG. 89 is the schematic diagram of the novel hybrid substrate 192 of FIG. 84. For example, tracing one of the quad polar circuits through, for example the circuit labeled 176, point "a" is toward the body fluid side of the lead wire 114 that connects from the hermetic seal 112 shown in FIG. 84. Typically, this would connect through a connector block or directly to a lead system where an electrode would come into contact with body tissue (in a unipolar pace or sense mode, the AIMD housing/can would serve as the return electrode). On the opposite side of the hermetic terminal, we have the same lead wire 114 which then connects to the via hole V.sub.1 of the flexible hybrid substrate 192'. The active electrode plate 176 enters the bandstop filter BSF which consists of the parallel inductor L.sub.1 and MLCC capacitor $C_1$, one sees that we have now entered the shielded part of the substrate meaning that the entire active electrode plate 176 is contained within grounded shield plates 194 and 194'. After exiting the bandstop filter BSF, we then go through inductor $L_2$, and then MLCC capacitor $C_2$ is connected to ground 194, 194'. MLCC $C_2$ is then connected with inductor $L_3$. After active electrode 176 exits inductor $L_3$, it is still shielded/sandwiched within the ground plates 194, 194' of the hybrid substrate 192. We then encounter the transient voltage suppression diode array DA. In this case, the diode array is shown connected to ground and acts as a high voltage suppression device. Diode arrays DA of this type are commonly used in AIMDs. The reason for this has to do with the use of either ICDs or automatic external defibrillators (AEDs). AEDs are now commonly deployed in government buildings, hotels, airplanes, and many other public places. These life saving devices are very important. If a person is unconscious, the AED electrodes are placed on the person's chest. The AED then automatically detects dangerous ventricular arrhythmias (such as ventricular fibrillation) and then an automated high voltage biphasic shock is applied to the electrodes. If the person has an implanted pacemaker (which is often the case) then the implanted leads pick up this high voltage shock that is being used to cardiovert the cardiac tissue. Since the implanted pacemaker is a low voltage device, this high voltage shock can damage sensitive internal circuits of the cardiac pacemaker. Accordingly, diode arrays, incorporating back to back diodes, zener diodes, transorbs or the like are commonly used to short the high voltage spike to ground before it can damage sensitive active electronic circuits (such as integrated circuits, hybrid chips and the like). Since the diode array that's typically used takes up a lot of space on the circuit board, it is a feature of the present invention that it could easily be integrated into the shielded three-terminal flat-through EMI/energy dissipating filter 190 of the present invention to save space by placing it on the interconnect circuit. We then exit the novel hybrid substrate 192 of the present invention at point "a" and make an electrical connection to the IC wire bond pad 139 as shown. Another way to think of the schematic diagram shown in FIG. 89 is that what we have is a bandstop filter for suppression of MRI or other powerful single frequency emitters in series with a three element T section filter as previously described in connection with FIG. 73 in series with a high voltage suppression diode. It will be obvious to those skilled in the art that the bandstop filter could be located to the right of the C, L, π., T or .η. element filter. It could also be placed in combination with L-C trap filter to ground. Accordingly, one can see that a number of components have been assembled into one convenient package.

Referring back to FIG. 84, there are a number of other features of the novel hybrid flex substrate 192 that need to be pointed out. One of the features is best described by referring back to FIG. 84 wherein the via holes have an enlarged rectangular portion A, B, C and D for suitable electrical probing or electrical testing. This section allows for a robot or a pogo spring connector to be placed on the pad to facilitate electrical testing, accelerated life testing, burn in, insulation test, dielectric withstanding voltage test or other suitable electrical tests as needed. These tests, often performed at elevated temperatures, are essential to assure the long term reliability of the novel shielded three-terminal flat-through EMI/energy dissipating filter of the present invention. In the opposite (right) end of the rigid part of the substrate 192", a similar enlarged pad area(s) 139 has been provided for similar electrical contact for test instruments as previously described. For ease of manufacturing, it is also convenient that the entire hybrid flex substrate 192 be laid flat as is shown. Being laid flat is particularly suitable to be placed into fixtures for modern robots. These robots are typically fed by tape and reel components or trays which house all of the electronic components. By having the basic hybrid substrate 192 laying flat, all of the components can be quickly placed by the robots. Assembly by hand is impractical due to the small size of the surface mounted components. For example, the MLCC chips can be 0201 or smaller which is the size of a grain of pepper (0.020 inch by 0.010 inch). It is then a matter of prior art wave-soldering or equivalent techniques to make the electrical and mechanical connections to all of the components. This is followed up by automated optical inspection, electrical test and even X-ray if needed.

Again referring to FIG. 84, so that adequate electromagnetic interference protection will be provided to sensitive AIMD electronics and sense circuits, the inductor $L_2$ will preferably be of a non-ferrite core and the capacitor $C_2$ would be of sufficient value working in conjunction with flat-through capacitance $C_P$ such that those components alone would provide adequate protection at MRI pulsed frequencies. For example, for 1.5 Tesla MR scanner, the RF pulsed frequency is 64 MHz. It would be desirable for component $C_P$, $L_2$ and $C_2$ to have over 40 dB attenuation at 64 MHz to provide adequate protection to device electronics. With the use of a very high value inductor $L_3$, as illustrated in FIG. 86, one can provide a very high degree of (attenuation) immunity to low frequency emitters, such as 58 kHz electronic article surveillance (security) gates that are typically used in retail stores. In addition, one can provide a great deal of immunity to low frequency (LF) RFID readers. These are typically used for automotive keyless entry systems and the like. Since neither RFID readers nor store security gates are present in an MR scan room, it does not matter if inductor $L_3'$ does saturate in the MR environment. Accordingly, a novel methodology is provided in the hybrid substrate 192 such that certain filter components do not saturate during the MR scan and others do. It will be obvious to those skilled in the art that capacitor elements $C_2$ could be a monolithic ceramic capacitor (MLCC), or a very high value aluminum electrolytic or tantalum capacitor. In other words, for very low frequency filtering, a capacitor of several microfarads could be used with a toroidal wound inductor of several hundred microhenries. This would provide attenuation down to very low frequencies.

In FIG. 89, one can see that $L_2$ working in combination with $C_2$ and $L_3$ form what is known in the art as a low-pass "T" filter. Any combination of active or passive circuit elements can be readily adapted to the shielded three-terminal flat-through EMI/energy dissipating filter of the present invention. This includes any of the low-pass filter circuits shown in FIG. 75, and any combinations of L-C traps and/or bandstop filters (BSFs). It is a feature of the present invention that the three terminal flat-through capacitance obtained by sandwiching large surface area through electrodes between surrounding ground plates result in a flat-through capacitance suitable to compensate for the self resonance characteristic (see FIG. 18) of prior art (and very low cost) MLCCs and allow them to be used in combination with the shielded three-terminal flat-through EMI/energy dissipating filter of the present invention to achieve a very broadband and effective EMI filter and highly effective energy dissipater.

Figure 90:
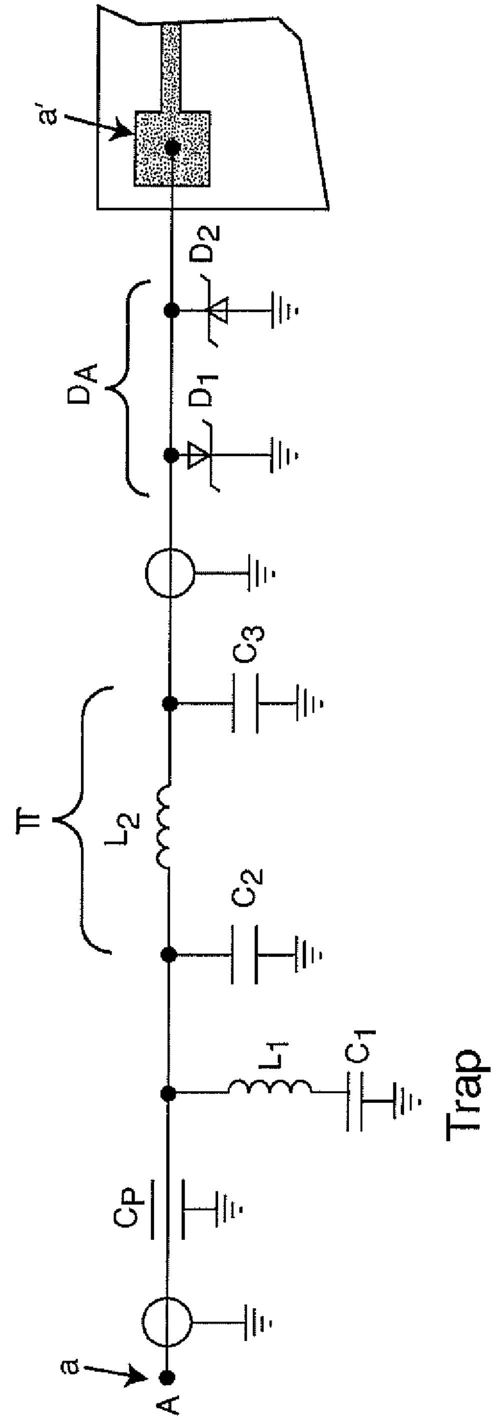
FIG. 90 is the same as one of the active circuits of FIG. 89 wherein the "T" circuit filter has been replaced with a it circuit filter.

FIG. 90 is an electrical schematic for one circuit A of FIG. 86. In this case, the T circuit low-pass filter has been replaced with a it circuit low-pass filter consisting of $C_2$, $L_2$ and $C_3$. In FIG. 90, the bandstop filter BSF consisting of components $L_1$ and $C_1$ acting in parallel, has been replaced by a L-C trap filter consisting of $L_1$ and $C_1$ that are wired in series to ground 194, 194'. It is well known that when L-C series components are in resonance; they ideally form a short circuit at the resonant frequency. This is more thoroughly described in U.S. Pat. No. 6,424,234 the contents of which are incorporated herein. Referring once again to FIG. 90, when one is designing the trap circuit, one has to be very careful of the parallel action of $C_P$ and $C_2$. One has to model the circuit very carefully to make sure that the trap filter functions properly in the presence of these parallel capacitances. It is often desirable, and well known in the art, to isolate the L-C trap filter with a series bandstop filter so that it will not interact with other parallel capacitances. It will be obvious to those skilled in the art that a bandstop filter could be inserted on one or both sides of the trap filter or between multiple trap filters to increase its or their efficacy.

Referring once again to FIG. 90, the use of a trap filter would be particularly advantageous if the AIMD were to be exposed to a MRI environment. For example, if the system were designed to be used in a 1.5 Tesla scanner, the trap filter could be designed to be resonant at 64 MHz. This would short out 64 MHz signals to ground (the titanium housing of the AIMD). This would not only provide a great deal of immunity and protection to device electronics, it would also desirably short MR energy to the metallic housing of the AIMD such that it cannot reflect back and cause overheating of the distal electrode tip to tissue interface. Using the housing to dissipate energy is described in U.S. Provisional Patent Application Nos. 61/144,102, the contents of which are incorporated herein.

Referring once again to FIG. 90, the π circuit could consist of an MLCC capacitor $C_2$ which would be very effective at high frequencies. $L_2$ could be a toroidally wound inductor with a ferrite core as previously described as $L_3'$ from FIG. 86. $C_3$ could be a high value tantalum capacitor. It would not matter if the it circuit was effective while the AIMD was operating in a MR scanner. This is because the L-C trap would be made of components which do not saturate in a magnetic field environment. In other words, inductor $L_1$ would be non-ferromagnetic and capacitor $C_1$ would generally be of MLCC construction. Therefore, the EMI filtering immunity for the MR environments would consist entirely of the operation of the trap filter operating in combination with the parasitic capacitance (flat-through capacitance) of the novel hybrid substrate 192 of the present invention. Accordingly, the π section filter would be very effective when the patient is outside of MR environments for attenuating low frequency signals and signals throughout the frequency range. In other words, the structure as illustrated in FIG. 90 would perform effective filtering from approximately 30 kHz all the way to 10 GHz while outside of an MR environment. While in an MR environment, it would perform effective filtering at selected frequencies of one or more trap filters as shown. Only one trap filter is shown, but it will be obvious to those skilled in the art that any number of trap filters could be placed in parallel in order to short circuit multiple RF frequencies. For example, if one were to want the AIMD to be compatible with both 1.5 and 3 Tesla scanners, then two trap filters would be required; one resonating at 64 MHz and the other one at 128 MHz. Again, as previously stated, the L-C trap filter can each be separated by a series bandstop filter consisting of a capacitor in parallel with an inductor so that the components of each individual trap filter do not interact with each other.

Reference is made to U.S. Provisional Patent Application Ser. No. 61/144,102, which describes a number of other frequency selective circuits that can be used to balance the energy during MRI scanning. The objective is to take as much energy off the implanted lead system and shunt it to the conductive housing of the AIMD which then becomes its own energy dissipating surface. It will be obvious to those skilled in the art that any and all of the schematics that are disclosed in U.S. Provisional Patent Application Ser. No. 61/144,102 can be embodied in the novel hybrid substrate 192 of the present invention.

Figure 91:
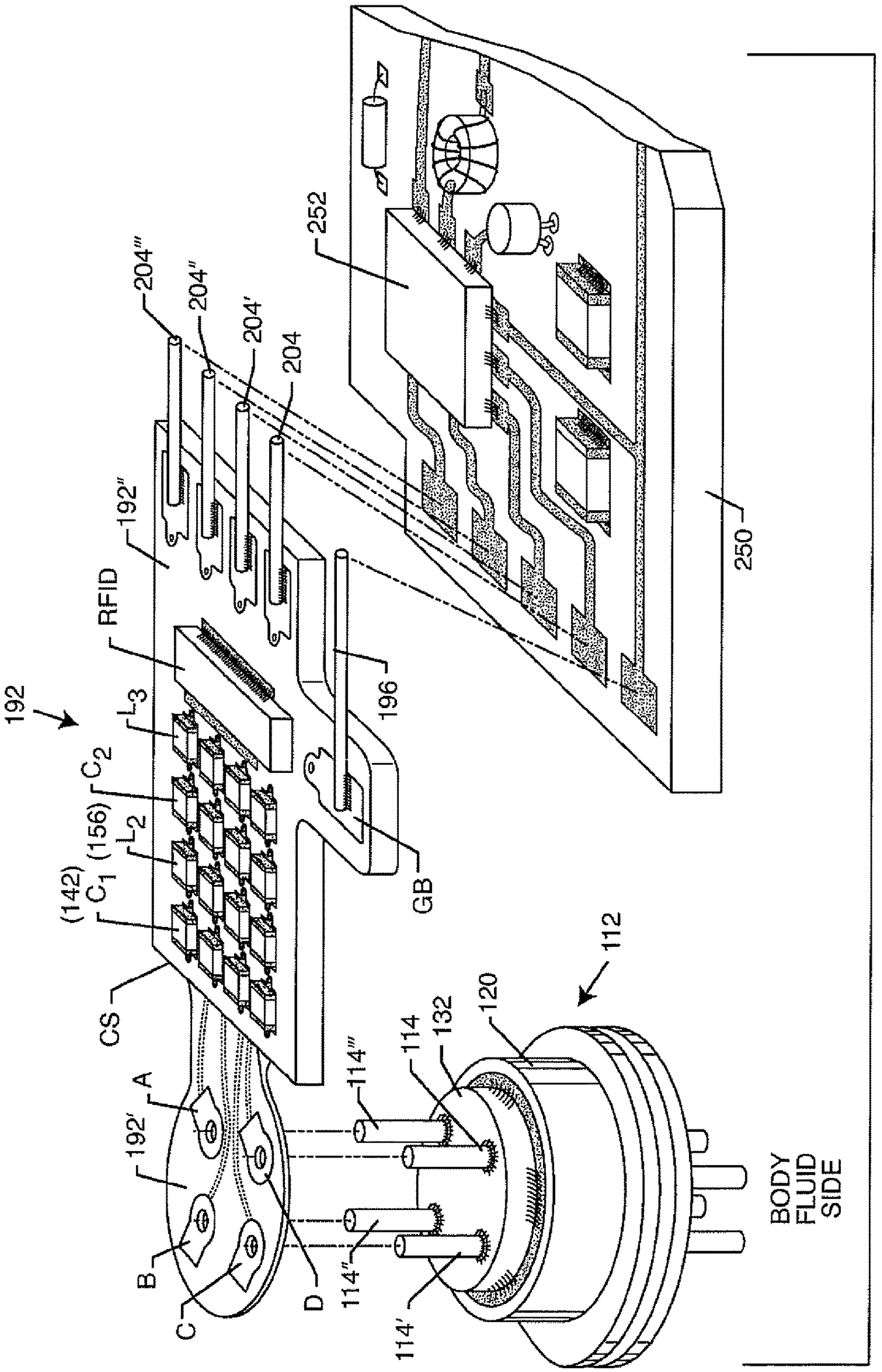
FIG. 91 is similar to FIG. 84, with the addition of a prior art quadpolar feedthrough capacitor.

FIG. 91 is very similar to FIGS. 84, 85 and FIG. 86. The difference is that a prior art feedthrough capacitor 132 is being used in conjunction with the hybrid substrate 192 of the present invention. Feedthrough capacitors are well known in the prior art, including U.S. Pat. Nos. 4,424,551; 5,333,095; 5,905,627; and 6,765,779, the contents all of which are incorporated. Referring once again to FIG. 91, the feedthrough capacitor 132 would provide high frequency filtering generally in the frequency range from 100-10,000 MHz. As described for FIG. 86, the other board mounted components could then all involve very high capacitance tantalum or aluminum electrolytic capacitors, or toroidal inductors using high permeability ferrite cores. For example, feedthrough capacitor 132 would provide sufficient immunity during an MRI scan such that the other components could all saturate. This would provide a very effective broadband filter operating generally in the frequency range from 10 kHz all the way to 10 MHz.

Figure 92:
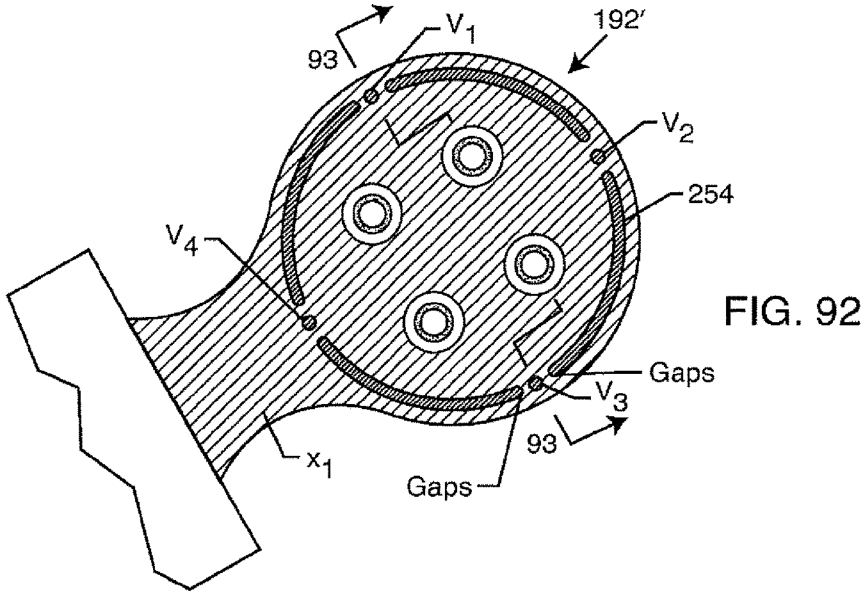
FIG. 92 is a plan view of the reverse side of the flexible portion of the hybrid substrate of FIGS. 84 and 88.

FIG. 92 illustrates the reverse side of the flexible portion 192' of the hybrid flex from FIG. 84. One can see that a robot has dispensed a circular portion of thermal-setting conductive thermal setting adhesive 254. This is designed to align precisely with the gold braze 124 of the hermetic terminal 112 of FIG. 84. Accordingly, the entire substrate can be laid down over the hermetic terminal assembly 112 and then the thermal-setting conductive material 254 can be cured in an oven, furnace or other equivalent process. This makes a suitable electrical and mechanical connection to the exposed ground shield electrode plate 194'. Referring back to FIG. 92, one will see that there are gaps left in the circumferential thermal-setting conductive polymer 254. These gaps are present to allow for a free flow of helium during fine leak detection as previously described. There are also via holes $V_1$, $V_2$, $V_3$ and $V_4$ which are used to connect to the other internal ground shield plates, including plate 194.

Figure 93:
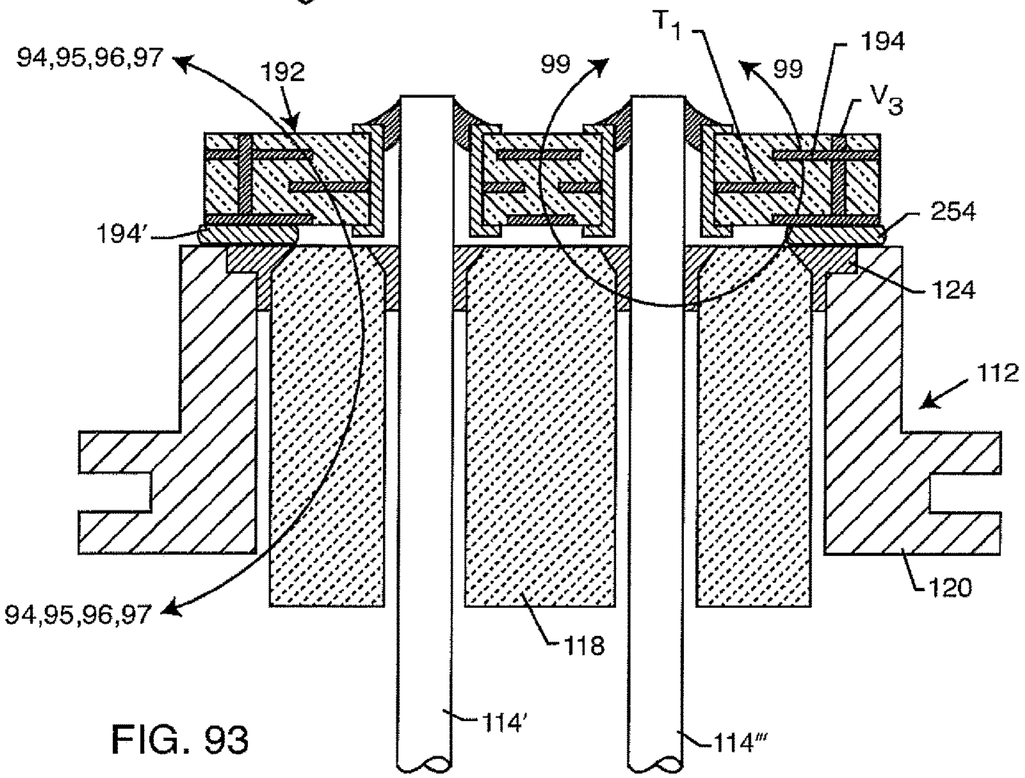
FIG. 93 is a sectional view taken generally along the line 93-93 of FIG. 92.

FIG. 93 is a sectional view taken along line 93-93 from FIGS. 84 and 92. One can see the electrical connection formed by thermal-setting conductive adhesive 254 between via hole $V_3$ and the gold braze 124, for example. Alternative methods of performing this low impedance RF electrical ground connection to the grounded shield plates 194, 194' of the shielded three-terminal flat-through EMI/energy dissipating filter of the present invention are illustrated in FIGS. 94 through 97.

Figure 94:
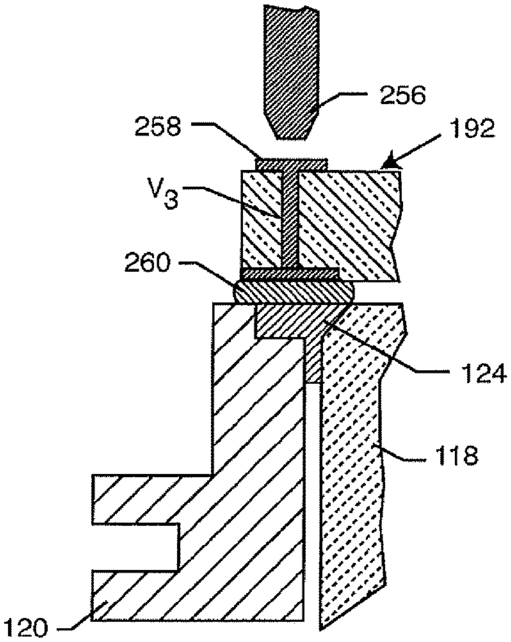
FIGS. 94-97 are fragmented sectional views taken generally of the area indicated by the line 94, 95, 96 and 97 in FIG. 93, showing alternative methods of making an electrical connection.

FIG. 94 illustrates a methodology of pushing a resistance welding electrode pad 256 onto a flex cable rivet eyelet 258 thereby creating a current flow in which an elevated temperature results sufficient to reflow a low temperature braze 260 solder or the like to the gold braze material 124.

Figure 95:
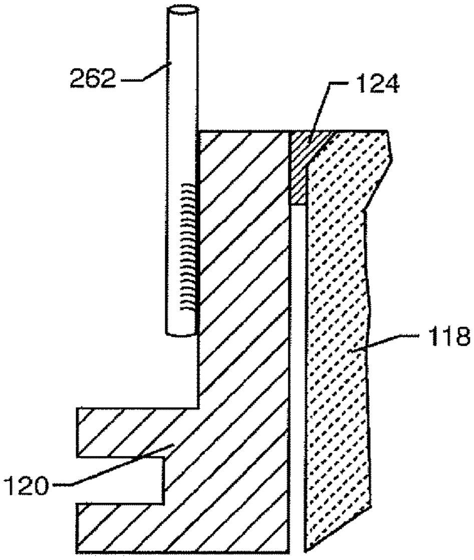

FIG. 95 illustrates an outer pin 262 which has been laser welded to the ferrule 120. The minimum number of pins is one, but an optimal number would be four to six to provide suitable RF connection to the internal grounded shield plates 194 and 194' of the present invention.

Figure 96:
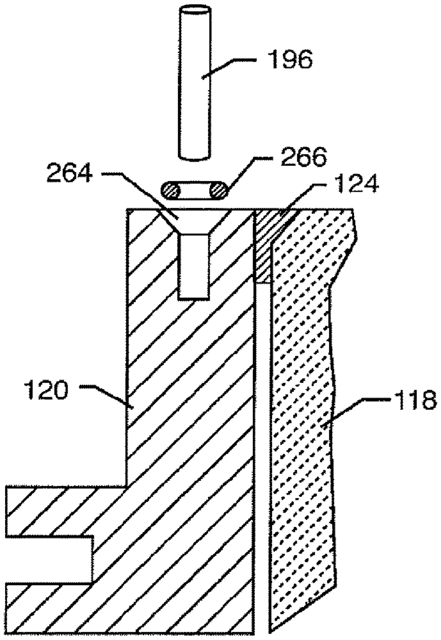

An alternative method is shown in FIG. 96 wherein a series of counterbores or countersinks 264 have been provided in the top of the flange 120 such that multiple lead wires 196 could be placed along with gold braze rings 266. A high temperature brazing furnace is used to reflow the gold preforms 266 and electrically and mechanically attach the pins/leads 196 to the ferrule 120. In this way, a number of ground pins 196 would be sticking up such that open via holes of the flexible portion 192' of hybrid substrate 192 of the present invention could be laid down and electrically attached to the grounded shield plates 194, 194'.

Figure 97:
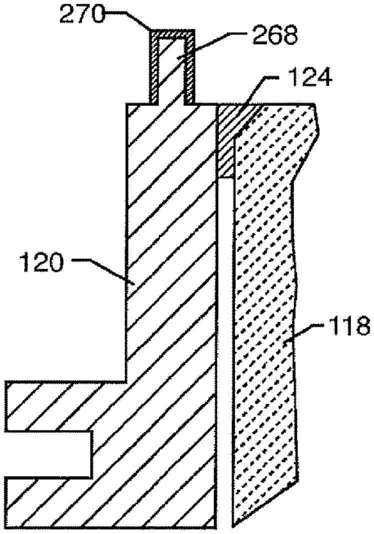

Another RF ground attach methodology is shown in FIG. 97 wherein the ferrule 120 is of a pressed powder metallurgy. In this case, a pedestal pin 268 (4 to 6 or more is the ideal number of pedestals) is formed as part of the powder metallurgy process. In this case, all the materials would be typically of titanium which is ideal for this purpose. Because of the problems with titanium oxide formation, a gold sputtering 270, plating or brazing is placed over the terminal pedestal 268 such that a proper oxide-free electrical connection can be made to the hybrid substrate 192 of the present invention.

Figure 98:
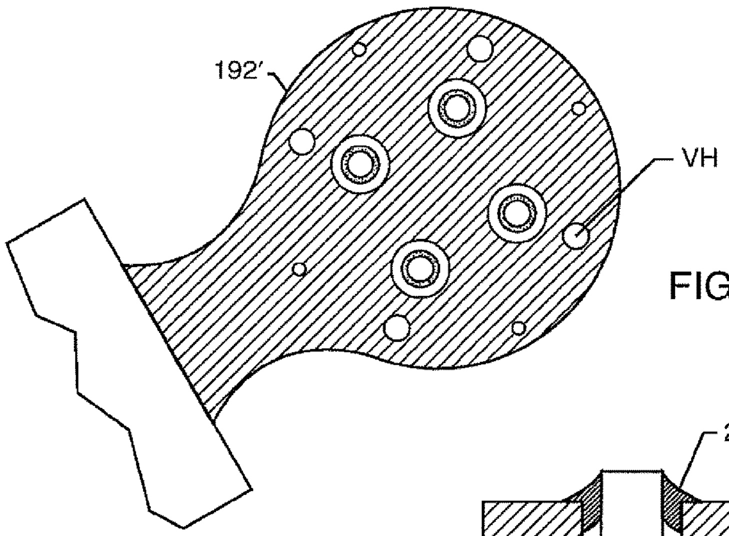
FIG. 98 is a plan view similar to FIG. 92 showing a modified version of flex cable assembly with four via holes.

FIG. 98 shows a modified version of the flexible portion 192' of the flex cable assembly of FIG. 84 with four (or more) via holes VH suitable for placement over any of the embodiments described in FIGS. 95 through 97 for electrical attachments to its grounded shield plates 194 and 194'.

Figure 99:
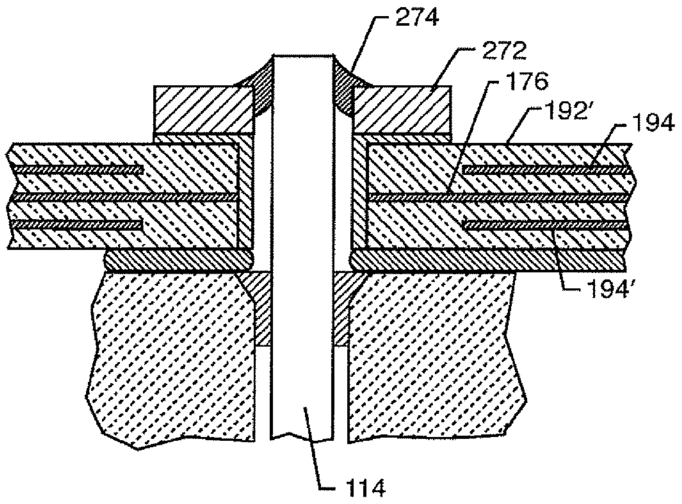
FIG. 99 is a cross-sectional view of the area indicated by line 99-99 in FIG. 93, showing type of yet another embodiment illustrating attachment of the substrate over a terminal pin utilizing a weld ring or a braze ring.

FIG. 99 illustrates a cross-section 99-99 from FIG. 93 of yet another embodiment illustrating attachment of the active electrodes of substrate 192' over a terminal pin 114 along with some sort of a weld ring 272 or a braze ring. An electrical connection with weld or solder material 274 is shown.

Figure 100:
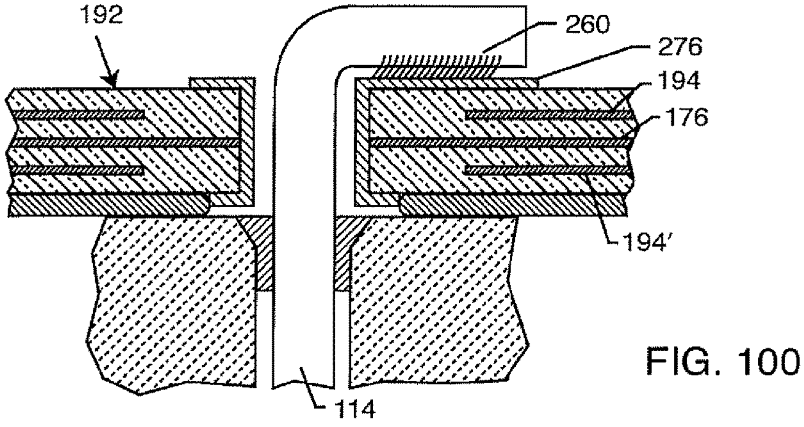
FIG. 100 is a view similar to FIG. 99 illustrating yet another methodology of attachment.

FIG. 100 illustrates another methodology wherein the lead wire 114 as previously shown in FIG. 84 could be bent over and then a low temperature braze 260 can be formed to an enlarged eyelet 276 of the novel hybrid flex substrate 192.

Figure 101:
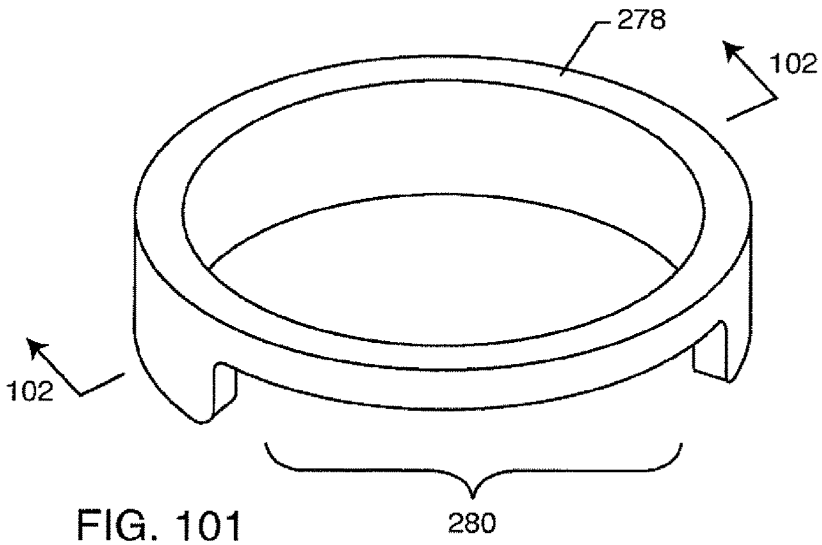
FIG. 101 is an isometric cross-section of a novel attachment cap used to connect the shielded three-terminal flat-through EMI/energy dissipating filter to various types of hermetic or non-hermetic seals.

FIG. 101 illustrates a novel laser weld cap 278 with a cut out section 280. The cut out area 280 is formed or cut so the metal cap 278 can slip down over the narrow section 192' of the flexible portion of the shielded three-terminal flat-through EMI/energy dissipating filter. The laser weld cap

278 can be a stamped titanium, machined titanium, injection molded titanium or a number of other metals.

Figure 102:
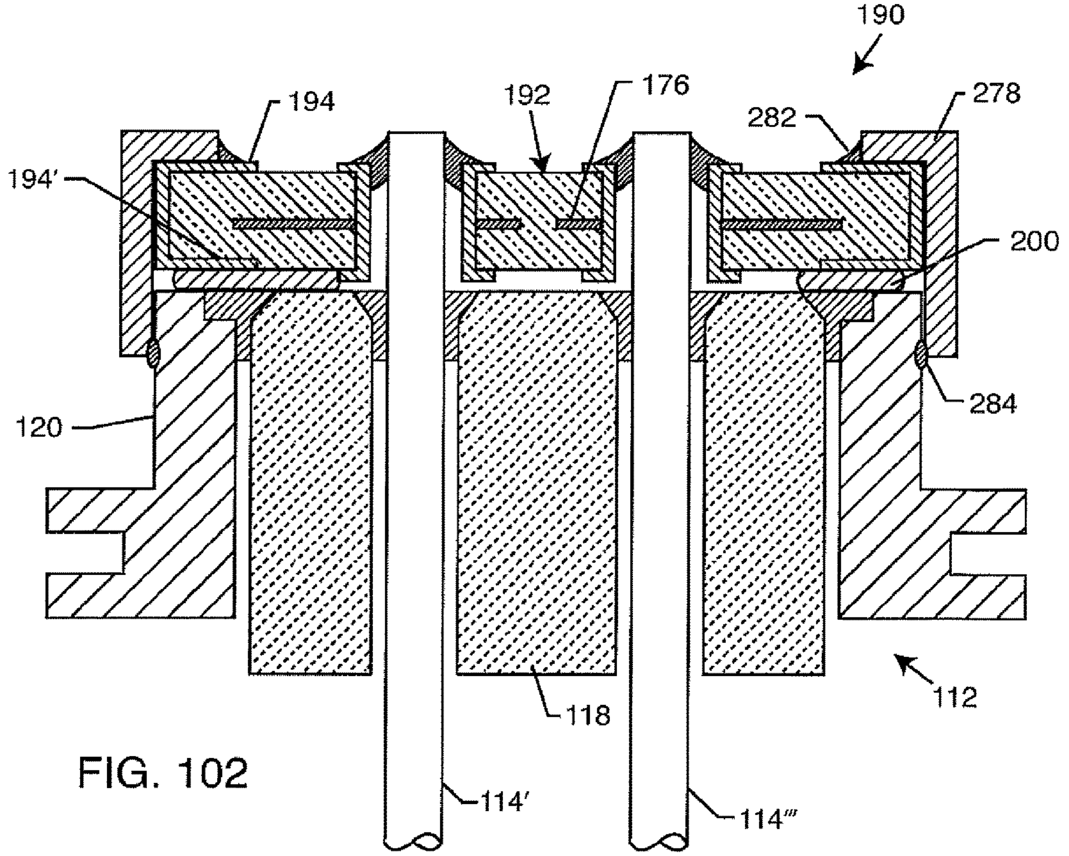
FIG. 102 is a cross-sectional view of a prior art hermetic seal embodying the novel cap from FIG. 101.

FIG. 102 is a combined cross-section taken generally from 102-102 from FIG. 101 and also from section 102-102 from FIG. 84. However, the hybrid substrate 192 has been modified to accommodate the novel laser weld cap 278 as illustrated in FIG. 101. In FIG. 102 one can see that the laser weld cap 278 is slipped down such that it comes into close contact with the flange 120 of the hermetic terminal 112. A continuous or discontinuous laser weld or braze 284 is formed, as shown. This makes a solid metallurgical and low impedance ground contact to the hermetic flange 120 and to the laser weld cap 278. An electrical connection 282 is then made to the ground metallization 194 of the shielded three-terminal flat-through EMI/energy dissipating filter 190 thereby providing a very low impedance RF ground. One can see in FIG. 102 that ground shield plates 194 and 194' are external for the purposes of this illustration; however, they could be internal plates as previously illustrated.

Figure 103:
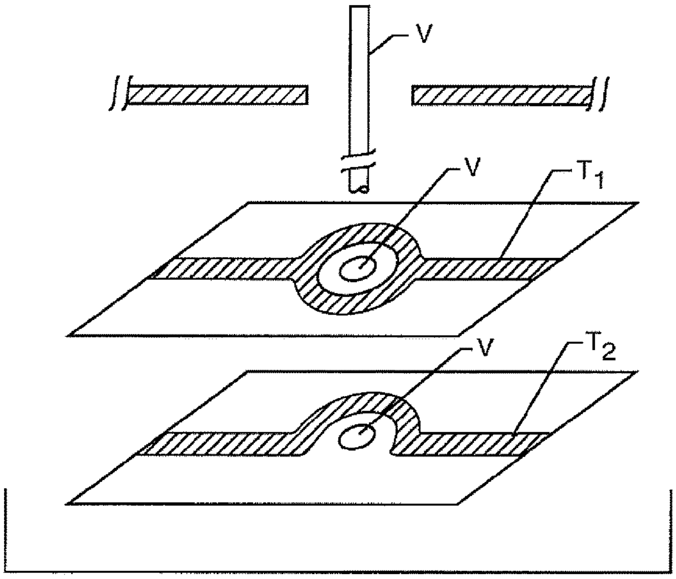
FIG. 103 is a schematic view illustrating a methodology of having a circuit trace or a portion of an electrode plate dodge around a via hole.

FIG. 103 is applicable to many of the illustrated embodiments of the present invention and simply illustrates a methodology of having a circuit trace $T_1$ or $T_2$ dodge around a via hole V such that it maintains a high surface area (to maximize ECA) and remains in electrical isolation. As one can see in the upper view, circuit trace $T_1$ can be routed in a circular manner all around the via hole or it can simply be routed around the via hole. To maximize flat-through capacitance ECA, the upper trace is the preferred embodiment.

Figure 104:
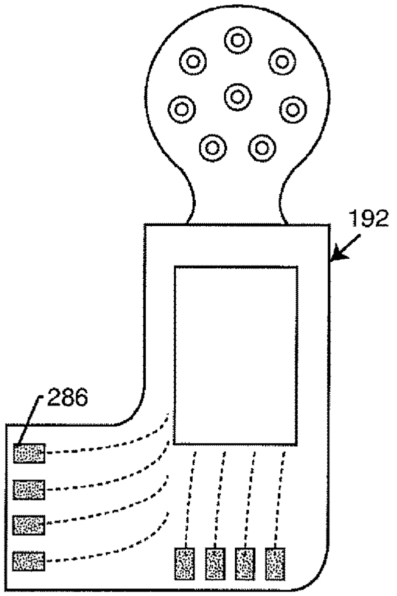
FIG. 104 is a schematic illustration of an alternative embodiment to FIG. 84.

FIG. 104 illustrates an alternative embodiment to FIG. 82 in that it is an octapolar design instead of a quadpolar design. Also, instead of having lead wires for transition to integrated circuit boards, it has wire bond pads 286 for convenient connection of jumper wires to other circuits.

Figure 105:
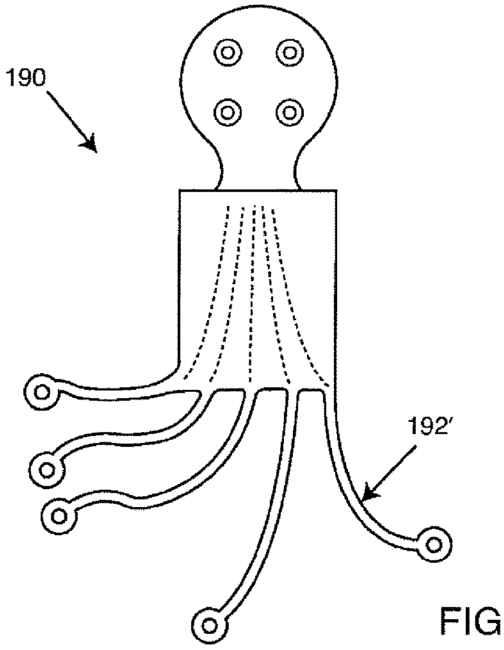
FIG. 105 is similar to FIG. 104, except that it illustrates the methodology of breaking up flex cable section of the hybrid substrate into flexible sections.

FIG. 105 is very similar to FIG. 104 except that it illustrates the methodology of breaking up the flex cable portion 192' of the hybrid substrate 192 into individual arms/traces for direct electrical connection to other locations, for example to an IC board, within a general electronics module or an AIMD.

FIG. 106 illustrates an in-line octapolar hermetic or non-hermetic terminal 112 with a hybrid substrate 192 of the present invention exploded away from it, but designed to be mounted to it. One can see that there are a number of MLCC capacitors 142 that are in series with an embedded inductor meander 158. Wire bond pads 139 are provided at the end for convenient connection of jumper wires to AIMD or other electronic device electrical circuits.

Figure 107:
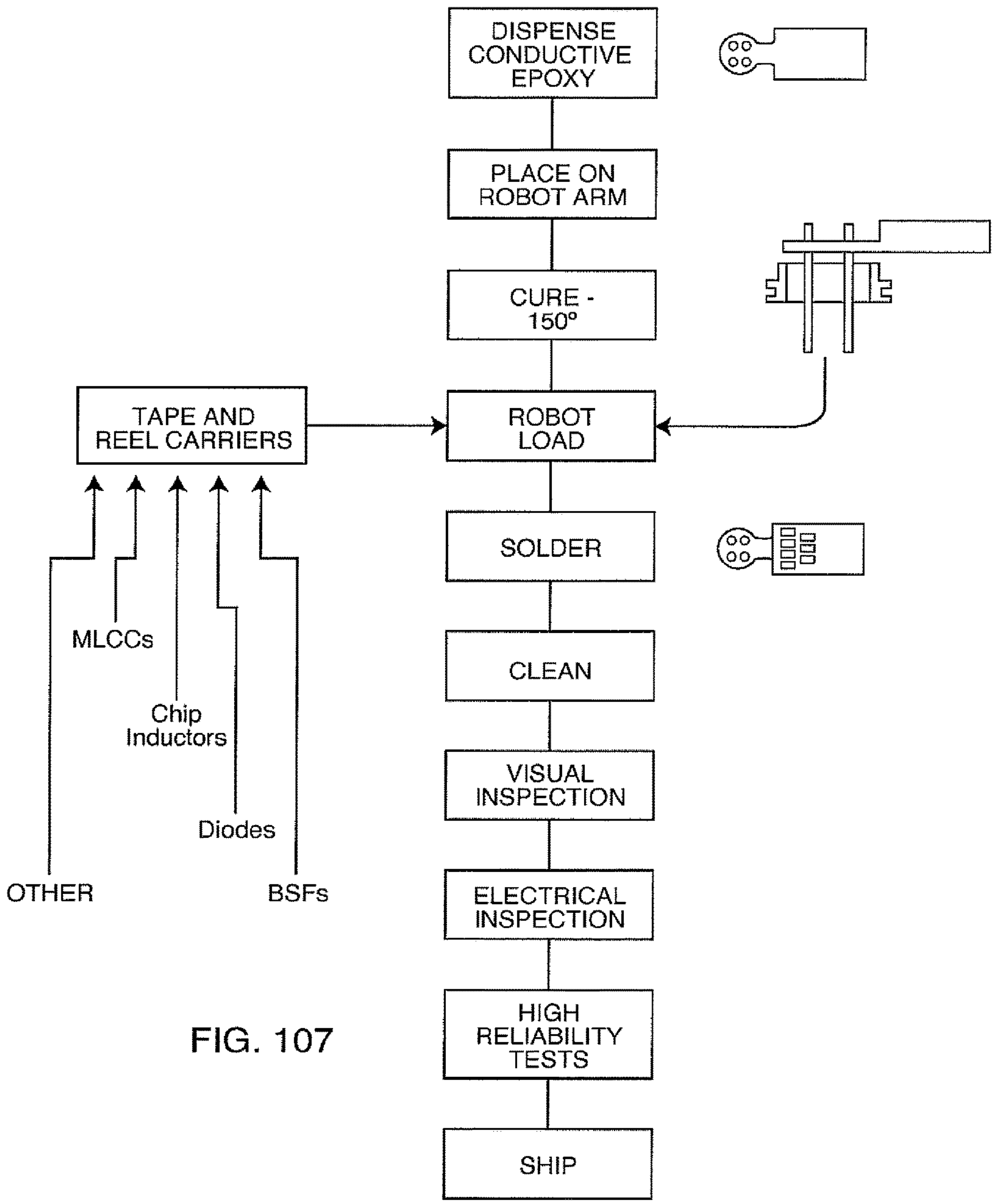
FIG. 107 is a flow chart illustrating a manufacturing production process.

FIG. 107 is a manufacturing production flow chart illustrating a very low cost and a very reliable way to manufacture the present invention. By way of illustration, we will be referring to the particular hybrid substrate 192 as previously illustrated in FIG. 84. As previously mentioned, it is highly desirable that during assembly that this substrate 192 be laid flat. It can then later be bent into any desired shape as shown in FIG. 87. The first step is to dispense conductive epoxy using a robot to achieve the ring of thermal-setting conductive adhesive 254 as previously described in connection with FIG. 92. This is then assembled into the hermetic seal 112 and cured at temperatures ranging from 150 to 300 degrees centigrade. The electrical chip components are then robot-loaded either from tape and reels or from carrier trays. The chip components can consist of any combination MLCC capacitors 142, chip inductors 156, diodes 154, bandstop filters, L-C trap filters, RFID chips or any other electronic components. These are then run through an automated soldering operation and cleaning operation where they go through an automated optical visual inspection. The electrical inspection is also automated. High reliability screening is then done automatically such as burn in, life testing and the like. Parts are then ready for packaging and shipping.

Figure 108:
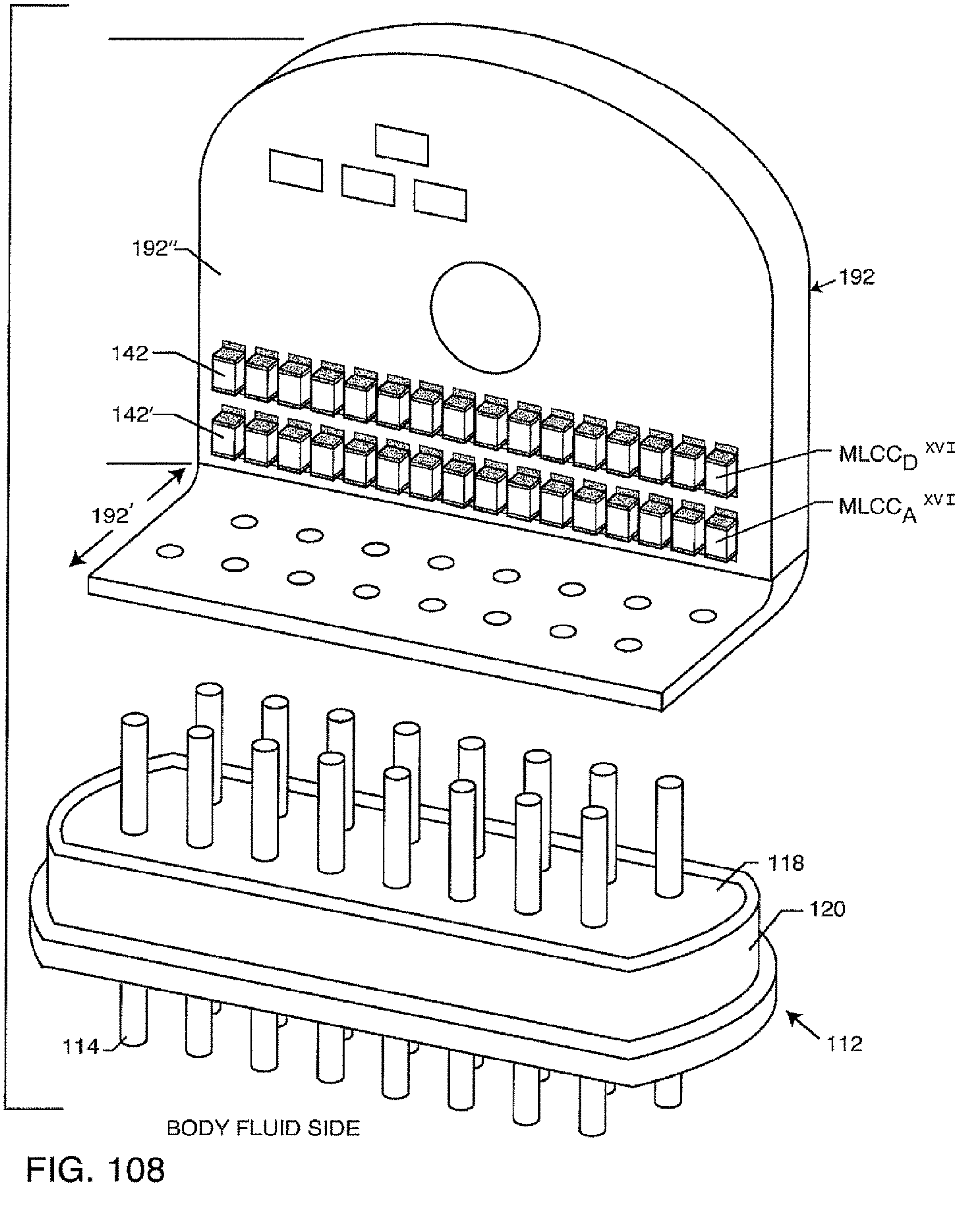
FIG. 108 is an exploded perspective view of a typical sixteen lead hermetic seal utilizing a novel hybrid shielded three-terminal flat-through EMI/energy dissipating filter embodying the present invention.

FIG. 108 illustrates a typical 16-lead glass hermetic seal 112 that would be typically found in a cochlear implant. Also shown is a novel hybrid substrate 192 of the present invention which consists of a rigid section 192" and a thin flexible section 192'. In this case, the thin flexible section 192' has been bent over into a 90 degree angle for convenient attachment to the hermetic seal assembly 112. A number $_A$ground shield plates of the present invention. The MLCC's 142 can support two purposes in this application. Some of the MLCC's 142 are used in series with the flat-through capacitor active electrodes, which are also known in the art as DC blocking capacitors. This is in order to protect body tissues from excessive electrical stimulation. Also shown are another row of MLCC capacitors 142' which are generally connected to ground to perform EMI filtering in accordance with the present invention. This is better understood by referring to the schematic diagram in FIG. 109.

Figure 109:
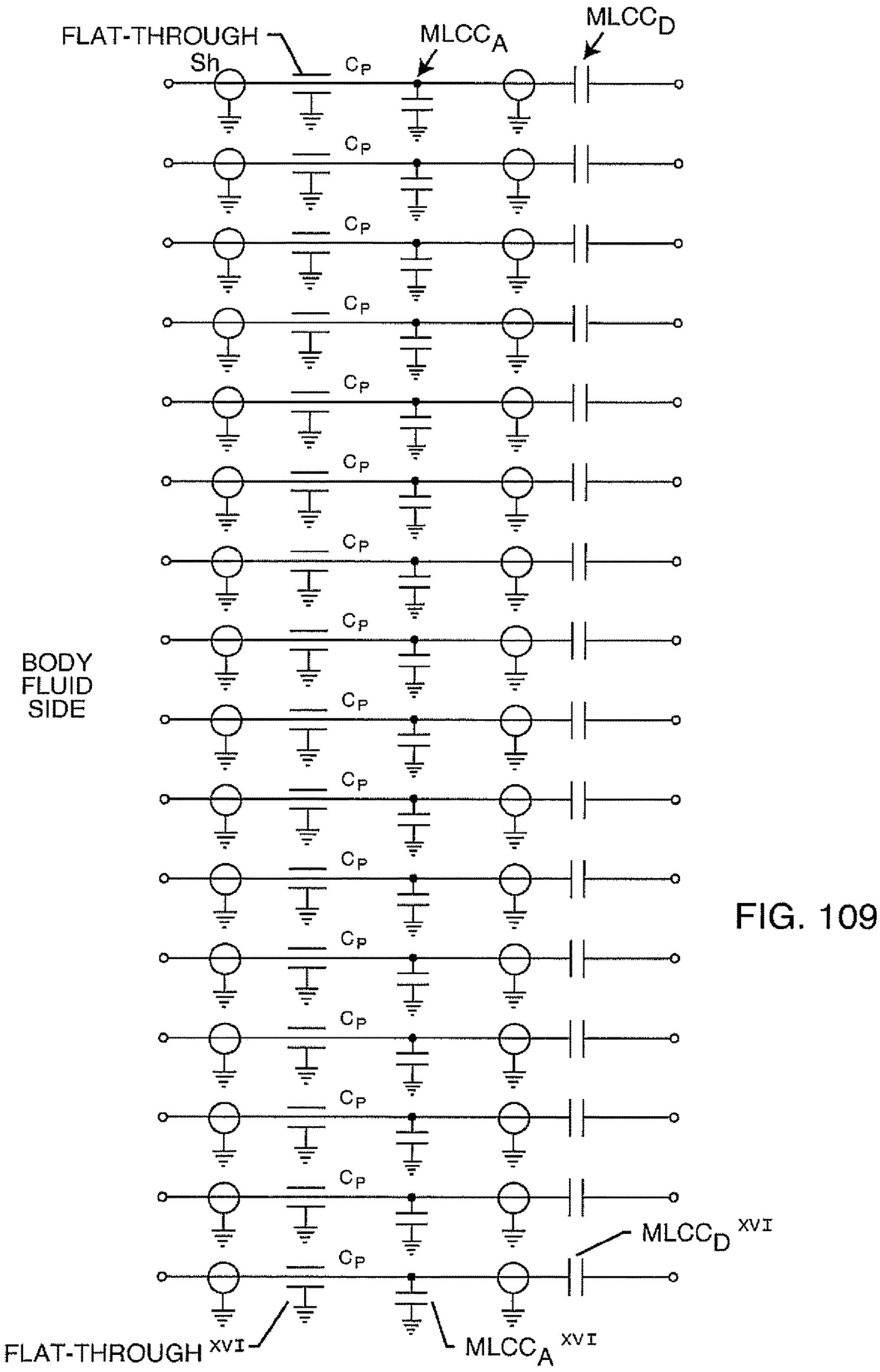
FIG. 109 is an electrical schematic diagram of the structure of FIG. 108.

Referring to the body fluid side of FIG. 109, starting with the top schematic, as we enter into the shielded area Sh, we first encounter the flat-through parasitic capacitances $C_P$ that are formed in the present invention between embedded ground shields (not shown) and the particular circuit electrode. We then encounter $MLCC_A$ which provides additional low frequency EMI filtering in accordance with the present invention. We then enter $MLCC_D$ in series which is a DC blocking capacitor which is placed in series with the circuit trace. Note that since they are both shielded, the order of $MLCC_A$ and $MLCC_D$ can be reversed without loss of EMI attenuation or body tissue protection. The purpose of series DC blocking capacitor $MLCC_D$ is to prevent DC bias from reaching body tissue and possibly causing damage or necrosis. In fact, these DC blocking capacitors are well known in the art and are generally required by regulatory agencies, such as the Federal Food and Drug Administration (FDA).

Figure 110:
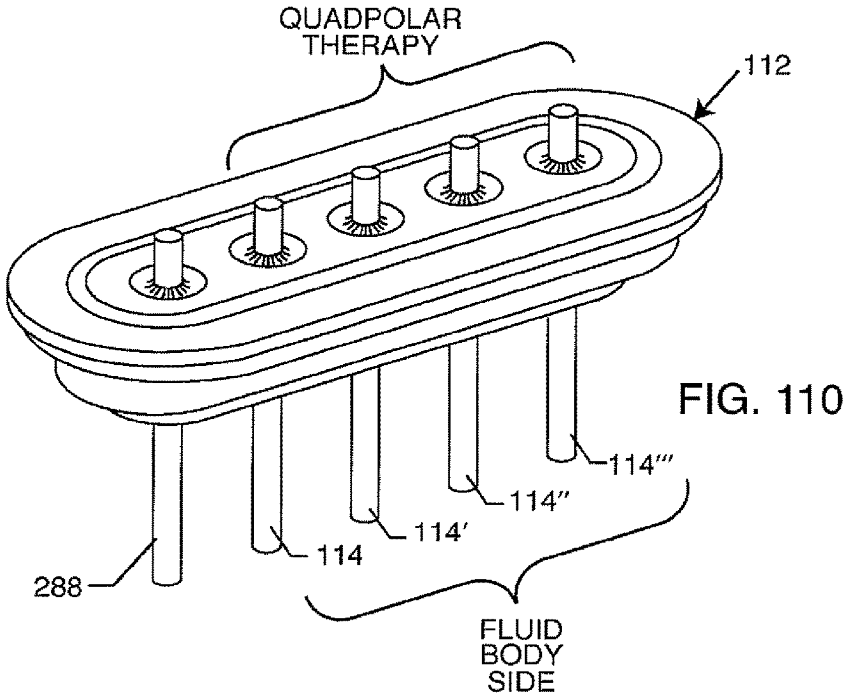
FIG. 110 is a perspective view of a five pin terminal.

FIG. 110 illustrates a 5-terminal pin hermetic seal 112 of the present invention incorporating four quadpolar lead wires 114-114''' which are designed to be connected to leads with electrodes that contact body tissue. Also shown is a fifth pin known as the RF antenna pin 288. RF distance telemetry is becoming very popular for AIMDs. In older devices, it was typical that telemetry was performed through embedded coils within the AIMD. A close coupled coil was brought up close to the skin over the implant which is also known as a telemetry wand. Signals were sent through this close coupled telemetry field in order to interrogate the implanted medical device, perform reprogramming and the like. A problem with this type of telemetry is that in order to effectively couple RF energy through the skin, it had to be very low in frequency (generally below 200 kHz). Because of the low frequency, the data transmission rate was quite slow. Since modern implantable medical devices often have over 4000 programmable functions and also store a great deal of data such as ECG wave forms, the slow transmission rate is very frustrating and time consuming for medical personnel. In addition, because of the relatively low coupling efficiency, it is necessary that the wand be placed in very close proximity to the implant. It often takes a little time to find the "sweet spot" so that one will be able to communicate with the AIMD properly. High frequency RF telemetry consisting of antenna 288 has become very popular and is generally accomplished in the 402 MHz (MICS band) or at higher frequencies. Because of the high frequency, energy transmission is very efficient. It is now possible for a doctor sitting at his desk to interrogate a pacemaker patient sitting in a chair across the room. Also because of the high frequency, the transmission data transfer rates are much higher. In other words, this system has much more bandwidth. However, a particular problem with this is that we now have a lead wire 288 that enters the interior of the AIMD which cannot, by definition, be EMI filtered. The presence of broadband EMI filtering would tend to strip off the desirable high frequency telemetry signal. Accordingly, it is important that this unfiltered antenna wire 288 be shielded and routed in such a way that EMI cannot enter into the active implantable medical device and cross-couple to sensitive circuits.

Figure 111:
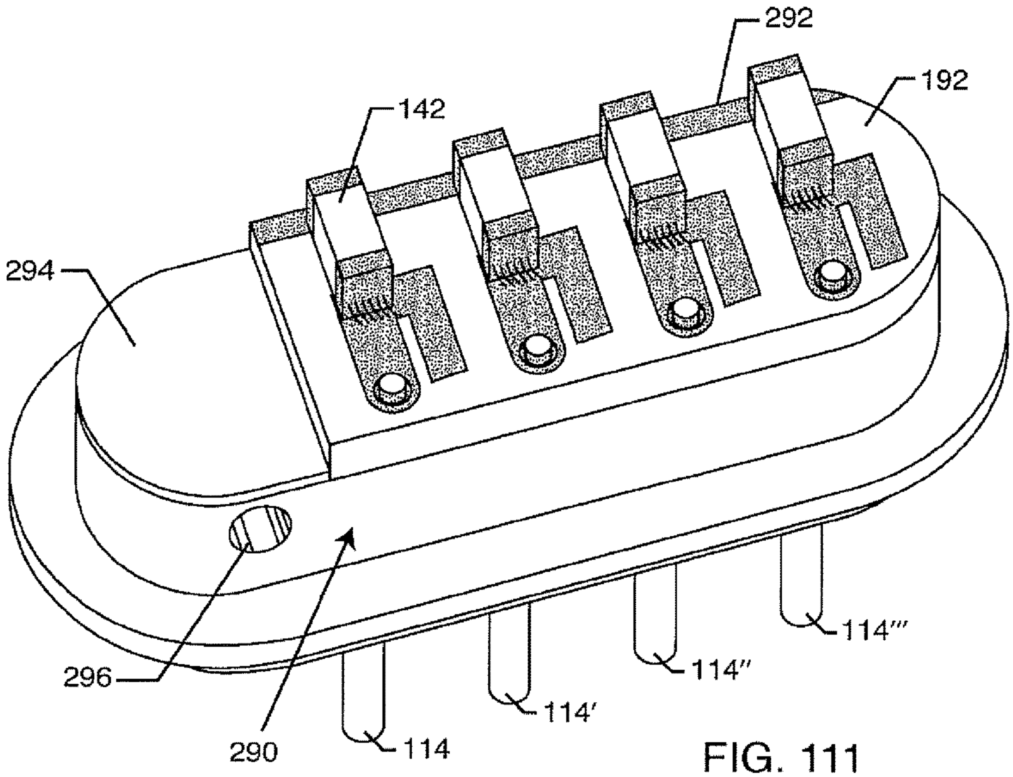
FIG. 111 is a perspective view of the five pin terminal of FIG. 110 to which a shielded three-terminal flat-through EMI/energy dissipating filter of the present invention is mounted.

Referring to FIG. 111, one can see that there is an outer metallic shield assembly 290 formed in an oval (can be any enclosed shape) that surrounds all of the terminal pins 114-114'''. This also provides a convenient location for the mounting of the hybrid substrate 192 of the present invention. Shown are MLCC capacitors 142 connected between the circuit traces and a ground metallization 292. Also shown is a novel lid assembly 294 which is metallic and is used to provide a shielded compartment which completely encapsulates or encloses the RF telemetry pin antenna 288. There is a convenient access port 296 shown which would be suitable for connection of a coaxial cable. The outer termination or shield of the coaxial cable would make electrical and mechanical connection to the ground shield 290. The interior pin of the coaxial cable would enter inside the cavity formed by the lid assembly 294 and make electrical connection to the RF telemetry pin at point 288. After all of this assembly work, the lid 294 would be attached to housing 290 by laser welding, soldering, brazing, conductive adhesives or the like. Another alternative to FIG. 111 would be to manufacture the cavity underneath the lid 294 sufficiently large to place the required electronic RF module to convert the high frequency RF telemetry signals picked up by the antenna 288 into digital signals. Then these digital signals would be EMI noise free and could be routed through either a connector pin or through the aperture 296.

Figure 112:
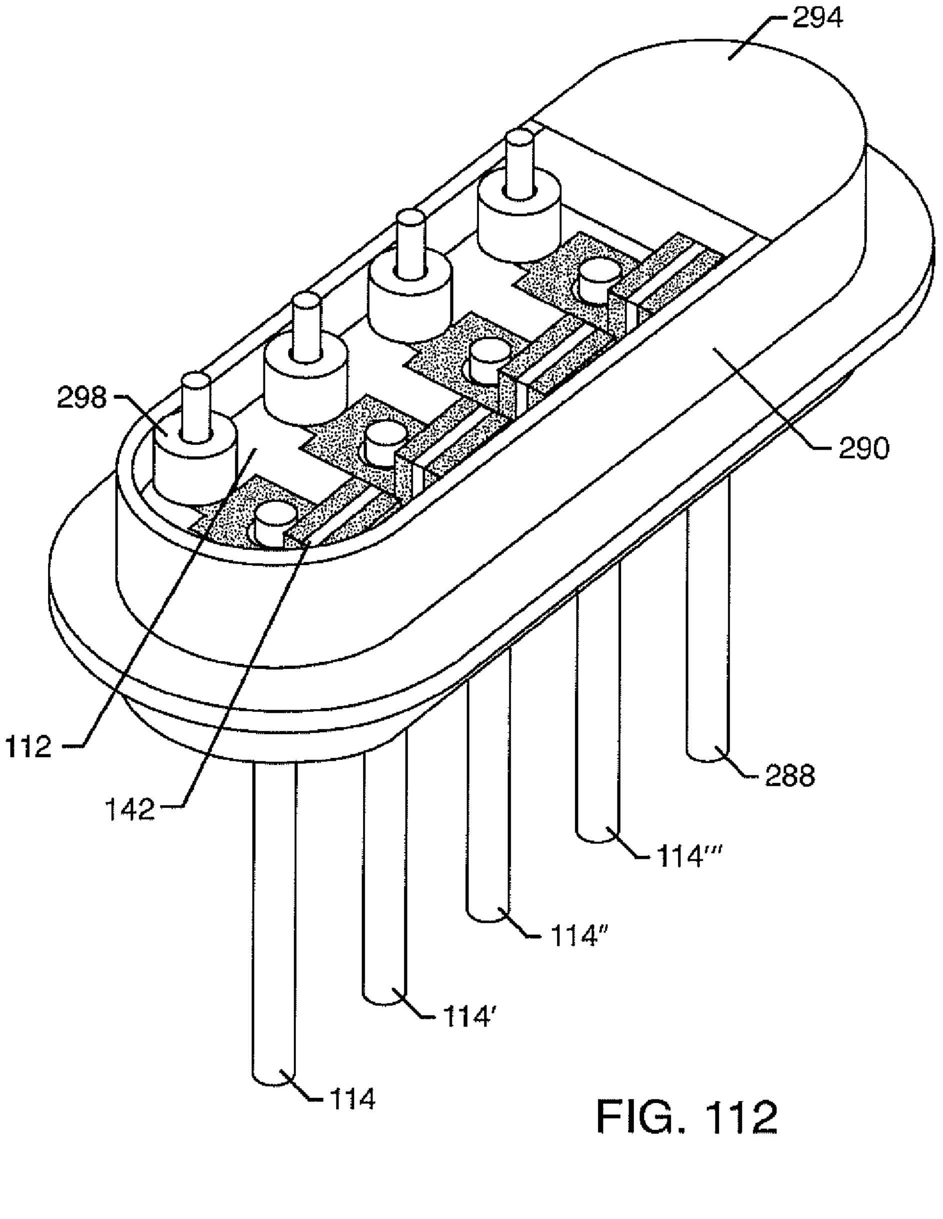
FIG. 112 is a perspective view similar to FIG. 111, showing an alternative embodiment wherein reversed geometry MLCC's are utilized to provide high frequency attenuation.

FIG. 112 is an alternative embodiment to the structure of FIG. 111, wherein reversed geometry MLCC's 142 are used to provide high frequency attenuation. In addition, optional ferrite beads 298 are used to further improve high frequency attenuation.

Figure 113:
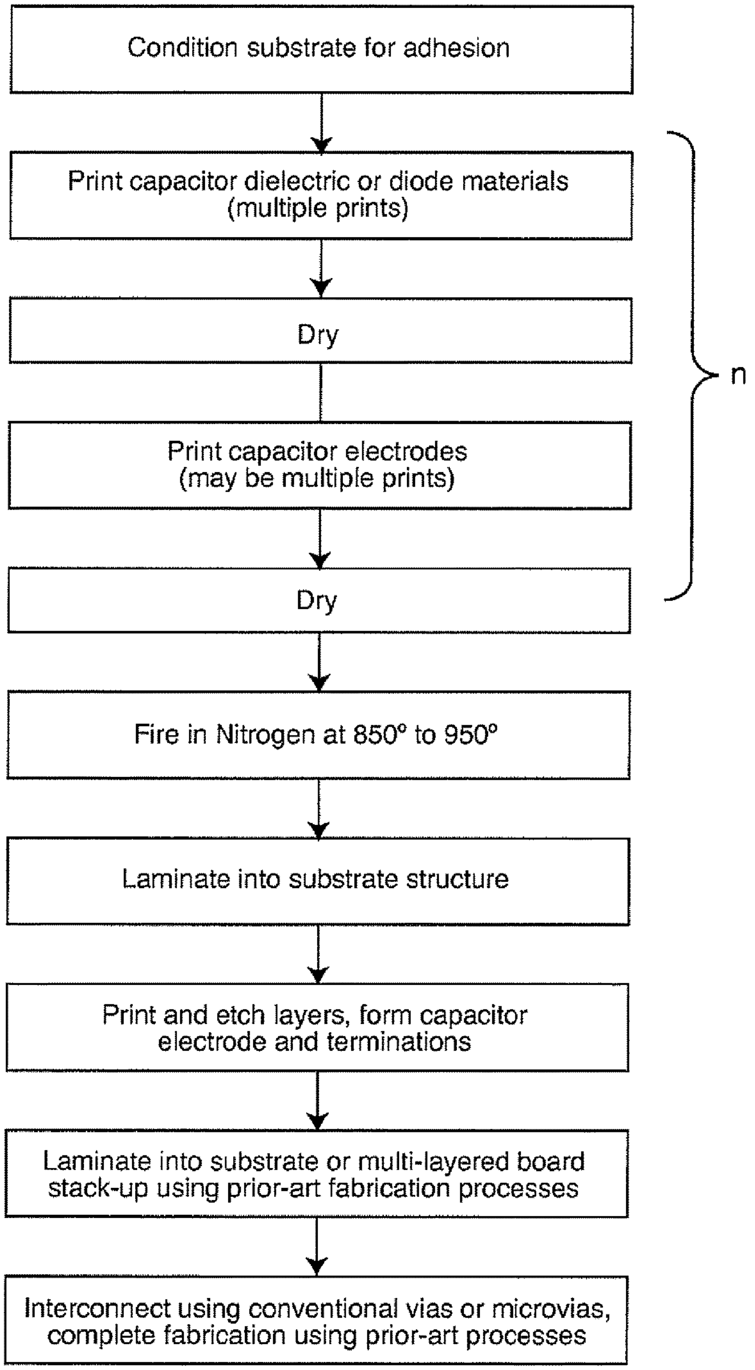
FIG. 113 is a flow chart illustrating an exemplary manufacturing process of the electronic components of the present invention.

FIG. 113 is a manufacturing flow chart that describes an alternative method of manufacturing any of the electronic components of the present invention. Monolithic ceramic capacitor manufacturing is well known in the art. However, a more efficient and cost effective way to do this would be to use thick film technology and lay down the components of the shielded three-terminal flat-through EMI/energy dissipating filter 190 all at one time all on one hybrid substrate 192. Referring to FIG. 113, you would first condition the substrate for adhesion of the various dielectric and electrode materials. Then you would print the capacitor dielectric or diode materials through multiple print operations. There is typically a drying operation between each multiple printing operation. This can be done literally in as many times (end times) as required until one reaches the desired capacitance value, inductance value or the like. The thick film component is then typically fired in nitrogen at temperatures ranging from 850 to 950 degrees C. This is then laminated into a substrate structure. The layers are printed and etched to form capacitor electrodes and terminations and this is laminated into a substrate or multi-layer board and stacked up using prior art application processes. There are then interconnects using conventional vias or micro-vias to complete the fabrication again using all prior art processes.

The novel hybrid substrate 192 of the shielded three-terminal flat-through EMI/energy dissipating filter 190 of the present invention can also be used to mount a variety of sensing circuits to be used in conjunction with external or lead-based sensors. For example, for a cardiac pacemaker application, a number of physiologic sensors could be mounted on the novel substrate, including respiration rate sensors, blood pH sensors, ventricular gradient sensors, cardiac output sensors, pre/post cardiac load sensors, contractility sensors, hemodynamics and pressure monitoring sensors. Such components could also be used in conjunction with blood gas or oxygen sensors.

Figure 114:
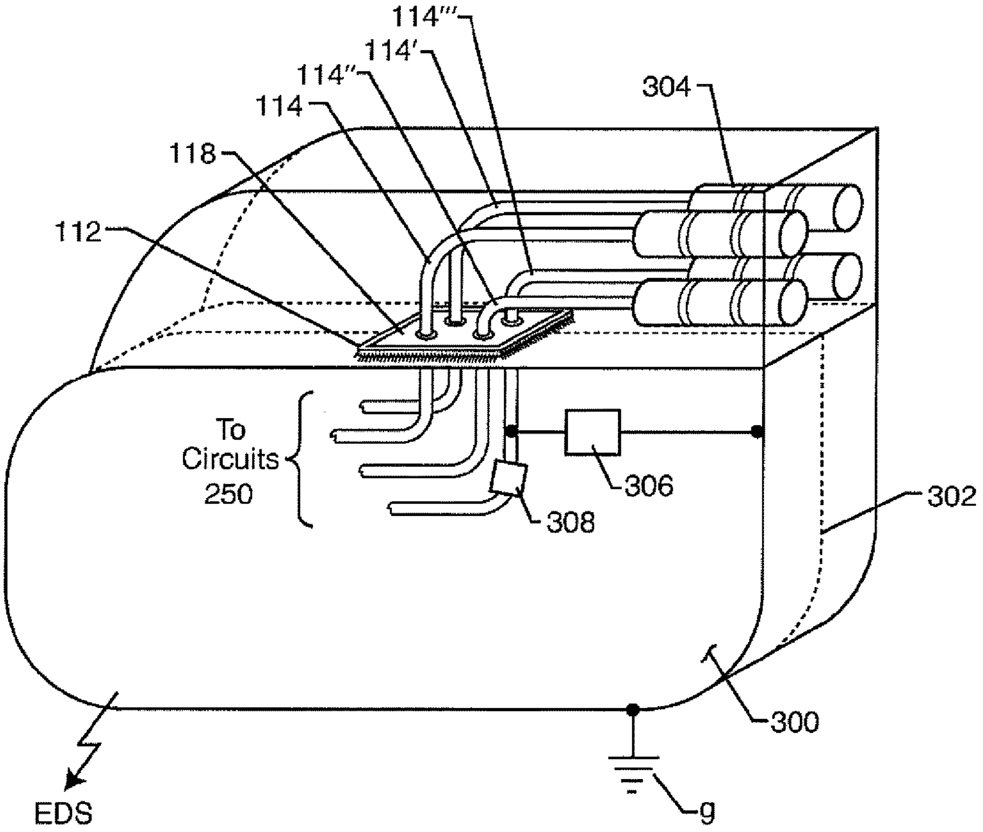
FIG. 114 is an illustration of an exemplary AIMD showing the use of variable impedance elements in connection with a lead wire within the housing of the AIMD.

FIG. 114 is an outline drawing of an AIMD such as a cardiac pacemaker. Shown is a metallic, typically titanium, housing 300. It is hermetically sealed with a laser weld 302 as shown. It has a hermetic seal 112, which is also laser welded to the titanium housing 300. The housing is also hermetically sealed by laser weld 302. The hermetic seal 112 has an insulator 118, which is well known in the prior art, through which lead wires 114-114''' pass through in non-conductive relationship with conductive housing 300. A typical pacemaker connector block 304 is shown. This can be in accordance with various ISO specifications such as IS-1, DF-1, IS-4 and the like. The female connector block 304 allows for convenient connection of a lead with a male proximal plug(s), which can be routed to the appropriate body tissue to be sensed or stimulated. The lead wires 114 through 114''' are generally routed to circuit boards, hybrid or integrated circuits or substrates 250 within the active implantable medical device housing 300. These can include cardiac sense circuits, pace circuits and the like. There are also variable impedance elements 306 and 308 as illustrated on lead wire 114'''. It should be noted that these variable impedance circuit elements would appear on all of the lead wires 114-114'''. They are only shown on lead wire 114''' to simplify the drawing. A novel feature is to use the metallic housing of the AIMD as a large surface area energy dissipating surface (EDS). This is also described in U.S. Provisional Patent Application Nos. 61/144,102 and 61/149,833, the contents of which are incorporated herein. The shielded three-terminal flat-through EMI/energy dissipating filter 190 of the present invention is an ideal way to reduce to practice and mount all of the various circuit components as described in U.S. Provisional Patent Application Nos. 61/144,102 and 61/149,833. Typically the AIMD is installed in a pectoral pocket, an abdominal pocket or in some other location that is not in intimate contact with a body organ. Accordingly, if the housing 300 were to overheat, it would be surrounded by fat and muscular tissue which is not nearly as sensitive to thermal damage as, for example, cardiac tissue or brain tissue. Also referring back to FIG. 114, one can see that for AIMDs, the relative surface area of the housing 300 is quite large in comparison to the electrode tip at the end of an implanted lead. In other words, it embodies a great deal of surface area over which to dissipate the MRI RF energy. Accordingly, the thermal rise will be very low (just a few degrees) as opposed to if the energy were concentrated over a small area in the electrode tip where the thermal rise can exceed 30 or even 60 degrees centigrade. Accordingly, it is a feature of the present invention that the housing of the AIMD be used as an energy dissipating surface optionally and ideally working in combination with bandstop filters installed at or near the distal electrode to tissue interface. In FIG. 114, this energy dissipation is represented by the arrow marked EDS. In fact, the energy is being dissipated at all points all around the metallic housing 300 to the surrounding body fluids and tissues.

Figure 115:
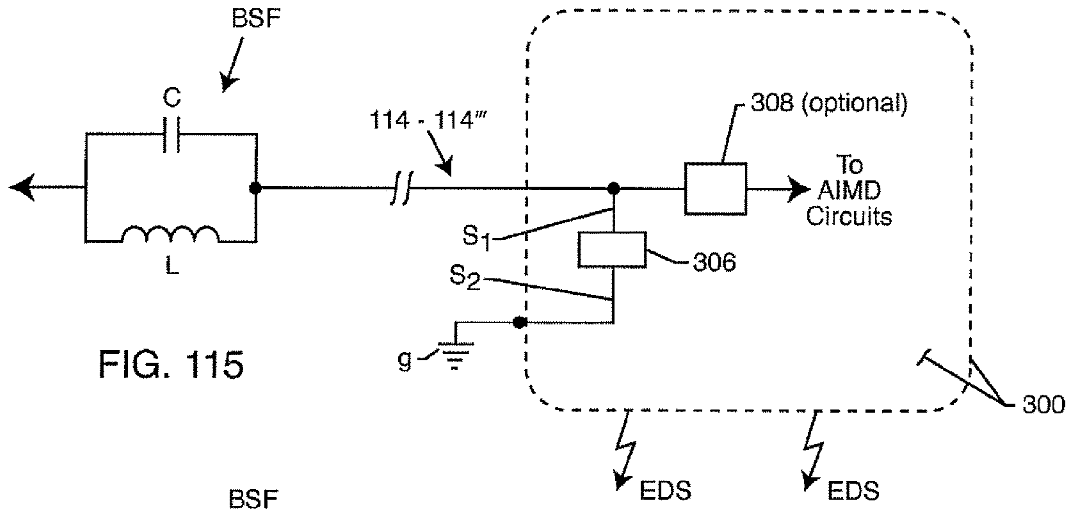
FIG. 115 is a schematic illustration of the structure shown in FIG. 114, showing use of variable impedance elements on leads that ingress and egress the AIMD.

FIG. 115 is a close-up view of the variable impedance elements 306 and 308 from FIG. 114 located within the housing 300 of the AIMD. As previously mentioned, the variable impedance elements 306 and 308 would be installed on all of the leads that ingress and egress the AIMD. The ground symbol g is shown to indicate that variable impedance element 306 is connected through the shielded ground plates of the three-terminal flat-through EMI/energy dissipating filter of the present invention to the metallic housing 300 of the AIMD. The lead wire lengths are not of particular concern since they will be embedded within the novel shielded three-terminal flat-through EMI/energy dissipating filter technology of the present invention. This is very important because each circuit electrode of the present invention is shielded such that a very high amplitude electromagnetic energy from MRI cannot re-radiate or cross-couple over to sensitive AIMD circuits (such as pacemaker sense circuits). The sections of lead wire $S_1$ and $S_2$ are kept within the shields 194 and 194' of the shielded three-terminal flat-through EMI/energy dissipating filter so that high frequency energy from MRI will not be reradiated to sensitive AIMD circuits. Ideally, circuit element 306 would be an MLCC chip 142 which would be bonded right at the point of lead wire ingress and egress.

Figure 116:
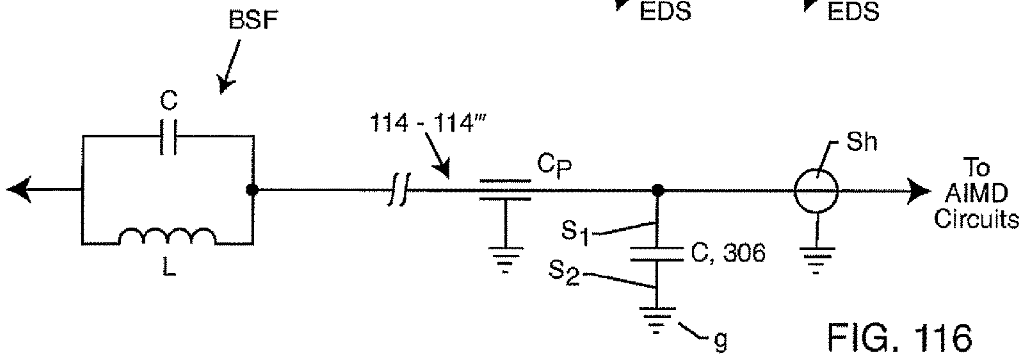
FIG. 116 is a schematic illustration showing that a variable impedance element can be a capacitor element.
Figure 117:
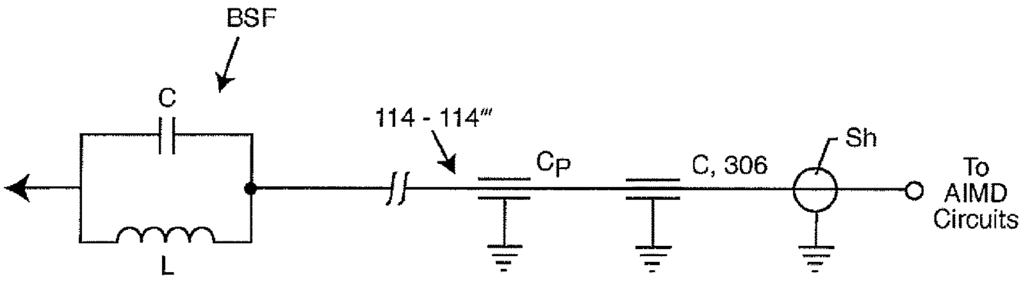
FIG. 117 is a schematic illustration similar to FIG. 116, showing that the variable impedance element can be a feedthrough capacitor element.

FIG. 116 illustrates that the variable impedance element 306 of FIG. 115 can be any type of capacitor (C) element, including MLCC chip capacitors 142 and the like. FIG. 117 illustrates that the variable impedance element 306 can also be a feedthrough capacitor C 132 as has been noted is in the prior art and illustrated in FIG. 91.

Figure 118:
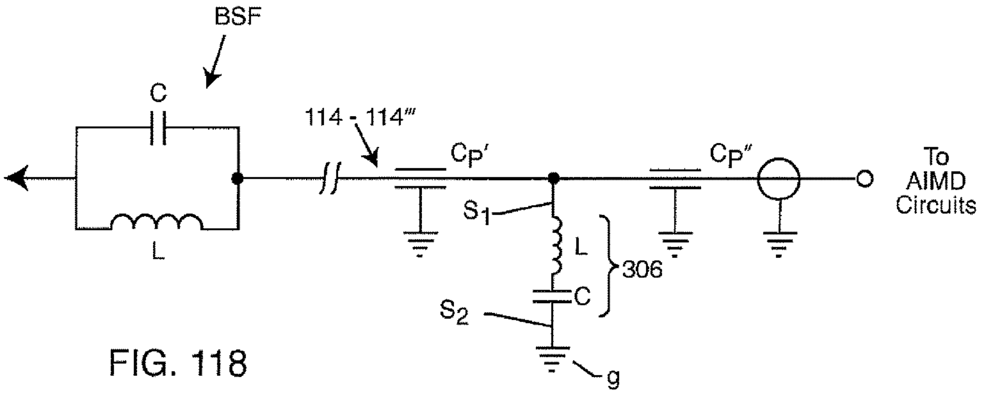
FIG. 118 is a schematic illustration similar to FIGS. 116 and 117, showing that the variable impedance element can be an L-C trap filter.

FIG. 118 indicates that variable frequency selective element 306 can also be an inductor (L) in series with a capacitor (C) also known as a L-C trap filter.

Figure 119:
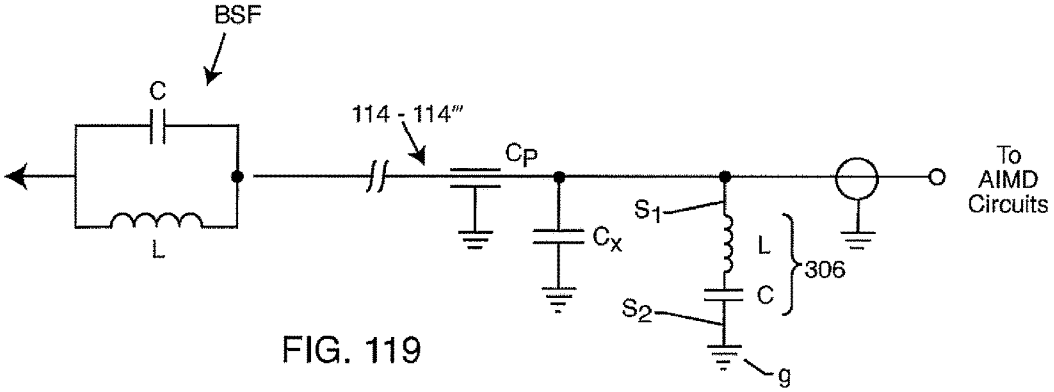
FIG. 119 is a schematic illustration similar to FIG. 118, showing use of a capacitor element in parallel with the L-C trap filter.

FIG. 119 illustrates that the trap filter of FIG. 118 can be used in combination with either a chip capacitor $C_X$ or equivalent capacitor as previously illustrated in FIG. 116 or a feedthrough capacitor as illustrated in FIG. 117. For a pacemaker or an ICD, this would be the most common embodiment. Typical capacitance value for the series resonant trap would be 270 nanohenries of inductance and 22 picofarads of capacitance. This would make the series trap filter series resonant at 64 MHz. It's also important that the designer realize that at a certain frequency, the combination of the trap filter 306 and the EMI filter $C_X$ will at some point become a parallel resonant bandstop filter. This happens at frequencies at which the trap filter becomes inductive. In other words, at resonance, the inductive reactance cancels out the capacitive reactance and the impedance of the series trap is essentially zero except for its real or resistive losses. However, at frequencies above resonance, the inductive reactance term tends to increase and dominate the capacitive reactance term. In other words, at frequencies above resonance the series LC trap will tend to look like an inductor which could then cause a secondary resonance in parallel with the feedthrough capacitor $C_X$. This means that there would be a minor degradation in the overall attenuation to electromagnetic interference. This resonant point should not appear at the frequency of a new and powerful emitter. Resonance at these emitter frequencies therefore should be avoided.

Figure 120:
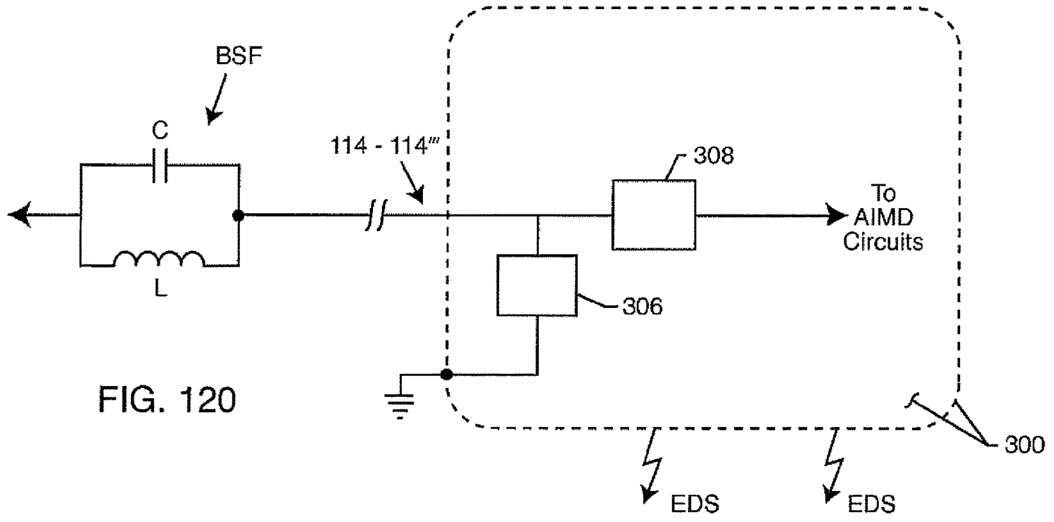
FIG. 120 is similar to FIG. 115 with emphasis on the series variable impedance element.

FIG. 120 is essentially the same as FIG. 115 except the focus is now on the series variable impedance element 308. The use of a series impedance element 308 is optional, but highly desirable for AMDs that have sense circuits.

Figure 121:
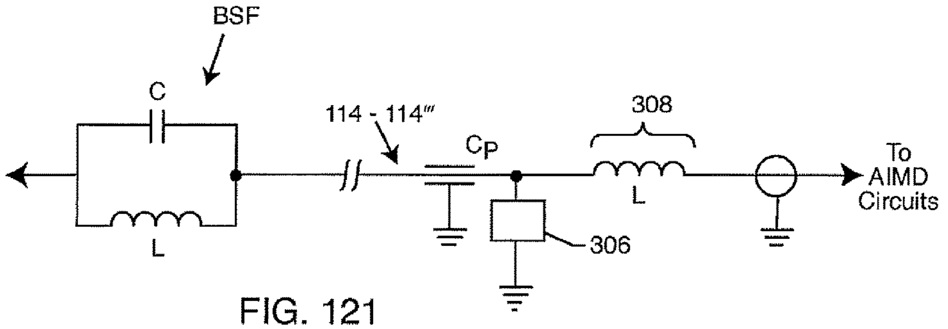
FIG. 121 illustrates that the variable impedance element can be an inductor.

FIG. 121 indicates that the variable impedance element 308 can be an inductor L as shown. This forms what is known in the art as a single element low-pass filter. The inductor element L would freely pass low frequencies such as biologic frequencies but would offer a higher impedance to high frequencies such as those of MRI RF pulse frequencies, cellular telephones and the like.

Figure 122:
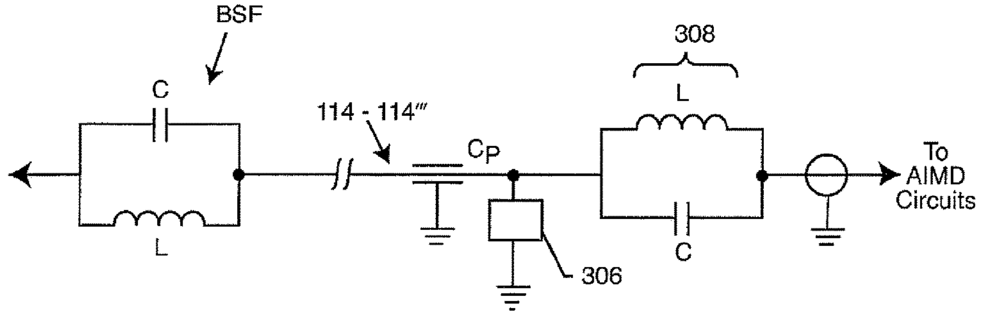
FIG. 122 illustrates that the variable impedance element can be an L-C bandstop filter.

FIG. 122 illustrates that the variable impedance element 308 can be a bandstop filter (BSF) consisting of parallel resonant L-C components as shown. The operation of the bandstop filter has been described in U.S. Patent Application Publication No. US 2007/0112398 A1, the contents of which are incorporated by reference herein.

Figure 123:
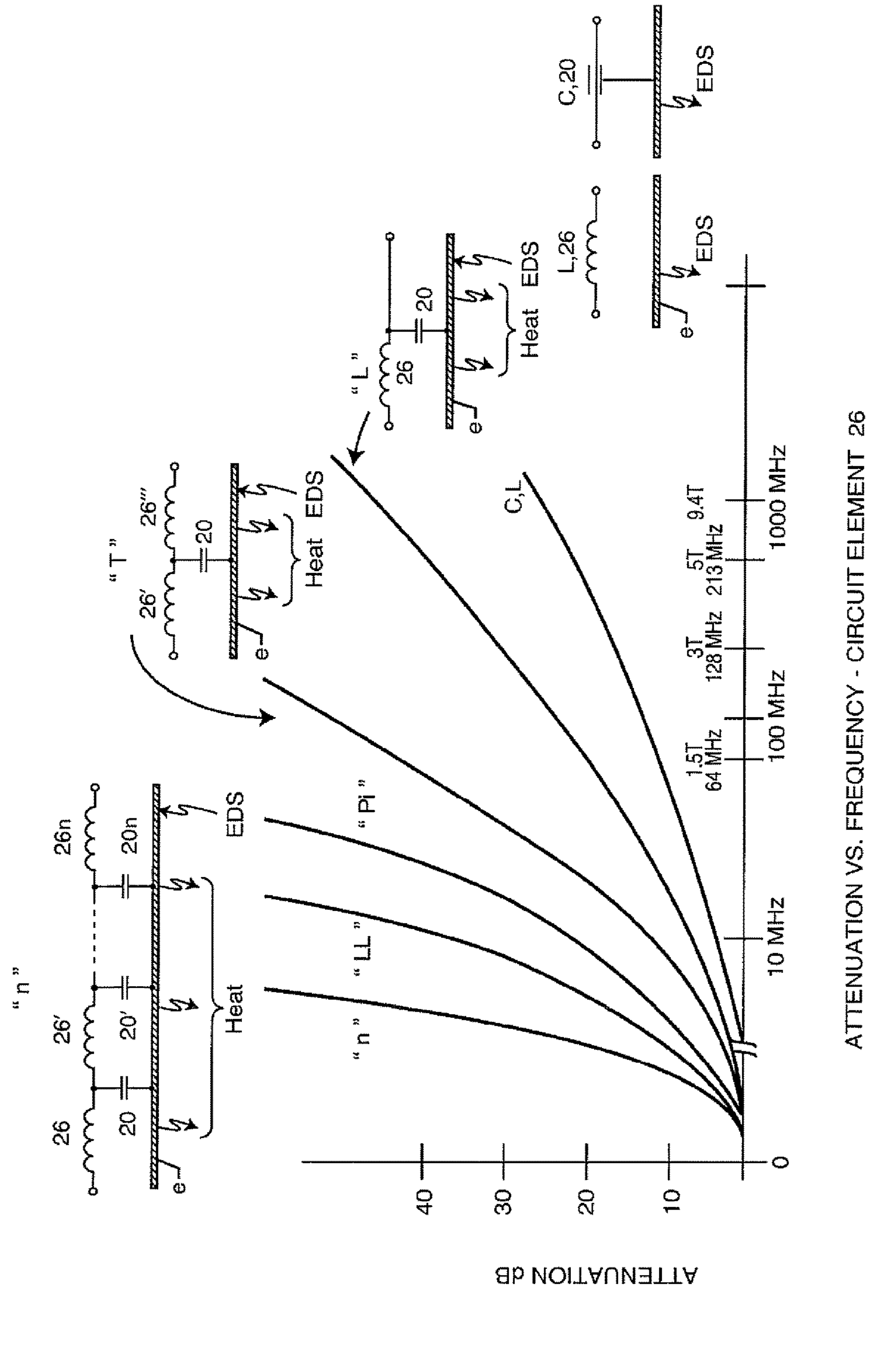

FIG. 123 illustrates that the optional series impedance element 308 can be any one of a family of low-pass filters. As previously described in connection with FIG. 121, this could be a single element low-pass filter consisting of a single inductor element L, 26 or a single capacitor element C, 20, 306. This could also be an L filter consisting of an inductor element 308, 26, and a second capacitor 304, 20. Variable reactance frequency selective element 308 could also be a T filter or an .η element filter which includes .π., LL, five element and the like-type low-pass filters. As one can see from FIG. 123, the attenuation versus frequency slope increases with increasing number of circuit elements. The other desirable effect is by having additional capacitors connected to the housing 300 of the AIMD, one creates additional circuit paths for dissipation of energy to the energy dissipating surface EDS. Accordingly, in the preferred embodiment, one would have one or more a parallel selective frequency element(s) 306 acting in cooperation with one or more series frequency reactive element(s) 308 as illustrated in FIGS. 115 and 120.

For a description of prior art feedthrough capacitors, one is referred to U.S. Pat. No. 4,424,551 or 5,333,095 or 6,765,779, wherein feedthrough capacitors having extremely low inductance are installed at the point of lead wire ingress to an active implantable medical device. For a further description of the L-C trap filter illustrated in FIG. 117, one is directed to U.S. Pat. No. 6,424,234 which illustrates very low inductance (leadless) methods of installing the trap filter at the point of lead wire ingress or egress of the AIMD or at any location in the shielded three-terminal flat-through EMI/energy dissipating filter.

Figures 124, 125:
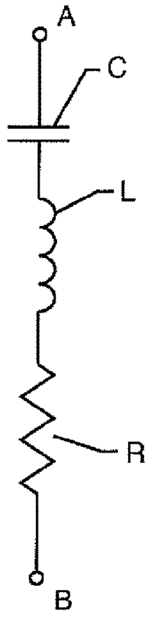

FIG. 124 illustrates a schematic diagram of a series inductor L-capacitor C filter which is commonly known in the industry as an L-C trap filter. The trap filter was previously described in FIG. 118. Referring once again to FIG. 124, there is a particular frequency for a trap filter when the capacitive reactance becomes equal and opposite to the inductive reactance. At this single frequency, the capacitive reactance and the inductive reactance cancel each other out to zero. At this point, all one has left is the parasitic resistance R. If one selects high quality factor (0) components, meaning that they are very low in resistance, then the trap filter of FIG. 124 ideally tends to look like a short circuit at its resonant frequency $f_r$ between points A and B which may comprise connections respectively to lead wires 114-114''' which are connected to active electrodes of the shielded three-terminal flat-through EMI/energy dissipating filter 190.

FIG. 125 gives the resonant frequency equation where $f_r$, in this case, was measured in hertz. Referring once again to FIG. 124, it is very important that the amount of resistance R be controlled. This is better understood by referring to FIG. 126.

Figure 126:
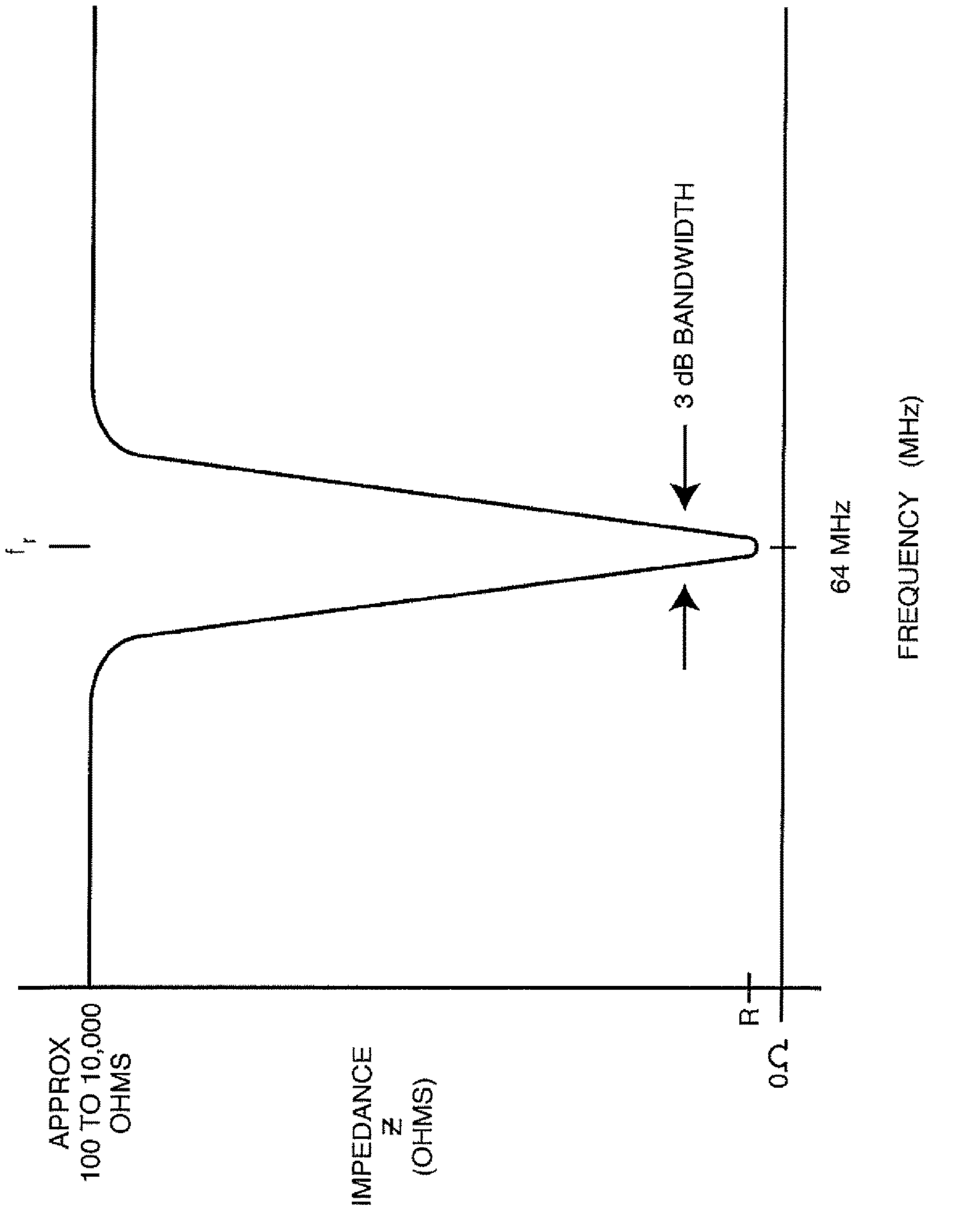

FIG. 126 is a graph that illustrates the impedance Z in ohms versus frequency of the series resonant L-C trap filter of FIG. 124. As one can see, the impedance is quite high until one reaches the frequency of resonance $f_r$. At this point, the impedance of the series L-C trap goes very low (nearly zero ohms). For frequencies above or below resonance $f_r$, depending on the selection of component values and their quality factor (Q), the impedance can be as high as 100 to 1000 or even 10,000 ohms or greater. At resonance, the impedance tries to go to zero and is limited only be the amount of parasitic resistance R (FIG. 124) that is generally composed of resistance from the inductor L and also the equivalent series resistance that comes primarily from the electrode plates of the capacitor C. There is a trade off in proper selection of the components that controls what is known as the 3 dB bandwidth. If the resistance is extremely small, then the 3 dB bandwidth will be narrower. However, this makes the trap filter more difficult to manufacture. Accordingly, the 3 dB bandwidth and the resistive element R are preferably selected so that it is convenient to manufacture the filter and tune it to, for example, 64 MHz while at the same time providing a very low impedance R at the resonant frequency. For an ideal L-C series resonant trap filter, wherein ideal would mean that the resistance R would be zero, then the impedance at resonance would be zero ohms. However, in this case, the 3 dB bandwidth would be so narrow that it would be nearly impossible to manufacture. Accordingly, some amount of resistance R is in fact desirable.

Figure 127:
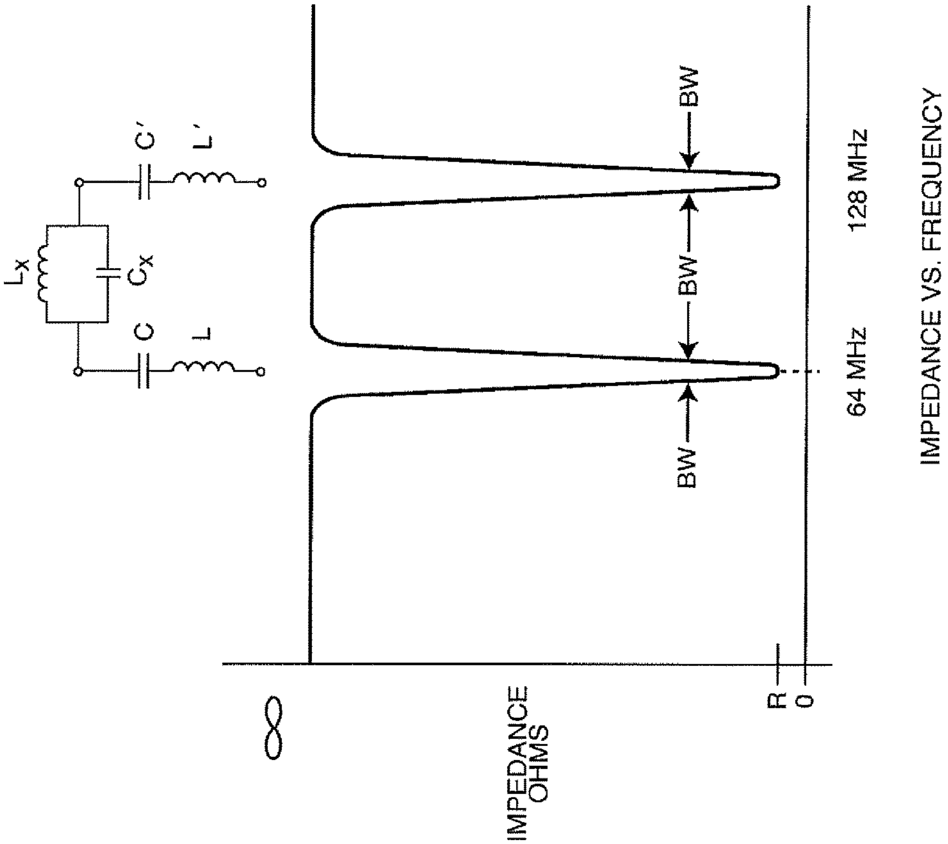

FIG. 127 is an impedance versus frequency curve wherein two trap filters have been installed which are designed to resonate at two different frequencies. In this case, the first trap filter consisting of capacitor element C and inductor element L, is designed to be self-resonant at the RF pulse frequency of a 1.5 Tesla MRI system (64 MHz). A second trap filter has been installed in parallel consisting of capacitor element C' and inductor element L' with component values designed to be self-resonant or have been designed such that the trap filter is self-resonant at 128 MHz (the operating frequency of a 3 Tesla MRI system). Referring once again to FIG. 127, one can see an optional bandstop filter BSF consisting of the parallel configuration of inductor $L_X$ and capacitor $C_X$. The purpose of the bandstop filter is to isolate the two trap filters so that they can work independently. The presence of the bandstop filter prevents secondary resonances from occurring because of the tendency for capacitors C and C' to appear in parallel along with inductors L and L' to appear in parallel. In other words, one gets a smoother double trap response when one uses a bandstop filter to electrically isolate the L-C traps into separate components at the frequency of interest.

Figure 128:
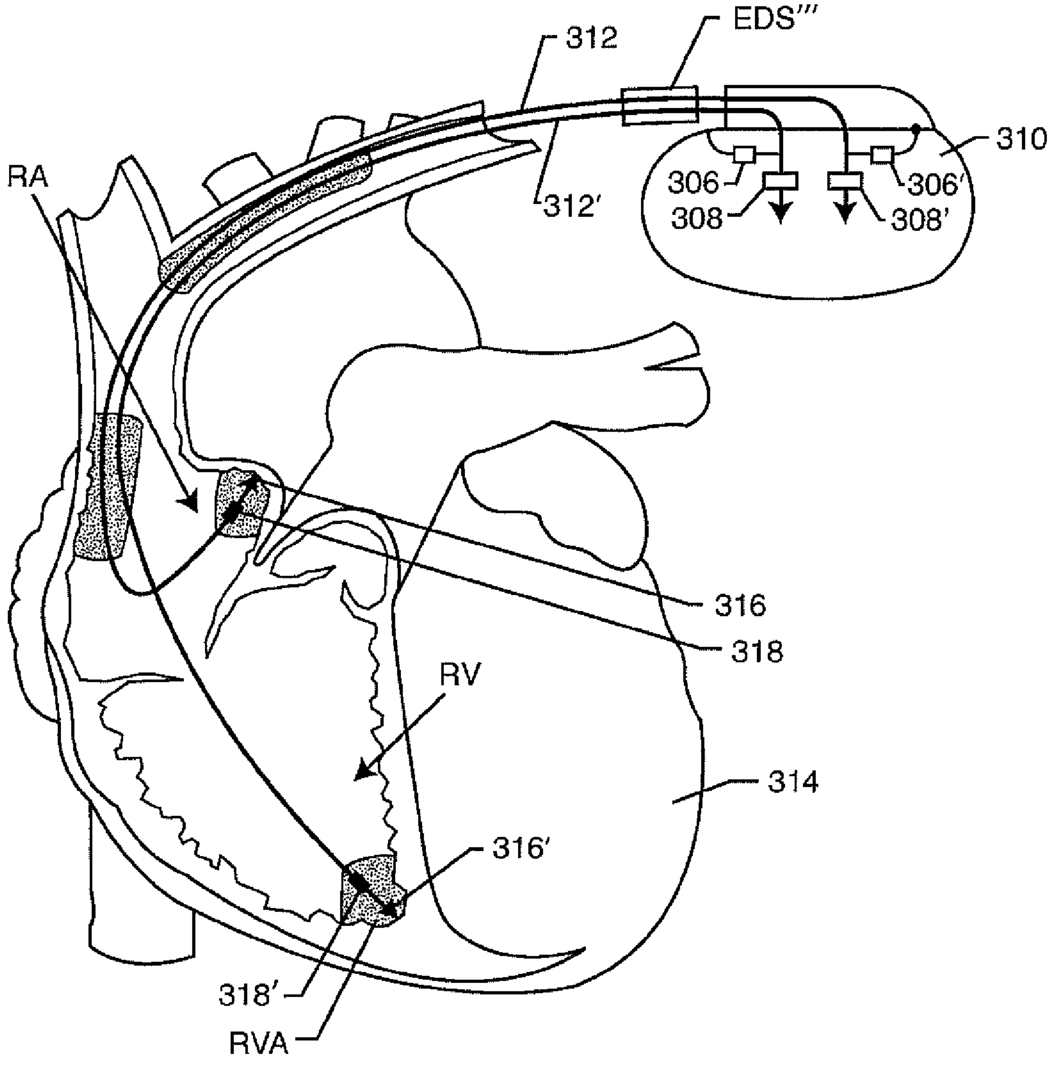

FIG. 128 is an overall outline drawing showing a cardiac pacemaker 310 with endocardial leads implanted into a human heart 314 as shown. Each lead is bipolar meaning that it contains two lead wires. One can see that lead 312 is routed into the right atrium and that lead wire 312' is routed into the right ventricular apex (RVA). The distal electrodes for the atrial lead are shown at tip 316 and ring electrode 318. In the right ventricle, the distal electrode tip 316' is shown in close proximity to distal ring electrode 318'. As previously mentioned, bandstop filters in accordance with U.S. Pat. No. 7,363,090 would be placed at or near the distal electrodes 316, 316' 318, 318' as needed. Referring to the AIMD housing 310, one can see that there are variable impedance elements 306 and 308 associated with each one of the lead wires which can be incorporated into the shielded three-terminal flat-through EMI/energy dissipating filter 190.

Figure 1:
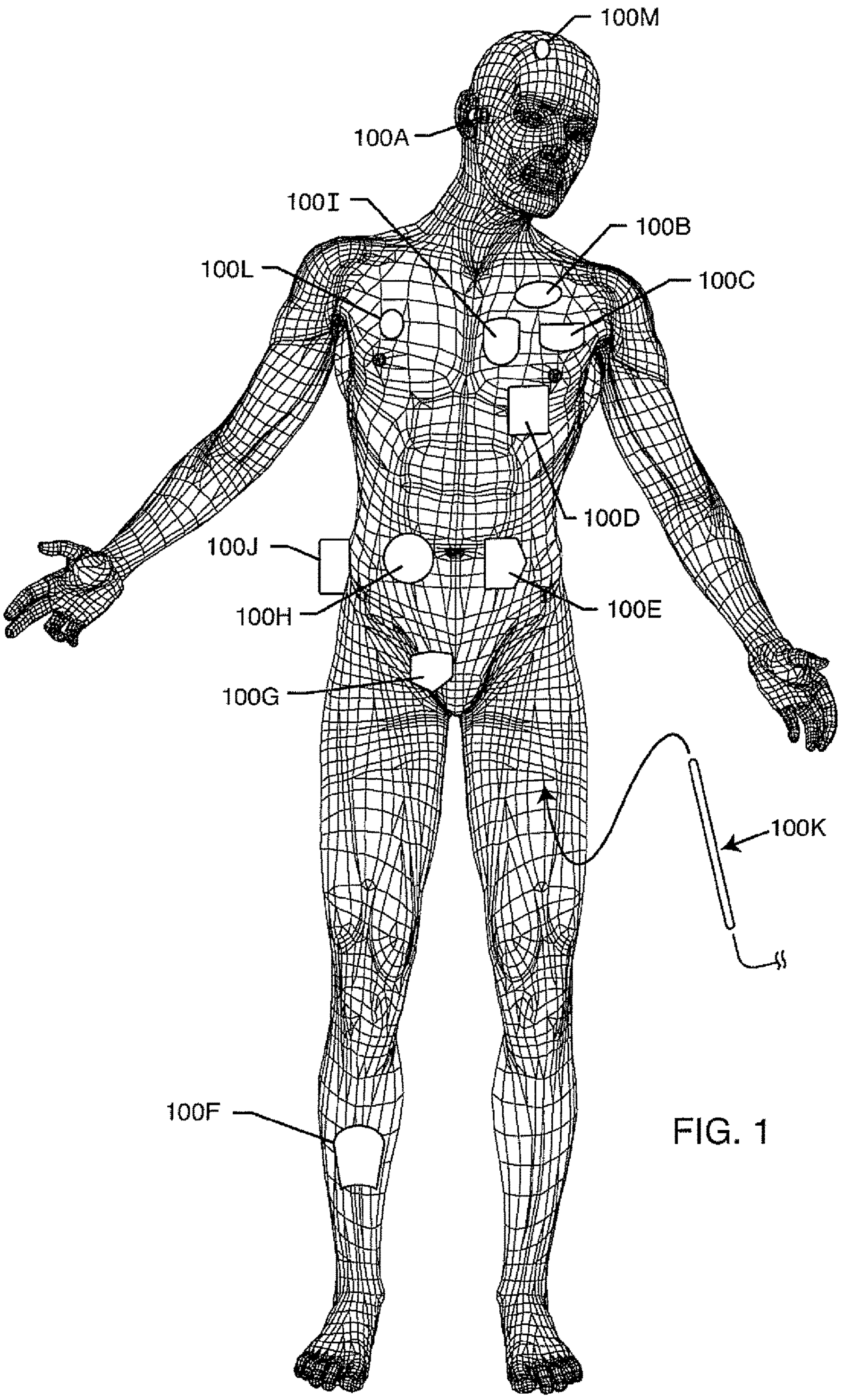
FIG. 1 is a wire formed diagram of a generic human body showing a number of implanted medical devices.
Figure 129:
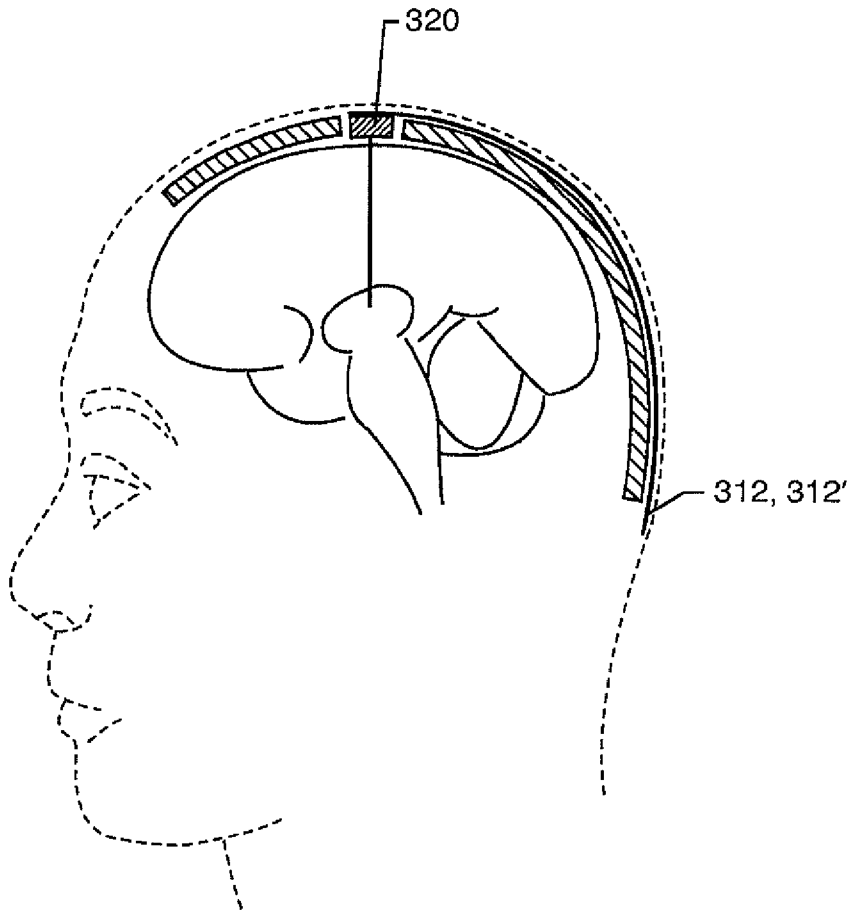

FIG. 129 is a cross-sectional view of a human head showing a deep brain stimulator electrode 320. Lead wires 312 and 312' are typically routed down the back of the neck and into the pectoral region and connected to an AIMD (brain neuromodulator). FIG. 129 is simply to illustrate that the properties of the present invention are not limited to cardiac pacemakers, but have wide applicability to a wide range of AIMDs as previously described with reference to FIG. 1. The frequency selective components described in FIG. 128 can be integrated into the shielded three-terminal flat-through EMI/energy dissipating filter of the present invention in a housing 320 in the skull burr hole which also supports the deep brain electrodes, or in the AIMD housing as shown in FIG. 114.

Figure 130:
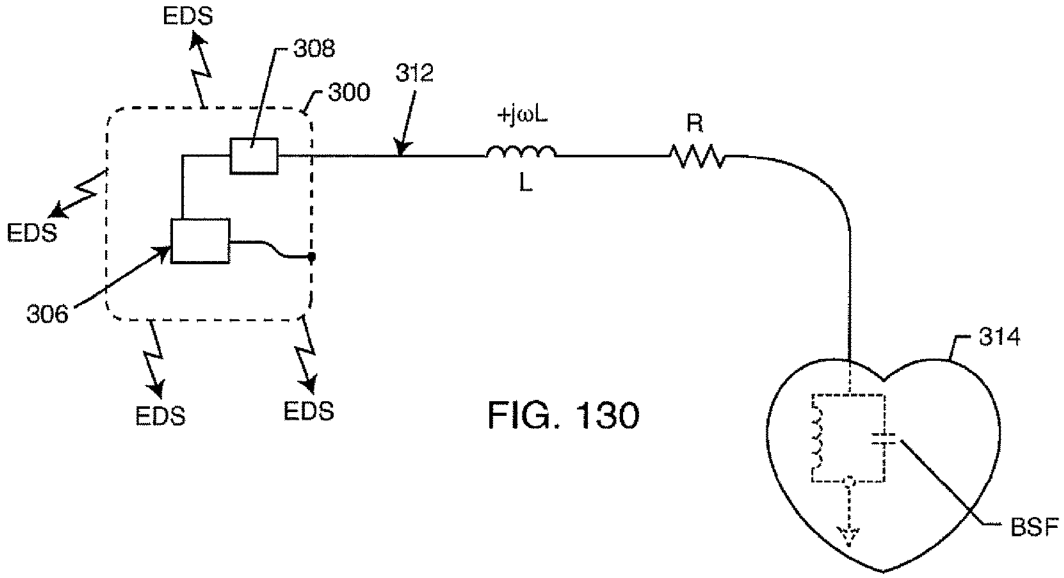

FIG. 130 shows a unipolar lead system 312 for an active implantable medical device. A unipolar lead system is shown for simplicity. It will be obvious to those skilled in the art that any number of lead wires 312 could be used. In FIG. 130, one will see that this system involves an AIMD and housing 300 attached to unipolar lead wire 312 to a human heart 314. At the distal tip or distal end of lead wire 312 is an optional bandstop filter BSF located at or near the stimulation/sense electrode. The optional bandstop filter BSF located near the distal electrode is more thoroughly described in U.S. Pat. No. 7,363,090 the contents of which are incorporated herein. The implanted lead 312 has inductive L and resistive R properties along its length. The total inductive reactance of lead 312 in ohms is given by the formula +j.omega.L as shown in FIG. 130. As mentioned, the bandstop filter BSF may or may not be present. Referring once again to FIG. 130, one can see that on the interior of the generally metallic housing 300 of the AIMD there are frequency selective components 306 and 308. These frequency selective elements can consist of various arrangements of capacitors, inductors and resistors or even short circuits as will be more fully described in FIGS. 131 though 133.

Figure 131:
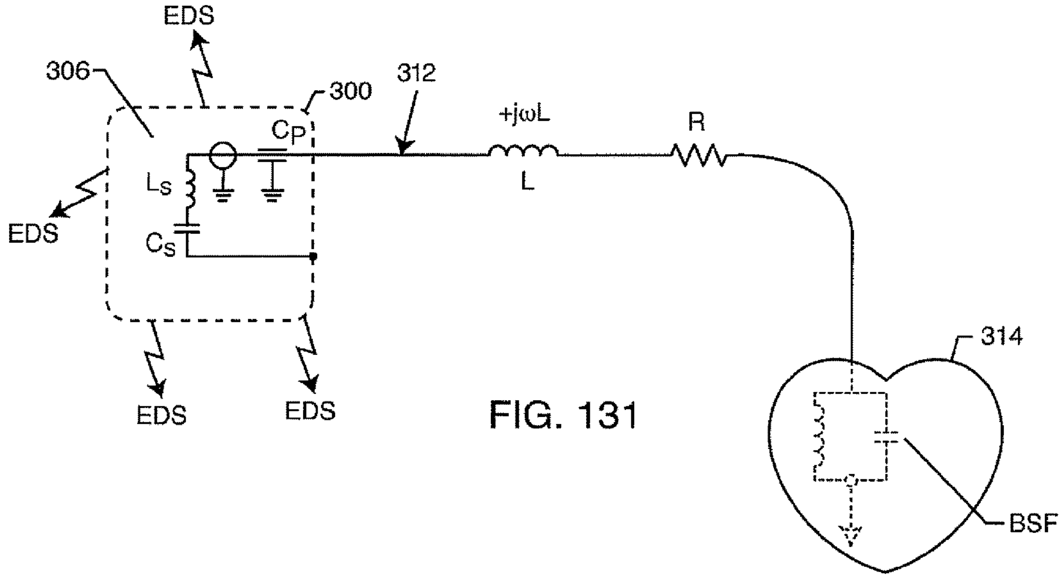

FIG. 131 illustrates the lead system of FIG. 130 wherein an L-C trap filter 306 has been placed inside of housing 300 in a shielded three-terminal flat-through EMI/energy dissipating filter assembly of the present invention. In this case, $L_S$. and $C_S$ have been designed as an L-C trap filter to be resonant at the pulsed RF frequency of the MRI equipment. Therefore, this forms an RF short to the AIMD housing 300 which becomes an energy dissipating surface EDS of the invention disclosed in U.S. Provisional Patent Application Nos. 61/144,102; and 61/149,833. It is desirable that the surface area of the AIMD housing 300 be relatively large so that very little temperature rise occurs on surface 300 as the MRI RF energy is being dissipated.

Figure 132:
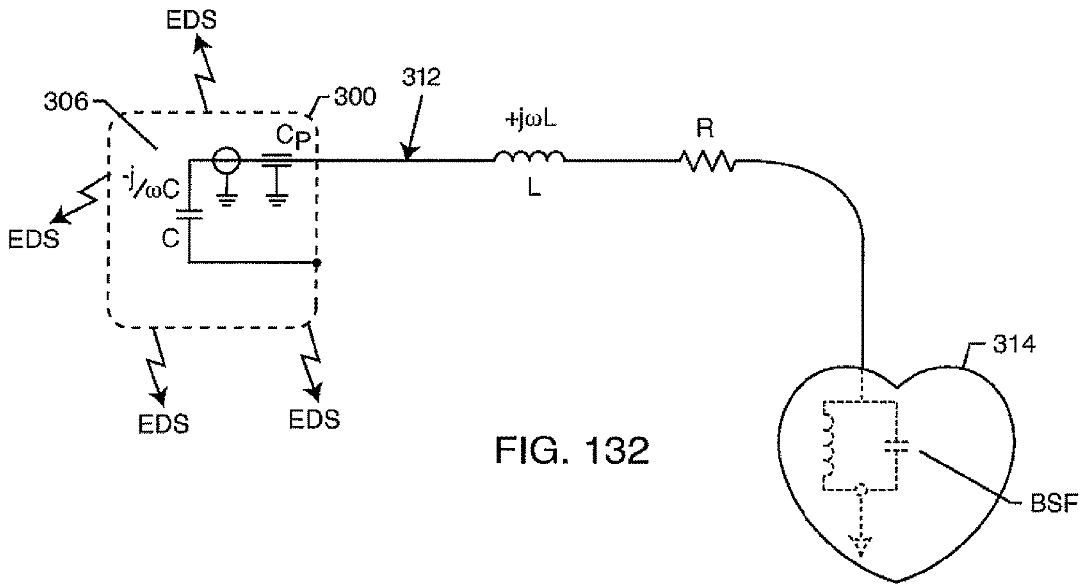

FIG. 132 is another illustration of the unipolar lead system of FIG. 130. In this case, element 306 features a capacitive element C whose capacitive reactance is given by the equation −j/.ω.C. In a preferred embodiment, the inductive reactance of the implanted lead would first be calculated (modeled) or measured in ohms. Therefore, the value of capacitance could be selected such that the capacitive reactance −j/ω.C is equal and opposite in ohms to the inductive reactance of the lead +j.ω.L. In this case, the reactances cancel each other so that one obtains maximal energy transfer to the energy dissipating surface 300.

Figure 133:
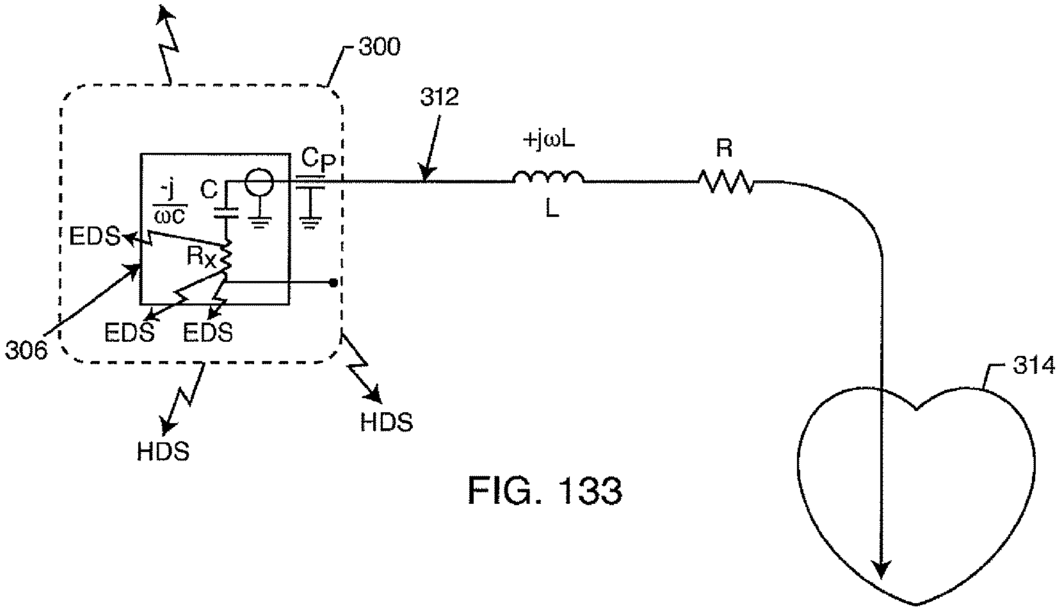

FIG. 133 is similar to the unipolar lead system previously described in FIGS. 130 and 132. In this case, as for FIG. 132, the capacitance value C has been selected such that the capacitive reactance will be equal and opposite to the inductive reactance of the implanted lead. However, in this case, the resistances are also balanced. In other words, the resistance R of the implanted lead is equal in value to a discrete resistor $R_X$ placed inside or outside of the housing 300 of the AIMD. Ideally, resistor $R_X$ would be incorporated into the shielded three-terminal flat-through EMI/energy dissipating filter of the present invention. In this case, maximum power transfer or energy will be dissipated by this discrete resistance $R_X$ as heat. In a preferred embodiment, a thermally conductive but electrically insulative material will be placed onto the shielded three-terminal flat-through EMI/energy dissipating filter over resistor $R_X$ and to the AIMD housing 300 such that maximum energy transfer from resistor $R_X$ will occur. In fact, in a preferred embodiment, resistor Rx shall have a finned high surface area housing for maximal heat transfer area to the surrounding encapsulant. Referring once again to FIG. 133, one can see that energy is radiated and conducted from a discrete resistance element Rx shown as EDS. This energy being dissipated turns to thermal (heat) energy. It is desirable to have a relatively large thermal mass located within housing 300. The AIMD housing 300 then becomes a secondary heat dissipating surface HDS. This thermal energy will be dissipated over the relatively large surface area 300 into body fluids and tissues that surround the AIMD. For example, in a cardiac pacemaker application, housing 300 would be in a pectoral muscle pocket.

Figure 134:
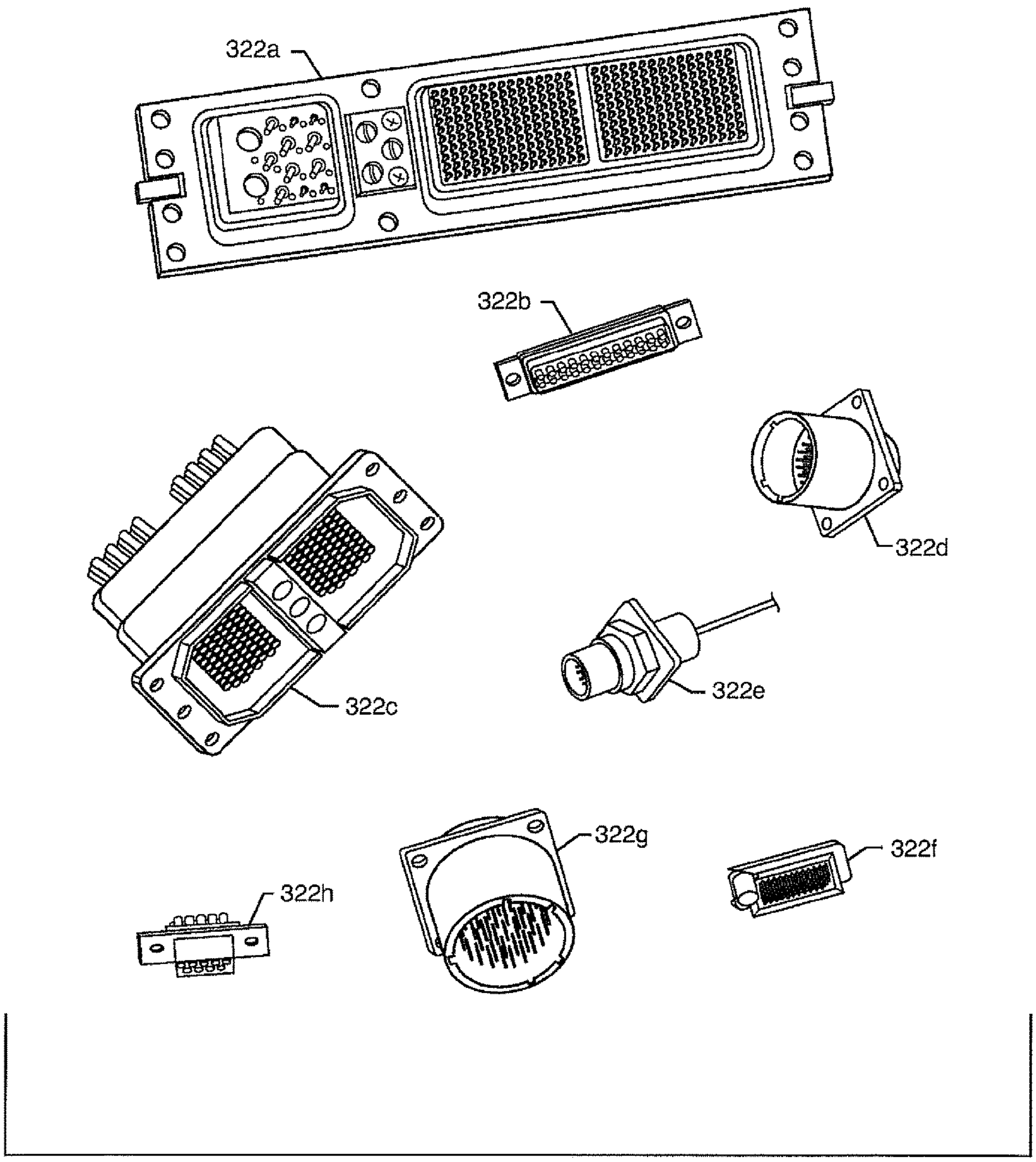

Referring back to FIGS. 132 and 133, it is not necessary that the reactances completely cancel, or in the case of FIG. 133, it's not particularly important that the resistances are exactly equal. In fact, there is a tradeoff between EMI filtering of the input capacitance and exact cancellation of the +j.ω.L component lead system. As it turns out, through actual testing, it is really only important that the impedance generally be cancelled in the lead system so that at least the bulk of the excess energy from the MRI RF pulse field will be dissipated to the housing 300 of the AIMD. For example, if one calculates that a 75 picofarad capacitor would exactly cancel the inductive reactance of the lead system, one may instead choose to use a 1000 picofarad capacitance for the flat-through and MLCCs of the shielded three-terminal flat-through EMI/energy dissipating filter. The 1000 picofarad total capacitance ($C_{P+C}$) would still draw a large amount of MRI RF energy from the lead system to the housing 300. The reason one would do this, is that a 1000 picofarad capacitor would offer much more effective EMI filtering to not only the RF pulse frequency (64 MH.sub.z or 1.4 Tesla MR system), but also for cell phones and other emitters commonly found in the pace environment. FIG. 134 illustrates filtered connectors **322*a*-322*h*** that are typically used in the military, aerospace, medical, telecommunication and other industries. In an EMI filtered connector, such as those typically used in aerospace, military, telecommunications and medical applications, it is very difficult to install a feedthrough capacitor type planar array to the connector housing or back shell without causing excessive mechanical stress to the ceramic capacitor. A number of unique mounting schemes are described in the prior art, which are designs that mechanically isolate the feedthrough capacitor while at the same time provide the proper low impedance ground connection and RF shielding properties. This is important because of the mechanical stresses that are induced in a filtered connector. It is problematic to install a relatively brittle ceramic feedthrough capacitor in a filtered connector because of the resulting mismatch in thermal coefficient of expansion of the surrounding materials, and also the significant axial and radial stresses that occur during connector mating.

By definition, connectors come in female and male versions to be mated during cable attach. The EMI filtering is typically done in either the female or the male portion, but usually not both. During the insertion or mating of the connector halves, significant mechanical forces are exerted which can be transmitted to the feedthrough capacitor. In summary, feedthrough capacitors or discrete capacitors in prior art filtered connectors involved very expensive mounting techniques. It is not unusual for the filtered connectors, as illustrated in FIG. 134, to cost hundreds or even thousands of dollars each. The present invention, using shielded three-terminal flat-through EMI/energy dissipating filter technology offers equal or even higher performance as compared to filtered connector planar array feedthrough capacitors but at a greatly reduced cost and size advantage.

With reference to FIGS. 135 and 136, there is shown a prior art sub D-type filtered connector 324 utilizing a planar array feedthrough capacitor (not shown).

FIGS. 137 and 138 illustrate other types of very common connectors. In this case, the prior art connectors 326 shown in FIGS. 137 and 138 are not filtered. In particular, in FIG. 137, one can see the exposed connector pins P. It is very common that these pins that protrude into a shielded housing in connection with the mounting of the connector. As one can see, these pins P can easily be connected to the shielded three-terminal flat-through EMI/energy dissipating filter of the present invention.

FIG. 139 shows a typical connector assembly 330 with an exploded view of a shielded three-terminal flat-through EMI/energy dissipating filter 190 of the present invention. The shielded three-terminal flat-through EMI/energy dissipating filter 190 can take any of the forms described in the present invention. For example, FIG. 141 is taken generally from partial section 141-141 from FIG. 139. One can see that the shielded three-terminal flat-through EMI/energy dissipating filter embodies an MLCC capacitor C,306. FIG. 140 illustrates the connector assembly 330, which can be hermetic or non-hermetic, which has been attached to the shielded three-terminal flat-through EMI/energy dissipating filter 190 of the present invention.

From the foregoing, it will be appreciated that the shielded three-terminal flat-through EMI/energy dissipating filters 190 of the present invention have broad application and may be used with a wide range of connectors, terminals and/or hermetic seals that support lead wires as they ingress/egress into electronic modules or shielded housings. The flat-through EMI/energy dissipating filters 190 of the present invention provide three-terminal capacitive filtering while simultaneously providing shielding of circuits and signals passing through the robust high current capability electrodes of the flat-through capacitor. The hybrid substrate 192 forming a major component of the energy-dissipating filter 190 of the present invention, functions in a very equivalent manner to prior art feedthrough capacitors in that: its internal ground plates act as a continuous part of the overall electromagnetic shield housing of the electronic device or module to physically block direct entry of high frequency RF energy through the hermetic seal or the equivalent opening for lead wire ingress and egress; and, the flat-through EMI/energy dissipating filter effective shunts undesired high frequency EMI signals off of the lead wire (electrodes) to the overall shield housing where such energy is dissipated in eddy currents resulting in a very small temperature rise.

In its most basic form, the shielded three-terminal flat-through EMI/energy dissipating filter comprises an active electrode plate through which a circuit current passes between a first terminal and a second terminal, and a plurality of shield plates substantially enveloping the active electrode plate, wherein the shield plates are collectively coupled to a grounded third terminal. More particularly, the plurality of shield plates include a first shield plate on a first side of the active electrode plate, and a second shield plate on a second side of the active electrode plate opposite the first shield plate.

Although several embodiments of the invention have been described in detail for purposes of illustration, various modifications of each may be made without departing from the spirit and scope of the invention. Accordingly, the invention is not to be limited, except as by the appended claims.

What is claimed is:

1. A filtered feedthrough assembly for an active implantable medical device, the filtered feedthrough assembly comprising:

a) a ferrule comprising an electrically conductive material, the ferrule comprising a ferrule opening, wherein a conductive ground pin is conductively and mechanically connected to the ferrule, and wherein the ferrule is configured to be attachable to an opening in a housing of an active implantable medical device;

b) an insulator at least partially residing in the ferrule opening where a first gold braze hermetically seals the insulator to the ferrule, wherein at least one insulator passageway extends through the insulator to an insulator first end surface and an insulator second end surface;

c) an electrically conductive lead wire residing in the insulator passageway where a second gold braze hermetically seals the lead wire to the insulator, the lead wire extending from a lead wire first portion to a lead wire second portion, wherein at least the lead wire second portion extends outwardly beyond the insulator second end surface;

d) a circuit board comprising spaced apart circuit board first and second sides, wherein the circuit board first side is adjacent to the insulator second end surface, and wherein the circuit board comprises at least one circuit board ground plate;

e) a circuit board first ground via hole extending through the circuit board ground plate, wherein a first ground via hole conductive material resides in the circuit board first ground via hole is conductively connected to the circuit board ground plate;

f) a circuit board second ground via hole spaced from the circuit board first ground via hole and extending through the circuit board ground plate, wherein at least a portion of the ground pin connected to the ferrule resides in the circuit board second ground via hole where a second ground via hole conductive material conductively connects the ground pin to the circuit board ground plate;

g) a circuit board active via hole extending through the circuit board, but being conductively isolated from the at least one circuit board ground plate, wherein at least a portion of the lead wire second portion extending outwardly beyond the insulator second end surface resides in the circuit board active via hole; and h) at least one two-terminal MLCC chip capacitor comprising a chip capacitor dielectric supporting at least one active electrode plate interleaved in a capacitive relationship with at least one ground electrode plate, wherein an active metallization is conductively connected to the at least one active electrode plate, and a ground metallization is connectively connected to the at least one ground electrode plate of the at least one two-terminal MLCC chip capacitor, i) wherein an active electrical path extends from the lead wire to the active metallization of the at least one two-terminal MLCC chip capacitor, and j) wherein a ground electrical path extends from the at least one two-terminal MLCC chip capacitor to the at least one circuit board ground plate and then to the ferrule, the ground electrical path comprising:

A) a ground electrical trace of the circuit board extending from a ground trace first portion to a ground trace second portion, wherein the ground trace first portion is conductively connected to the ground metaiiization of the at least one two-terminal MLCC chip capacitor, and wherein the ground trace second portion is conductively connected to the first ground via hole conductive material residing in the circuit board first ground via hole and being conductively connected to the circuit board ground plate; and B) the ground pin residing in the circuit board second ground via hole being conductively connected to the circuit board ground plate by the second ground via hole conductive material, the ground pin being conductively and mechanically connected to the ferrule.

2. The filtered feedthrough assembly of claim 1, wherein the conductive ground pin is conductively and mechanically connected to the ferrule by one of the group consisting of a third gold braze, a laser weld, and being integral with the ferrule.

3. The filtered feedthrough assembly of claim 1, wherein the ground pin resides in a countersink in the ferrule.

4. The filtered feedthrough assembly of claim 1, wherein the at least one circuit board ground plate resides at least partially on the circuit board first side adjacent to at least one of the ferrule and the insulator.

5. The filtered feedthrough assembly of claim 1, wherein the circuit board comprises at least one circuit board internal ground plate and at least one circuit board external ground plate, and wherein the first ground via hole conductive material residing in the circuit board first ground via hole conductively connects the ground trace second portion to the circuit board internal and external ground plates, and wherein the second ground via hole conductive material residing in the circuit board second ground via hole, spaced from the circuit board first ground via hole, conductively connects the circuit board internal and external ground plates to the ground pin.

6. The filtered feedthrough assembly of claim 1, wherein an active electrical trace of the circuit board extends from an active trace first end to an active trace second end, and wherein the active conductive path extending from the lead wire to the at least one two-terminal MLCC chip capacitor comprises:

a) the lead wire second portion in the circuit board active via hoie being conductively connected to the active trace first end; and b) the active trace second end being conductively connected to the active metallization of the at least one two-terminal MLCC chip capacitor.

7. The filtered feedthrough assembly of claim 6, wherein the active trace first end resides in the circuit board active via hole.

8. The filtered feedthrough assembly of claim 1, wherein the at least one two-terminal MLCC chip capacitor is spaced closer to the insulator second end surface than the insulator first end surface.

9. The filtered feedthrough assembly of claim 1, including at least one telemetry antenna wire hermetically sealed within a second insulator passageway of the insulator, wherein the telemetry antenna wire is not conductively connected to the at least one two-terminal MLCC chip capacitor.

10. The filtered feedthrough assembly of claim 1, wherein the circuit board comprises a rigid section, and wherein the circuit board rigid section comprises at least one material selected from the group consisting of a ceramic, an alumina, and an FR4 material.

11. The filtered feedthrough assembly of claim 1, wherein the circuit board comprises a flexible section, and wherein the circuit board flexible section comprises at least one material selected from the group consisting of a polyimide, a Kapton, and an acrylic material.

12. A filtered feedthrough assembly for an active implantable medical device, the filtered feedthrough assembly comprising:

a) a ferrule comprising an electrically conductive material, the ferrule comprising a ferrule opening, wherein a conductive ground pin is conductively and mechanically connected to the ferrule, and wherein the ferrule is configured to be attachable to an opening in a housing of an active implantable medical device;

b) an insulator at least partially residing in the ferrule opening where a first gold braze hermetically seals the insulator to the ferrule, wherein at least one insulator passageway extends through the insulator to an insulator device end surface and an insulator body fluid end surface;

c) an electrically conductive lead wire residing in the insulator passageway where a second gold braze hermetically seals the lead wire to the insulator, the lead wire extending from a lead wire first portion to a lead wire second portion, wherein at least the lead wire second portion extends outwardly beyond the insulator device end surface;

d) a circuit board comprising spaced apart circuit board first and second sides, wherein the circuit board first side is adjacent to the insulator device side, and wherein the circuit board comprises at least one circuit board ground plate;

e) a circuit board first ground via hole extending through the circuit board ground plate, wherein a first ground via hole conductive material residing in the circuit board first ground via hole is conductively connected to the circuit board ground plate;

f) a circuit board second ground via hole spaced from the circuit board first ground via hole and extending through the circuit board ground plate, wherein at least a portion of the ground pin connected to the ferrule resides in the circuit board second ground via hole where a second ground via hole conductive material conductively connects the ground pin to the circuit board ground plate;

g) a circuit board active via hole extending through the circuit board, but being conductively isolated from the at least one circuit board ground plate, wherein at least a portion of the lead wire second portion extending outwardly beyond the insulator device end surface resides in the circuit board active via hole; and h) at least one two-terminal MLCC chip capacitor comprising a chip capacitor dielectric supporting at least one active electrode plate interleaved in a capacitive relationship with at least one ground electrode plate, wherein an active metallization is conductively connected to the at least one active electrode plate, and a ground metallization is conductively connected to the at least one ground electrode plate of the at least one two-terminal MLCC chip capacitor, i) wherein an active conductive path extends from the lead wire to the at least one two-terminal MLCC chip capacitor, the active conductive path comprising an active electrical trace of the circuit board, the active trace extending from an active trace first portion to an active trace second portion, wherein the lead wire second portion residing in the circuit board active via hole is conductively connected to the active trace first portion, and wherein the active trace second portion is conductively connected to the active metallization of the at least one two-terminal MLCC chip capacitor, and j) wherein a ground conductive path extends from the at least one two-terminal MLCC chip capacitor to the at least one circuit board ground plate and then to the ferrule, the ground conductive path comprising:

A) a ground electrical trace of the circuit board, the ground trace extending from a ground trace first portion to a ground trace second portion, wherein the ground trace first portion is conductively connected to the ground metallization of the at least one two-terminal MLCC chip capacitor, and wherein the ground trace second portion is conductively connected to the first ground via hole conductive material residing in the circuit board first ground via hole and being conductively connected to the circuit board ground plate; and B) the ground pin residing in the circuit board second ground via hole being conductively connected to the circuit board ground plate by the second ground via hole conductive material, the ground pin being conductively and mechanically connected to the ferrule.

13. The filtered feedthrough assembly of claim 12, wherein the conductive ground pin is conductively and mechanically connected to the ferrule by one of the group consisting of a third gold braze, a laser weld, and being integral with the ferrule.

14. The filtered feedthrough assembly of claim 12, wherein the ground pin resides in a countersink in the ferrule.

15. The filtered feedthrough assembly of claim 12, wherein the at least one circuit board ground plate resides at least partially on the circuit board first side adjacent to at least one of the ferrule and the insulator.

16. The filtered feedthrough assembly of claim 12, wherein the circuit board comprises at least one circuit board internal ground plate and at least one circuit board external ground plate, and wherein the first ground via hole conductive material residing in the circuit board first ground via hole conductively connects the ground trace second portion to the circuit board internal and external ground plates, and wherein the second ground via hole conductive material residing in the circuit board second ground via hole, spaced from the circuit board first ground via hole, conductively connects the circuit board internal and external ground plates to the ground pin.

17. The filtered feedthrough assembly of claim 12, wherein the active trace first portion resides in the circuit board active via hole.

18. The filtered feedthrough assembly of claim 12, wherein the at least one two-terminal MLCC chip capacitor is spaced closer to the insulator device end surface than the insulator body fluid end surface.

19. The filtered feedthrough assembly of claim 12, wherein the lead wire first portion is spaced outwardly beyond the insulator body fluid surface.

20. The filtered feedthrough assembly of claim 12, including at least one telemetry antenna wire hermetically sealed within a second insulator passageway serving as an insulator telemetry passageway, wherein the telemetry antenna wire is not conductively connected to the at least one two-terminal MLCC chip capacitor.

21. The filtered feedthrough assembly of claim 12, wherein the circuit board comprises a rigid section, and wherein the circuit board rigid section comprises at least one material selected from the group consisting of a ceramic, an alumina, and an FR4 material.

22. The filtered feedthrough assembly of claim 12, wherein the circuit board comprises a flexible section, and wherein the circuit board flexible section comprises at least one material selected from the group consisting of a polyimide, a Kapton, and an acrylic material.

23. A filtered feedthrough assembly for an active implantable medical device, the filtered feedthrough assembly comprising:

a) a ferrule comprising an electrically conductive material, the ferrule comprising a ferrule opening, wherein a conductive ground pin is conductively and mechanically connected to the ferrule, and wherein the ferrule is configured to be attachable to an opening in a housing of an active implantable medical device;

b) an insulator at least partially residing in the ferrule opening where a first gold braze hermetically seals the insulator to the ferrule, wherein at least one insulator passageway extends through the insulator to an insulator first end surface and an insulator second end surface;

c) an electrically conductive active lead wire residing in the insulator passageway where a second gold braze hermetically seals the lead wire to the insulator, the lead wire extending from a lead wire first portion to a lead wire second portion, wherein at least the lead wire second portion extends outwardly beyond the insulator second end surface;

d) a circuit board comprising spaced apart circuit board first and second sides, wherein the circuit board first side is adjacent to the insulator second end surface, and wherein the circuit board comprises at least one circuit board ground plate extending from a circuit board ground plate first portion spaced from a circuit board ground plate second portion;

e) a circuit board first ground via hole extending through the circuit board ground plate first portion, wherein a first ground via hole conductive material residing in the circuit board first ground via hole is conductively connected to the circuit board ground plate first portion;

f) at least one circuit board second ground via hole spaced from the circuit board first ground via hole and extending through the circuit board ground plate second portion, wherein at least a portion of the ground pin connected to the ferrule resides in the circuit board second ground via hole where a second ground via hole conductive material conductively connects the ground pin to the circuit board ground plate second portion;

g) a circuit board active via hole extending through the circuit board, but being conductively isolated from the at least one circuit board ground plate, wherein at least a portion of the lead wire second portion extending outwardly beyond the insulator second end surface resides in the circuit board active via hole; and h) at least one two-terminal MLCC chip capacitor comprising a chip capacitor dielectric supporting at least one active electrode plate interleaved in a capacitive relationship with at least one ground electrode plate, wherein an active metallization is conductively connected to the at least one active electrode plate, and a ground metallization is conductively connected to the at least one ground electrode plate of the at least one two-terminal MLCC chip capacitor, i) wherein the lead wire second portion residing in the circuit board active via hole is conductively connected to the active metallization of the at least one two-terminal MLCC chip capacitor, and j) wherein:

A) the ground metallization of the at least one two-terminal MLCC chip capacitor is conductively connected to the first ground via hole conductive material residing in the circuit board first ground via hole, the first ground via hole conductive material being conductively connected to the circuit board ground plate first portion; and B) the ground pin residing in the circuit board second ground via hole being conductively connected to the circuit board ground plate second portion by the second ground via hole conductive material, the ground pin being conductively and mechanically connected to the ferrule.

24. A filtered feedthrough assembly for an active implantable medical device, the filtered feedthrough assembly comprising:

a) a ferrule comprising an electrically conductive material, the ferrule comprising a ferrule opening, wherein a plurality of conductive ground pins are conductively and mechanically connected to the ferrule by respective first gold brazes, and wherein the ferrule is configured to be attachable to an opening in a housing of an active implantable medical device;

b) an insulator at least partially residing in the ferrule opening where a second gold braze hermetically seals the insulator to the ferrule, wherein a plurality of insulator passageways extend through the insulator to an insulator first end surface and an insulator second end surface;

c) a plurality of electrically conductive lead wires residing in respective ones of the insulator passageways where a plurality of respective third gold brazes hermetically seals each of the lead wires to the insulator, each lead wire extending from a lead wire first portion to a lead wire second portion, wherein at least the lead wire second portion extends outwardly beyond the insulator second end surface;

d) a circuit board comprising spaced apart circuit board first and second sides, wherein the circuit board first side is adjacent to the insulator second end surface, and wherein the circuit board comprises at least one circuit board ground plate;

e) a plurality of circuit board first ground via holes extending through the circuit board ground plate, wherein a first ground via hole conductive material resides in each of the circuit board first ground via holes;

f) a plurality of circuit board second ground via holes spaced from the plurality of circuit board first ground via holes and extending through the circuit board ground plate, wherein at least a portion of one of the ground pins connected to the ferrule resides in a respective one of the circuit board second ground via holes where a second ground via hole conductive material conductively connects the ground pin to the circuit board ground plate;

g) a plurality of circuit board active via holes extending through the circuit board, but being conductively isolated from the at least one circuit board ground plate, wherein at least a portion of one of the plurality of lead wire second portions extending outwardly beyond the insulator second end surface resides in a respective one of the circuit board active via holes;

h) a plurality of two-terminal MLCC chip capacitors, each comprising a chip capacitor dielectric supporting at least one active electrode plate interleaved in a capacitive relationship with at least one ground electrode plate, wherein each two-terminal MLCC chip capacitor has an active metallization conductively connected to the at least one active electrode plate, and a ground metallization conductiveiy connected to the at least one ground electrode plate;

i) a plurality of active electrical traces of the circuit board, each active trace extending from an active trace first portion to an active trace second portion; and j) a plurality of ground electrical traces of the circuit board, each ground trace extending from a ground trace first portion to a ground trace second portion, k) wherein there are a plurality of active conductive paths, each active path extending from one of the plurality of lead wires to a respective one of the two-terminal MLCC chip capacitors, each active conductive path comprising:

A) the lead wire second portion residing in a respective one of the circuit board active via holes being conductively connected to a respective one of the active trace first portions; and B) the active trace second portion being conductively connected to the corresponding active metallization of a respective one of the two-terminal MLCC chip capacitors, and l) wherein there are a plurality of ground conductive paths, each ground path extending from the two-terminal MLCC chip capacitor of the corresponding active path to the at least one circuit board ground plate and then to the ferrule, each of the ground conductive paths comprising:

C) the ground trace first portion being conductively connected to the ground metallization of the corresponding two-terminal MLCC chip capacitor;

D) the ground trace second portion being conductively connected to the first ground via hole conductive material residing in the circuit board first ground via hole, the first ground via hole conductive material being conductively connected to the circuit board ground plate; and E) the ground pins residing in the circuit board second ground via holes being conductively connected to the circuit board ground plate by the second ground via hole conductive material, spaced from the circuit board first ground via holes, the ground pins being conductively and mechanically connected to the ferrule.

25. The filtered feedthrough assembly of claim 24, wherein the plurality of lead wires reside between at least two of the plurality of ground pins.

26. The filtered feedthrough assembly of claim 24, wherein the at least one circuit board ground plate resides at least partially on the circuit board first side adjacent to at least one of the ferrule and the insulator.

27. The filtered feedthrough assembiy of claim 24, wherein the circuit board comprises at least one circuit board internal ground plate and at least one circuit board external ground plate, and wherein the first ground via hole conductive material residing in the circuit board first ground via holes is conductively connected to the circuit board internal and external ground plates, and wherein the second ground via hole conductive material residing in the circuit board second ground via holes, spaced from the circuit board first ground via holes, conductively connects the circuit board internal and external ground plates to the ground pins.

28. The filtered feedthrough assembly of claim 24, wherein the active trace first portions reside in a respective one of the circuit board active via holes.

29. The filtered feedthrough assembly of claim 24, wherein the plurality of two-terminal MLCC chip capacitors are spaced closer to the insulator second end surface than the insulator first end surface.

30. The filtered feedthrough assembly of claim 24, wherein the lead wire first portions are spaced outwardly beyond the insulator first end surface.

31. The filtered feedthrough assembly of claim 24, including at least one telemetry antenna wire hermetically sealed within an insulator passageway of the insulator, wherein the telemetry feedthrough conductor is not conductively connected to any one of the plurality of two-terminal MLCC chip capacitors.

32. The filtered feedthrough assembly of claim 24, wherein the circuit board comprises a rigid section, and wherein the circuit board rigid section comprises at least one material selected from the group consisting of a ceramic, an alumina, and an FR4 material.

33. The filtered feedthrough assembly of claim 24, wherein the circuit board comprises a flexible section, and wherein the circuit board flexible section comprises at least one material selected from the group consisting of a polyimide, a Kapton, and an acrylic material.

34. The filtered feedthrough assembly of claim 24, wherein the ground pins and first gold brazes are each located at least partially within a ferrule countersink.

35. A filtered feedthrough assembly for an active implantable medical device, the filtered feedthrough assembly comprising:

a) a ferrule comprising an electrically conductive material, the ferrule comprising a ferrule opening, wherein a conductive ground pin is conductively and mechanically connected to the ferrule by a first gold braze, and wherein the ferrule is configured to be attachable to an opening in a housing of an active implantable medical device;

b) an insulator at least partially residing in the ferrule opening where a second gold braze hermetically seals the insulator to the ferrule, wherein at least one insulator passageway extends through the insulator to an insulator first end surface and an insulator second end surface;

c) an electrically conductive lead wire residing in the insulator passageway where a third gold braze hermetically seals the lead wire to the insulator, the lead wire extending from a lead wire first portion to a lead wire second portion, wherein at least the lead wire second portion extends outwardly beyond the insulator second end surface;

d) a circuit board comprising spaced apart circuit board first and second sides, wherein the circuit board first side is adjacent to the insulator second end surface, and wherein the circuit board comprises at least one circuit board ground plate;

e) at least one two-terminal MLCC chip capacitor comprising a chip capacitor dielectric supporting at least one active electrode plate interleaved in a capacitive relationship with at least one ground electrode plate, wherein an active metallization is conductively connected to the at least one active electrode plate, and a ground metallization is conductivelp connected to the at least one ground electrode plate;

f) a circuit board first ground via hole extending through the circuit board ground plate, wherein a first ground via hole conductive material residing in the circuit board first ground via hole is conductively connected to the circuit board ground plate and to the ground metallization of the two-terminal chip capacitor;

g) a circuit board second ground via hole spaced from the circuit board first ground via hole and extending through the circuit board ground plate, wherein at least a portion of the ground pin connected to the ferrule resides in the circuit board second ground via hole where a second ground via hole conductive material conductively connects the ground pin connected to the ferrule to the circuit board ground plate; and h) a circuit board active via hole extending through the circuit board, but being conductively isolated from the at least one circuit board ground plate, wherein at least a portion of the lead wire second portion extending outwardly beyond the insulator second end surface resides in the circuit board active via hole, and wherein an active conductive material conductively connects the lead wire to the active metallization of the at least one two-terminal chip capacitor.

* * * * *

UNITED STATES PATENT AND TRADEMARK OFFICE

CERTIFICATE OF CORRECTION

PATENT NO. : 9,895,534 B2
APPLICATION NO. : 15/375235
DATED : February 20, 2018
INVENTOR(S) : Robert A. Stevenson, Christine A. Frysz and Richard L. Brendel It is certified that error appears in the above-identified patent and that said Letters Patent is hereby corrected as shown below:

In the Specification

Column 16, Line 60 delete “it” and insert --π--

Column 44, Line 27 delete “it” and insert --π--

Column 54, Line 33 delete “though” and insert --through--

Column 55, Line 42 delete “MH.sub.z” and insert --MHz--

In the Claims

Column 57, Line 43 (Claim 1, Line 30) delete “resides” and insert --residing--

Column 58, Lines 11-12 (Claim 1, Lines 65-66) delete “metaiiization” and insert --metallization--

Column 58, Line 53 (Claim 6, Line 8) delete “hoie” and insert --hole--

Column 63, Line 15 (Claim 24, Line 57) delete “conductiveiy” and insert --conductively--

Column 63, Line 65 (Claim 27, Line 1) delete “assembiy” and insert --assembly--

Column 65, Line 5 (Claim 35, Line 34) delete “conductivelp” and insert --conductively--

Signed and Sealed this
Tenth Day of September, 2019

Andrei Iancu
*Director of the United States Patent and Trademark Office*